US009232997B2

(12) United States Patent
Sugimoto et al.

(10) Patent No.: US 9,232,997 B2
(45) Date of Patent: Jan. 12, 2016

(54) DEVICES AND METHODS FOR RETRIEVABLE INTRA-ATRIAL IMPLANTS

(71) Applicant: Corvia Medical, Inc., Tewksbury, MA (US)

(72) Inventors: Hiroatsu Sugimoto, Cambridge, MA (US); Stephen J. Forcucci, Winchester, MA (US); Edward McNamara, Chelmsford, MA (US); Matthew J. Finch, Medford, MA (US); Christopher Magnin, Andover, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 150 days.

(21) Appl. No.: 13/838,192

(22) Filed: Mar. 15, 2013

(65) Prior Publication Data

US 2014/0012368 A1   Jan. 9, 2014

Related U.S. Application Data

(63) Continuation-in-part of application No. 13/167,502, filed on Jun. 23, 2011, now abandoned, which is a continuation-in-part of application No. 12/954,468, filed on Nov. 24, 2010, now Pat. No. 8,752,258, which (Continued)

(51) Int. Cl.
*A61F 2/24* (2006.01)
*A61L 31/02* (2006.01)
(Continued)

(52) U.S. Cl.
CPC ........... *A61F 2/2427* (2013.01); *A61B 17/0057* (2013.01); *A61B 17/221* (2013.01);
(Continued)

(58) Field of Classification Search
CPC ...... A61F 2/24; A61F 2/2418; A61B 17/0057
USPC .................... 623/2.1–2.19; 606/151
See application file for complete search history.

(56) References Cited

U.S. PATENT DOCUMENTS 3,874,388 A   4/1975 King et al.
4,018,228 A   4/1977 Goosen
(Continued)

FOREIGN PATENT DOCUMENTS

AU   2007317191 A1   5/2008
CN   1556719 A   12/2004
(Continued)

OTHER PUBLICATIONS

Ling et al.; Implantable magnetic relaxation sensors measure cumulative exposure to cardiac biomarkers; Nat Biotechnol; 29(3); pp. 273-277; Mar. 2011.
(Continued)

*Primary Examiner* — Suzette J Gherbi
(74) *Attorney, Agent, or Firm* — Shay Glenn LLP

(57) ABSTRACT

Devices and methods to enhance the implantation, retreivability, or repositionability are provided. Embodiments of devices include pivotable sections providing the ability to maintain the device's engagement with a delivery system during implantation where the deliver system approaches an opening of the septum at an angle. Embodiments of devices also include configurations that allow for improved retrieval into a delivery system in the event that a malfunction or a problem with the patients physiology is detected.

30 Claims, 73 Drawing Sheets

Related U.S. Application Data is a continuation-in-part of application No. 12/719,843, filed on Mar. 8, 2010, now Pat. No. 8,157,860, application No. 13/838,192, which is a continuation-in-part of application No. 13/290,295, filed on Nov. 7, 2011, now Pat. No. 8,460,372, said application No. 13/167,502 is a continuation-in-part of application No. 12/954,541, filed on Nov. 24, 2010, now Pat. No. 8,740,962.

(60) Provisional application No. 61/449,566, filed on Mar. 4, 2011, provisional application No. 61/299,559, filed on Jan. 29, 2010, provisional application No. 61/240,085, filed on Sep. 4, 2009.

(51) Int. Cl.
*A61B 17/00* (2006.01)
*A61B 17/221* (2006.01)
*A61F 2/91* (2013.01)
*A61B 18/14* (2006.01)
*A61B 17/22* (2006.01)
*A61B 18/00* (2006.01)
*A61F 2/06* (2013.01)
*A61F 2/95* (2013.01)

(52) U.S. Cl.
CPC .............. *A61F 2/2412* (2013.01); *A61F 2/2418* (2013.01); *A61F 2/2436* (2013.01); *A61F 2/2493* (2013.01); *A61F 2/91* (2013.01); *A61L 31/022* (2013.01); *A61B 18/1492* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/2215* (2013.01); *A61B 2017/22035* (2013.01); *A61B 2018/00023* (2013.01); *A61B 2018/00351* (2013.01); *A61B 2018/144* (2013.01); *A61F 2002/061* (2013.01); *A61F 2002/9522* (2013.01); *A61F 2210/0076* (2013.01); *A61F 2220/005* (2013.01); *A61F 2220/0008* (2013.01); *A61F 2220/0041* (2013.01); *A61F 2220/0058* (2013.01); *A61F 2220/0066* (2013.01); *A61F 2230/005* (2013.01); *A61F 2230/006* (2013.01); *A61F 2230/0017* (2013.01); *A61F 2230/0019* (2013.01); *A61F 2230/0054* (2013.01); *A61F 2230/0058* (2013.01); *A61F 2230/0067* (2013.01); *A61F 2230/0078* (2013.01); *A61F 2250/0098* (2013.01)

(56) References Cited

U.S. PATENT DOCUMENTS

| | | |
|---|---|---|
| 4,373,216 A | 2/1983 | Klawitter |
| 4,491,986 A | 1/1985 | Gabbay |
| 4,705,507 A | 11/1987 | Boyles |
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,556,386 A | 9/1996 | Todd |
| 5,578,045 A | 11/1996 | Das |
| 5,693,090 A | 12/1997 | Unsworth et al. |
| 5,702,412 A | 12/1997 | Popov et al. |
| 5,725,552 A | 3/1998 | Kotula et al. |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich, Jr. et al. |
| 6,059,827 A | 5/2000 | Fenton |
| 6,068,635 A | 5/2000 | Gianotti |
| 6,077,281 A | 6/2000 | Das |
| 6,120,534 A | 9/2000 | Ruiz |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,241,678 B1 | 6/2001 | Afremov et al. |
| 6,258,119 B1 | 7/2001 | Hussein et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,301 B1 | 10/2002 | Amplatz et al. |
| 6,468,303 B1 | 10/2002 | Amplatz et al. |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,641,610 B2 | 11/2003 | Wolf et al. |
| 6,645,143 B2 | 11/2003 | VanTassel et al. |
| 6,666,885 B2 | 12/2003 | Moe |
| 6,712,836 B1 * | 3/2004 | Berg ................ A61B 17/0057 606/213 |
| 6,719,768 B1 | 4/2004 | Cole et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,001,409 B2 | 2/2006 | Amplatz |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,159,593 B2 | 1/2007 | McCarthy et al. |
| 7,226,466 B2 | 6/2007 | Opolski |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,524,330 B2 | 4/2009 | Berreklouw |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |

(56) References Cited

U.S. PATENT DOCUMENTS

| | | |
|---|---|---|
| 7,766,966 B2 | 8/2010 | Richelsoph |
| 7,819,890 B2 | 10/2010 | Russo et al. |
| 7,842,026 B2 | 11/2010 | Cahill et al. |
| 7,871,419 B2 | 1/2011 | Devellian et al. |
| 7,905,901 B2 | 3/2011 | Corcoran et al. |
| 7,927,370 B2 | 4/2011 | Webler et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,252,042 B2 | 8/2012 | McNamara et al. |
| 8,303,623 B2 | 11/2012 | Melzer et al. |
| 8,313,505 B2 | 11/2012 | Amplatz et al. |
| 8,366,088 B2 | 2/2013 | Allen et al. |
| 8,398,670 B2 | 3/2013 | Amplatz et al. |
| 8,460,372 B2 | 6/2013 | McNamara et al. |
| 8,777,974 B2 | 7/2014 | Amplatz et al. |
| 9,005,155 B2 | 4/2015 | Sugimoto |
| 2001/0029368 A1 | 10/2001 | Berube |
| 2002/0029061 A1 | 3/2002 | Amplatz et al. |
| 2002/0062135 A1 | 5/2002 | Mazzocchi et al. |
| 2002/0072765 A1 | 6/2002 | Mazzocchi et al. |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0095173 A1 | 7/2002 | Mazzocchi et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1* | 11/2002 | Keren ............... A61B 17/00234 604/9 |
| 2002/0177894 A1 | 11/2002 | Acosta et al. |
| 2002/0183826 A1 | 12/2002 | Dorn et al. |
| 2002/0198563 A1 | 12/2002 | Gainor et al. |
| 2003/0093072 A1 | 5/2003 | Friedman |
| 2003/0125798 A1 | 7/2003 | Martin |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065548 A1 | 3/2005 | Marino et al. |
| 2005/0065589 A1 | 3/2005 | Schneider et al. |
| 2005/0070934 A1 | 3/2005 | Tanaka et al. |
| 2005/0075655 A1 | 4/2005 | Bumbalough et al. |
| 2005/0080400 A1 | 4/2005 | Corcoran et al. |
| 2005/0096735 A1 | 5/2005 | Hojeibane et al. |
| 2005/0113868 A1 | 5/2005 | Devellian et al. |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0165344 A1* | 7/2005 | Dobak ............... A61F 2/01 604/8 |
| 2005/0187616 A1 | 8/2005 | Realyvasquez |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267523 A1 | 12/2005 | Devellian et al. |
| 2005/0267524 A1 | 12/2005 | Chanduszko |
| 2005/0273075 A1 | 12/2005 | Krulevitch et al. |
| 2005/0288722 A1 | 12/2005 | Eigler et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0085060 A1* | 4/2006 | Campbell ............... A61F 2/06 623/1.26 |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0016250 A1 | 1/2007 | Blaeser et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0168019 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1* | 12/2007 | Rottenberg ........ A61B 17/00234 600/16 |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249397 A1 | 10/2008 | Kapadia |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018562 A1 | 1/2009 | Amplatz et al. |
| 2009/0018570 A1 | 1/2009 | Righini et al. |
| 2009/0025820 A1 | 1/2009 | Adams |
| 2009/0030495 A1 | 1/2009 | Koch |
| 2009/0054984 A1* | 2/2009 | Shortkroff ......... A61F 2/30756 |

(56) References Cited

U.S. PATENT DOCUMENTS

| | | | |
|---|---|---|---|
| | | | 623/16.11 |
| 2009/0062841 A1 | 3/2009 | Amplatz et al. | |
| 2009/0082803 A1 | 3/2009 | Adams et al. | |
| 2009/0099647 A1 | 4/2009 | Glimsdale et al. | |
| 2009/0112050 A1 | 4/2009 | Farnan et al. | |
| 2009/0112244 A1 | 4/2009 | Freudenthal | |
| 2009/0112251 A1 | 4/2009 | Qian et al. | |
| 2009/0131978 A1 | 5/2009 | Gainor et al. | |
| 2009/0171386 A1 | 7/2009 | Amplatz et al. | |
| 2009/0177269 A1 | 7/2009 | Kalmann et al. | |
| 2009/0187214 A1 | 7/2009 | Amplatz et al. | |
| 2009/0209855 A1 | 8/2009 | Drilling et al. | |
| 2009/0209999 A1 | 8/2009 | Afremov | |
| 2009/0210047 A1 | 8/2009 | Amplatz et al. | |
| 2009/0210048 A1 | 8/2009 | Amplatz et al. | |
| 2009/0234443 A1 | 9/2009 | Ottma et al. | |
| 2009/0264991 A1 | 10/2009 | Paul, Jr. et al. | |
| 2009/0270840 A1 | 10/2009 | Miles et al. | |
| 2009/0270909 A1 | 10/2009 | Oslund et al. | |
| 2010/0022940 A1 | 1/2010 | Thompson | |
| 2010/0023046 A1 | 1/2010 | Heidner et al. | |
| 2010/0023048 A1 | 1/2010 | Mach | |
| 2010/0023121 A1 | 1/2010 | Evdokimov et al. | |
| 2010/0030259 A1 | 2/2010 | Pavcnik et al. | |
| 2010/0030321 A1 | 2/2010 | Mach | |
| 2010/0049307 A1 | 2/2010 | Ren | |
| 2010/0051886 A1 | 3/2010 | Cooke et al. | |
| 2010/0057192 A1 | 3/2010 | Celermajer | |
| 2010/0063578 A1 | 3/2010 | Ren et al. | |
| 2010/0094335 A1 | 4/2010 | Gerberding et al. | |
| 2010/0106235 A1 | 4/2010 | Kariniemi et al. | |
| 2010/0121370 A1 | 5/2010 | Kariniemi | |
| 2010/0131053 A1 | 5/2010 | Agnew | |
| 2010/0179491 A1 | 7/2010 | Adams et al. | |
| 2010/0211046 A1 | 8/2010 | Adams et al. | |
| 2010/0234881 A1 | 9/2010 | Blaeser et al. | |
| 2010/0249490 A1 | 9/2010 | Farnan | |
| 2010/0249491 A1 | 9/2010 | Farnan et al. | |
| 2010/0249909 A1 | 9/2010 | McNamara et al. | |
| 2010/0249910 A1 | 9/2010 | McNamara et al. | |
| 2010/0256548 A1 | 10/2010 | McNamara et al. | |
| 2010/0256753 A1 | 10/2010 | McNamara et al. | |
| 2010/0268316 A1 | 10/2010 | Brenneman et al. | |
| 2010/0274351 A1* | 10/2010 | Rolando | A61F 2/06 |
| | | | 623/1.26 |
| 2010/0298755 A1 | 11/2010 | McNamara et al. | |
| 2010/0305685 A1* | 12/2010 | Millwee | A61F 2/2412 |
| | | | 623/1.26 |
| 2010/0324588 A1 | 12/2010 | Miles et al. | |
| 2011/0004239 A1 | 1/2011 | Russo et al. | |
| 2011/0004296 A1 | 1/2011 | Lutter et al. | |
| 2011/0022079 A1 | 1/2011 | Miles et al. | |
| 2011/0071623 A1 | 3/2011 | Finch et al. | |
| 2011/0071624 A1 | 3/2011 | Finch et al. | |
| 2011/0087261 A1 | 4/2011 | Wittkampf et al. | |
| 2011/0093062 A1 | 4/2011 | Cartledge et al. | |
| 2011/0106149 A1 | 5/2011 | Ryan et al. | |
| 2011/0112633 A1 | 5/2011 | Devellian et al. | |
| 2011/0130784 A1 | 6/2011 | Kusleika | |
| 2011/0184439 A1 | 7/2011 | Anderson et al. | |
| 2011/0190874 A1 | 8/2011 | Celermajer et al. | |
| 2011/0213364 A1 | 9/2011 | Davis et al. | |
| 2011/0218477 A1 | 9/2011 | Keren et al. | |
| 2011/0218478 A1 | 9/2011 | Keren et al. | |
| 2011/0218479 A1 | 9/2011 | Rottenberg et al. | |
| 2011/0218480 A1 | 9/2011 | Rottenberg et al. | |
| 2011/0218481 A1 | 9/2011 | Rottenberg | |
| 2011/0257723 A1 | 10/2011 | McNamara | |
| 2011/0270239 A1 | 11/2011 | Werneth | |
| 2011/0283871 A1 | 11/2011 | Adams | |
| 2011/0295182 A1 | 12/2011 | Finch et al. | |
| 2011/0295183 A1 | 12/2011 | Finch et al. | |
| 2011/0295362 A1 | 12/2011 | Finch et al. | |
| 2011/0295366 A1 | 12/2011 | Finch et al. | |
| 2011/0306916 A1 | 12/2011 | Nitzan et al. | |
| 2011/0307000 A1 | 12/2011 | Amplatz et al. |
| 2011/0319989 A1 | 12/2011 | Lane et al. |
| 2012/0022427 A1 | 1/2012 | Kapadia |
| 2012/0053686 A1 | 3/2012 | McNamara et al. |
| 2012/0130301 A1 | 5/2012 | McNamara et al. |
| 2012/0165928 A1 | 6/2012 | Nitzan et al. |
| 2012/0259263 A1 | 10/2012 | Celermajer et al. |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0267885 A1 | 10/2013 | Celermajer et al. |
| 2013/0281988 A1 | 10/2013 | Magnin et al. |
| 2014/0012181 A1 | 1/2014 | Sugimoto et al. |
| 2014/0194971 A1 | 7/2014 | McNamara |
| 2014/0257167 A1 | 9/2014 | Celermajer et al. |
| 2014/0277045 A1 | 9/2014 | Fazio et al. |
| 2014/0277054 A1 | 9/2014 | McNamara et al. |
| 2015/0039084 A1 | 2/2015 | Levi et al. |
| 2015/0119796 A1 | 4/2015 | Finch |
| 2015/0148731 A1 | 5/2015 | McNamara et al. |

FOREIGN PATENT DOCUMENTS

| | | |
|---|---|---|
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| CN | 102905626 A | 1/2013 |
| CN | 102908213 A | 2/2013 |
| EP | 1264582 A2 | 2/2002 |
| EP | 1470785 A1 | 10/2004 |
| EP | 1849440 A1 | 10/2007 |
| EP | 2528646 A2 | 12/2012 |
| EP | 2537490 A1 | 12/2012 |
| EP | 2642954 A1 | 10/2013 |
| JP | 58-27935 U | 6/1983 |
| JP | 2003530143 | 10/2003 |
| WO | 9527448 A1 | 10/1995 |
| WO | WO98/08456 A1 | 3/1998 |
| WO | WO98/42403 A1 | 10/1998 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | 2008055301 A1 | 5/2008 |
| WO | 2008058940 A1 | 5/2008 |
| WO | 2010111666 A1 | 9/2010 |
| WO | 2010128501 A1 | 11/2010 |
| WO | 2010129089 A2 | 11/2010 |
| WO | WO2010/129511 A | 11/2010 |
| WO | 2011093941 A2 | 8/2011 |
| WO | 2011094521 A2 | 8/2011 |
| WO | 2011093941 A3 | 10/2011 |
| WO | 2011093941 A4 | 12/2011 |
| WO | 2011094521 A3 | 12/2011 |
| WO | 2012071075 A1 | 5/2012 |
| WO | 2012109557 A2 | 8/2012 |
| WO | 2012109557 A3 | 1/2013 |
| WO | 2013096965 A1 | 6/2013 |

OTHER PUBLICATIONS

Roven et al.; Effect of compromising right ventricular function in left ventricular failure by means of interatrial and other shunts; Am J Cardiol.; 24(2); pp. 209-219; Aug. 1969.

Sambhi et al.; Pathologic Physiology of Lutembacher Syndrome; Am J Cardiol.; 2(6); pp. 681-686; Dec. 1958.

Trafton, Anne; Detecting whether a heart attack has occurred; MIT News; 3 pgs.; Feb. 14, 2011; retrieved from the internet Sep. 20, 2014 (http://newsoffice.mit.edu/2011/cardiac-implant-0214).

(56) References Cited

OTHER PUBLICATIONS

Celermajer et al.; U.S. Appl. No. 14/498,903 entitled "Apparatus and methods to create and maintain an intra-atrial pressure relief opening," filed Sep. 26, 2014.
European Application Serial No. 10772411.4, European Search Opinion and Supplementary European Search Report mailed Mar. 16, 2012, DC Devices, Inc., 6 pages.
European Application Serial No. 11843665.8, Notification re Publication and Provisional Protection mailed Sep. 4, 2013, DC Devices, Inc., 1 page.
U.S. Appl. No. 12/954,521, Ex Parte Quayle Action mailed Sep. 11, 2013, Matthew J. Finch et al., 6 pages.
Australian Application Serial No. 2010245215, Examiners Report mailed Mar. 27, 2012, DC Devices, Inc., 2 pages.
Australian Application Serial No. 2010245215, Further Examination Report mailed Nov. 14, 2012, DC Devices, Inc., 3 pages.
Australian Application Serial No. 2011210741, First Examiner Report mailed Nov. 5, 2012, DC Devices, Inc., 3 pages.
Australian Application Serial No. 2012202952, First Examiner Report mailed Aug. 16, 13, DC Devices, Inc., 3 pages.
AD et al., "A One Way Valved Atrial Septal Patch: A New Surgical Technique and Its Clinical Application", The Journal of Thoracic and Cardiovascular Surgery, vol. 111, No. 4, Apr. 1996, pp. 841-848.
Althoff et al., "Long-Term Follow Up of a Fenestrated Amplatzer Atrial Septal Occluder in Pulmonary Arterial Hypertension", American College of Chest Physicians 2008, Chest, vol. 133, No. 1, Jan. 2008, 5 pages.
Atz et al., "Preoperative Management of Pulmonary Venous Hypertension in Hypoplastic Left Heart Syndrome with Restrictive Atrial Septal Defect", The American Journal of Cardiology, vol. 83, Apr. 15, 1999, pp. 1224-1228.
Bailey, Steven R., "Nanotechnology in Prosthetic Heart Valves", EuroPCR 2005, May 24-27, 2005, 31 pages.
Bolling, Steven F., "Direct Flow Medical-My Valve is Better", Direct Flow medical Inc., Apr. 23, 2009, 21 pages.
Caselli, Joseph S., "No! Valve Replacement; Patient Prosthetic Mismatch Rarely Occurs", Texas Heart Institute, Apr. 25, 2009, 75 pages.
Cheatham, John P., "Intervention in the Critically III Neonate and Infant with Hypoplastic Left Heart Syndrome and Intact Atrial Septum", Journal of Interventional Cardiology, vol. 14, No. 3, 2001, pp. 357-366.
Design News, "Low Power Piezo Motion", http://www.designnews.com/document.asp?doc_id=229053&dfpPParams=ht_13,aid_229053&dfpLayout=article, May 14, 2010, 3 pages.
European Application Serial No. EP12180631.9, Extended European Search Report and European Search Opinion mailed Nov. 19, 2012, DC Devices, Inc., 6 pages.
Gaudiani et al., "A Philosophical Approach to Mitral Valve Repair (with Data)", Dallas-Leipzig International Valve Congress, Apr. 24, 2009, 28 pages.
Hijazi, Ziyad M., "Valve Implantation", Pediatric & Adult Interventional Therapies for Congenital and Valvular Heart Disease, Jul. 22-25, 2007, 36 pages.
Larios et al., "The Use of an Artificial Foraminal Valve Prosthesis in the Closure of Interatrial and Interventricular Septal Defects", American College of Chest Physicians, Dis. Chest. 1959, vol. 36, Dec. 1959, 12 pages.
Leon, Martin B., "Transcatheter Aortic Valve Therapy: Summary Thoughts", Transcatheter Valve Therapies, Jun. 24-26, 2009, 19 pages.
McMahon, Jim, "Piezo Motors and Actuators: Streamlining Medical Device Performance", DesignFax News, Mar. 23, 2010, 5 pages.
Merchant et al., "Implantable Sensors for Heart Failure; Advances in Arrhythmia and Electrophysiology", Circ. Arrhythm. Electrophysiol., vol. 3, Dec. 2010, pp. 657-667.
Moses, Jeffrey W., "The Good, The Bad and The Ugly of Transcatheter AVR", Jul. 10, 2009, 28 pages.
O'Loughlin et al., "Insertion of a Fenestrated Amplatzer Atrial Septostomy Device for Severe Pulmonary Hypertension", Heart, Lung and Circulation, vol. 15, 2006, pp. 275-277.
Park et al., "Blade Atrial Septostomy: Collaborative Study", Circulation, Journal of the American Heart Association, vol. 66, No. 2, Aug. 1982, pp. 258-266.

International Application Serial No. PCT/AU2007/001704, International Search Report mailed Jan. 16, 2008, The University of Sydney, 4 pages.
International Application Serial No. PCT/AU2007/001704, International Preliminary Report on Patentability completed Aug. 22, 2008, The University of Sydney, 5 pages.
International Application Serial No. PCT/AU2007/001704, Written Opinion mailed Jan. 16, 2008, The University of Sydney, 5 pages.
International Application Serial No. PCT/US10/58110, International Preliminary Report on Patentability mailed Nov. 27, 2012, DC Devices, Inc., 11 pages.
International Application Serial No. PCT/US12/024680, International Preliminary Report on Patentability mailed Aug. 22, 2013, DC Devices, Inc., 7 pages.
International Application Serial No. PCT/US2010/026574, International Preliminary Report on Patentability mailed Nov. 10, 2011, DC Devices, Inc., 7 pages.
International Application Serial No. PCT/US2010/026574, International Search Report and Written Opinion mailed Nov. 19, 2010, DC Devices, Inc., 9 pages.
International Application Serial No. PCT/US2010/058110, International Search Report and Written Opinion mailed Dec. 26, 2011, DC Devices, Inc., 14 pages.
International Application Serial No. PCT/US2011/041841, International Preliminary Report on Patentability mailed Jan. 6, 2013, DC Devices, Inc., 8 pages.
International Application Serial No. PCT/US2011/041841, International Search Report and Written Opinion mailed Feb. 9, 2012, DC Devices, Inc., 12 pages.
International Application Serial No. PCT/US2011/022895, International Search Report and Written Opinion mailed Oct. 24, 2011, DC Devices, Inc., 11 pages.
International Application Serial No. PCT/US2012/024680, International Search Report and Written Opinion mailed Oct. 23, 2012, DC Devices, Inc., 11 pages.
International Application Serial No. PCT/US2012/071588, International Search Report and Written Opinion mailed Apr. 19, 2013, DC Devices, Inc., 19 pages.
Pedra et al., "Stent Implantation to Create Interatrial Communications in Patients with Complex Congenital Heart Disease", Catheterization and Cardiovascular Interventions, vol. 47, 1999, pp. 310-313.
Perry et al., "Creation and Maintenance of an Adequate Interatrial Communication in left Atrioventricular Valve Atresia or Stenosis", The American Journal of Cardiology, vol. 58, Sep. 15, 1986, pp. 622-626.
Philips et al., "Ventriculofemoroatrial Shunt: A Viable Alternative for the Treatment of Hydrocephalus", J. Neurosurg., vol. 86, Jun. 1997, pp. 1063-1066.
Physik Instrumente, "Piezo for Motion Control in Medical Design and Drug Research", Physik Instrumente (PI) GmbH & Co. KG, Nov. 21, 2010, 22 pages.
RPI Newswire, "Implantable, Wireless Sensors Share Secrets of Healing Tissues", http://news.rpi.edu/update.do, Feb. 21, 2012, 1 page.
Sommer et al., "Transcatheter Creation of Atrial Septal Defect and Fontan Fenestration with "Butterfly" Stent Technique", Supplement to Journal of the American College of Cardiology, vol. 33, No. 2, Supplement A, Feb. 1999, 3 pages.
Stone, Gregg W., "Transcatheter Devices for Mitral Valve Repair Surveying the Landscape", Columbia University Medical Center, Jul. 10, 2009, 48 pages.
Stormer et al., "Comparative Study of in vitro Flow Characteristics between a Human Aortic Valve and a Designed Aortic Valve and Six Corresponding Types of Prosthetic Heart Valves", Eur. Surg. Res., vol. 8, 1976, pp. 117-131.
Watterson et al., "Very Small Pulmonary Arteries: Central End-to-Side Shunt", Ann. Thorac. Surg., vol. 52, 1991, pp. 1132-1137.
Weber, Ralph, "Piezo Motor Based Medical Devices", Medical Design Technology, http://www.mdtmag.com/articles/2009/04/piezo-motor-based-medical-devices, Apr. 2, 2009, 5 pages.

* cited by examiner

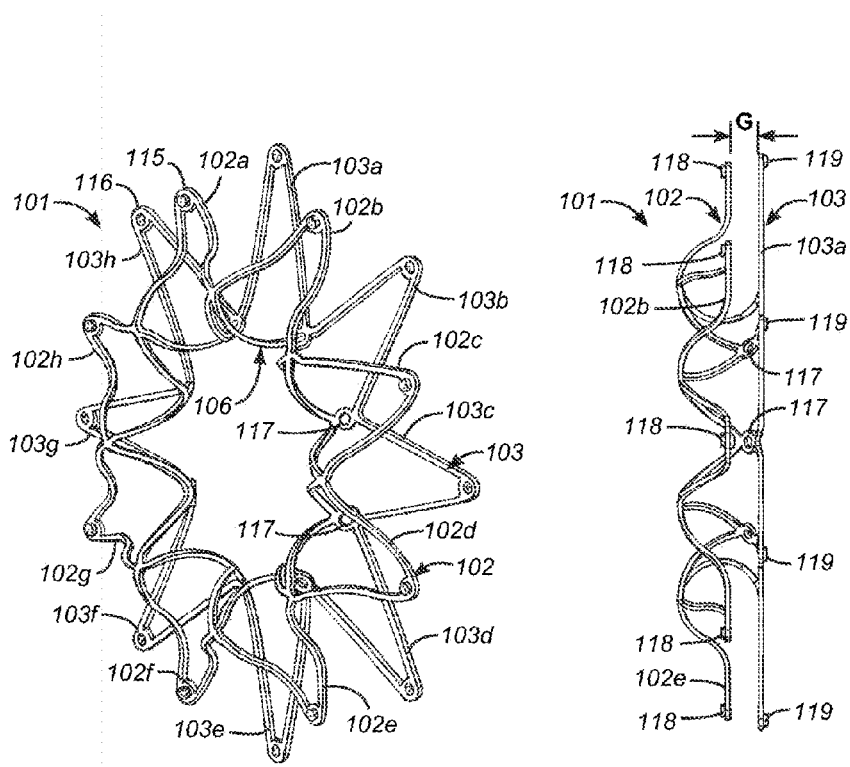
FIG. 4
FIG. 5
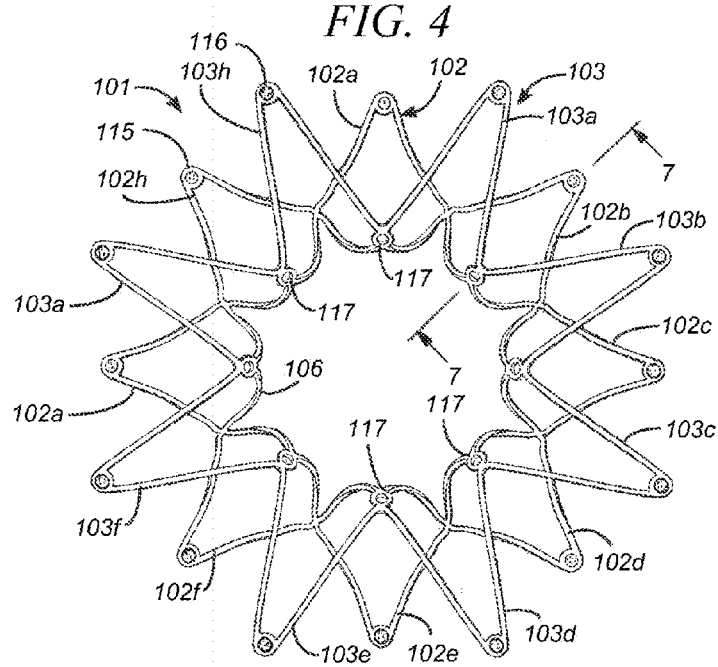
FIG. 6
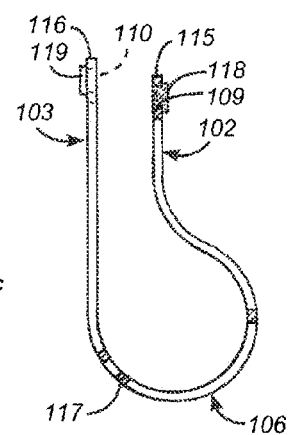
FIG. 7

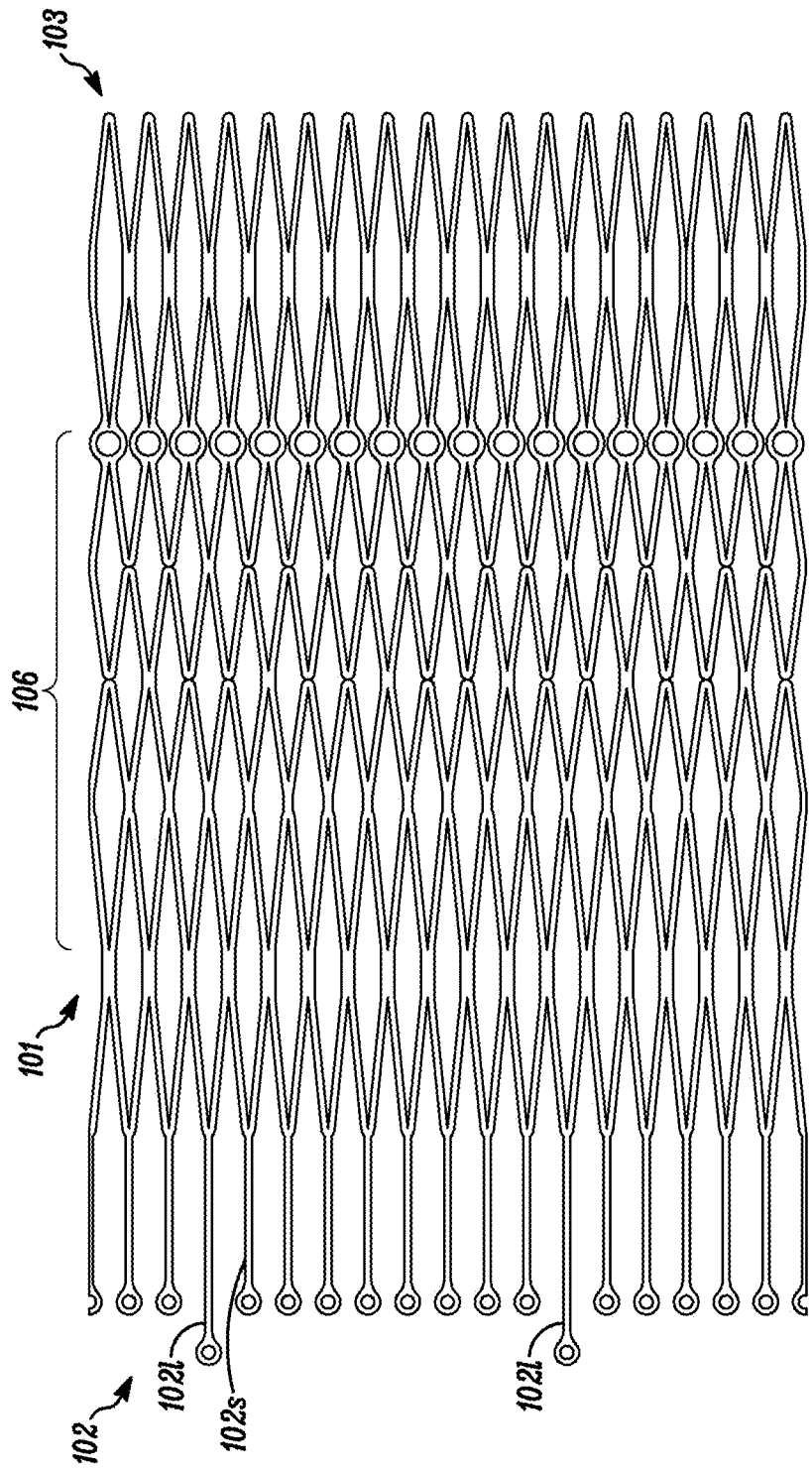

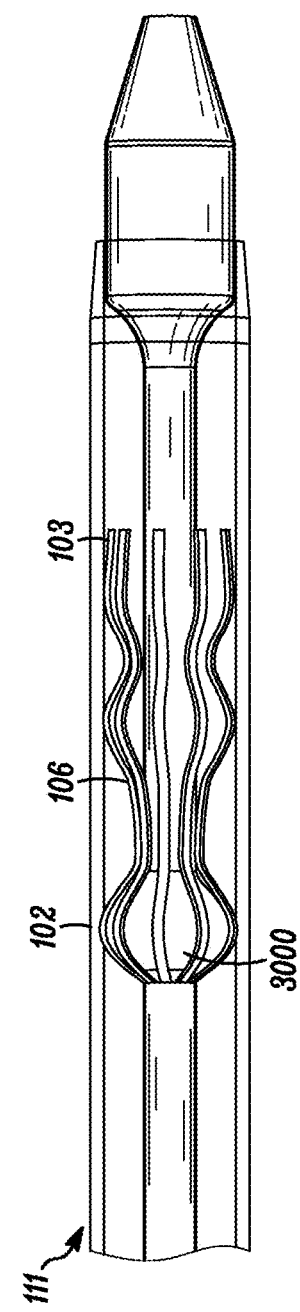

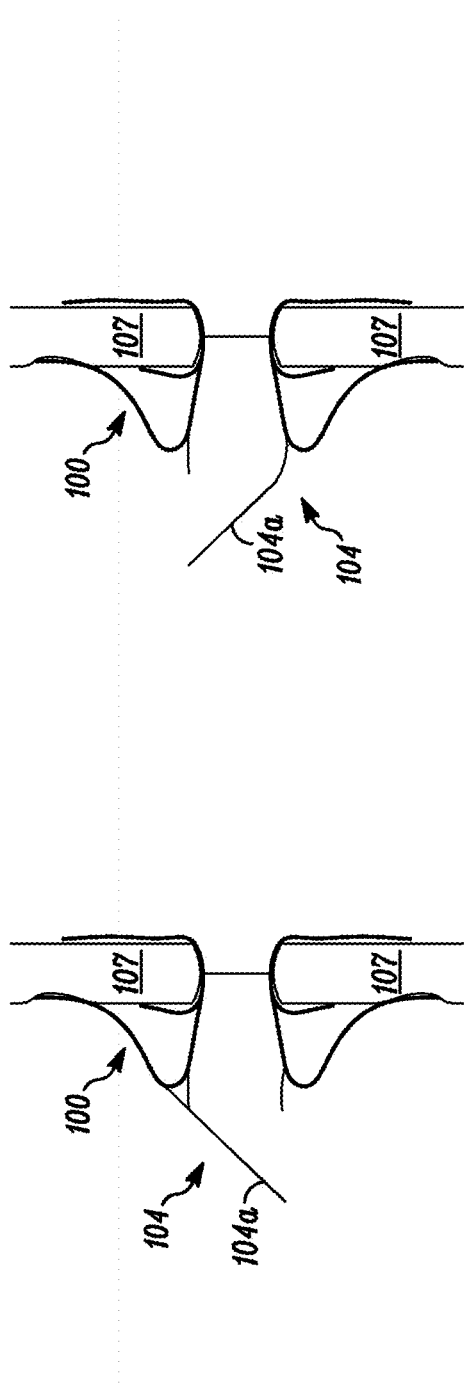

DEVICES AND METHODS FOR RETRIEVABLE INTRA-ATRIAL IMPLANTS

CROSS REFERENCE TO RELATED APPLICATIONS

This application is a continuation-in-part of U.S. patent application Ser. No. 13/167,502, filed Jun. 23, 2011, which claims the benefit of U.S. Provisional Appl. No. 61/449,566, filed Mar. 4, 2011, and is a continuation-in-part of U.S. patent application Ser. No. 12/954,468, filed on Nov. 24, 2010, now U.S. Pat. No. 8,752,258, which is a continuation-in-part of U.S. patent application Ser. No. 12/719,843, filed on Mar. 8, 2010, now U.S. Pat. No. 8,157,860, and claims the benefit of U.S. Provisional Application No. 61/299,559, filed on Jan. 29, 2010. U.S. patent application Ser. No. 12/719,843 claims the benefit of U.S. Provisional Application No. 61/240,085 filed Sep. 4, 2009. This application is also a continuation-in-part of U.S. patent application Ser. No. 13/290,295, filed on Nov. 7, 2011, now U.S. Pat. No. 8,460,372. U.S. application Ser. No. 13/167,502, filed Jun. 23, 2011 is also a continuation-in-part of U.S. patent application Ser. No. 12/954,541, filed Nov. 24, 2010, now U.S. Pat. No. 8,740,962. Each application is herein incorporated by reference in its entirety.

INCORPORATION BY REFERENCE

This application incorporates by reference the following applications: U.S. patent application Ser. No. 12/447,617 filed Apr. 28, 2009; International Patent Application No. PCT/AU2007/001704 filed Nov. 7, 2007; and Australian Patent Application No. AU 2006906202 filed Nov. 7, 2006.

FIELD OF THE INVENTION

The present invention relates generally to devices and methods for treating heart failure. In particular, the invention relates to interatrial pressure vents, shunts and the like, which reduce elevated pressure on one side of the heart thus mitigating the symptoms that result, as well as placement devices, systems, and methods therefore.

BACKGROUND

The functioning of the heart and the opening and closing of heart valves occur primarily as a result of pressure differences. For example, the opening and closing of the mitral valve between the left atrium and the left ventricle occurs as a result of the pressure differences between the left atrium and the left ventricle. During ventricular diastole (ventricular filling), when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole (ventricular emptying), the intraventricular pressure rises above the pressure in the atrium and pushes the mitral valve shut. Blood then is pumped from the ventricles to the arteries.

The heart has four valves to ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

Blood flowing back from the left ventricle into the left atrium, or systolic dysfunction of the left ventricle and valve disease, as mentioned in the background, may cause high atrial pressure and reduce the flow of blood into the left atrium from the lungs. As blood backs up into the pulmonary system, fluid leaks into the lungs and causes pulmonary edema. Blood volume going to the atrium reduces volume of blood going forward into the aorta causing low cardiac output. Excess blood in the atrium over-fills the ventricle during each cardiac cycle and causes volume overload in the left ventricle.

Heart failure with such symptoms is a common and potentially lethal condition affecting humans, with sub-optimal clinical outcomes often resulting in symptoms, morbidity and/or mortality, despite maximal medical treatment.

Congestive heart failure (CHF) is a condition affecting millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, (2) assisting systems, and (3) surgical treatments. Pharmacological treatments, e.g., with diuretics, are used to reduce the workload of a heart by reducing the blood volume and preload. While pharmacological treatments improve quality of life, they have little effect on survival. Assisting devices, e.g., mechanical pumps, are used to reduce the load on the heart by performing all or part of the pumping function normally done by the heart. However, in a chronic ischemic heart, a high-rate pacing may lead to increased diastolic pressures, calcium overload, and damage to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into systolic heart failures (SHF) or diastolic heart failures (DHF). In a SHF, the pumping action of a heart is reduced or weakened. A normal ejection fraction (EF), which is a function of the volume of blood ejected out of the left ventricle (stroke volume) divided by the maximum volume remaining in the left ventricle at the end of a diastole or relaxation phase, is greater than 50%. In a SHF, the EF is reduced to less than 50%. A patient with a SHF may have an enlarged left ventricle because of cardiac remodeling developed to maintain an adequate stroke-volume. This pathophysiological phenomenon is often associated with increased atrial pressure and left ventricular filling pressure.

DHF is a heart failure without any major valve disease even though the systolic function of the left ventricle is preserved. Generally, DHF is a failure of the ventricle to adequately relax and expand, resulting in a decrease in the stroke volume of the heart. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments. Presently, there are very few treatment options for patients suffering from DHF. DHF afflicts between 30% and 70% of patients with CHF.

There are several known techniques used to treat symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left side circulation. Dobak also discloses a conduit with a one-way valve that directs the blood flow from the left atrium to the right atrium.

The constantly evolving nature of heart failures represents a significant challenge for developing an efficient treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat a patient.

In the past, strategies have been described for the relief of high pressure in the right atrium, such as the creation of hole(s) in the native or surgically created septum between the left and right atria. These have been designed for the rare conditions of pulmonary hypertension or cavopulmonary connections for certain complex congenital heart diseases. Accordingly, there still exists a need for devices and methods to treat heart failure, particularly diastolic and/or systolic failure of the left ventricle and its consequences.

BRIEF SUMMARY

Embodiments of the present invention include an implantable device, which can be referred to herein as a device, vent, venting device, stent, implantable, implantable device, valve, shunt, prosthesis, interatrial pressure vent, intercardiac pressure vents/devices, (the above terms and synonyms of such terms will be used herein interchangeably and shall have the same meaning unless an alternate meaning is made explicitly clear). In some embodiments, the implantable device may comprise may comprise a body assembly. In embodiments, the body assembly refers to the primary structural portion of the device which may comprise, or otherwise itself be, what is referred to herein as a core segment. In embodiments, optionally a flow control element is included. A flow control element is sometimes referred to as a valve. Not all embodiments comprise a flow control element or the like, and those skilled in the art will appreciate that even embodiments described in connection with a flow control element need not necessarily contain a flow control element or the like. To that end, the designs, methods, configurations of components, etc. disclosed herein have been described along with various configurations. For example, embodiments may be described which include flow control elements or features of the implantable device; however, those skilled in the art will appreciate where the designs, components, configurations or components described herein can be used in combination, or interchangeably, and that the description herein does not limit such interchangeability or combination of components to only that which is described herein.

The present invention provides implantable devices for treating heart conditions in a patient. The device may have a first elongated, or collapsed, profile for percutaneously delivery and a second expanded profile upon deployed from the delivery catheter. The device may have a hub or other attachment mechanism that is adapted to cooperate with a complementary mechanism on a deployment and/or retrieval device. In some embodiments, this hub or other attachment device is located at an apex of the implantable device. In some instances, the hub or other attachment device is comprised of a cardiac-environment compatible machinable material.

The device may comprise a proximal flange, a distal flange, a core segment, and a hub. Each of the proximal and distal flanges may comprise a plurality of flange segments each with a first end and a second end. In some embodiments, the proximal flange comprises a proximal curvy portion, which allows the device to curve, turn, bend or twist. The core segment defines a passage which is adapted to permit fluid to flow therethrough from one side of said septal wall to another side of said septal wall. In some embodiments, the second ends of the first flange and the second ends of the second flange are contiguous with the core segment. In some embodiments, the core segment has a first diameter when deployed. The hub may be configured to releasably attach to a delivery catheter. In some embodiments, the first end of the proximal flange is configured to rotate against the hub.

In some embodiments, the implanted device may be removed after being (a) fully deployed and disengaged from its delivery system (such as a catheter delivery system including the type described herein) and/or (b) within, near, or implanted in the targeted anatomy of the subject. In some embodiments, the device may be repositioned from being partially or fully deployed at one location to a being deployed at another location.

In some embodiments, the device comprises a plurality of struts, a hub that is connected to an end of at least one of the struts, at least three pluralities of fork sections each having two or more prongs, a first flange that is formed at least in part from a first set of fork prong junctions, a second flange that is formed at least in part from a second set of fork prong junctions, and a core segment. The device may be configured to be collapsible about its longitudinal axis so that the device may be stored in a delivery apparatus for percutaneous delivery to a hole in the septal wall of a patient's heart and to be expandable upon deployment so that it takes on its pre-collapsed shape. In some embodiments of the present invention, the hub and the struts of the device form an apex at the proximal end of the device.

In some embodiments, the device includes a hub and a first portion which is operably connected to the hub. The first portion comprises a continuous, metal sheet material which has a plurality of contiguous primary strands each of which branches into at least two secondary strands. The first portion has at least a first flange section, a second flange section, and a core segment and is configured such that at least part of the core segment is positioned between the first and second flange sections. In such embodiments, the device is adapted to be delivered by a catheter into the patient's heart such that the device expands during the delivery to an expanded configuration, and the device is further adapted to be collapsed from its expanded configuration by withdrawing the device back into the catheter.

In some embodiments, the device comprises a plurality of interconnected units, a hub that is connected to the near end of at least one of the units, a first flange that is at least in part formed by the junctions of arm sections of adjacent units, a second flange that is at least in part formed by the far ends of at least some of the units, and a core segment. Each of the units includes a first diamond section connected at its far end to the near end of a second diamond section. Each of the units is connected together by way of its arm sections, which extend from the first diamond section of the unit, and by interconnections of their respective second diamond sections. The device is configured to be collapsible about its longitudinal axis so that the device may be stored in a delivery apparatus for percutaneous deliver to a hole in the septal wall of a patient's heart. Like other embodiments described herein, the device is expandable upon deployment and will take on its pre-collapsed shape. The hub and the units in some instances form an apex at what would be the near end of the device which is within right atrium of the patient's heart when implanted.

In some other embodiments, the device comprises a plurality of struts, a hub that is connected to an end of at least one of the struts, at least two pluralities of fork sections each having two prongs, a first flange that is formed from at least two of the struts, a second flange that is formed at least in part of at least two of a set of fork prong junctions, and a core segment.

The present invention also includes techniques, systems, and methods for deployment of the devices described herein.

In some embodiments, the device comprises a core segment, which may comprise a self expanding mesh. In embodiments the device may be collapsible so as to fit into a placement catheter described herein. In some embodiments, the device may be both self-explaining and collapsible.

Some embodiments include a delivery system for the implantable device. The delivery system may comprise a delivery sheath and a delivery catheter. The delivery sheath may have a distal end, a proximal end, and a center lumen-like cavity. The delivery catheter may be slidably disposed within the center lumen-like cavity. The distal end of the delivery catheter distal end of the delivery catheter may be configured to releasably attach to an implantable device.

In some embodiments, the implantable device is designed to safeguard against portions of the flange that are to engage the proximal side of the septum from entering into the portion of the heart that is on the distal side of the septum. This safeguard is best understood by considering the implantable device in its state of collapse along its longitudinal axis for percutaneous delivery to the patient's heart. The safeguard is to provide a minimum longitudinal distance between the distal end of the proximal flange and the distal end of the core segment of the implantable device. This longitudinal distance is to be the quotient of the longitudinal length of the septal aperture into which the device is expected to be implanted divided by the cosine of the angle the longitudinal axis of the device is expected to make during delivery in relation to the longitudinal axis of the septal aperture. Due to the dynamic nature of the heart and the delivery apparatus during the deployment of the device, in some instances this minimum distance is increased by a factor ranging between 1.1 and 2.0.

The body assembly may be constructed from preformed wire braid. The wire braid may be formed from nitinol with a martensite/austenite transition temperature is below 37° C. so it remains in its superelastic, austenitic phase during use. The transition temperature is below about 25+/−5° C. The wire should have a diameter of at least about 0.0035 (about 2 lbs of breaking strength at 200 ksi tensile). The wire should have a very smooth surface to reduce thrombogenicity or irritation response from the tissue. The surface finish may be 63 μin RA or better. This surface may be obtained either by mechanical polishing, by electropolishing or a combination. In embodiments, the surface may be cleaned with detergents, acids and/or solvents to remove residual oils or contamination and then controllably passivated to insure minimal corrosion.

The implantable device, or a part thereof, e.g., the body portion, may be formed from grade 1 or grade 6 titanium. In embodiments, the body may be formed of grade 9 titanium. In embodiments, the body may be formed of 316L stainless steel. In embodiments, the body may be formed of 416L stainless steel. In embodiments, the body may be formed of nitinol or cobalt-chromium-nickel alloy (such as Elgiloy®). In embodiments, the body is formed of platinum iridium. In embodiments, the body may be formed of a cobalt chromium alloy. In embodiments, the body may be formed of MP35N®. In embodiments, the body may be formed of Vitalium™. In embodiments, the body may be formed of Ticonium™. In embodiments, the body may be formed of Stellite®. In embodiments, the body may be formed of tantalum. In embodiments, the body may be formed of platinum. Materials disclosed with reference to the body or any component of the device disclosed herein are not meant to be limiting. The skilled artisan will appreciate that other suitable materials may be used for the body or any other component of the device.

In embodiments, the body assembly may be formed from a length of cylindrical tubing that is precut with slots at specific locations and then formed in a series of processes to produce a shape suited for the purpose of containing a flow control element within the interatrial septum.

As an example, a first process might be to stretch the cylinder to expand its internal diameter to a uniform target dimension. This can be done with a balloon or a standard tubing expander consisting of a segmented sleeve and tapered conical inserts that increase the diameter of the sleeve when the cones are advanced toward the center. In order that the shape of the stretched tubing be preserved, the cylinder should be annealed while held into this stretched shape by heating it beyond 300° to 600° for at least about 20 minutes to allow the internal stresses to be relieved. A second process might be to form one flange end shape using a similar process as the first process but using a tool shape specially designed for the first flange shape. A third process might be to form the second flange end shape using a similar process as the first process but using a tool specially designed for the third flange shape. These shapes must be annealed using a similar process as the first shape, either in separate steps or altogether.

In some embodiments of the device, pre-selected areas of the sheet material of which device is comprised have reduced through-thicknesses in relation to the through-thickness of sheet material of other areas of the implantable device. These areas of reduced through-thickness are selected based upon a desire to provide these areas with greater flexibility. In some method embodiments, a device having reduced through-thickness in preselected areas is made by a process in which a tube of a particular wall thickness is machined in preselected areas to locally reduce the through-thickness of the tube, and then a pre-selected pattern is cut into the machined tube to form a patterned tube which is then thermomechanically formed into the shape the device is to have in use after implantation. Such variations of thickness may be used on any portions of embodiments of the device disclosed herein where variations in flexibility are desirable.

In embodiments, the internal diameter of the finished interatrial pressure vent is larger than about 5 mm to enable adequate venting of the left atrium and minimize damage to blood components from excessive shear stress, but enabling the interatrial pressure vent to stow in a placement catheter of smaller than about 14 F.

In embodiments, the flow control element opening is at least about 50 sq. mm. In embodiments, the flow control element opening is 50 sq. mm+−10 sq. mm. In another embodiment, the cylindrical section is formed with an inside diameter of between 3 and 15 mm.

The internal diameter of the body segment may be a constant dimension along the center, longitudinal axis of the interatrial pressure vent and is long enough to isolate the flow control element from deflection or damage as a result of contact with other structural elements of the heart.

In embodiments, the body segment is formed into a substantially toroidal shape, the inner diameter tapering down and then up again from one side of the implant to the other. In embodiments, the length of the body section may be about 4 mm. In embodiments, the length of the body section may be between about 3 mm and about 40 mm.

Other embodiments and advantages of the invention will become more apparent from the following detailed description when taken in conjunction with the accompanying drawings.

BRIEF DESCRIPTION OF THE DRAWINGS

The present invention will become more fully apparent from the following description and appended claims, taken in conjunction with the accompanying figures. Understanding that these figures merely depict exemplary embodiments, they are, therefore, not to be considered limiting. It will be readily appreciated that the components of the present invention, as generally described and illustrated in the figures herein, could be arranged and designed in a wide variety of different configurations. Nonetheless, embodiments will be described and explained with additional specificity and detail through the use of the accompanying figures in which:

FIG. 4 is perspective view of the interatrial pressure vent by itself;

FIG. 5 is a right side view of implantable device of FIG. 4;

FIG. 6 is a distal end view of the implantable device of FIG. 4;

FIG. 7 is an enlarged fragmentary cross-sectional view taken along line 7-7 of FIG. 6;

FIGS. 7A through 7C are a side elevational views of embodiments of the device in the stowed position;

FIG. 11A is a side view of another embodiment of a placement catheter with an interatrial pressure vent stowed therein;

FIGS. 28A through 28C depict other embodiments of the device that direct the flow of blood in a desired direction;

DETAILED DESCRIPTION

Figure 1:
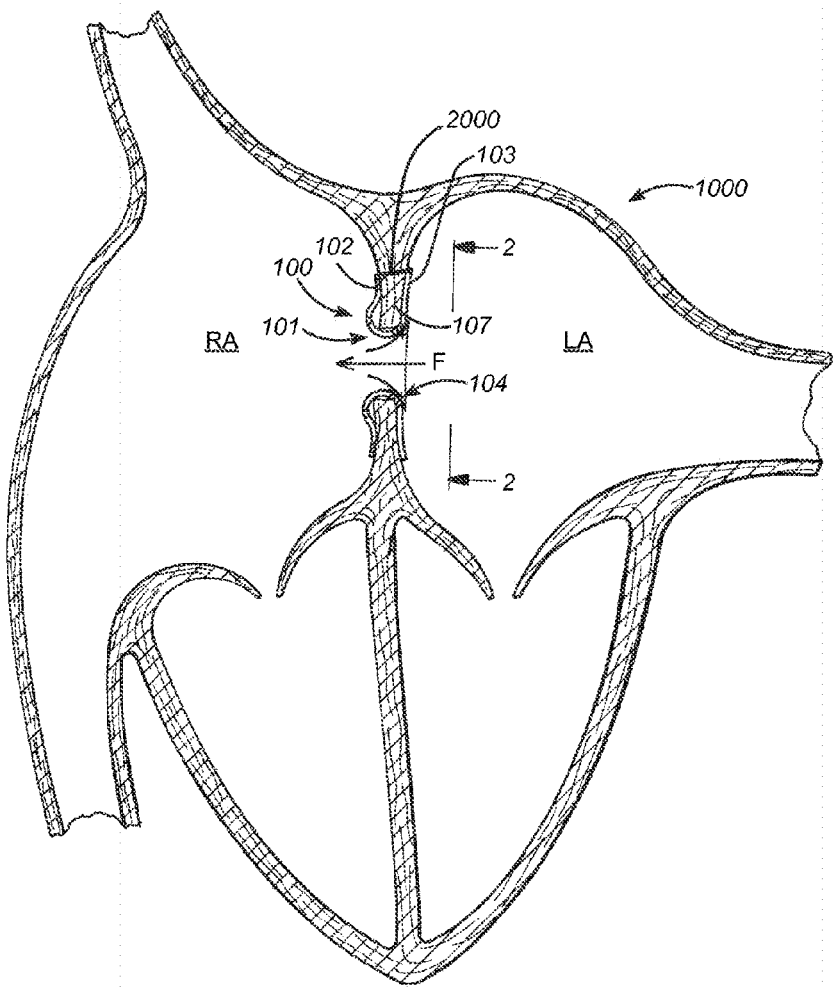
FIG. 1 is a schematic cross-sectional view of a patient's heart with an interatrial pressure vent in situ.

Certain specific details are set forth in the following description and Figures to provide an understanding of various embodiments. Those of ordinary skill in the relevant art will understand that they can practice other embodiments without one or more of the details described below. Further, while various processes are described herein with reference to steps and sequences, the steps and sequences of steps are not be understood as being required to practice all embodiments of the present invention.

Unless otherwise defined, explicitly or implicitly by usage herein, all technical and scientific terms used herein have the same meaning as those which are commonly understood by one of ordinary skill in the art to which this present invention pertains. Methods and materials similar or equivalent to those described herein may be used in the practice or testing of the present invention. In case of conflict between a common meaning and a definition presented in this document, latter definition will control. The materials, methods, and examples presented herein are illustrative only and not intended to be limiting.

Certain specific details are set forth in the following description and Figures to provide an understanding of various embodiments. Those of ordinary skill in the relevant art will understand that they can practice other embodiments without one or more of the details described below. Further, while various processes are described herein with reference to steps and sequences, the steps and sequences of steps are not be understood as being required to practice all embodiments of the present invention.

Unless expressly stated otherwise, the term "embodiment" as used herein refers to an embodiment of the present invention.

Unless a different point of reference is clear from the context in which they are used, the point of reference for the terms "proximal" and "distal" is to be understood as being the position of a practician who would be implanting, is implanting, or had implanted a device into a patient's atrial septum from the right atrium side of a patient's heart. An example of a context when a different point of reference is implied is when the description involves radial distances away from the longitudinal axis or center of a device, in which case the point of reference is the longitudinal axis or center so that "proximal" refers to locations which are nearer to the longitudinal axis or center and "distal" to locations which are more distant from the longitudinal axis or center.

As used herein, the terms "subject" and "patient" refer to any animal, such as a mammal like livestock, pets, or humans. Specific examples of "subjects" and "patients" include, but are not limited, to individuals requiring medical assistance, and in particular, requiring treatment for symptoms of heart failure.

As used herein, the term "pressure differential" means the difference in pressure between two points or selected spaces; for example between one side of a flow control element and another side of the flow control element.

As used herein, the term "embolic particle" means any solid, semi-solid, or undissolved material, that can be carried by the blood and cause disruption to blood flow when impacted in small blood vessels, including thrombi.

As used herein, the terms "radially outward" and "radially away" means any direction which is not parallel with the central axis. For example, considering a cylinder, a radial outward member could be a piece of wire or a loop of wire that is attached or otherwise operatively coupled to the cylinder that is oriented at some angle greater than 0 relative to the center longitudinal axis of the cylinder.

As used herein, the term "axial thickness" means the thickness along an axis parallel to the center longitudinal axis of a shape or component.

As used herein, the term "axial direction" means direction parallel to the center longitudinal axis of a shape or component.

As used herein, a "sealable connection" is an area where components and/or objects meet wherein the connection defines provides for an insubstantial leakage of fluid or blood through the subject area.

As used herein, the term "lumen" means a canal, duct, generally tubular space or cavity in the body of a subject, including veins, arteries, blood vessels, capillaries, intestines, and the like.

As used herein, the term "sealably secured" or "sealably connected" means stably interfaced in a manner that is substantially resistant to movement and provides resistance to the flow of fluid through or around the interface.

As used herein, the term "whole multiple" means the product contains no decimal.

It is to be understood that whenever relational numbers are used herein, e.g., "first," "second," etc., they are used for convenience of description and so they are to be interpreted with regard to the particular embodiment or claim in which they are presented, rather than as applying globally throughout this document to all embodiments or all claims. Thus, for example, in one embodiment it may be more convenient to use the term "first flange" to describe a flange that would be located in the right atrium when the device of that embodiment is implanted in an atrial septum, whereas it might be more convenient to use the term "first flange" in another embodiment to refer to refer to a flange that would be located in the left atrium when the implantable device of that embodiment is implanted.

The present invention provides structures that enable several unique intracardiac and intraluminal valve devices, loaders, controls and placement devices and catheters therefor. In some embodiments directed toward the intra-cardiac setting, these valve devices are intended to allow sufficient flow from the left atrium to the right atrium to relieve elevated left atrial pressure and resulting patient symptoms but also prevent the amount of flow from the right atrium to the left atrium to minimize the potential for thrombi or other embolic material from entering the arterial circulation. For example, the device can be used to regulate the pressure in a heart chamber. Specifically, the device can be used to treat elevated chamber pressures in a patient suffering from CHF or having a Patent Foramen Ovale (PFO) or an Atrial Septal Defect (ASD) that needs repair but is preferably left with residual flow between atria so as not to traumatize the heart hemodynamics but still prevent embolization from the right to left atria.

However, it should be appreciated that embodiments are applicable for use in other parts of the anatomy or for other indications. For instance, a device such as that described in this disclosure could be placed between the coronary sinus and the left atrium for the same indication. Also, a pressure vent such as is described in this disclosure could be placed between the azygous vein and the pulmonary vein for the same indication.

The present invention may include a percutaneously deliverable device. In some embodiments, the device has a straightened, elongated, low-profile delivery configuration suitable for delivery via a delivery system. The device may have a generally radially expanded and sometimes shortened deployed profile. For example, it can have a distal expanded portion positioned on the left atrial side of the septum, a right expanded portion positioned on the right atrial side of the septum, and/or a shunt portion, sometimes referred to as a "core segment", positioned through an aperture in the septum.

The present invention also provides attachment mechanisms between percutaneous delivery systems and the implantable devices. Such attachment mechanisms may allow the device to conform to the heart anatomy prior to and during deployment from the percutaneous delivery system, to be repositioned during deployment, and/or to be retrieved during or repositioned after deployment.

The device may have a hub or other attachment mechanism that is adapted to cooperate with a complementary mechanism on a deployment and/or retrieval apparatus. This hub or other attachment device may be located at an apex of the device. The hub or other attachment device may comprise a cardiac-environment-compatible machinable material, e.g., a stainless steel, a particular example of which being 316 LVM stainless steel.

Referring now to FIG. 1, one embodiment of an interatrial pressure vent is shown. FIG. 1 depicts the heart 1000 of a human subject. "LA" refers to the left atrium, and "RA" refers to the right atrium. The interatrial septum is depicted as 107. The embodiment of the interatrial pressure vent 100 shown includes a body element 101 and flow control element 104, embodiments of which will be described in further detail below. The body element 101 may comprise flanges 102 and 103. In this and other embodiments described herein, flanges 102 and 103 may be annular flanges, which define a gap 2000 into which the septum 107 fits. In embodiments, after insertion, the interatrial pressure vent is securely situated in an opening created in the interatrial septum. Arrow F in FIG. 1 shows the direction of flow. It can be thus seen that a build up of pressure in the LA can be vented, by way of the inventive device, to the RA.

Figure 63:
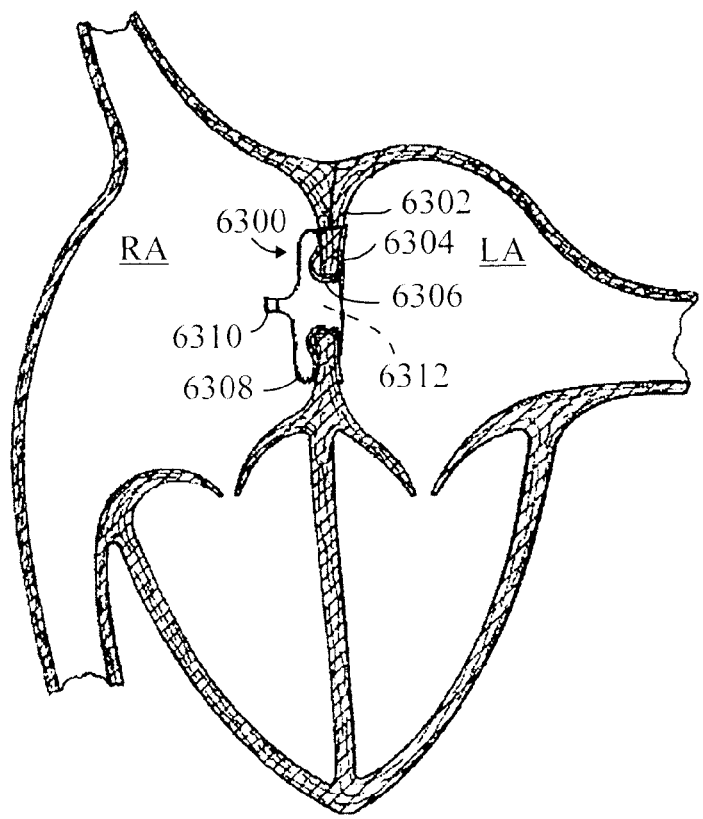
FIG. 63 depicts an embodiment of an implantable device implanted in the atrial septum.

As illustrated in FIG. 63, another embodiment of an implantable device 6300 is deployed across the atrial septum 6302. The device 6300 includes an expanded distal flange 6304, a core segment 6306, an expanded proximal flange 6308, and a hub 6310. The distal flange 6304 is apposed to the septum 6302 on the left atrial side, and as will become more apparent in reference to discussion and figures below, all flange segments extend radially outward from the longitudinal axis of the device 6300. The core segment 6306 is placed through the aperture 6312 on the septum 6302, connecting to the distal and proximal flanges 6304, 6308. The core segment 6306 may be generally tubular, but also may be of any suitable shape that allows blood communication between the left atrium LA and the right atrium RA. The proximal flange 6308 is apposed to the septum 6302 on the right atrium RA side with all of its flange segments extending radially outward. A distal end of all the proximal flange segments connects the proximal end of the core segment 6306, and the proximal ends of the all proximal flange segments connect the hub 6310. The hub 6310 connects to the proximal end of the proximal flange 6308. The hub 6310 allows the device 6300 to be connected to a delivery system. As illustrated in FIG. 63, the device 6300 is securely situated across the aperture 6312 on the atrial septum 6302.

In some embodiments, the distal and proximal flanges may be attached or adjacent to the respective ends of the core segment and extend radially outward from the longitudinal axis of the core segment. The distal and proximal flanges may be integral with the core segment and need not be "attached" thereto but may be fabricated from the same material that defines the core segment (including in the manners described herein) and thus may be contiguous therewith.

In some embodiments, one or more segments of either or both of the distal and proximal flanges may be in the shape of a petal or a loop. Other design, shape, size, and configurations of flange segments are also encompassed by the present invention. A flange may be in the shape of an annular ring in which a continuous loop or a helical curve expands radially outward when deployed. Each flange segment may be formed of multiple individual struts or may be formed of a single strut. The shape and configurations of a distal or proximal flange may be the same as or different from that of the other flange.

Figure 2:
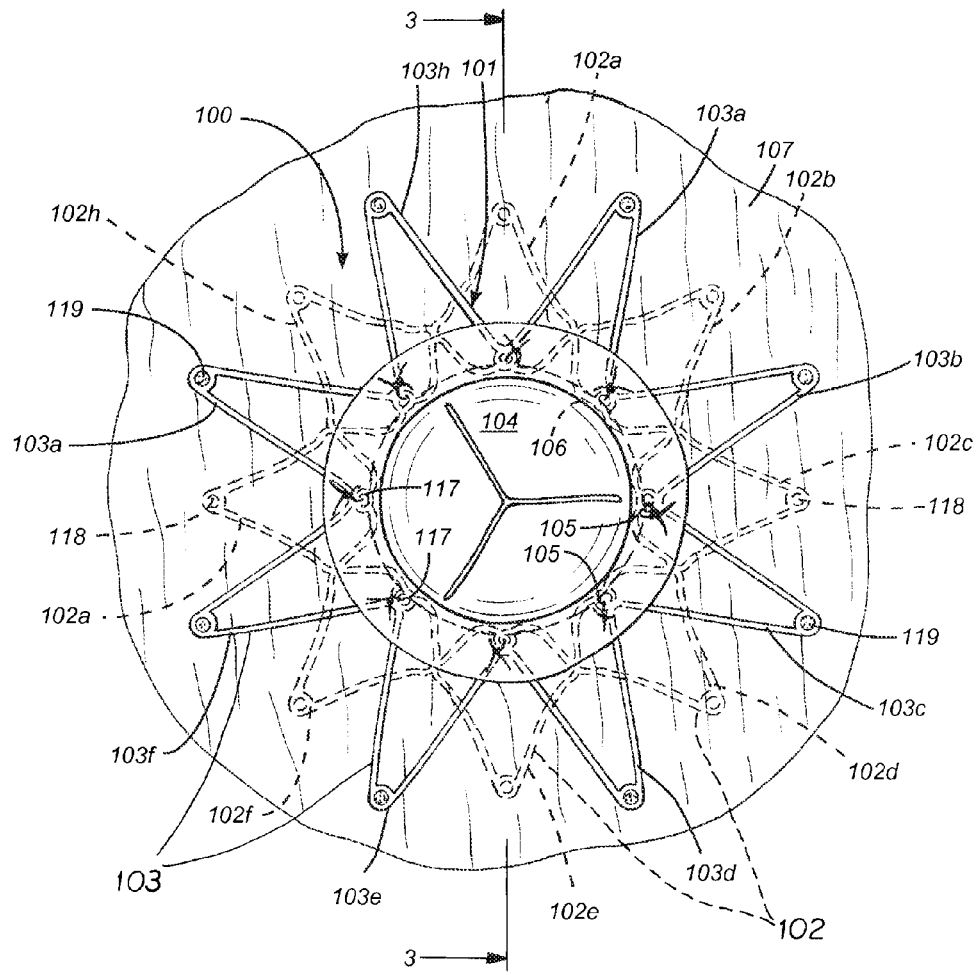
FIG. 2 is an end view of the interatrial pressure vent of FIG. 1 in situ as seen along line 2-2 of FIG. 1.

Referring now to FIG. 2, an embodiment of the interatrial pressure vent is illustrated. This embodiment of an interatrial pressure vent 100 includes body element 101 comprising a substantially open mesh and including a substantially cylindrical core segment (shown end on) 106 and substantially annular flanges 102 and 103. Flanges 102 and 103 may be comprised of any number of flange segments (or "flange elements" or "flange members") 102a-102h and 103a-103h, that are attached adjacent to the end of the core segment and extend radially outward from longitudinal axis of the core segment and flow control element 104. "Flange segments" may also be referred to as "legs" herein. The flanges 102 and 103 (and thus the segments which comprise them 102a-h and 103a-h) in this and all embodiments disclosed herein, may also be integral with the core segment. That is, they need not be necessarily "attached" thereto but may be fabricated from the same material that defines the core segment (including in the manners described above and herein) and thus may be contiguous therewith. The flow control element may be attached to the body element, for example at locations 105. The flange segments in this and any embodiment of any annular flange may be formed of two individual strut elements or also can be formed of a single element. The flange segments may be generally rectangular in cross section, circular in cross section, oval in cross section or some other geometric shape.

Figure 64:
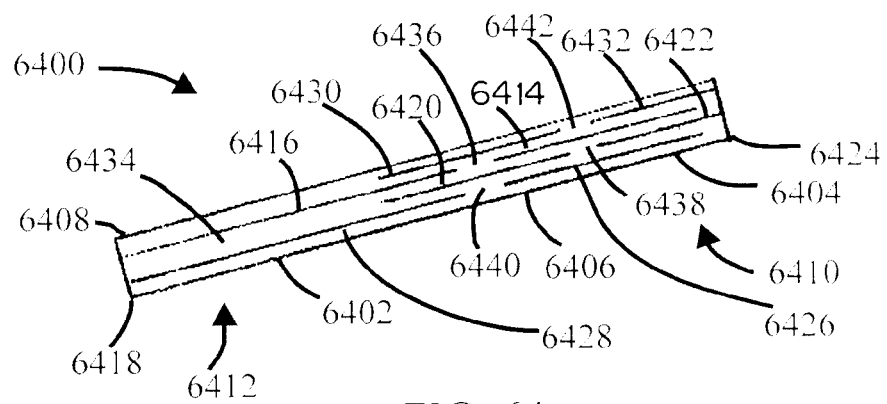
FIG. 64 depicts an embodiment of an implantable device in its low profile configuration.

FIG. 64 shows an embodiment of the device 6400 is in a elongated, low-profile delivery configuration. This configuration is sometimes referred to herein as a "delivery profile" and the configuration that the device has when it is deployed from the delivery system is sometimes referred to herein as the "deployed profile". It should be understood that a device may have its delivery profile configuration when it is being stretched on both ends or when it is constrained within a delivery catheter. Both the distal and proximal flanges align with the core segment along the longitudinal axis of the device. In some embodiments, the core segment may also be stretched longitudinally to a smaller overall diameter in the delivery profile. In some other embodiments, the overall size of the core segment remains unchanged from the delivery profile to the deployed profile.

Still referring to FIG. 64, an embodiment of the device 6400 is shown in its delivery profile where its proximal flange 6402, distal flange 6404, and core segment 6406 are aligned with each other to form a general tubular shape 6408. The distal portion 6410 of the tube 6408 forms the distal flange 6404 of the device 6400 upon deployment, and the proximal portion 6412 of the tube 6408 forms the proximal flange 6402 of the device 6400 upon deployment. The proximal portion 6412 of the tube 6408 is configured to connect to a hub (not shown). Several slits, e.g., first and second slits 6414, 6416, extend along the tube 6408 from one spot to another spot. The slits which are next to one another and are parallel to each other on tube surface and are offset longitudinally from each other. The first slit 6414 extends from a first location to a second location on the distal portion 6410 of the tube. The second slit 6416 extends from a third location, proximal to the first location, to the proximal end 6418 of the tube 6408. The second slit 6414 longitudinally aligns with the first slit 6414 parallel to the longitudinal axis of the tube. A third slit 6420 extends from a fourth location to a fifth location on the tube 6408. The third slit 6420 is parallel to the first and second slits 6414, 6416, and is radially next to the first and the second slits 6414, 6416. The fifth location on the tube is proximal to the second location. A fourth slit 6422 extends from a sixth location, distal to the fifth location, to the distal end 6424 of the tube 6408. The fourth slit 6420 longitudinally aligns with the third slit 6418 and they both are parallel to the longitudinal axis of the tube 6408. The tube 6408 also has additional sets of slits, e.g. fifth and sixth slits 6426, 6428, that are similarly situated and aligned as are first and second slits 6414, 6416 but which are circumferentially transposed along the surface of the tube 6408 as well as additional sets of slits, e.g. seventh and eighth slits 6430, 6432, that are similarly situated and aligned as are third and fourth slits 6420, 6422 but which are circumferentially transposed along the surface of the tube 6408.

As shown in FIG. 64, a strut, e.g., strut 6434, is formed between two slits radially next to each other, e.g. second and sixth slits 6416, 6428. The struts may bow or bend outward during the deployment so as to form the distal and proximal flanges 6404, 6402. Struts may have cross sections in the shape of a rectangle, circle, oval, or some other geometric shapes. As shown in FIG. 64, a first junction 6436 is formed between the first, second, third, and seventh slits 6414, 6416, 6420, 6430, and a second junction 6438 is formed between the first, third, fourth, and fifth slits 6414, 6420, 6422, 6426. The first junction 6436 is part of the proximal flange 6402 of the device 6400 and the second junction 6438 part of the core segment 6406 of the device 6400. The tube 6408 has additional sets of junctions, e.g. third and fourth junctions 6440, 6442, which are similar to the first and second junctions 6436, 6438 but which are circumferentially transposed along the surface of the tube 6408 from the first and second junctions 6436, 6438. Those skilled in the art will understand that the slit pattern and locations described above will vary with respect to the desired deployed shape of the device.

Figure 65:
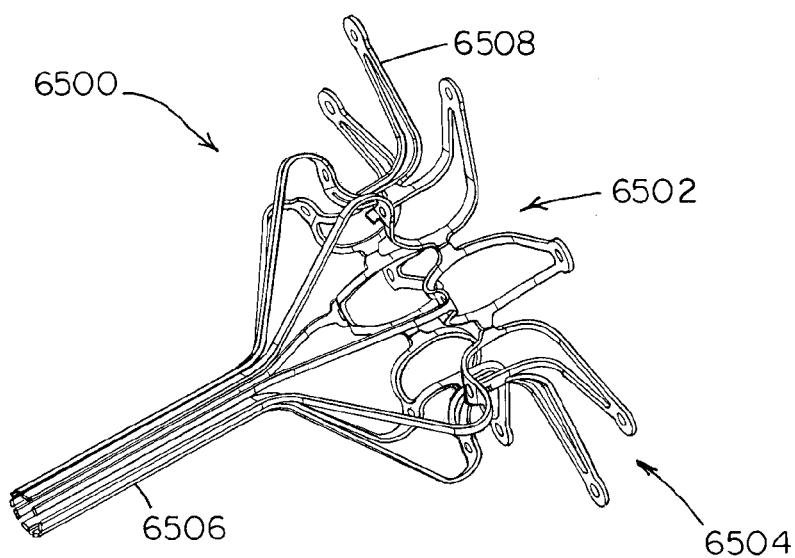
FIG. 65 depicts an expanded embodiment of an implantable device.
Figure 66:
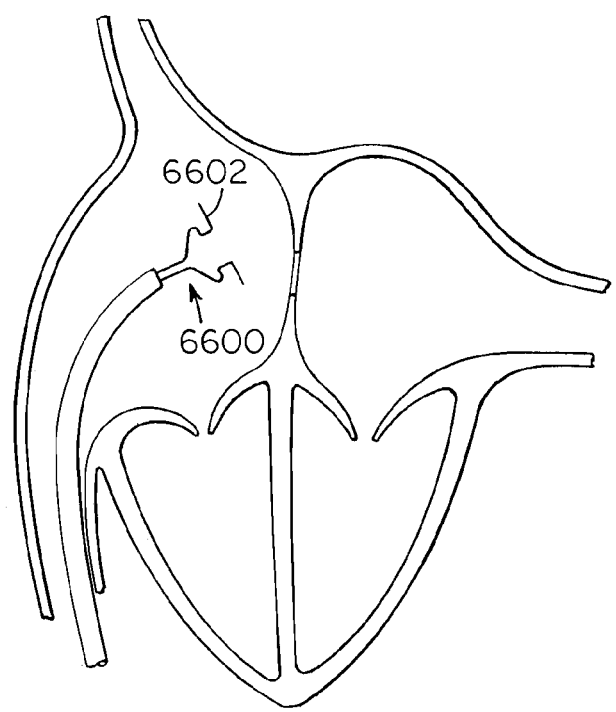
FIG. 66 depicts a partially deployed implantable device embodiment.
Figure 67:
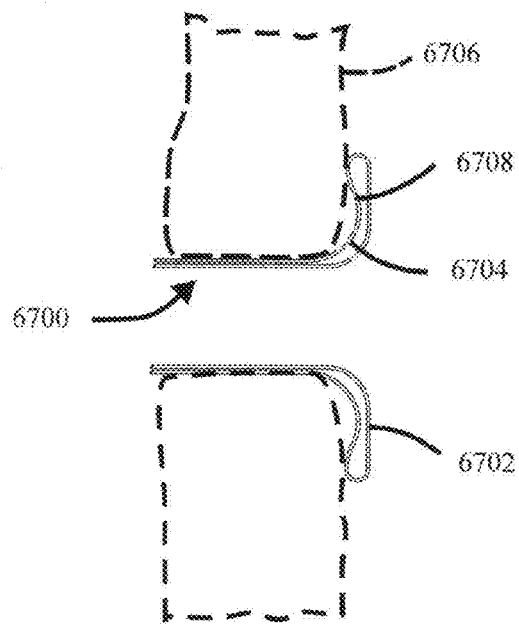
FIG. 67 depicts a cross-sectional view of a device implanted in an atrial septum.

FIGS. 65-67 schematically illustrate partially-deployed devices according to embodiments of the present invention. Referring to FIG. 65, which shows an embodiment in the deployed shape. The distal portion 6502 of the device 6500 expands radially to form the distal flange 6504 while the proximal end 6506 of the device 6500 is still confined to its tube shape. In embodiments, proximal end 6506 is trimmed to shorten it to a length desired for a device to be implanted. The segments of the distal flange 6504, which has flange segments one such flange segment shown as 6508, are formed from struts between slits of the distal portion 6502 of the device 6500. One end of each distal flange segment originates from the core segment of the device 6500, while the other end originates from the distal end of the tube. In some embodiments, the distal flange segments device 6500 upon deployment form a generally planar distal flange 6602 that is parallel to the septum (not shown).

Referring to FIG. 66, there is shown a schematic side-view of a partially-deployed device 6600. The distal flange segments of device 6600 upon deployment form an distal flange 6602 with the distal flange segments curved from the core segment toward the septum. As illustrated in FIG. 67 which shows a portion of device 6700 as it is being deployed in use, each distal flange segment 6702 of the device 6700 may have a first curved section 6704 extending into the left atrium so as to form a space between itself and the septal wall 6706 and a second curved section 6708 extending from the first curved section 6704 toward the septal wall 6708. The distal flanges can have other shapes and forms.

Figure 68:
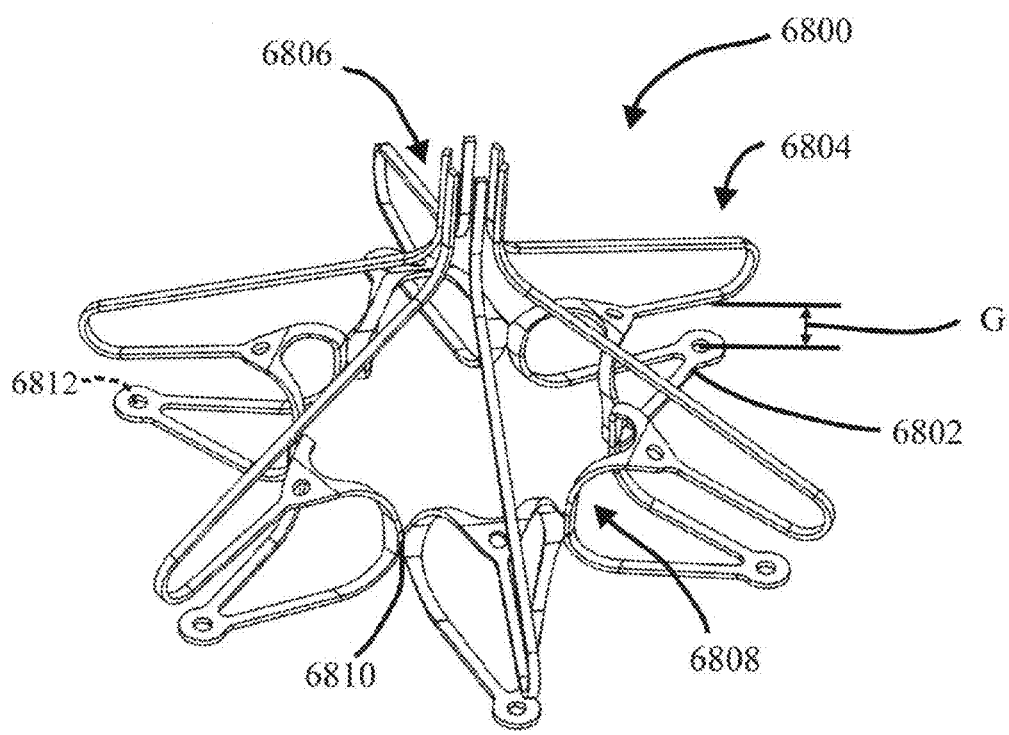
FIG. 68 depicts an expanded embodiment of an implantable device.

FIG. 68 illustrates a fully deployed device 6800 without a hub according to one embodiment of the present invention. Upon the distal portion of the tube being released from the delivery device, the distal portion of the tube expands radially, shortening its axis distance. The struts formed between slits at the proximal portion of the tube bend outward forming the segments of the distal flange 6802. The proximal portion of the tube behaves similarly and forms the proximal flange 6804. The proximal ends of the proximal flange segments form a tubular proximal end 6806 of the device, which is configured to connect to a hub (not shown). One end of each of the segments of proximal flange 6804 originates at the proximal end of the core segment 6808, while the other end originates at the proximal end of the device 6800.

In the embodiment illustrated in FIG. 63, upon deployment, the segments proximal flange 6308 each have a first curved section extending into the right atrium which forms a space between the segment and the septum 6302, and a second curved section extending from the first curved section toward the septum 6302. The proximal flange may have other shapes and forms and the specific disclosures in the present invention should not be viewed as limiting.

Referring again to FIG. 68, the core segment 6808 is between the distal and proximal flanges 6802, 6804. The core segment 6808 is formed by a portion of the tube between the distal and proximal portions of the tube expanding radially and shortening longitudinally. The diameter of the core segment 6808 may remain the same or it may expand, e.g., by a factor up to 3. Referring to FIG. 81, the second junction 8138 is on the core segment 6808 of FIG. 68 and correlates to junction 6810 in FIG. 68. The core segment 6808 has a general tubular profile with a central passageway extending therethrough. The cross section of a core segment and its central passageway may be circular, oval or polygonal, such as square or hexagonal, or any other suitable shape as will be apparent to those skilled in the art. Typically, the cross section of a core segment has a diameter generally ranging from 5 mm to 30 mm, and the cross-sectional area of the central passageway ranges from 19 $mm^2$ to 700 $mm^2$.

Returning to embodiments of the implantable device, the distal flanges and proximal flanges may define a gap into which the septum fits. Such a gap, the gap G is indicated in FIG. 68 between the distal and proximal flanges 6802, 6804 of device 6800. Such gaps may be smaller than the thickness of the septum in some embodiments. In such embodiments, as the device is being deployed across the septum, the proximal and distal flanges may flex to accommodate the septal tissue and the gap may expand when tissues is positioned therein. The gap may be zero in some embodiments. The gap may be negative in some embodiments. In such embodiments, the flange segments on each side of the core segment cross one another in a relaxed radially expanded form so that when the device is implanted, they exert a pressure against the septum. The gap may be larger than the thickness of the septum to avoid abrasion to the septal tissue. The above description of the characteristics of gap G may apply to any of the embodiments disclosed herein.

In some embodiments, the most radially outward end of the at least one or both of the distal and proximal flanges of the device may be folded toward the core segment longitudinally, so that the distance between most outward tips of the distal and proximal flanges is shorter than the distance between the ends of the distal and proximal flanges where they connect the core segment in the deployed configuration. In some embodiments, the most outward tips of the distal and proximal flanges press the septum and thereby secure the device in place.

The proximal flange segments may be oriented so they are not directly opposed to the distal flange segments on the opposite side of the core segment. This may be referred to as "radially off-set" or "angularly off-set" flanges or flange segments. This design eliminates pinching points on the septum and reduces the chance for tissue injury. The distal flange segments may be arranged midway between two adjacent proximal flange segments.

The length of distal flange segments may be similar to the length of proximal flange segments. The lengths of distal flange segments may be identical to the lengths of proximal flange segments; the length of distal flange segments may be longer than the length of proximal flange segments; or the length of distal flange segments may be shorter than the proximal flange segments.

According to some embodiments, each of the distal and proximal flanges includes at least two flange segments. In particular embodiments, the distal flange includes eight loops. Devices having between four and ten flanges may be formed. Devices according to the present invention may include any number of flange segments. The most desirable number of flange segments on each distal and proximal flange depends on a variety of anatomical and manufacturing factors. In some embodiments, the distal and proximal flanges have the same number of flange segments. In some other embodiments, the distal and proximal flanges have different numbers of flange segments.

The most outward ends of the distal flange and/or proximal flange may be designed to have a large area of contact with the septal wall in order to minimize the stress concentration against the septal wall. The ends of distal and proximal flange segments may be rounded at their radially outward ends to reduce stress concentrations against the atrial septum after placement. This rounded shape can easily be formed as part of the integral shape of the flange segment. While rounded shapes at the ends of the flange segments reduce stress on the septum, one skilled in the art should also understand that other variations are also contemplated The thickness of a flange segment near its radially outer end may be decreased to achieve less stress against the septal wall. A different material of higher flexibility could be used for the end portions of the flange segments. Varying the thickness of components of implantable devices or selecting different materials to achieve desired flexibility/stiffness properties is discussed multiple times herein and each method applies to any and all embodiments of implantable devices discussed herein.

The distal and/or proximal flange segments may be designed to be more flexible than the core segment. In such embodiments, the increased flexibility may be achieved in several ways. The struts forming the distal and proximal flange segments may be smaller than the struts forming the core segment such that an increased flexibility of the flanges in relation to the core segment or other flange members can be achieved. Flange segments may be made from a different material from the core segment, for example, the flange segments may be made of material with a greater flexibility than that of the core segment material. The flange segments may have a greater flexibility than the core segment (or the remaining portion of the flange segment or the flange itself as the case may be). This can reduce the probability of causing damage to the tissue of the septum while allowing the core segment to maintain a strong outward force against the septal opening and thus decrease the probability that the device will become dislodged.

Referring to FIG. 68, the proximal flange 6804, distal flange 6802, and core segment 6808 of the device 6800 include a substantially open surface area. In some embodiments, each opening 6812 has a size of 1 mm² to 5 mm². In some embodiments, the opening surface area is 50-95% of entire surface of the device.

The implantable device may be fabricated by methods described herein including laser-cutting or acid-etching a pattern into a preformed tube, then shape-setting to the intended deployed configuration. A device having an open structure may be formed from a hollow tube that has been slotted using, for example, a machining laser or water drill or other method, and then expanded to form the open structure. The device may also be formed of a woven, knitted, or braided tubular metallic fabrics made out of metallic strands. The term "strand" used here can be wires, cords, fibers, yarns, filaments, cables, threads, or the like, and these terms may be used interchangeably. The device having an open structure may be formed from wire that is pre-bent into the desired shape and then bonded together to connect elements either by welding them or adhesively bonding them. They could be welded using a resistance welding technique or an arc welding technique, preferably while in an inert gas environment and with cooling control to control the grain structure in and around the weld site. The welded joints may be conditioned after the welding procedure to reduce grain size and coining or upset forging may be employed to optimize fatigue performance.

In some embodiments, the device comprises a sheet material that may have a constant through-thickness. In some embodiments, pre-selected areas of the sheet material have reduced through-thicknesses in relation to the through-thickness of sheet material in other areas of the implantable device. The areas of reduced through-thickness are selected based upon a desire to provide these areas with greater flexibility. In embodiments, the through-thickness of the device may vary in magnitude between a high value where greater stiffness is desired and a low value where greater flexibility is desired, wherein the low value is in the range of between 40 and 99 percent of the high value.

Figure 69:
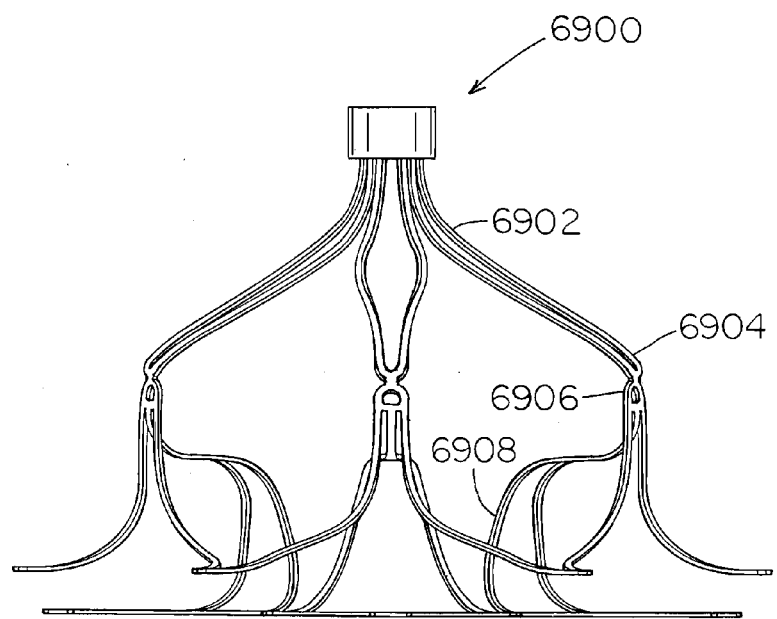
FIG. 69 depicts an elevational view of a expanded device embodiment.

FIG. 69 illustrates this feature of the invention. The device 6900 shown in FIG. 69 has some areas, such as first and second areas 6902, 6904, at which greater flexibility is desirable and some areas, such as third and fourth areas 6906, 6908 at which greater stiffness is desirable. Accordingly, the present invention contemplates providing one or more of the first and second, with thinner through-thicknesses in relation to that of one or more of the third and fourth areas 6906, 6908. In some embodiments of the present invention, the through-thickness of one or more of the first and second areas 6902, 6904 is in the range of between 40 and 99 percent of the maximum through-thickness in one or more of the third and fourth areas 6906, 6908.

The present invention contemplates that through-thickness may be locally reduced in selected areas by way of any conventional means, e.g., grinding, turning, etching, electrochemical machining. In some method embodiments, a device having reduced through-sections in preselected areas is made by a process in which a tube of a particular wall thickness is machined in preselected areas to locally reduce the through-thickness of the tube, and then a pre-selected pattern is cut into the machined tube, e.g., by laser cutting, electrodischarge machining, or etching, to form a patterned tube which is then thermomechanically formed into the shape the device is to have in use after implantation. In some instances of this method, the reduced through-thickness areas have magnitudes which are in the range of between 40% and 99% of the magnitudes of the maximum through-thickness area of the device.

Figure 2A:
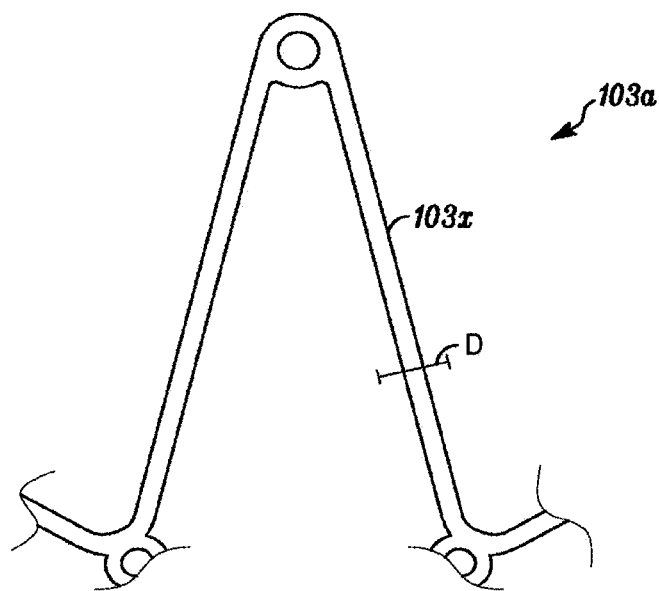
FIG. 2A is an end-on close up view of a flange segment of an embodiment.
Figure 2B:
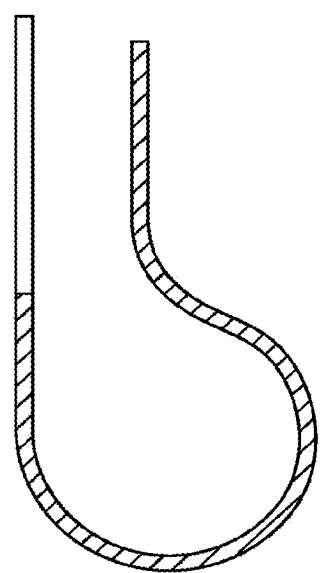
FIG. 2B is an enlarged side cross-sectional view of an embodiment to illustrate variations in flexibility in a flange.

As described in connection with FIGS. 2A and 2B, varying the width of a strut or segment or the diameter of a strut or segment can allow for variations in flexibility. Such methods of varying the through-thickness may be implemented along with those described above to achieve a varying flexibility profile for any embodiment disclosed herein, including the varying flexibility profile mentioned above.

In some embodiments, the device is fabricated from a tube and then shaped to its final configuration. If a sufficiently elastic and resilient material or a shape memory material such as nitinol, is used, the device can be preformed into the finished shape, i.e., deployed profile, and then stowed during delivery in delivery profile and the deployed profile will be regained after deployment. In some embodiments, the core segment and/or one or both of the distal and proximal flanges may be manually expanded to the desired diameter and/or curved to a pre-set shape, heat set in an oven while constrained to the desired shape to memorize the desired device shape. The surface of the finished assembly should be carefully prepared to insure is passivated and free of surface imperfections that could be nidus for thrombus formation.

The device may be made of a biocompatible metal or polymer. In some embodiments, the device in whole or in part is made of a elastic material, super-elastic material, or shape-memory alloy which allows selected portions to distort into a generally straightened profile during the delivery process and resume and maintain its deployed profile in vivo once it is deployed from the delivery catheter. Some of the materials device may be made of in whole or in part include stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys or other metallic alloys, and polymers such as PTFE, UHMPE, HDPE, polypropylene, polysulfone, or other biocompatible polymers. Part or all of the device may be fabricated from a resorbable polymer such as polyactic acid, polyglycolic acid, polycaprolactone, a combination of two or more of these or a variety of other resorbable polymers that are well known to those skilled in the art. The surface of the device may be textured to induce tissue response and tissue in-growth for improved stabilization.

The device (open or monolithic) may comprise porous materials to encourage tissue ingrowth or to act as a reservoir for containing one or more compounds that will be released over time after implant to address numerous issues associated with the product performance. These compounds may be used to diminish calcification, protein deposition, thrombus formation, or a combination of some or all of these conditions. The compound may be used to stimulate an irritation response to induce tissue ingrowth. The compound may be an anti-inflammatory agent to discourage tissue proliferation adjacent to the device. The material that is used to make the device may be multilayered and comprise a coating of resorbable polymer or semipermeable polymer that may comprise various compounds that may be released, and in some embodiments in a controlled manner over time, after implant to address numerous issues associated with product performance.

In embodiments, the distal flange, proximal flange, and core segment may include integral marker holes or slots in which at least one radioopaque markers can be positioned so the device may more easily be visualized using radiographic imaging equipment such as with x-ray, magnetic resonance, ultrasound, or fluoroscopic techniques. Radiopaque markers may be swaged, riveted, or otherwise placed and secured in the hole and thereby dimensioned to be flush with the end of the material surrounding the hole.

A device may have a hub which is configured to join the proximal ends of the proximal flanges segments. A hub may provide releasable attachment point between the device and a delivery system.

A hub may include a hub body and hub cap. The hub body may be configured to connect to the proximal end portions of the proximal flange segments. The hub cap may be configured to be fasten to the hub body so that the proximal end portions of the proximal flanges segments are secured inside the hub.

Each proximal end portion of each proximal flange segments may join to a hub. The proximal end portions of the proximal flange segments may be joined with one another to form two proximal end joints with one or both of the proximal end joints being joined to the hub. The proximal end portion of proximal flange segments may be joined to form more than three proximal end joints with one or more of the proximal end joints being joined to the hub.

The hub body and the hub cap are attached together by a variety of means. For example, the hub cap and hub body may be joined together by mechanical means such as by an interference connection between the inside of the hub cap and the outside of the hub body, by threaded connection where the hub cap and the hub body have complementary threads, or by crimping. The hub cap and hub body may be joined by energy means such as heat, ultrasonic, or other types of welding etc. The hub cap and hub body may be joined by chemical means such as adhesive etc. Other means of the attachment known to those skilled in the art can also be incorporated.

The hub cap may have cup shape comprising a tubular body with an open end and a closed end. The closed end of the hub cap may have an orifice that accommodates the delivery catheter-hub connection. The hub cap may have a sleeve shape. Although the term "tubular" has been used to describe the exemplary configuration of the hub body and hub cap, it is to be understood that the cross section of the hub cap and hub body may be circular, oval or polygonal, such as rectangular, square, or hexagonal. Other shapes and configurations can be used for the hub body and hub cap without departing the design principle disclosed herein.

Figure 70:
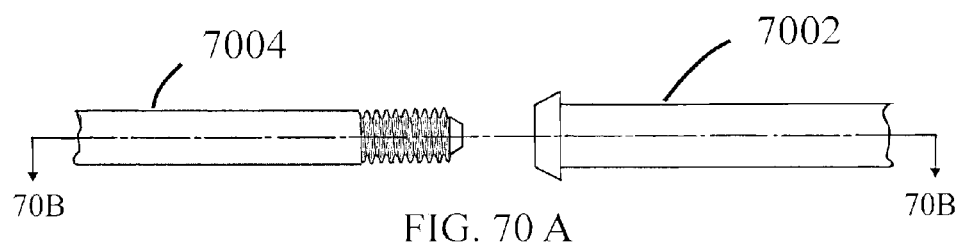
FIG. 70A depicts a means by which a hub of a device may connect to a catheter.
FIG. 70B depicts a cross-section of the means of FIG. 70A.
Figure 70:
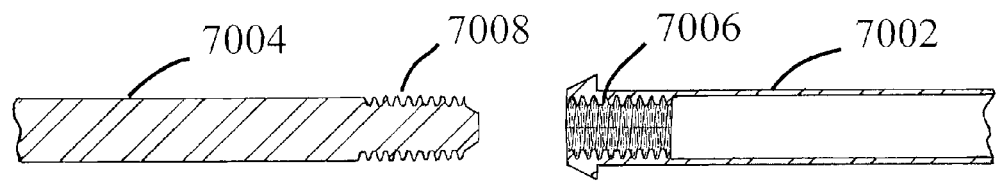
Figure 71A:
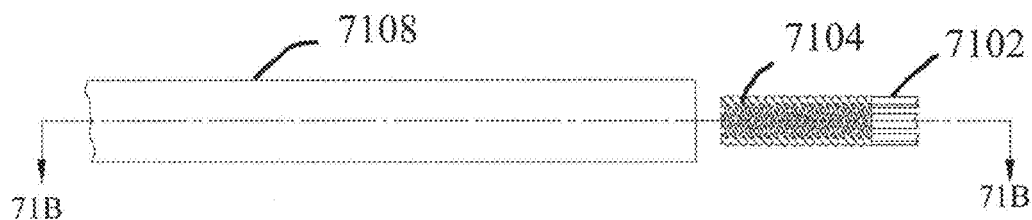
FIG. 71A depicts another means by which a hub of a device may connect to a catheter.
Figure 71B:
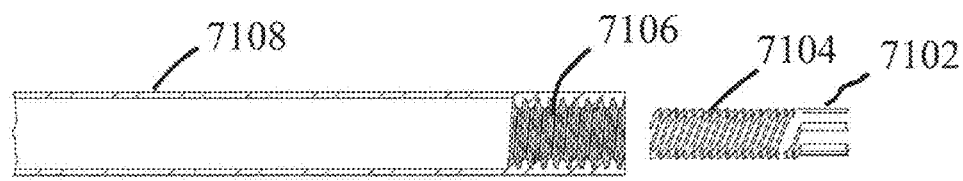
FIG. 71B depicts a cross-section of the means of FIG. 71A.

The present invention includes embodiments in which the hub is connected to a delivery catheter. As is illustrated in FIGS. 70A-B and 71A-B, the hub may be threadably connected to a delivery catheter. FIG. 70B shows a cross-sectional view taken along parting line 70B-70B of the hub 7002 and the delivery catheter 7004. The hub 7002 includes a female thread 7006 which is configured to connect to the male thread 7008 which is located at the distal end of the delivery catheter 7004. FIG. 71A illustrates the hub 7102 having male threads 7104 which are configured to connect to the female threads 7106 located at the distal end of the delivery catheter 7108. FIG. 71B shows a cross-sectional view taken along parting line 71B-71B of the hub 7102 and the delivery catheter 7108.

Figure 72:
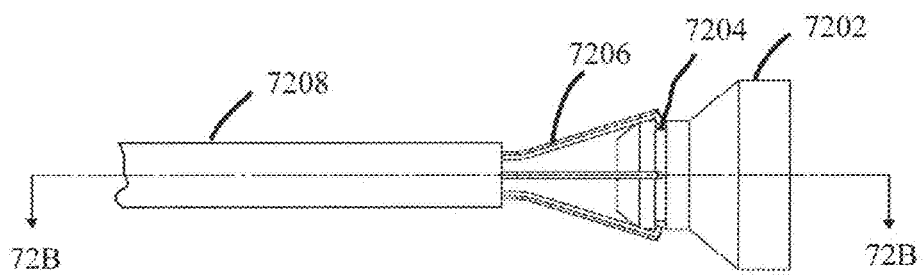
FIG. 72A depicts yet another means by which a hub of a device may connect to a catheter.
FIG. 72B depicts a cross-section of the means of FIG. 72A.
Figure 72:
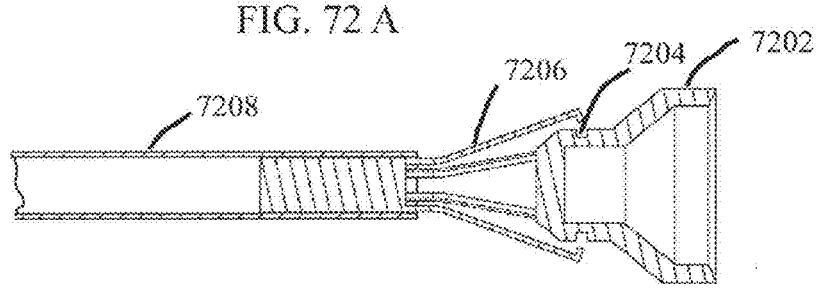

FIGS. 72A-B illustrates a hub 7202 having a groove 7204 which is configured to cooperate with a collet system 9806 at the distal end of the delivery catheter 7208. FIG. 72B shows a cross-sectional view taken along parting line 72B-72B of the hub 7202 and the delivery catheter 7208.

Figure 73:
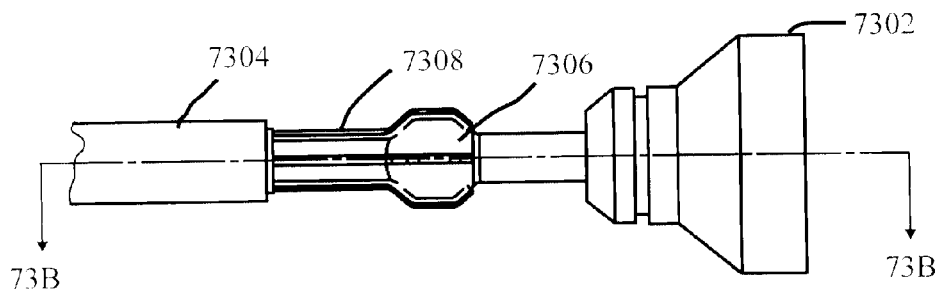
FIG. 73A depicts another means by which a hub of a device may connect to a catheter.
FIG. 73B depicts a cross-section of the means of FIG. 73A.
Figure 73:
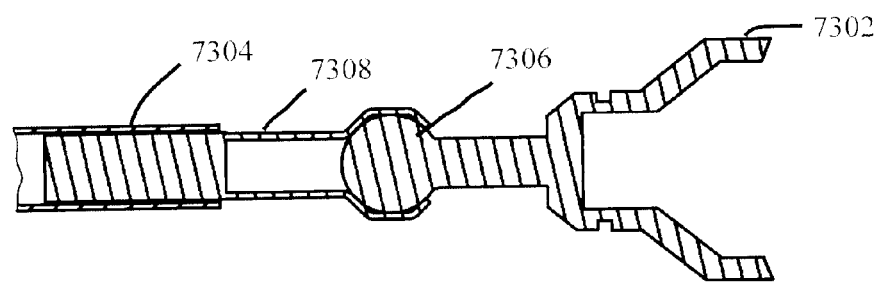

FIGS. 73A-B illustrate a ball-and-claw connection between a hub 7302 and a delivery catheter 7304 in which the hub 7302 includes a ball 7306 configured to be secured by claws 7308 at the distal end of the delivery catheter 7310. FIG. 73B shows a cross-sectional view taken along parting line 73B-73B of the hub 7302 and the delivery catheter 7304.

Figure 74:
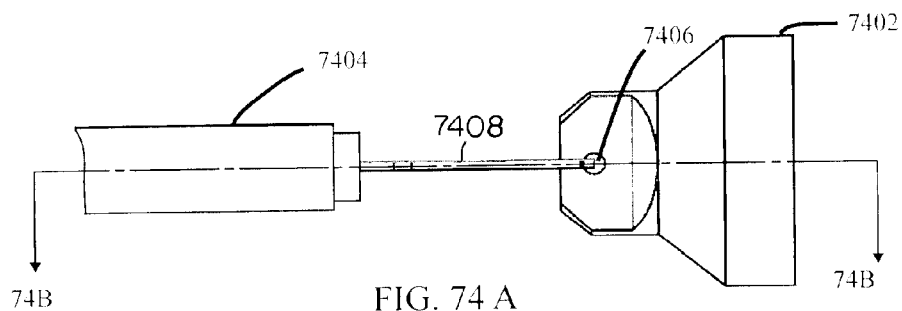
FIG. 74A depicts yet another means by which a hub of a device may connect to a catheter.
FIG. 74B depicts a cross-section of the means of FIG. 74A.
Figure 74:
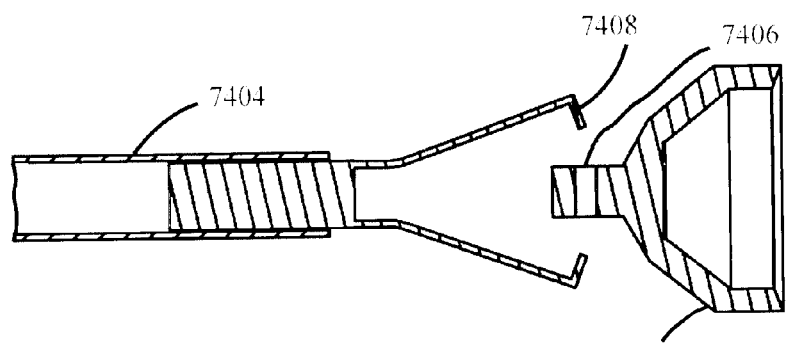

FIGS. 74A-B illustrate a pin-through-hole connection between a hub 7402 and a delivery catheter 7404 in which the hub 7402 has an aperture 7406 which is configured to receive fingers and/or pins, e.g., pins 7408, at the distal end of the delivery catheter 7404. FIG. 74B shows a cross-sectional view taken along parting line 74B-74B of the hub 7402 and the delivery catheter 7404.

Figure 75:
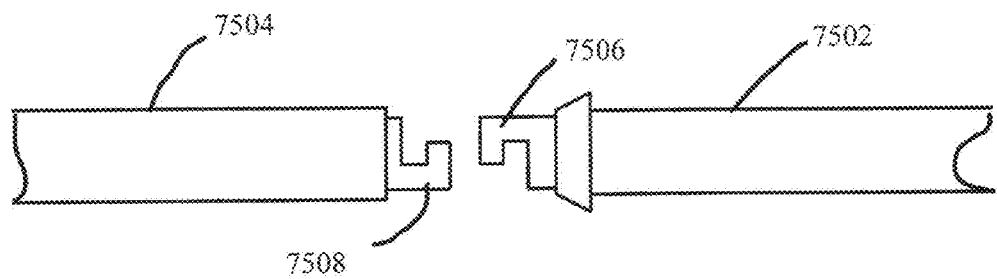
FIG. 75A depicts another means by which the hub of the device may connect to a catheter.
FIG. 75B depicts the means of FIG. 75A in a connected state.
FIG. 75C depicts a cross-section of the means of FIG. 75B.
Figure 75:
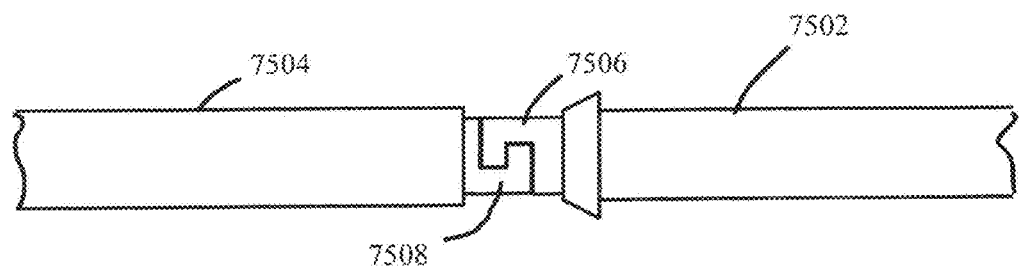
Figure 75:
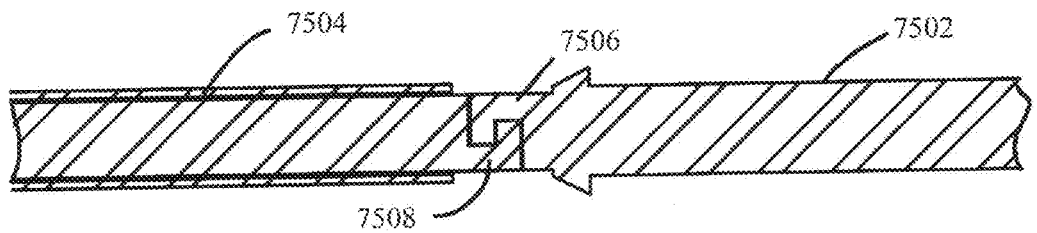

75A-C illustrate an interlocking connection between a hub 7502 and a delivery catheter 7504 in which each of the hub 7502 and the distal end of the delivery catheter 7504 has a C-shaped element, i.e., hub C-shaped element 7506 and delivery catheter C-shaped element 7508, wherein the C-shaped elements 7506, 7508 are configured to interconnect with each other. FIG. 75A shows the hub 7502 and the delivery catheter 7504 prior to interconnecting. FIG. 75B shows the hub 7502 and the delivery catheter 7504 after their respective C-shaped elements 7506, 7508 have interconnected. FIG. 75C shows a cross-sectional view along the vertical midplanes of the hub 7502 and delivery catheter 7504 shown in FIG. 75B.

It is to be understood that connection mechanisms other than those described above may be used for connecting the hub and the delivery catheter in accordance with the present invention.

Figure 76:
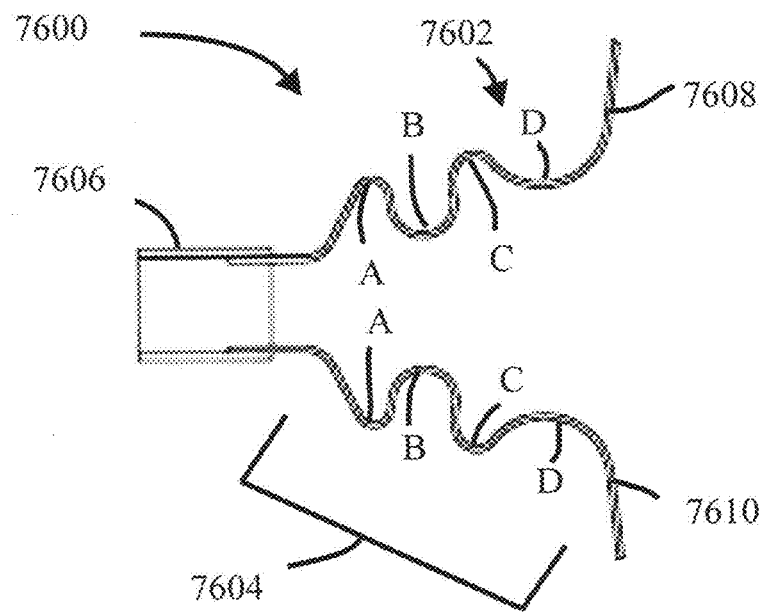
FIG. 76 depicts a cross-section of the proximal end of a device embodiment.
Figure 77:
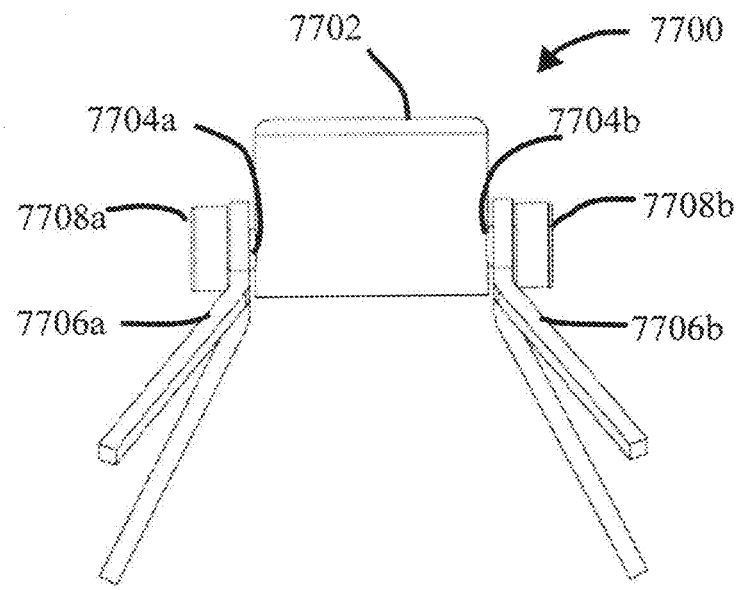
FIG. 77 depicts a side view of the proximal end of a device embodiment in which the hub has posts to which the flange segments are attached.

In some embodiments, the end of the various embodiments of the implantable device that is connected to or otherwise in engagement with the delivery catheter is configured to allow some degree of freedom to the device when such end is connected to or otherwise engaged with the delivery catheter. For example, as the delivery catheter enters the right atrium, the delivery catheter may extend toward the atrial septum at a non-zero angle of up to 180 degrees "θ". Embodiments allow the portion of the device that is primarily engaged with the septum to be free from distortion imposed by the delivery catheter. Such embodiments permit the device to conform to the natural anatomy of the atrial septum as much as possible while still giving the clinician the ability of retrieving the device if necessary due to the fact that the device can be engaged with or otherwise connected to the delivery catheter as long as possible while deployed in the septum, but also while maintaining a delivery catheter angle that would compromise the delivery or other prior art devices. FIGS. 76 and 77 illustrate two such embodiments.

FIG. 76 illustrates a mid-plane cross-sectional view of the proximal end 7600 of a device described herein. The proximal end 7600 herein described can be made part of the implantable devices described herein such as those discussed in connection with FIGS. 22, 23, 46A, 46B, 63, 65, 68, 69, and 83A. According to an embodiment in which each of the proximal portions, e.g. section 7602, of the proximal flange segments has a flexible section or pivotable section e.g, pivotable section 7604 (as indicated by the bracket) optionally connected to a hub 7606. The flexible section 7604 may allow the device 7600 to curve, turn, bend, or twist as the proximal and distal flanges of the device 7600 are deployed across and conform to the atrial septum. Such deployment may take place while the device 7600 is still connected to, or otherwise in engagement with, the delivery catheter and the end of the delivery catheter (and consequently the end of the device that is in engagement with the delivery catheter) is angled away from the longitudinal axis of the rest of the device. Such embodiments allow for a clinician to determine, while the proximal end of the device and the catheter delivery mechanism maintain a non-zero angle up to 180 degrees with respect to the longitudinal axis of the core segment of the device, whether deployment of the portions of the device is satisfactory prior to releasing the device from engagement with the delivery mechanism.

The flexible section 7604 may also permit rotational displacement of the section 7604 about the longitudinal axis of the core segment, for example, allowing a clockwise or counter-clockwise displacement relative to the proximal end of the proximal flange. Thus, the flexible section 7604 may accommodate twisting relative to the remainder of the device while allowing the remainder of the device to be satisfactorily deployed.

In embodiments of the device having the general structure of those described herein the device may be configured to have a distal flange adapted to be in contact with the left atrial side of the atrial septum; a core segment adapted to be in contact with the opening in the atrial septum; a proximal flange having a portion adapted to be in contact with the right atrial side of the atrial septum; and a pivotable end mentioned above. The pivotable or flexible end is connected to a proximal end of the proximal flange. Such connection may be integral. As mentioned above, the pivotable end may adapted to be in releasable engagement with the delivery system while maintaining a non-zero angle up to 180 degrees with respect to the longitudinal axis of the core segment of the device or a rotational displacement angle relative to the remainder of the deployed device, said displacement being about the longitudinal axis. As mentioned above, the clinician may determine if the device is satisfactorily deployed prior to release. In embodiments, satisfactory deployment may mean that a portion of the distal flange is adapted to maintain contact with the left atrial side of the atrial septum and a portion of the core segment is adapted to be in contact with the opening in the atrial septum upon pivoting of the pivotable end. It may also mean that a portion of the proximal flange is adapted to maintain contact with the right atrial side of the atrial septum upon pivoting of the pivotable end. Satisfactory deployment may also occur upon measurement of a physiological parameter prior to releasing the device from the deliver system. Such measurement may include the measurement of the blood flow through the core segment, or the pressure in left atrium, the pressure in the right atrium, or both.

In embodiments, to achieve the flexibility/pivotability discussed herein, the end 7600 comprises a plurality of parallel struts wherein each of the struts within the longitudinal length of the flexible section has a plurality of alternating radially concave inward and radially concave outward curves. For example, referring to FIG. 76, curvy section 7604 includes first and second struts 7608, 7610, each of which has a radially concave inward section A, a radially concave outward section B, a radially concave inward section C, and a radially concave outward section D.

Another embodiment which gives the device freedom of movement at its proximal end is shown in FIG. 77. FIG. 77 schematically illustrates the proximal end 7700 of a device. This proximal end 7700 comprises a hub 7702 which has two posts 7704a, 7704b extending radially outward from the longitudinal axis of the device. Two sets of flexible flange sections 7706a, 7706b, each of which forms a collar at their junction, is rotatably attached to the posts 7704a, 7704b and held in place by endcaps 7708a, 7708b. This configuration permits the main portion of the device to rotate out of alignment with a delivery catheter to which the hub 7702 is attached.

Figure 78A:
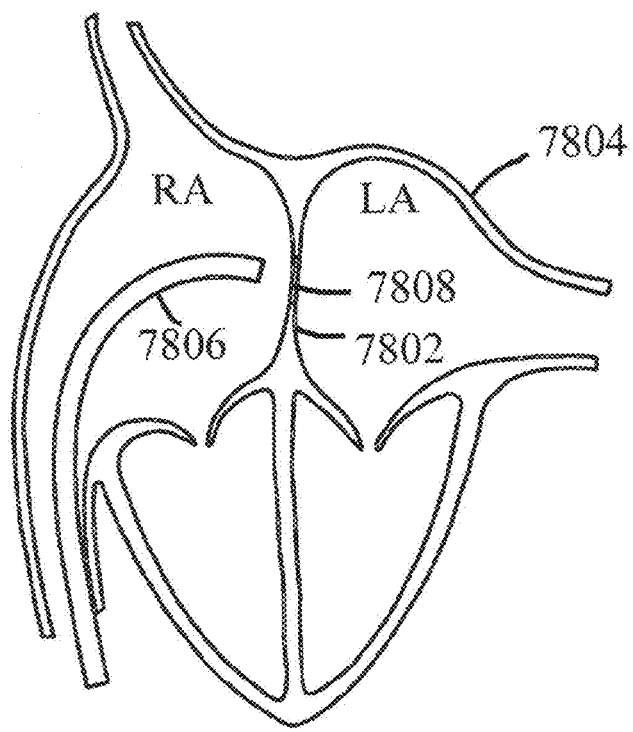
FIGS. 78A-78F depict an insertion sequence of a device embodiment into an atrial septum.
Figure 78B:
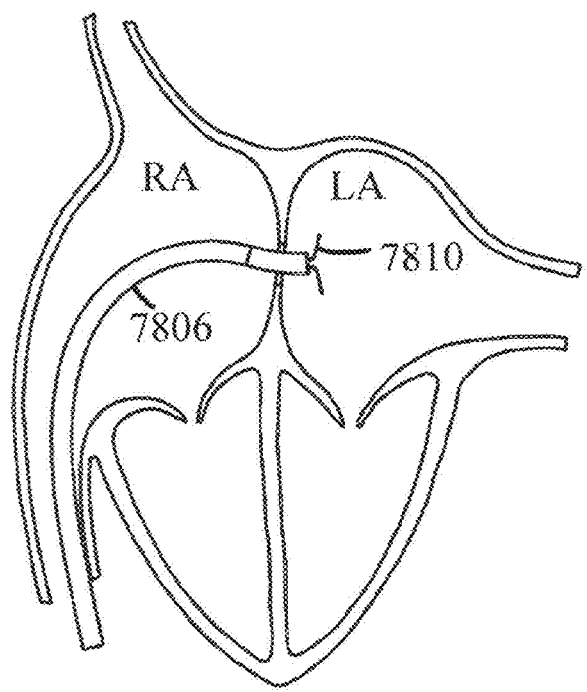

FIGS. 78A-F schematically illustrate an embodiment of a device 7800 which is being delivered to and deployed at a treatment site in the atrial septum 7802 of a patient's heart 7804. In FIG. 78A the device 7800 is not visible as it is in its delivery profile and contained within the distal end portion of a delivery system 7806, which includes a delivery catheter and a sheath. The device 7800 is secured to the delivery system 7806 so that the device 7800 can be placed accurately at the desired delivery location, e.g., the treatment site 7802. Although hidden from view, the hub of the device is attached to the distal end of the delivery system 7806. The attachment mechanism also is configured to provide a controlled deployment of the device 7800 so that the position of the device 7800 as it is being deployed can be monitored. The device 7800 may be withdrawn into the delivery system 7806 or repositioned until the final stage of the deployment process. Under some circumstances, the device 7800 also may be retrieved after deployment has been completed. The manner in which the device 7800 is secured to the delivery system 7806 and the process for deployment and/or retrieval of the device are described in detail below.

The delivery catheter of the delivery system 7806 is slidably disposed within the longitudinal passageway of the delivery sheath. The distal end of the delivery catheter releasably attaches to the hub of the device 7800. The device 7800 in its elongated delivery profile is constrained within the distal end portion of the delivery sheath. The delivery sheath containing the device 7800 is first inserted into the right atrium RA of the patient's heart 7804. The distal end of the delivery system 7806, including the delivery sheath may then be passed through an aperture 7808 which is located in the atrial septum 7802 and into the left atrium LA of the patient's heart 7804. The distal portion of the device 7800 may then be exposed into the left atrium LA by moving the delivery sheath proximally while holding delivery catheter steady or by advancing the delivery catheter distally while maintaining delivery sheath in place or by moving the delivery sheath proximally while distally advancing the delivery catheter. (Note that general methods of delivery are described herein and others are known to the skilled artisan). As it becomes exposed, the distal portion 7810 of the device 7800 begins to expand into the left atrium LA—see FIG. 78B.

Figure 78C:
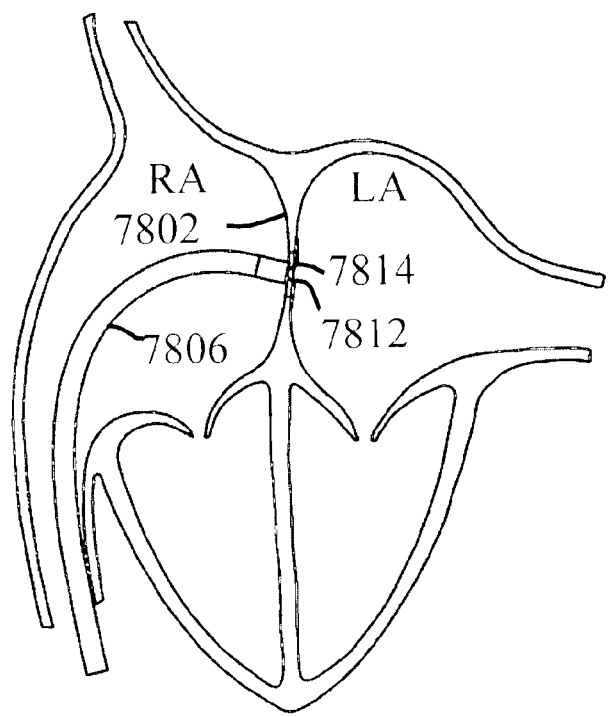

The delivery sheath holding the proximal portion of the device 7800 and the delivery catheter attached to the device 7800 may then be pulled back through the aperture 7808 and into the right atrium RA so that the core segment 7812 of the device 7800 is positioned within the aperture 7808 and the distal flange 7814 of the device 7800 seats against the left atrium LA side of the atrial septum 7802, as shown in FIG. 78C.

Figure 78D:
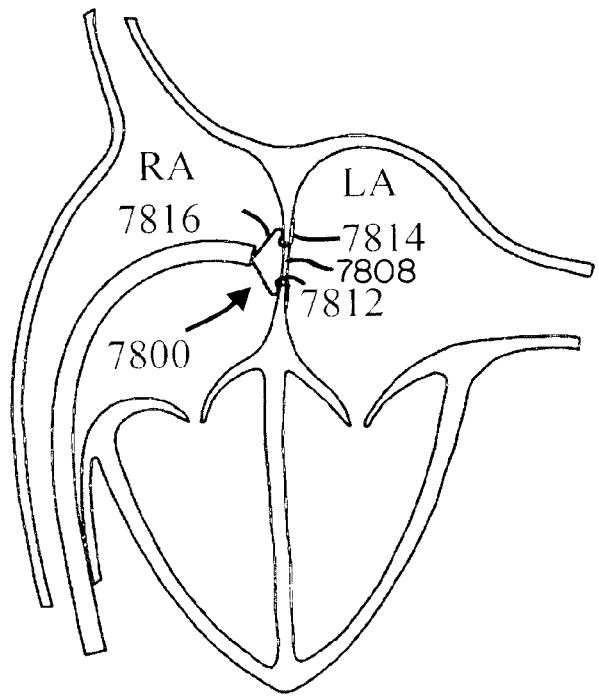

Referring now to FIG. 78D, the proximal portion of the device 7800 is then exposed into the right atrium RA by withdrawing the delivery sheath further proximally while holding delivery catheter steady or by advancing the delivery catheter distally, while maintaining delivery sheath in place or by moving the delivery sheath proximally and distally advancing the delivery catheter. When properly deployed, the core segment 7812 of the device 7800 is disposed within or through the aperture 7808 with the device's 7800 distal flange 7814 on the left atrium LA side of the atrial septum 7802 and the device's 7800 proximal flange 7816 on the right atrial side of the atrial septum 7802. The distal flange 7814 and proximal flange 7816 may exert a compressive force against the atrial septum 7802 securing the core segment across the aperture 7808. The positioning of the device 7800 can be evaluated using fluoroscopy or other appropriate techniques.

Figure 78E:
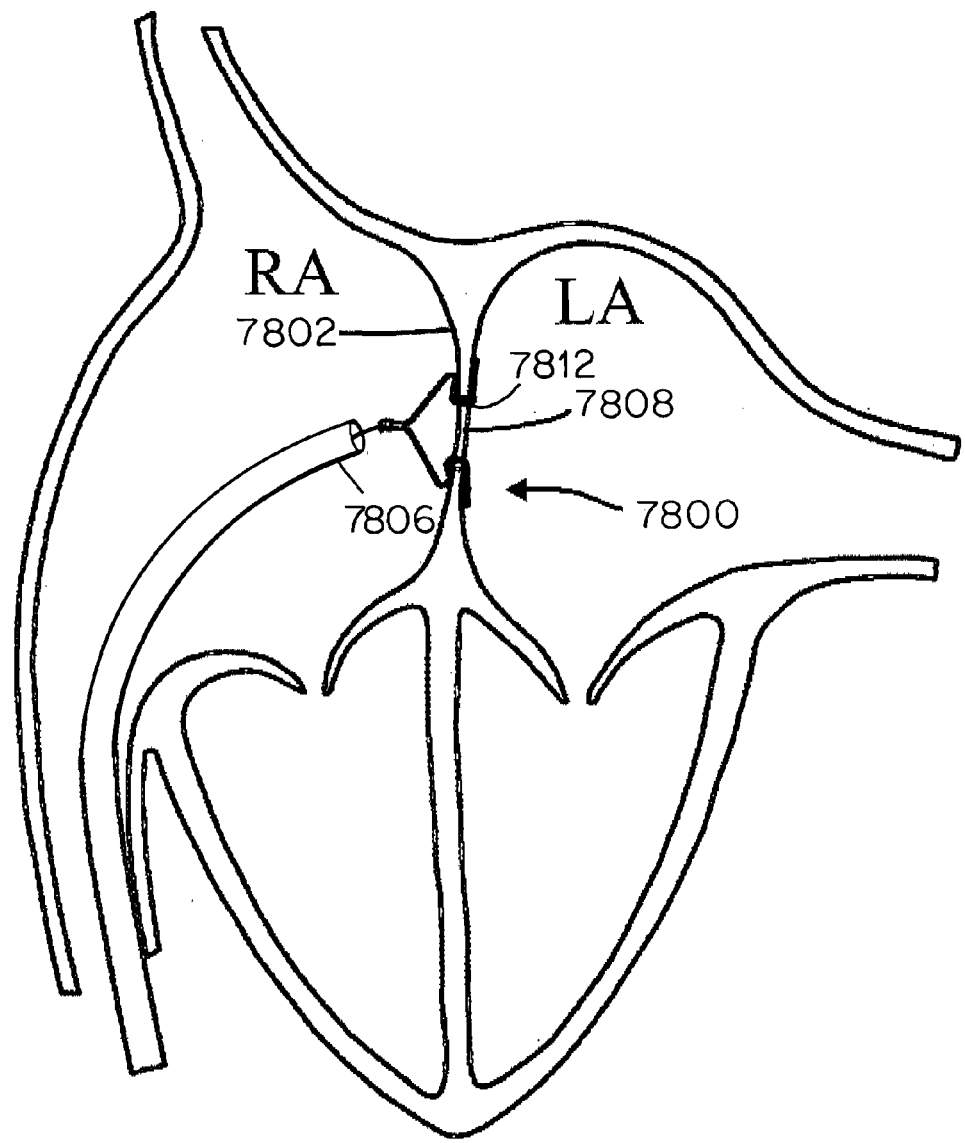
Figure 78F:
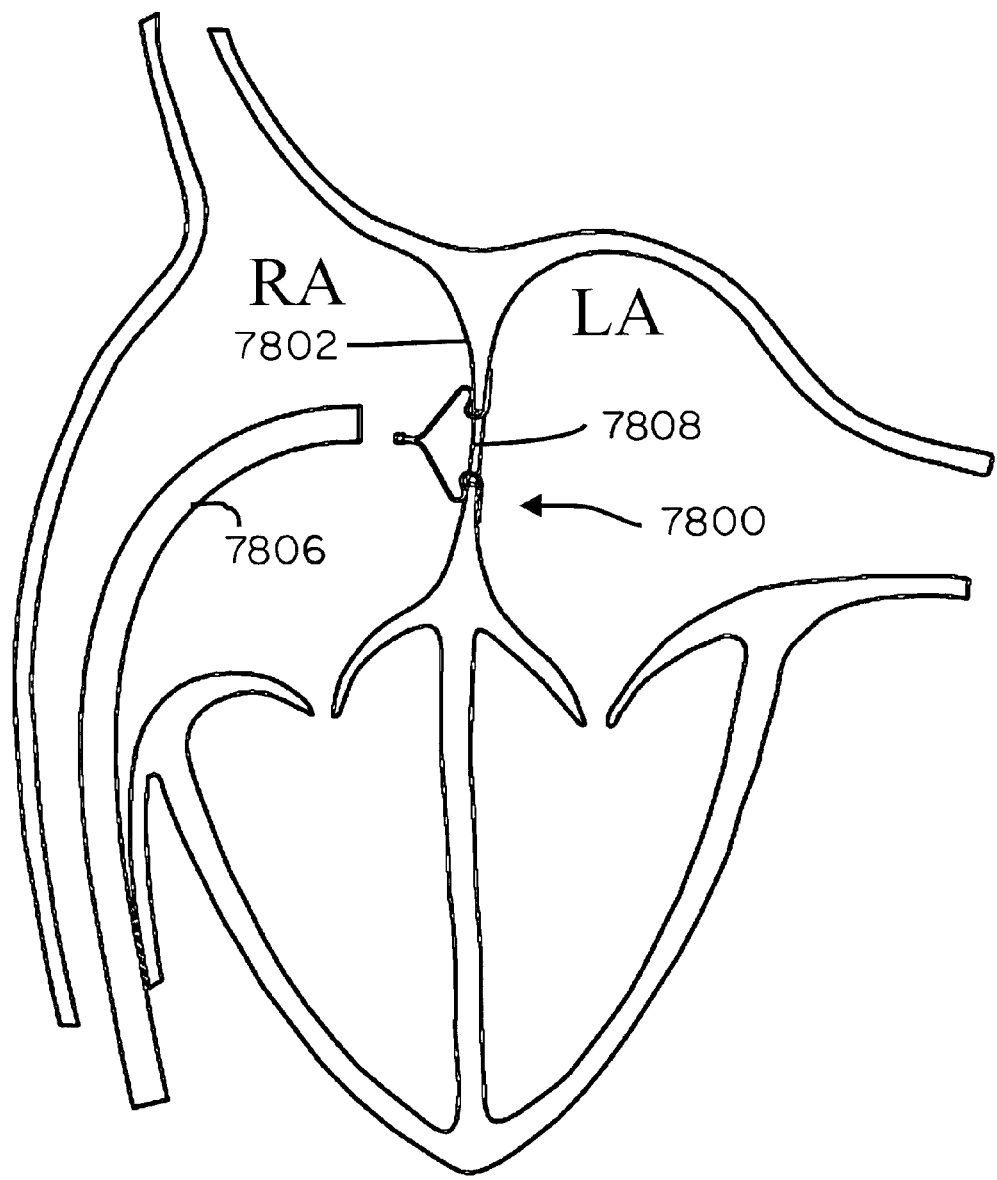

FIG. 78E shows the device still connected to or engaged with the delivery system 7608. As can be seen the angle of approach (θ of FIG. 79) of the delivery system 7608 is non-zero with respect to the longitudinal axis of the core segment 7812 of the device. As discussed above, the pivotable end of the device allows for the device 7800 to maintain its connection to, or engagement with, the delivery system while (a) the significant operable features of the device are deployed in the septum, and (b) accommodating the angle mentioned above. In this way, the clinician can determine if the device 7800 is satisfactorily deployed and/or if the physiology of the patient is such that the device 7800 may be released from engagement with the delivery system. Before disengaging, if deployment is incorrect or questionable, or if the measured physiological parameters of the patient reveals a problem, the device may be retrieved by retracting the device back into the delivery system as discussed below.

When the clinician who is implanting the device is satisfied with the device's location and deployment characteristics and/or physiology of the patient upon deployment, the attachment between the hub of the device and the distal end of the catheter is then detached to release the device 7800 from the delivery system 7806 and the delivery system 7806 pulled distally away from the device 7800, as illustrated in FIG. 78E.

The device 7800 remains implanted in the aperture 7808 of the atrial septum 7802. The delivery system is then removed from the heart. However, in some cases, if the clinician is not satisfied with the location of the device 7800, the delivery system 7806 may be used to retrieve the device 7800.

To retrieve the proximal portion of a device back into the delivery system before the hub of the device has been detached from the delivery catheter, the delivery sheath may be advanced distally while the delivery catheter is pulled proximally or the delivery sheath may be advanced distally while the delivery catheter is held steady or the delivery catheter may be pulled proximally while the delivery sheath is held steady. Any of these actions will cause the proximal flange to enter into the distal end of the delivery sheath and resume its elongated delivery profile within the delivery sheath. To retrieve the distal portion of the device back into the delivery system, the delivery sheath may be advanced distally while the delivery catheter is pulled proximally or the delivery sheath may be advanced distally while the delivery catheter is held steady or the delivery catheter may be pulled proximally while the delivery sheath is held steady. After the device is fully withdrawn into the delivery system, the delivery system may be removed from the body or the device can be redeployed according to steps of the delivery sequence described above.

In embodiments, the flange segments are designed to be more flexible than the core segment. In such embodiments, the increased flexibility may be achieved in several ways. In embodiments, a dimension of the surface of the strut elements that make up the flange segments is altered relative to the corresponding dimension of the struts (or elements, or members) that make up the core segments. FIG. 2A illustrates such embodiments. FIG. 2A shows an example flange segment 103a viewed end on. As shown, the end-facing dimension of strut element of 103x has a width D. By decreasing the width D in relation to the width of the outward-facing dimension of the struts that comprise the core segment, an increased flexibility of the flanges in relation to the core segment or other flange members (or portions thereof) can be achieved. FIG. 2B shows an enlarged fragmentary cross-section of an embodiment of the device substantially shown in FIG. 6. The view is taken along line 7-7 of FIG. 6. In this figure, the cross hatched area shows the area of increased flexibility. It can be seen that one area of the flange segment is thus more flexible than another area. In embodiments where the strut elements are circular, then in a similar fashion, the diameter of the strut element could be made to have a diameters less than the diameter of the strut (or similar elements) comprising the mesh-like configuration of the core segment.

In embodiments where the flange element is made from a different section of material and is attached to the core segment, the segment material could be chosen to have a greater flexibility than the core segment (or remaining portion of the flange segment or flange itself as the case may be). The choice of materials based on their flexibility will be apparent to those skilled in the art. In the ways described above, the flange segments can achieve greater flexibility than the core segment (or the remaining portion of the flange segment or the flange itself as the case may be) thereby reducing probability of damage to the tissue of the septum while allowing the core segment to maintain a strong outward force against the septal opening and thus decrease the probability that the device could become dislodged.

In embodiments having an open-mesh configuration for the body element 101, the body element can be formed from a number of materials suitable for use in a patient, such as titanium, nitinol, stainless steel, Elgiloy®, MP35N®, Vitalium, Mobilium, Ticonium, Platinore, Stellite®, tantalum, platinum, or other resilient material. Alternatively, in such embodiments, the body element 101 can be formed from a polymer such as PTFE, UHMWPE, HDPE, polypropylene, polysulfone, or other biocompatible plastic. The surface finish of the body element may be smooth with no edges or sharp discontinuities. In other embodiments, the surface finish is textured to induce tissue response and tissue in growth for improved stabilization. In embodiments, the open mesh of body element 101 can be fabricated from a resorbable polymer such as polylactic acid, polyglycolic acid, polycaprolactone, a combination of two or more of these or a variety of other resorbable polymers that are well known to those skilled in the art.

In embodiments, the structure of the body element may be uniform and monolithic.

In other embodiments, the body element (mesh or monolithic) may comprise porous materials to encourage tissue ingrowth or to act as a reservoir for containing one or more compounds that will be released over time after implant to address numerous issues associated with the product performance. These compounds can be used to diminish calcification, protein deposition, thrombus formation, or a combination of some or all of these conditions. The compound can also be used to stimulate an irritation response to induce tissue ingrowth. In embodiments, the compound can be an anti-inflammatory agent to discourage tissue proliferation adjacent to the device. Numerous agents are available for all of such uses and are familiar to those who are skilled in the art.

In embodiments, the material that may comprise the body may be multilayered comprising a coating of resorbable polymer or semipermeable polymer that may comprise various compounds that may be released, and in some embodiments in a controlled manner over time, after implant to address numerous issues associated with product performance.

The mesh can be formed from wire that is pre-bent into the desired shape and then bonded together to connect the component elements either by welding them or adhesively bonding them. They could be welded using a resistance welding technique or an arc welding technique, preferably while in an inert gas environment and with cooling control to control the grain structure in and around the weld site. These joints can be conditioned after the welding procedure to reduce grain size using coining or upset forging to optimize fatigue performance.

In other embodiments, the mesh can be formed from a hollow tube that has been slotted using, for example, a machining laser or water drill or other method and then expanded to form the open structure. If a sufficiently elastic and resilient material, such as nitinol, is used, the structure can be preformed into the finished shape and then elastically deformed and stowed during delivery so the shape will be elastically recovered after deployment. The surface of the finished assembly must be carefully prepared to insure is passivated and free of surface imperfections that could be a nidus for thrombus formation.

In embodiments, the flow control element 104 is a tissue valve such as a tricuspid valve, a bicuspid valve or a single flap valve formed from pericardial tissue from a bovine, porcine, ovine or other animal. Any number of cusps may be used. The flow control element is formed using a number of processing steps and auxiliary materials such as are well known in the art.

The flow control element 104 can also be a ball valve, a duckbill valve, a leaflet valve, a flap valve, a disc in cage type valve, a ball in cage type valve or other type of valve formed from a polymer or polymers or a combination of polymers, ceramics and metals such as Dacron (polyester), PTFE (such as Teflon®), polyurethane, PET or other suitable polymer; titanium, stainless steel, nitinol, MP35N®, cobalt-chromium-nickel alloy (such as Elgiloy®), or other suitable metal; zirconia, silicone nitride, or other suitable ceramic. Valves or portions thereof may comprise different stiffness/flexibly properties with respect to other valves or portions thereof in the flow control element.

The flow control element 104 preferably extends to a point along the flange assembly 103 to enable creation of a sealable connection to the septum wall after placement. This is more particularly shown in FIG. 3 where it can be seen that in embodiments, the flow control element extends beyond the length of the core segment and is folded and attached to the core segment so as to create a lip that extends in a direction center of the opening in the vent. When the device is abutted against the septal wall, this lip forms said sealable connection and thus can reduce the likelihood that blood can flow through the septal opening via pathways between the outer surface (septal-facing surface) of the interatrial pressure venting device and the septal opening. The flow control element 104 is attached to the body element 101. This can be accomplished by using a suture material, such as silk, nylon, polypropylene, polyester, polybutylester or other materials such as are well known to those skilled in the art. In embodiments, flow control element 104 can be attached to body element 101 using adhesive bonding agents such as cyanoacrylate, polymethylmethacrylate, or other materials such as are well known to those skilled in the art. In other embodiments, flow control element 104 can be attached to body element 101 via staples, rivets, rings, clamps or other similar methods as are well known to those skilled in the art.

As mentioned above, flow control element can be made of material selected for its flexibility/stiffness. In embodiments where a loose valve is desired that resonates more closely with the cycle of the heart, a however stiffness material may be chosen. In embodiments where it is desired to open the valve when the pressure differential reaches a selected value, the material of the flow control element can be selected and/or processed in a manner to open at the desired differential. The leaflets or sections of the flow control element itself may also comprise areas of variable stiffness, and or may be more flexible or less flexible than other leaflets or components of the flow control element.

Figure 3:
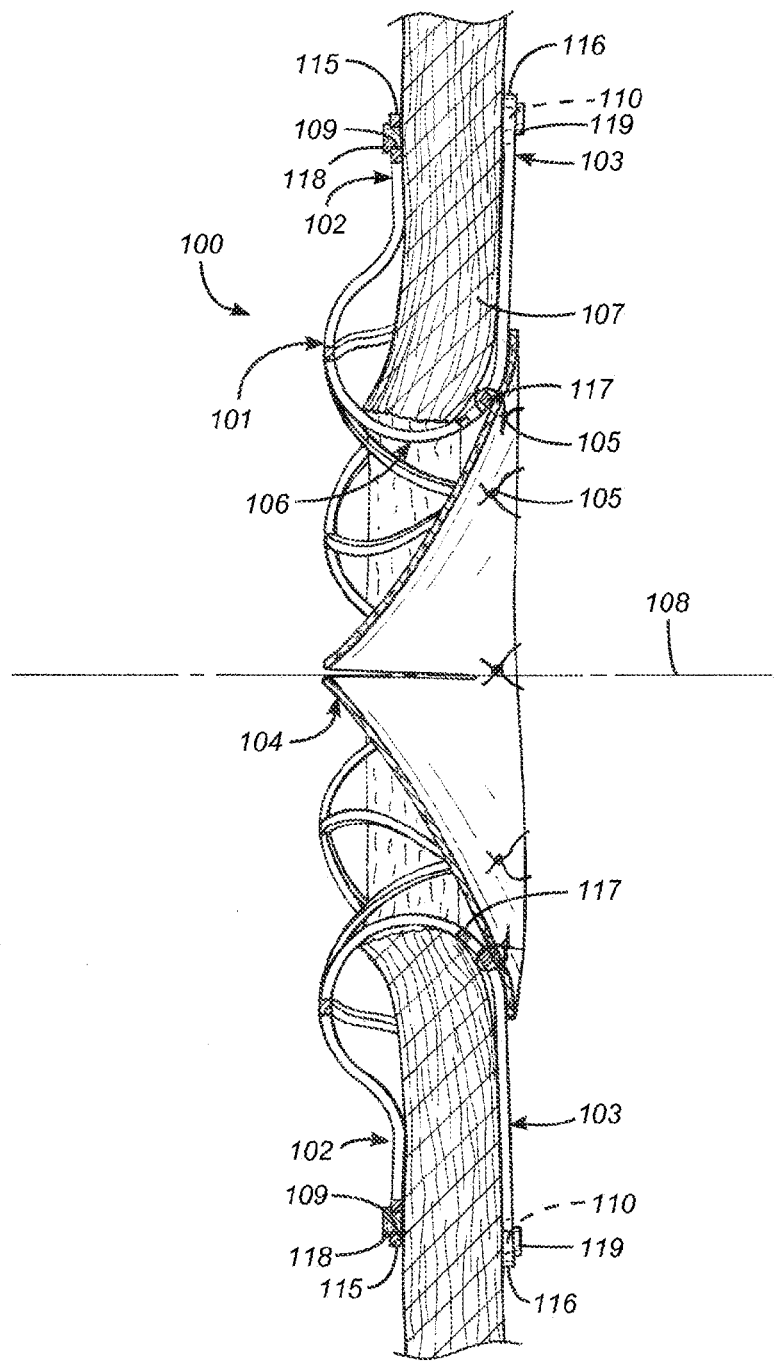
FIG. 3 is a cross-sectional side view taken along line 3-3 of FIG. 2.

FIG. 3 shows an embodiment of the device implanted in the atrial septum of the heart of a patient. As can be seen from the figure, the core segment 106 can be formed contiguously with flanges 102 and 103 and thus flange segments 102a-102h and 103a-103h respectively. In the embodiment shown, flow control element 104 is contained within the core segment 106 so it does not extend beyond the face of the body element 101, thereby insulating it from contact from other body structures or peripheral tissue. In embodiments, the core segment 106 can be extended to protrude beyond the interatrial septum 107 and the flange assembly 102 and/or 103 on at least one side of the interatrial septum 107 and can be formed with a shape that extends to create a lip in the manner described above. In embodiments, the ends of the flange assemblies 102, 103 are formed to lie at a parallel angle to and against the septal wall along at least a part of its length to increase the area of contact and thereby decrease the stress concentration against the septal wall.

Referring now to FIG. 4, an embodiment of the implantable device is shown. This perspective view implantable device 101 shows how, in embodiments, the ends of flange segments 102a-102h, 103a-103h are rounded at their distal ends 115 and 116 to reduce stress concentrations against the interatrial septum after placement. This rounded shape can easily be formed as part of the integral shape of the flange segment. In other embodiments, the thickness of the segment in this area may be decreased to decrease the stress further against the interatrial septum, which is similar to embodiments described above. Also similar to embodiments described above, if the segment is round, the diameter can be decreased in order to increase flexibility. Also, as described above a different material of higher flexibility could be used for the end portions of the segments.

Figure 7B:
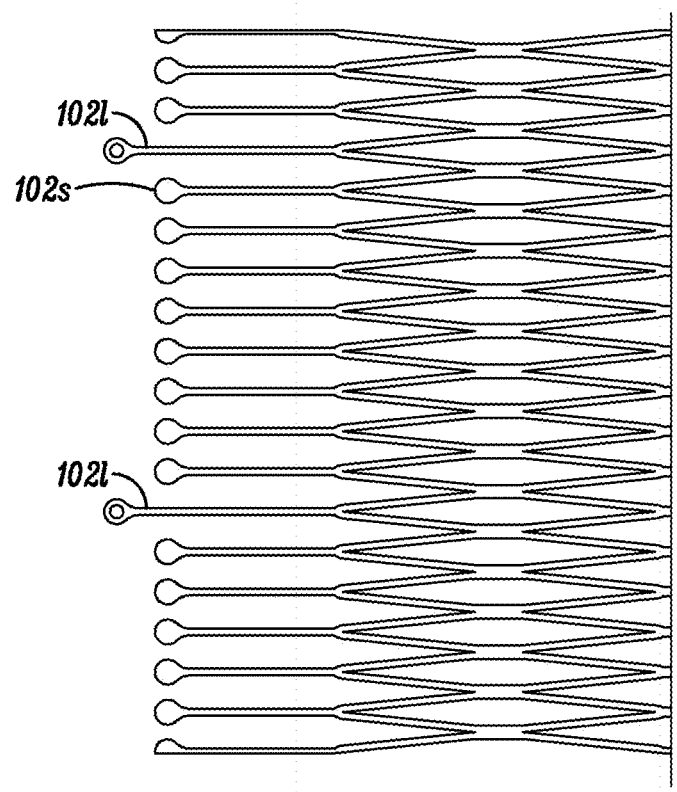
Figure 7C:
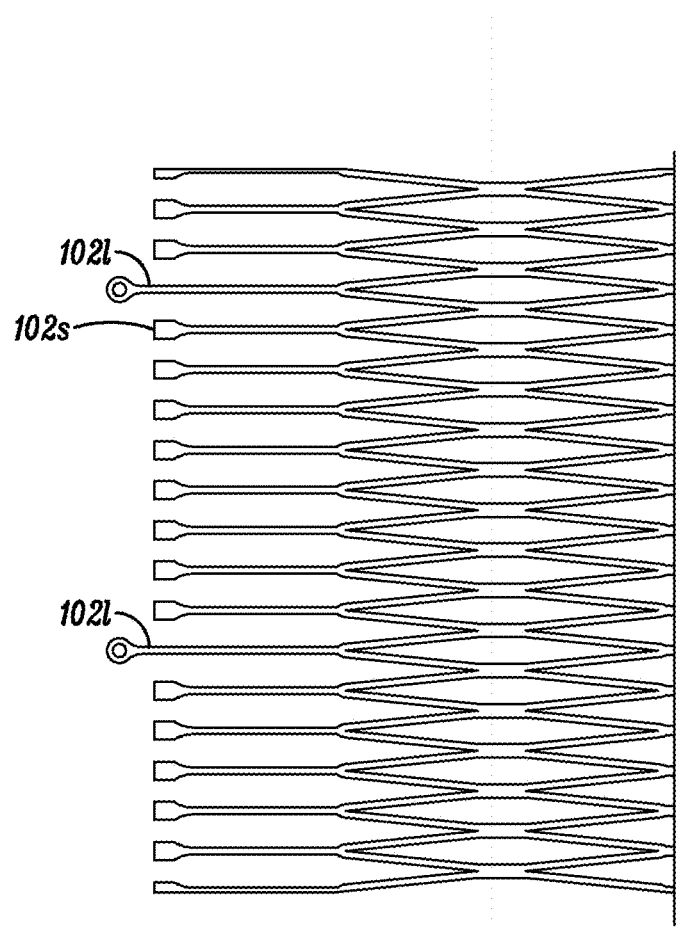

While rounded shapes at the ends of the flange segments reduce stress on the septum, other variations on this theme are contemplated. FIGS. 7A through 7C illustrate embodiments where the shape of the end portions of the flange segments has configurations to achieve less stress against the septal wall— among other goals. FIG. 7A is a side elevational view of embodiment of the pressure venting device in its stowed configuration. Core segment 106 of body element 101 is shown and, in this embodiment, is integral with flanges 103 and 102. The individual flange segments are not labeled; however, it is easily seen that flange 103 comprises segments substantial similar to those described above. There is no eyelet or opening at the end of the segment in the embodiment shown. Flange 102 shows an embodiment where the flange segment is not comprised of a triangular or multi-strut arrangement as described above but rather a single-member segment. Any flange may be constructed with single-member segment. An example single member is referred to as 103s. In this example, at the end of each single-member flange segment (102s) for example, there is an eyelet. FIG. 7B shows an embodiment similar to that shown in FIG. 7A where the end of the segments 102s are not eyelets but rather pads. FIG. 7C shows another embodiment where the ends of the segments 102 are paddle shaped. Other smooth-edged shapes could be used, and it should be understood that such shapes and configurations apply to all manner of flange segment ends, not only single-member segments. This would include the ends of flange segments shown and described herein, for example with reference to FIGS. 2 through 7.

FIGS. 7A-C also show embodiments having at least one flange segment being longer than the other flange segments. Again, while represented as single-member flange segments they need not be and as such a configuration with at least one longer segment may apply to any flange-segment configuration disclosed herein. The benefits and purpose of having at least one longer flange segment will be described more fully below.

In embodiments, the outer ends of the flange segments 102a-102h, 103a-103h are formed with integral marker holes or slots 109 and 110 (shown in FIGS. 3 and 7 for example) in which markers 118 and 119 can be positioned so the device may more easily be visualized using radiographic imaging equipment such as with x-ray, magnetic resonance, ultrasound or other imaging techniques. Markers as disclosed herein may be applied to the ends of any segments, not just those with holes or eyelets therein. A radiopaque marker 118 and 119 can be swaged, riveted, or otherwise placed and secured in the hole and thereby dimensioned to be flush with the end of the segment. Markers may also be simply attached or to end of a segment not having a hole. In all embodiments having markers, flange ends 115 and 116 are more visible when imaged. In other embodiments, the markers 118 and 119 can be bonded with an adhesive agent such as cyanoacrylate or epoxy or a variety of other materials that are available and suitable for implant as are well known. The markers may be proud (as shown for example in FIG. 7) or flush with the end of the flange segment. The radiopaque markers 118 and 119 may be formed of tantalum, tungsten, platinum iridium, gold, alloys of these materials or other materials that are known to those skilled in the art. Also markers 118 and 119 comprising cobalt, fluorine or numerous other paramagnetic materials or other echogenic materials that are known to those skilled in the arts can be incorporated together with the radiopaque materials, or in alternating locations of the flange segments to enable both x-ray and echographic imaging of the interatrial pressure vent. Alternatively, the ends of the flange elements 102a-102h and 103a-103h can be wrapped with a foil made of the same marker materials. In embodiments, the radiopaque material can be laminated to the flange segments and bonded through a welding process or using an adhesive such as cyanoacrylate or numerous other adhesives known to those skilled in the art.

Suture rings 117 can be formed in the body element to locate and fix the attachment site along the body element to the flow control element. The suture rings can be circular holes formed into the structure or they could also be some other shape such as rectangular or triangular and also can be formed as a secondary step, for example by standard machining techniques, using a secondary laser machining step, or with electrochemical etching. Preferably the connection between a segment and any other segment of the body element are formed with as large a radius as possible to increase resistance to fatigue failure. Also, preferably, all edges of the formed device are rounded to improve biocompatibility and hemocompatibility.

The pattern of suture rings as well as which of the rings are selected during suturing may affect the properties of the flow control element. For example, in embodiments where it is desired to have the flow element loose and flappable, less suture rings may be utilized and, in such embodiments, RA-side end of the flow control element may contain relatively less sutures than the LA side. In other embodiments, it may be desirable to keep the flow control element affixed to the core segment for a increased length of the segment thereby reducing the amount of flow control element material that affecting flow. Still in other embodiments the top or bottom portion the flow element at the RA side may be sutured in such a way so as to allow the top or bottom portion of the flow control element to affect flow more than the other portion respectively. Embodiments discussed below where the flow is "aimed" may utilize suturing patterns effective to enable the desired flow control element configuration.

Returning to the flange segments, in an embodiment, the interatrial pressure vent 100 is comprised of an equal number of flange segments on each side of the interatrial septum. In embodiments, there are eight flange segments on each side of the core segment. In another aspect there are an equal number of suture rings and flange segments on one side of the interatrial pressure vent. In other embodiments, there are seven flange segments on each side of the core segment. In other embodiments, there are six flange segments on each side of the core segment. In other embodiments, there are five flange segments on each side of the core segment. In other embodiments there are four flange segments on each side of the core segment. In other embodiments there are three flanges on each side of the core segment. In other embodiments there are two flanges on each side of the core segment. In other embodiments, there is one flange on each side of the core segment. Still in other embodiments there are more flange segments as compared to flange segments. And in other embodiments, there are more flange segments as compared to flange segments. As can be seen there are a number of variations for the number of flange segments and the skilled artisan will appreciate that any number could be used while not deviating from the scope and spirit of this invention.

Referring now to FIG. 5, an embodiment of the implantable device is displayed in side view. The flange segments can be formed to produce a gap G (also referred to as an annular gap) between the ends of flange segments on one side of the body and flange segments on the other side of the body, when the device is in its "native" or un-deployed state. When the device is deployed, it flexes to accommodate the tissue and as such the gap may expand when tissue is positioned therein. In embodiments, this gap is slightly smaller than the thickness of the interatrial septum. In other embodiments, the gap can be larger than the thickness of the interatrial septum. In other embodiments the gap can be zero. In another aspect the gap can be negative: in this case the flange segments on each side of the body can be formed to cross each other in order to exert more pressure between the deployed flange segments and the interatrial septum. Also shown in FIG. 5 are radiopaque markers 118 and 119, which in embodiments are shown to be located adjacent to the end of the flange segments.

Referring now to the embodiment shown in FIG. 6, the flange segments 102*a*-102*h* are oriented so they are not directly opposed to flange segments 103*a*-103*h* on the opposite side of the body element so that after placement there is no pinching points thereby reducing the chance for tissue injury. In embodiments, flange segments 102*a*-102*h* are arranged midway between adjacent ends of flange segments 103*a*-103*h*. In embodiments the length of flange segments 102*a*-102*h* are similar to the length of flange segments 103*a*-103*h*. However, in other embodiments the length of flange segments 102*a*-102*h* are identical to the length of flange segments 103*a*-103*h*; the length of flange segments 102*a*-102*h* are longer than 103*a*-103*h*; and the length of flange segments 102*a*-102*h* are shorter than flange segments 103*a*-103*h*.

Referring now to FIG. 7, in embodiments having radiopaque markers it can be seen that the radiopaque markers 118 and 119 may be placed into the marker holes 109 and 110 (or placed on the ends of flange segments that do not have holes) to locate the ends of the flange segments 102*a*-102*h* and 103*a*-103*h* with a non-invasive imaging technique such as with x-ray or echo sound during or after the procedure. In embodiments, the markers 118 and 119 can be formed to be flush in an axial direction with the outer surface and the inner surface of the flange segments 102*a*-102*h* and 103*a*-103*h*. In another aspect, the markers 118 and 119 can be formed to extend in an axial direction beyond the outer surface of the flange segments 102*a*-102*h* and 103*a*-103*h*, away from the interatrial septum. In embodiments, the markers 118 and 119 can be formed to extend in an axial direction beyond the inside of the flange segments 102*a*-102*h* and 103*a*-103*h*, toward the interatrial septum. In embodiments, the markers 118 and 119 can be formed to extend in an axial direction beyond the inside and the outside of the flange segments 102*a*-102*h* and 103*a*-103*h*. In embodiments, the markers 118 and 119 can be formed to be recessed in an axial direction within the surface of the inside of the flange segments 102*a*-102*h* and 103*a*-103*h*. In embodiments, the markers 118 and 119 can be formed to be recessed in an axial direction within the outside of the flange segments 102*a*-102*h* and 103*a*-103*h*. In embodiments, the markers 118 and 119 can be formed to be recessed in an axial direction within both the inside and the outside of the flange segments 102*a*-102*h* and 103*a*-103*h*. In embodiments, the markers 118 and 119 can be formed to extend in a radial direction within the width of the flange segments 102*a*-102*h* and 103*a*-103*h*. In embodiments, the markers 118 and 119 can be formed to extend in a radial direction flush with the width of the flange segments 102*a*-102*h* and 103*a*-103*h*.

Figure 8:
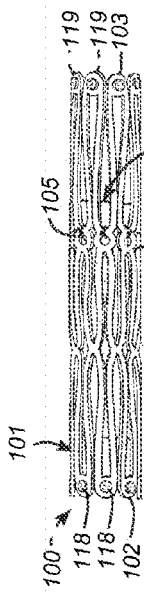
FIG. 8 is a side elevational view of the interatrial pressure vent of FIG. 1 in a collapsed configuration prior to loading in a placement catheter.

Referring now to FIG. 8, an interatrial pressure vent 100 is shown in its stowed configuration. In embodiments, the interatrial pressure vent can be collapsed to a substantially cylindrical shape for stowing in a delivery catheter during placement. Flange segments 102*a*-102*h* and 103*a*-103*h* can be fabricated to be substantially equal in length. The "stowed position" is not meant to apply only to devices having flange segments of equal length but rather to all embodiments of the venting device disclosed herein. Devices having flange segments of varying length and orientation such as those described herein are also designed to stow in substantially the same manner as shown in FIG. 8. In an embodiment 200 seen in FIG. 20, flange segments 202*a*-202*h* and 203*a*-203*h* are formed on a slanted angle so that, when marker elements are secured to the ends of the flange segments, the flange segments can be stowed into a smaller volume. In embodiments 300 seen in FIG. 21, flange segments 302*a*-302*h* are formed of alternating length to allow stowage into a smaller volume.

Figure 9:
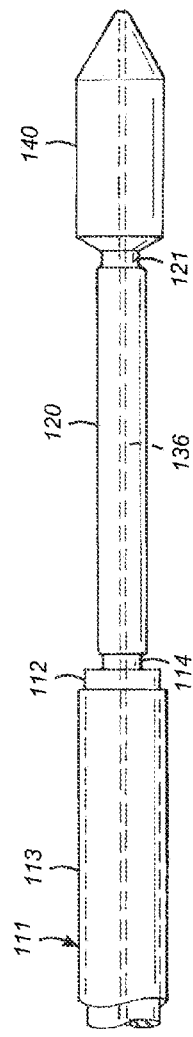
FIG. 9 is a side view of the distal end of a placement catheter in its open position.

Referring now to FIG. 9, an embodiment of the distal end of the placement catheter 111 is shown in its open position. The inner shaft 112 is fabricated with a center lumen 136 of sufficient diameter to contain a guidewire 138 or also for use in injecting contrast or other liquid. Commonly, the lumen would be sized for a guidewire of 0.010", 0.011", 0.014", 0.018", 0.021", 0.028", 0.035", 0.038", 0.042" or 0.045". This lumen 136 can also be used to measure pressure at the distal end of the catheter using other equipment and techniques that are well known to those skilled in the art. The lumen 136 preferably extends through the entire length of the inner shaft 112. Alternatively, the guidewire lumen 136 can extend for a shorter length in the proximal direction and then through a side hole (not shown) of the inner sheath. A corresponding side hole (not shown) is placed on the outer shaft 113 adjacent to the side hole in the inner shaft 112 to create a pathway between the center lumen 136 of the inner shaft 112 and the outside of the outer shaft 113. In this way it is possible to pass a guidewire from this distal end of the inner lumen 136 through the side hole and exchange the catheter over a guidewire that is less than twice the length of the catheter 111 while securing the guidewire position during exchange.

In embodiments, the inner shaft 112 is configured with a waist section 120 to contain the folded interatrial pressure vent 100 between the gap formed in the space outside of this section of inner shaft 112 and the inside of the outer shaft 113. The inner shaft 112 may be formed to contain at least one circumferential groove 114 at the proximal end of waist section 120 that forms a recess between the inside of the outer shaft 113 and the smallest diameter of the groove that is greater than the gap formed in the space between the waist section 120 and the inside of the outer shaft 113. Radiopaque markers 118 can extend in a radial direction past the outer surface of the flange segments 102*a*-102*h* and in embodiments, when interatrial pressure vents are folded into their stowed configuration and placed into position over inner shaft 112, radiopaque markers 118 are dimensioned to fit into groove 114. Other similarly dimensioned sections may be used; that is, that which fits into the groove need not necessarily be a radiopaque marker. In embodiments, when interatrial pressure vents are stowed in this manner, the gap between waist section 120 and the inside of outer shaft 113 is not sufficient to allow radiopaque markers 118 beyond the distal end of groove 114 unless the outer sheath 113 is retracted beyond the proximal end of groove 114.

The inner shaft 112 may be formed with a groove 121 on the distal end of the waist section 120 adjacent to the location of the distal end of the interatrial pressure vents are radiopaque markers 119 (or similar dimensioned members) can extend in a radial direction past the outer surface of the flange segments 102a-102h and in embodiments, when interatrial pressure vents are folded into its stowed configuration and placed into position over inner shaft 112, radiopaque markers 119 are dimensioned to fit into groove 121. In another aspect, the inner shaft 112 may be formed with a circumferential groove 114 on the proximal end of waist section 120 and a circumferential groove 121 on the distal end of the waist section 120 The inner shaft can be formed of a variety of polymers or metals or combinations of polymers and metals that are suitable for use in a patient. The inner shaft can be fabricated from a single length of PTFE, UHMWPE, FEP, HDPE, LDPE, polypropylene, acetal, Delrin, nylon, Pebax, other thermoplastic rubber, aliphatic or aromatic polyurethane, or a variety of other engineering resins that are well known to those skilled in the art. In embodiments, the inner shaft can be fabricated using multiple layers of two or three of the above-mentioned polymers to combine desirable properties of each. For example, the outer surface could be composed of polyurethane to enable easier bonding of auxiliary components to the inner shaft. The inner layer could be PTFE to convey better lubricity to the inner shaft. In embodiments, the inner shaft and or the outer shaft could be coated on the inner and or outer surface with a coating material that conveys specific properties to the shaft like antithrombogenicity or lubricity. There are numerous available coating materials suitable for these purposes as are well known to those skilled in the art. The inner shaft can be compounded with a radiopacifier to increase the visibility of the inner shaft under fluoroscopy using bismuth salts such as bismuth subcarbonate, bismuth oxychloride, bismuth trioxide, tungsten powder, molybdenum powder or other radiopacifier such as are well known to those skilled in the arts. Similarly, the outer sheath can be fabricated from the same set of materials as the inner sheath, in the same manner and using the same coatings. Embodiments described below in connection with a flange rather than circumferential groove operate in substantially the same manner as described above and herein, except the device does not necessarily have projections that fit into and are retained by the grooves.

Figure 10:
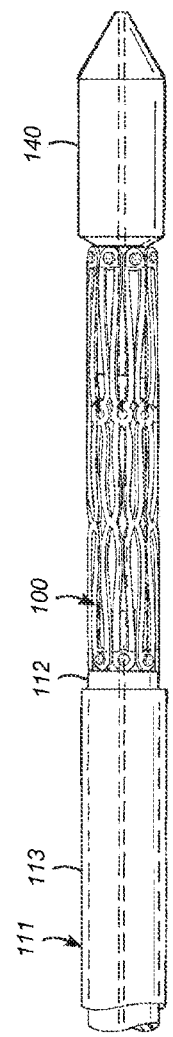
FIG. 10 is a side view of the distal end of a placement catheter in its open position and with an interatrial pressure vent in its stowed configuration and in position over the inner shaft of the catheter.
Figure 17:
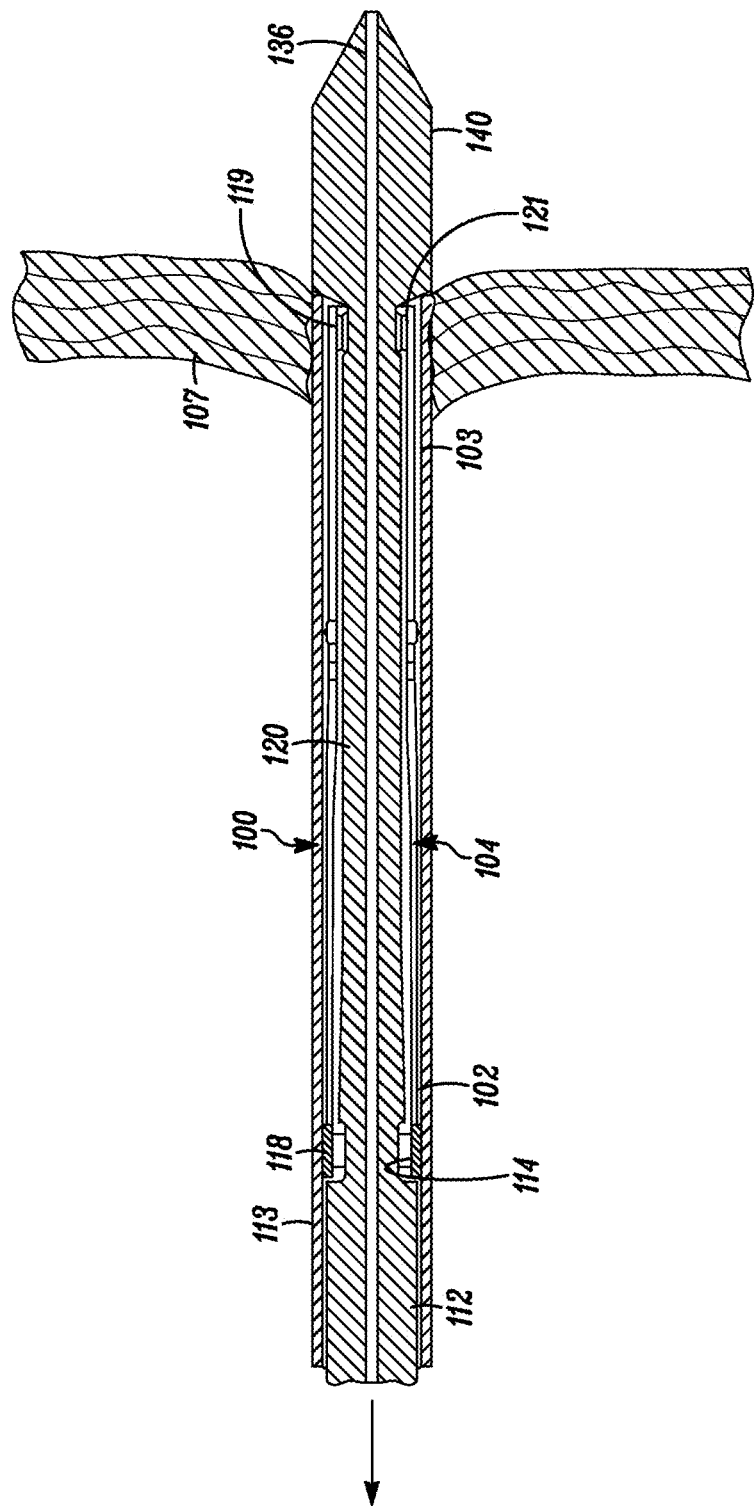
FIG. 17 is an enlarged cross-sectional detail view of the distal end of the placement catheter of FIG. 16 but showing the distal flange segments of the interatrial pressure vent being retracted from the interatrial septum as if it were determined to be in an undesirable position by imaging the radiopaque markers and going to be redeployed.

Referring now to FIG. 10, a folded representative interatrial pressure vent 100 is shown in its stowed position with the placement catheter 111 shown in its open position. In practice, if the body of the interatrial pressure vent is fabricated of nitinol or other elastic material, when the placement catheter is in its fully open position, the flange segments 102a-102h and 103a-103h would automatically recover into a shape like that shown in, for example, FIG. 4, hence this Figure is shown to illustrate the position of the interatrial pressure vent 100 relative to the waist section 120 and grooves 114 and 121. When radiopaque markers (or similarly dimensioned members) 118 extend beyond the thickness of the inside of body segment 101 of interatrial pressure vent 100, they form a projection within interatrial pressure vent 100 that can be captured within groove 114 to secure the position of the interatrial pressure vent 100 during placement. During deployment, the outer shaft 113 of placement catheter 111 is retracted a sufficient distance to reveal the distal portion of the interatrial pressure vent 100 allowing the flange segments 103a-103h to dilate radially away from the central longitudinal axis of body 101. By capturing the radiopaque 118 markers within the groove 114, the device can be repositioned easily without further deployment, or the device can be completely retracted and removed from the patient without deployment as indicated in FIG. 17.

Figure 11:
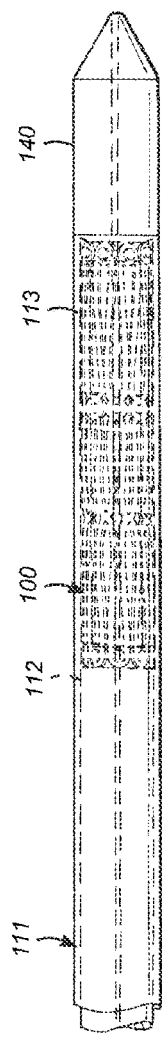
FIG. 11 is a side view of the distal end of a placement catheter in a closed configuration with an interatrial pressure vent in its stowed configuration loaded onto the placement catheter.

Referring now to FIG. 11, an interatrial pressure vent 100 is shown completely stowed within the placement catheter 111.

FIG. 11A shows an embodiment of the placement catheter similar in operation to those described herein but operative to engage an interatrial pressure vent by way of a slightly different mechanism than described above in connection with circumferential grooves. This figure shows a schematic depiction of a stowed interatrial vent. Rather than having the grooves as described above, this embodiment of a placement catheter may comprise an inner shaft having a flange or member 3000 (rather than a groove) which has a diameter larger than that of the inner shaft to grip and hold an end of the interatrial vent device as shown. As shown in the figure, the flange and its segments (collectively referred to in the figure as 102) wrap around the ball-shaped flange 3000 and allow the interatrial pressure vent to be moved with the placement device in the manners described herein.

Figure 12:
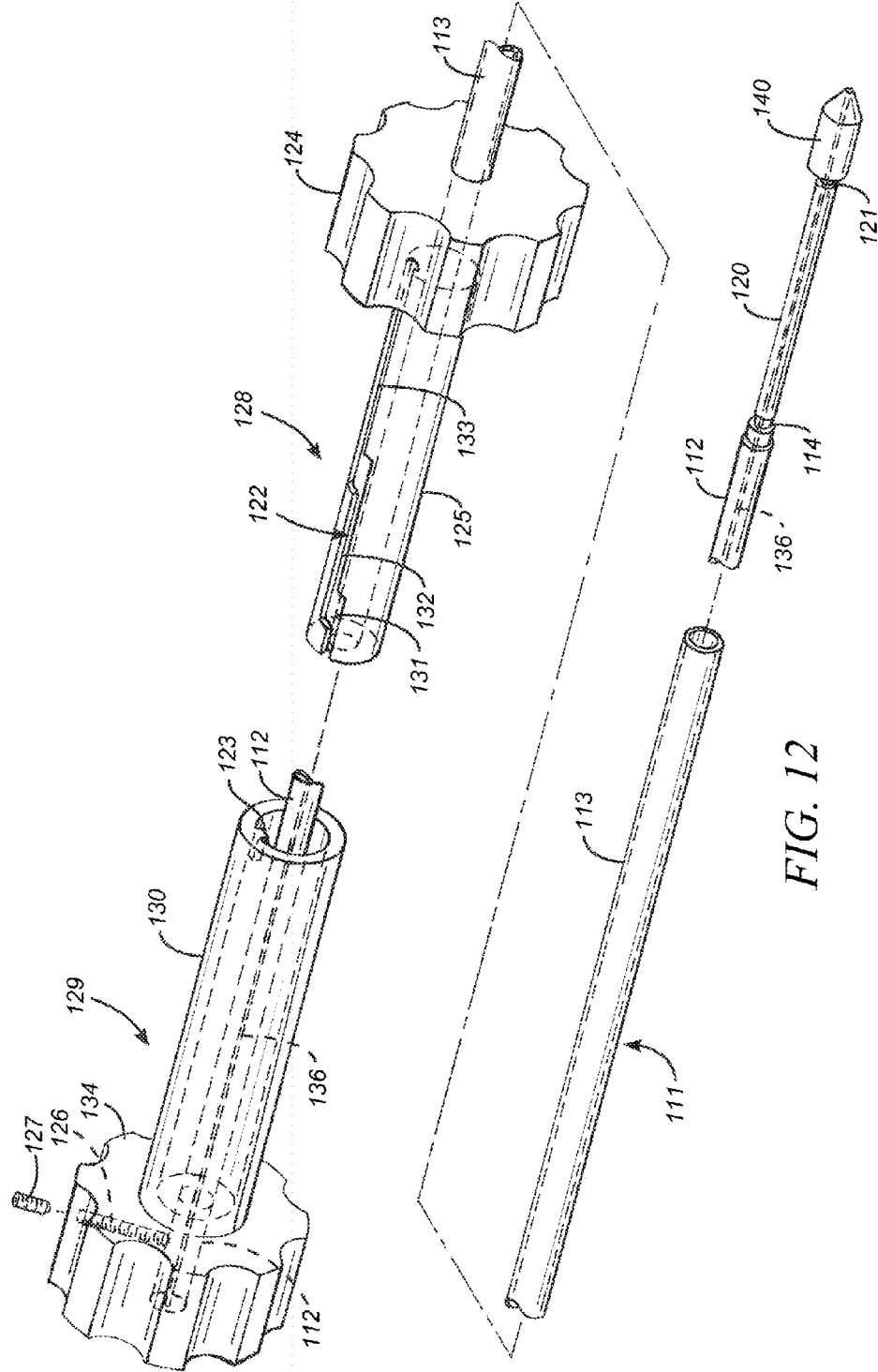
FIG. 12 is an exploded perspective view of the proximal and distal ends of a placement catheter.

Referring now to FIG. 12, a placement catheter 111 is shown. It should be noted that while the inner shaft is depicted as having grooves in FIG. 12, the inner shaft may comprise the flange 3000 as described above in connection with FIG. 11A. The skilled artisan will appreciate that the operation of the device is substantially similar whether grooves or flanges are utilized. The placement catheter 111 may comprise a first handle component 128 that can be attached to outer shaft 113. The first handle component can be attached to the outer shaft 113 using a variety of adhesive methods such as solvent bonding using a solvent for both the handle and outer shaft material; an organosol consisting of a solvent and polymer in solution that is compatible with both the outer shaft and the first handle component; a polymerizable adhesive, such as polyurethane, cyanocrylate, epoxy or a variety of other adhesives as are well known to those skilled in the art. The first handle component can be fabricated from a variety of metals such as aluminum, stainless steel, titanium or a number of other metals and alloys as are well known to those skilled in the art. In embodiments, the first handle component 128 is fabricated from a polymer such as polycarbonate, or a variety of engineering resins, such as Lexan®, or others as are well known to those skilled in the art.

The first handle component may comprise hand grip section 124 and tubular shaft section 125. The tubular shaft section 125 can contain keyway 122 that is formed or machined into the shaft section. The keyway is preferably formed with three linear sections; a first linear section 131, a second linear section 132 and a third linear section 133. Each of these sections is formed to traverse along a path primarily parallel with the center axis along the length of the first handle component but each is displaced radially from one another by at least about half of the width of the keyway. The placement catheter 111 also can comprise a second handle component 129 that can be attached to inner sheath 112. The second handle component can be fabricated from the same variety of metals and polymers as the first handle component. The two handles can be fabricated from the same materials or from different materials. The second handle component can be attached to the inner sheath in the same manner and using the same materials as the first handle component attaches to the outer sheath. In embodiments, the second handle component can contain threaded hole 126 for containing set screw 127. The set screw can be twisted to capture the inner shaft against the second handle component. The second handle component 129 also can comprise a second hand grip section 134 and second tubular shaft section 130. The second tubular shaft section can contain key 123 that is formed or machined of suitable dimension to adapt to keyway 122 of first handle component 128. When assembled, second handle component 129 can be slideably moved relative to first handle component 128 in a manner controlled by the shape and length of the key way 122. As the second handle 129 is advanced relative to the first handle 128, it can be appreciated that the inner sheath 112 will slide in a distal direction out from the outer sheath 113. It can be appreciated that when the second handle component 129 is assembled, the key 123 is slid into the first linear section 131 and advanced until it hits the edge of the keyway formed between the first linear section 131 and the second linear section 132. In order for the second handle component 129 to advance further, it must be rotated and, once rotated, it can be advanced further but will stop when the key 123 hits the edge of the keyway formed between the second linear section 132 and the third linear section 133. The keyway dimensions are preferably selected with consideration for the combination of lengths of other components in the placement device.

A first position, defined as the position when the key 123 is in contact with the proximal edge formed between the first linear section 131 and the second linear section 132, is preferably determined so, when fully assembled and with the interatrial vent in its stowed position within the placement catheter, the outer shaft 113 will completely cover the length of the interatrial pressure vent 100 as is desired during catheter placement. The keyway dimensions can also be selected to result in a second position, defined as the position when the key 123 is in contact with the distal edge formed between the second linear section 132 and third linear section 133. The second position would preferably be selected to reveal the full length of flange segments 103a-103h but retain flange segments 102a-102h within the outer shaft 113 of the catheter. The length of the third linear section 133 would preferably be selected so that, when the second handle component 129 was advanced completely against the first handle component 128, the full length of the interatrial vent 100 would be uncovered by the outer shaft 113 and the device would be deployed. A variety of other configurations of the first and second handle components could be used for this same purpose. The first handle component tubular shaft section 125 and the second handle component tubular shaft section 130 could be threaded (not shown) so the first handle component 128 could be screwed into the second handle component 129. Alternatively, gear teeth (not shown) could be formed in the first tubular shaft section 125 of the first handle component 128 and a gear wheel (not shown) could be incorporated into the second shaft tubular section 130 of the second handle component 129. The gear wheel would preferably be chosen to mesh with the gear teeth and the second handle component 129 could be advanced toward the first handle component 128 by rotating the gear wheel. A variety of other design configurations could be utilized to control the relative location between the first handle component and the second handle component as are well known to those skilled in the art.

FIGS. 13 through 17 show embodiments of a system for treating heart failure. More specifically FIGS. 12 through 19 show how the placement catheter is introduced and positioned in a patient and methods for placing the interatrial valve in a patient. The interatrial pressure vent 100 is presterilized and packaged separately from the placement catheter 111. Sterilization can be performed by exposing the device to a sterilizing gas, such as ethylene oxide, by exposing the device to elevated temperature for an adequate period of time, by using ionizing radiation, such as gamma rays or electron beam or by immersing the device in a fluid that chemically crosslinks organic molecules, such as formaldehyde or glutaraldehyde and then rinsed in sterile water or sterile saline. For each of these sterilization methods, consideration must be given to compatibility of the materials so device performance is not adversely affected as a result of the sterilization process. Also, the packaging design and materials must be carefully considered with the sterilization procedure, post sterilization handling and storage, environmental exposure during storage and shipment, and ease of handling, opening, presentation and use during the procedure.

In embodiments, interatrial pressure vent 100 can be assembled using components that have been pre-sterilized using one of the above methods or others that are well known and the final assembly may be accomplished in an aseptic manner to avoid contamination.

In embodiments, the interatrial pressure vent 100 can be supplied non-sterile and be sterilized around the time of use using one of the above methods or by other methods well known by those skilled in the art.

Similarly, the placement catheter 111 may be pre-sterilized and packaged separately from the interatrial pressure vent 100. Sterilization can be performed using a similar method to the interatrial pressure vent 100 or using a different method from the same choices or using some other method as is well known by those skilled in the art.

In embodiments, an interatrial pressure vent 100 and the placement catheter 111 can be supplied pre-sterile and in the same package. In another aspect, the interatrial pressure vent 100 and the placement catheter 111 can be preloaded and supplied pre-sterile.

Prior to insertion, the interatrial pressure vent 100 is preferably folded and stowed onto the placement catheter 111. This can be accomplished in a sterile field and using aseptic techniques in the following steps. First the interatrial pressure vent 100 is presented to the sterile field and the placement catheter 111 is presented to the sterile field. Second, the interatrial pressure vent 100 and placement catheter 111 are inspected for visible signs of damage, deterioration or contamination. Third, the second handle component 129 of the placement catheter 111 is retracted fully so the outer shaft 113 exposes the inner shaft 112 to the maximum extent allowed. Fourth, the interatrial pressure vent 100 is positioned in the correct orientation over the inner shaft 113 of the placement catheter 111 with the inner shaft 113 oriented through the center of the flow control element 104. Fifth, the flange segments 102 a-h and 103 a-h are folded away from each other and the flange segments 102 a-h and 103 a-h and the core segment 106 are compressed radially to fold the interatrial pressure vent 100 into a size and shape that will fit over and onto the waist section 120 of the inner shaft 112 with the distal ends 115 of flange segments 102a-h aligning with the proximal groove 114 of inner shaft 112.

In embodiments comprising a flange as described in FIG. 11A the flange segments 102 a-h and 103 a-h are folded away from each other and the flange segments 102 a-h and 103 a-h and the core segment 106 are compressed radially to fold the interatrial pressure vent 100 into a size and shape that will fit over the flange 3000 described on FIG. 11A. This folding may be accomplished with the aid of an insertion tool (not shown) that retains the interatrial pressure vent 100 in a stowed position on inner shaft 112 and then advancing outer shaft 113 over the stowed interatrial pressure vent 100 and displacing the insertion tool, thereby leaving the outer shaft 113 completely covering the interatrial pressure vent 100 and mating with the distal tapered tip 140 of the inner shaft 112. In other embodiments, this can be accomplished by hand using the fingers of one hand to hold the distal ends 115 of the flange segments 102a-102h in position at groove 114 of the inner shaft 112 and advancing the outer shaft 113 over the inner shaft 112 enough to hold the flange segments 102a-102h in place. Completion of the loading procedure is accomplished by progressively advancing the outer shaft 113 until it completely covers the interatrial pressure vent 100 as shown in FIGS. 11 and 11A. While the below discussion regarding placement of the interatrial pressure vent uses the placement device shown in FIGS. 9-11 as an example, the description on placement and the procedure therefore is also meant to apply to embodiments where the inner shaft comprises a flange rather than grooves.

Figure 13:
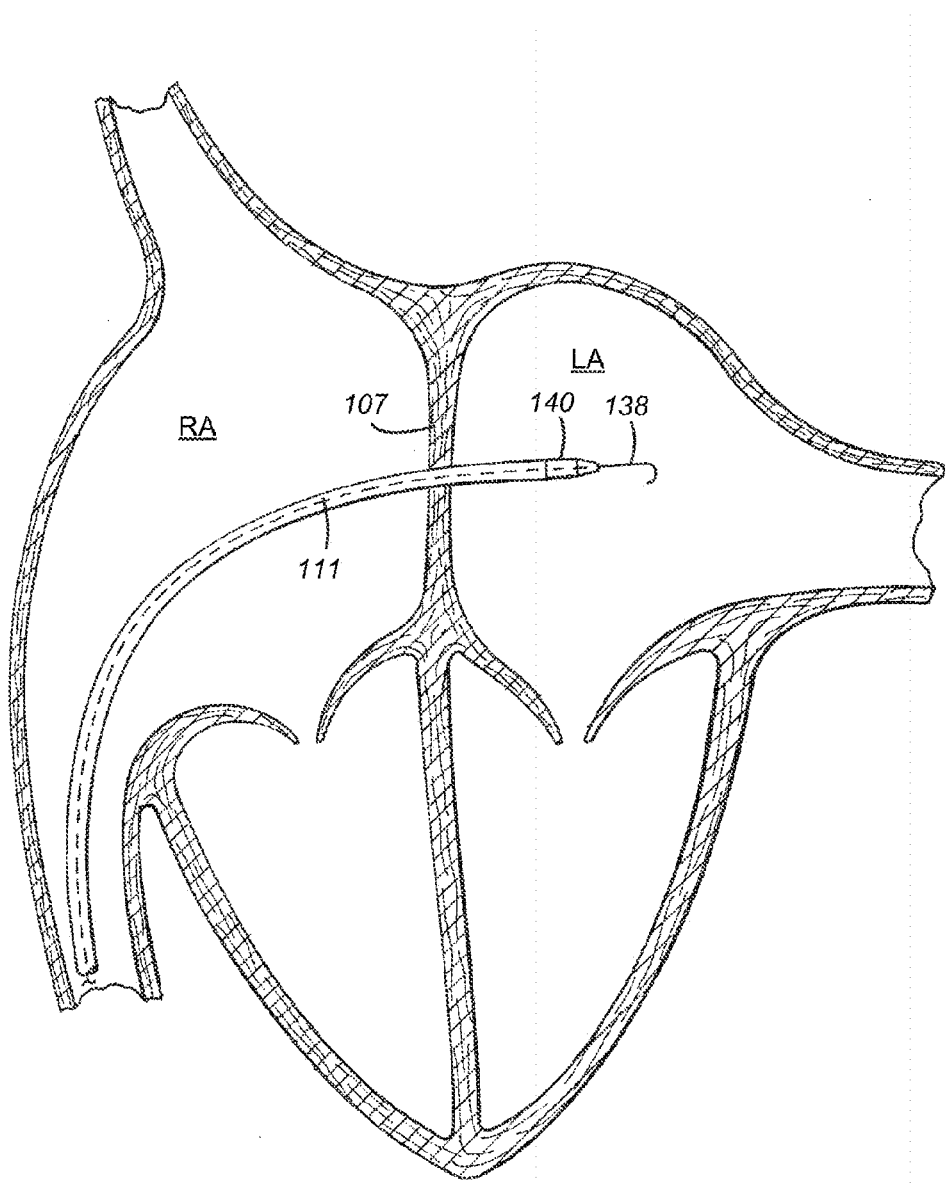
FIG. 13 is a cutaway view of a heart of a patient and the distal end of a placement catheter in position across the interatrial septum.

Positioning of the loaded interatrial valve 100 and placement catheter 111 in preparation for implanting the interatrial valve 100 in the patient can be accomplished by: first gaining vascular access; second, positioning a guidewire 121 in the right atrium of the patient; third, positioning an introducer (not shown) into the patients right atrium; fourth, locating the interatrial septum; fifth, advancing the introducer through the interatrial septum and into the patient's left atrium; sixth, advancing the guidewire 138 into the left atrium; seventh, retracting the introducer; eighth, advancing the loaded placement catheter 111 and interatrial pressure vent 100 into position so the distal end and approximately half of the stowed length of the interatrial pressure vent 100 is protruding through the interatrial septum and into the patient's left atrium as shown in FIG. 13.

In embodiments, positioning of the loaded interatrial valve 100 and placement catheter 111 in preparation for implanting the interatrial valve 100 in the patient can be accomplished by: first gaining vascular access; second, positioning a guidewire 138 in the right atrium of the patient; third, advancing the loaded interatrial valve 100 and placement catheter 111 over guidewire 138 by inserting the guidewire into and through lumen 136 and advancing placement catheter 111 into the patient's right atrium; fourth, locating the interatrial septum; fifth, advancing the placement catheter 111 through the interatrial septum and into the patient's left atrium so the distal end and approximately half of the stowed length of the interatrial pressure vent 100 is protruding through the interatrial septum and into the patient's left atrium as shown in FIG. 13.

Figure 14:
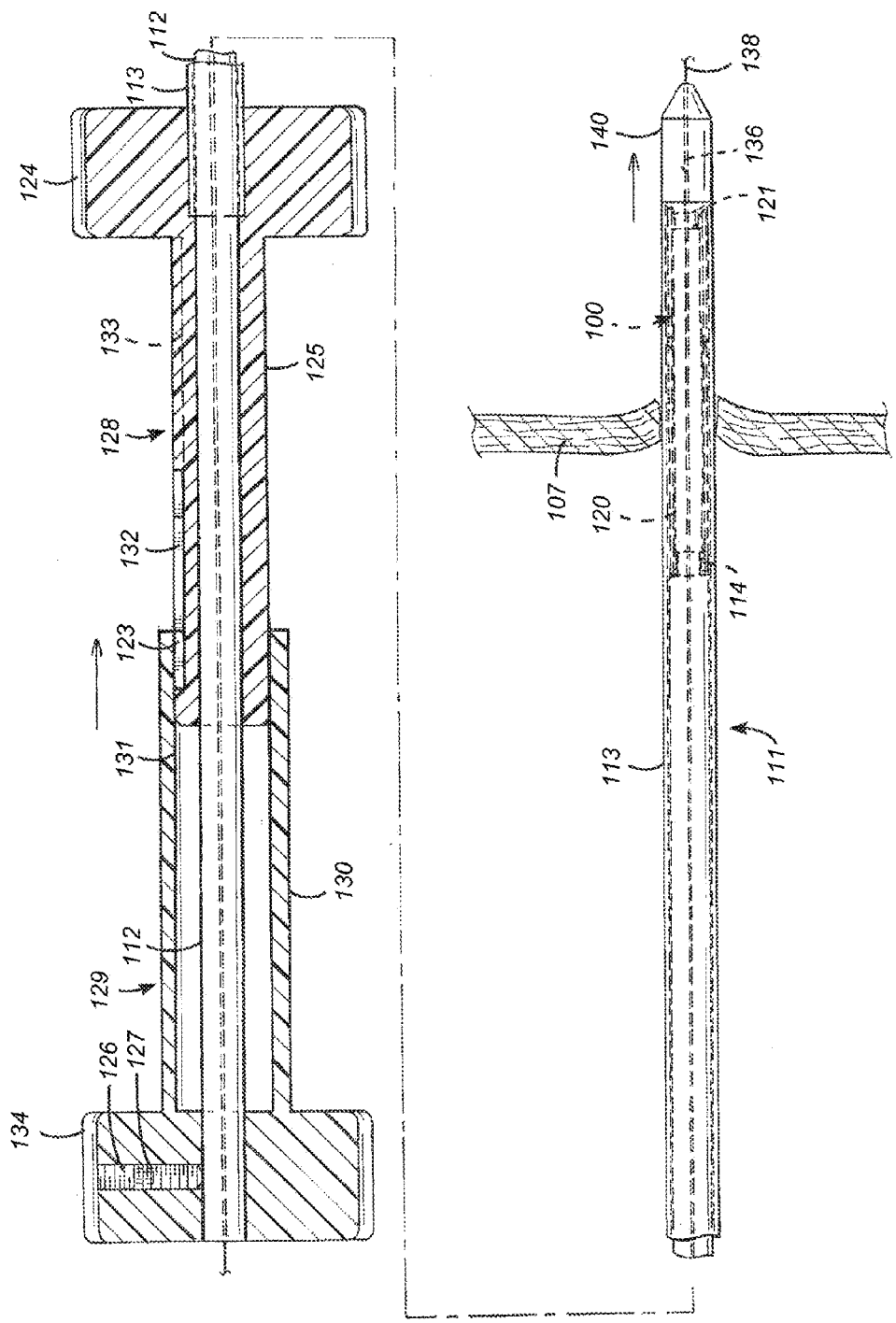
FIG. 14 is a schematic cross sectional side view of the proximal and distal end of a placement catheter in a closed position and positioned across the interatrial septum of the heart of a patient.
Figure 15:
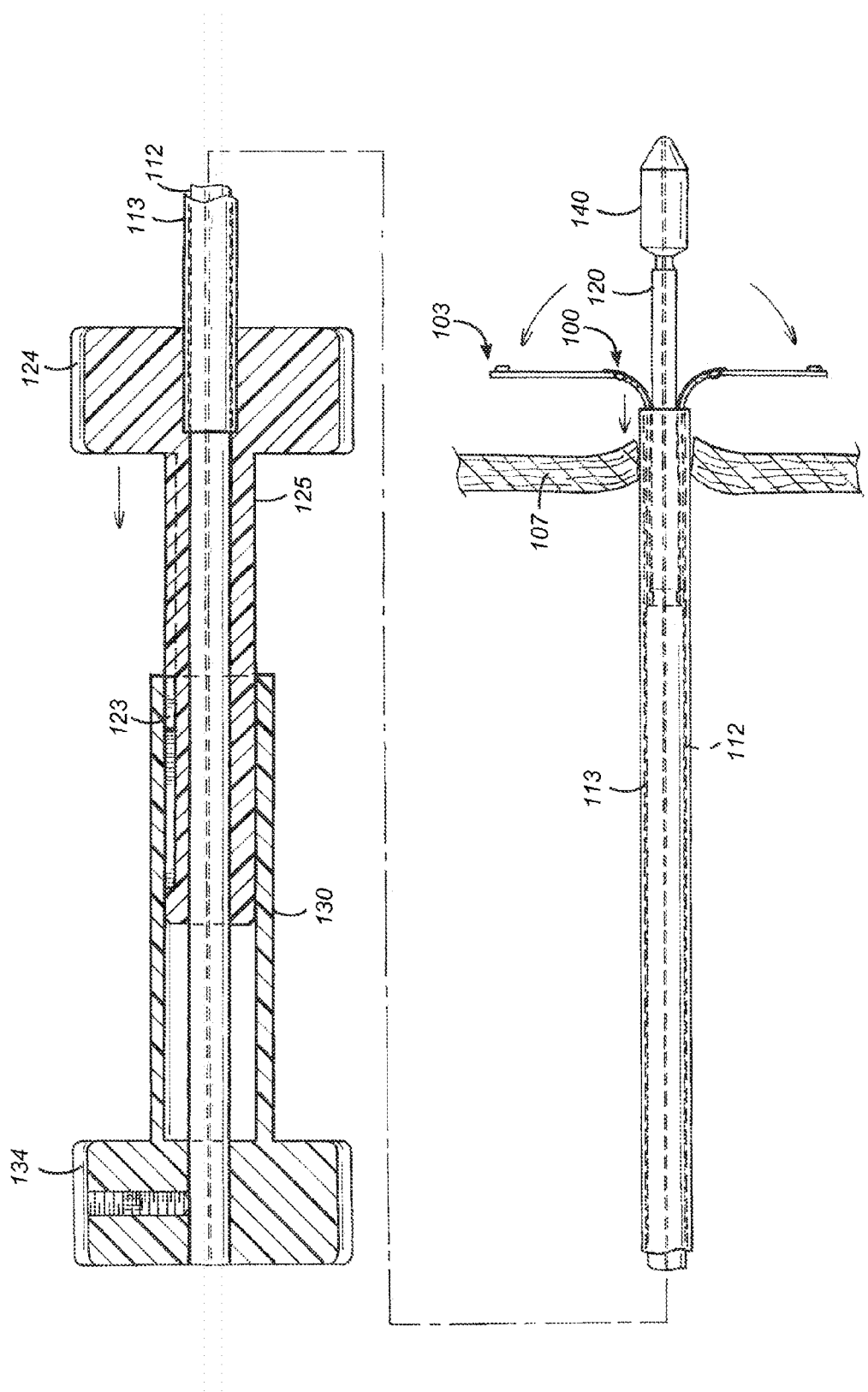
FIG. 15 is a view similar to FIG. 14 but showing the distal end of the placement catheter in a partially open position and the distal flange segments of the interatrial pressure vent deployed.
Figure 16:
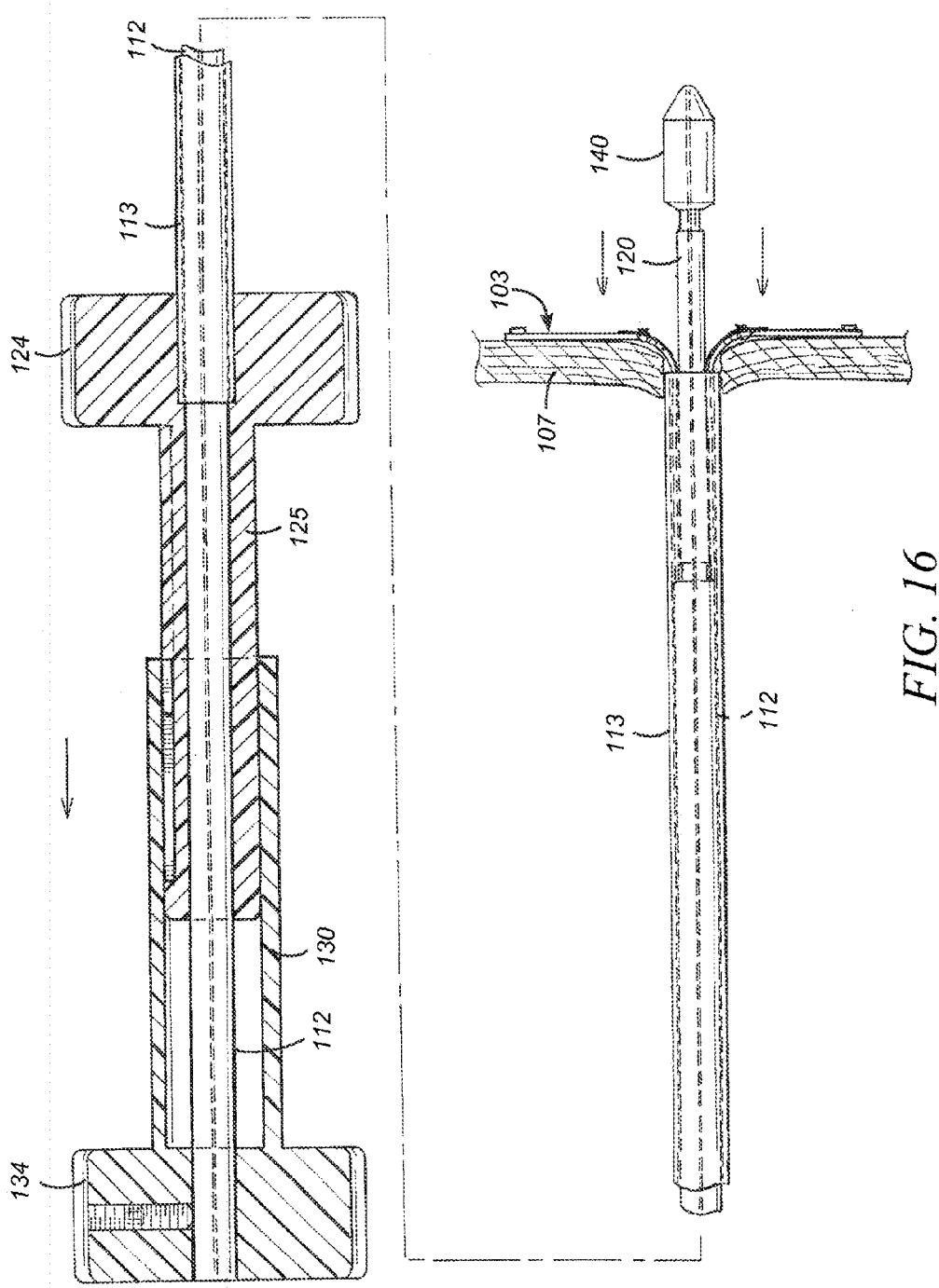
FIG. 16 is a view similar to FIG. 15 but showing the distal flange segments of the interatrial pressure vent in position against the wall of the interatrial septum.
Figure 18:
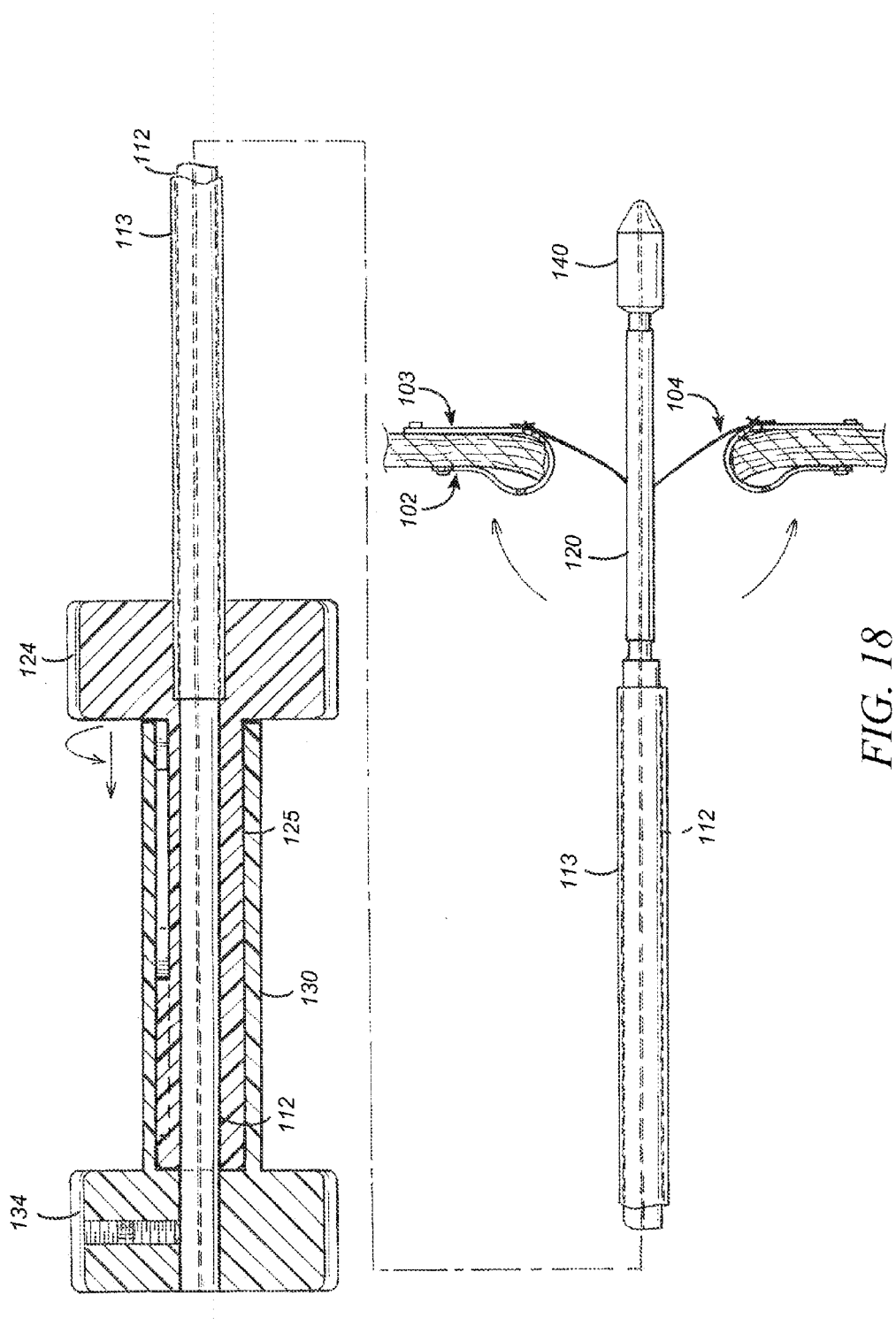
FIG. 18 is a view similar to FIG. 16 but showing further deployment of the interatrial pressure vent by releasing the proximal flange segments if imaging determines a correct positioning of the distal flange segments.
Figure 19:
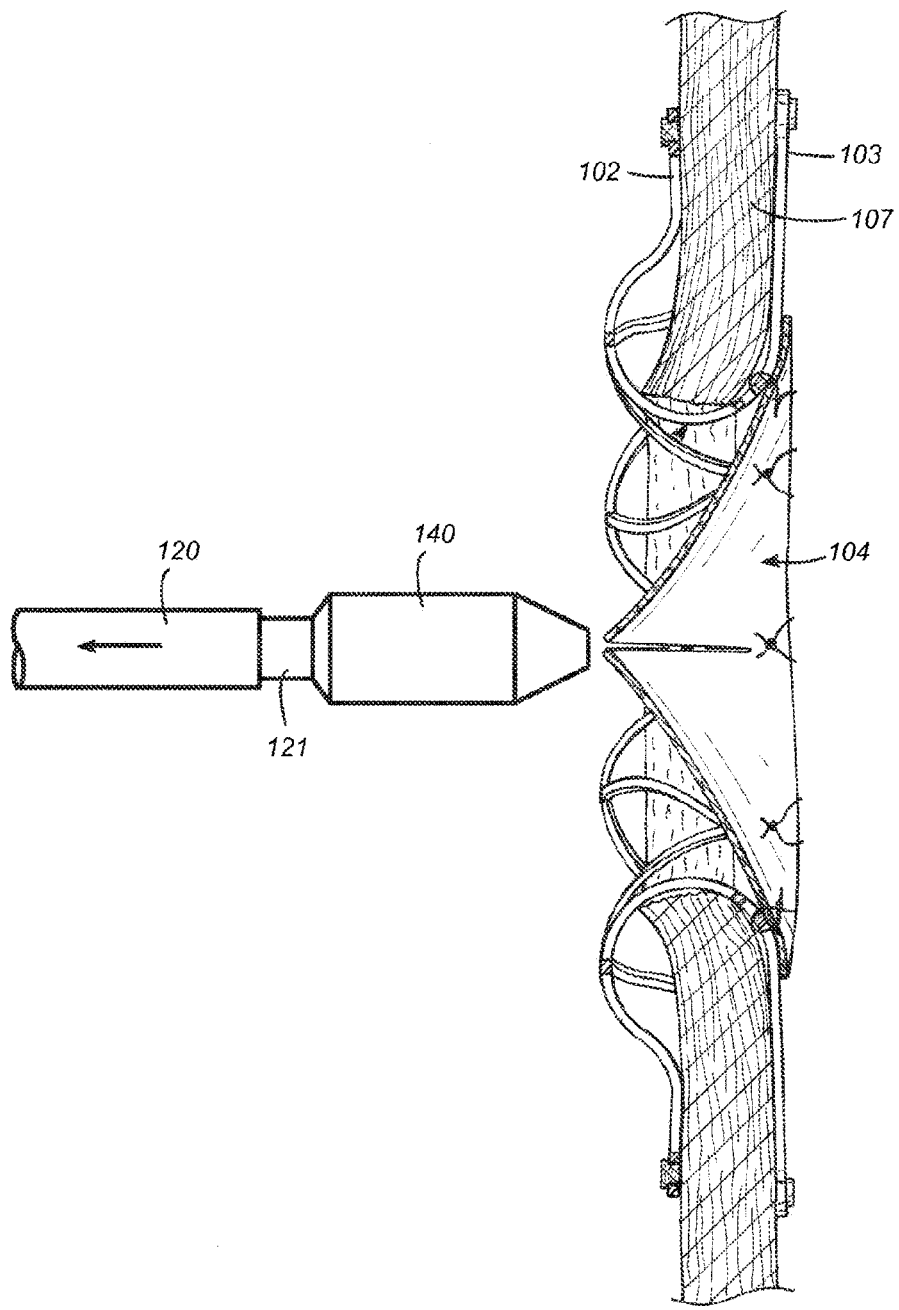
FIG. 19 is an enlarged cross-sectional detail view of the placement catheter of FIG. 18 but showing the interatrial pressure vent fully released in position and the placement catheter being removed.

Implanting interatrial pressure vent 100 into a patient can be accomplished, once the loaded interatrial pressure vent 100 and placement catheter 111 are in position as shown in FIG. 14, by first, retracting first handle component 128 toward second handle component 129 while holding second handle component 129 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by retracting first handle 128 toward second handle 129 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fourth, the inner sheath is retracted through the flow control element 104 of interatrial pressure vent 100, into the patient's right atrium as shown in FIG. 19; fifth the first handle component 128 is advanced away from the second handle component 129 to reposition inner shaft 112 into the position relative to outer shaft 113 it was in during placement and the placement catheter is removed from the patient and the procedure is completed.

In other embodiments, implanting interatrial pressure vent 100 into a patient can be accomplished, once the loaded interatrial pressure vent 100 and placement catheter 111 are in position as shown in FIG. 14, by first, advancing second handle component 129 toward first handle component 128 while holding first handle component 128 until flange segments 103a-h are fully uncovered as shown in FIG. 15, and as can be verified by visualizing the markers 119 using fluoroscopy or using echocardiography; second, retracting the placement catheter 111 with partially deployed interatrial pressure vent 100 toward the patient's right atrium until the flange segments 103a-h are in contact with the left atrial side of the interatrial septum, as shown in FIG. 16, and as can be verified using the same techniques mentioned or as can be perceived by the user based on the resistance felt against further proximal movement of the placement catheter 111; third, continuing to retract the outer sheath 113 by advancing second handle 129 toward the first handle 128 until the outer sheath 113 is retracted beyond the proximal end of groove 114 of inner shaft 112 and also uncovers flange segments 102a-h, at which time the flange segments 102a-h of interatrial pressure vent 100 will deploy returning to the preloaded geometry and capture the interatrial septum between the flange segments 103a-h and flange segments 102a-h as shown in shown in FIG. 18; fourth, the inner sheath is retracted through the flow control element 104 of interatrial pressure vent 100, into the patients right atrium as shown in FIG. 19; fifth, the second handle component 129 is retracted away from the first handle component 128 to reposition inner shaft 112 into the position relative to outer shaft 113 it was in during placement and the placement catheter is removed from the patient and the procedure is completed.

For a variety of reasons, it may be necessary or desirable to remove interatrial pressure vent 100 and placement catheter 111 during any part of the procedure without further risk or injury to the patient. This is possible as follows: if, for any reason, it is desired for the device to be removed before outer shaft 113 is retracted and flange segments 103a-h are deployed, then the placement catheter 111 with interatrial valve 100 can simply be retracted out through the same pathway as introduced.

If, following deployment of flange segments 103a-h it is necessary or desirable to remove the device, then the interatrial valve 100 can be retracted into the placement catheter 111 by advancing first handle 128 away from second handle 129, while holding second handle 129 stationary, thereby advancing outer sheath 113 distally through the interatrial septum and over the flange segments 103a-h. In embodiments, radiopaque markers 118 placed in marker holes 109 are captured in groove 114 (see FIG. 17) and cannot fit in the gap between waist 120 of inner shaft 112 and inner surface of outer shaft 113, so as outer sheath 113 is advanced, flange segments 103a-h are forced to fold inward toward their stowed position and are retracted back onto inner shaft 112 and within outer sheath 113. Once outer shaft 113 is fully advanced, catheter 111 can be retracted as shown in FIG. 17 to be removed out through the interatrial septum and out through the same pathway as introduced.

Figure 19A:
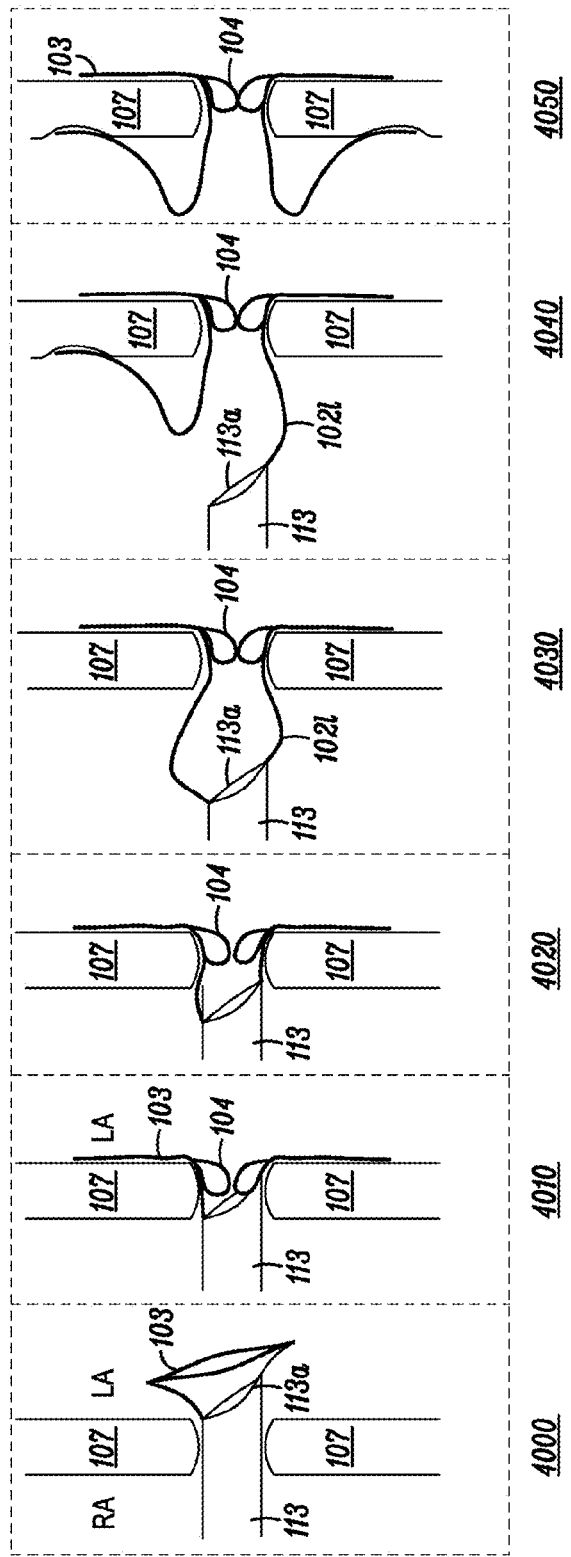
FIG. 19A is schematic depiction of another embodiment of a placement catheter system and interatrial pressure device along with the deployment process therefor.

FIG. 19A is an embodiment designed to enhance the retrievability of the device. The procedure for implanting the device is substantially similar to that which is described above; however, there are variations to the placement catheter and the device, which will be described below. As discussed in connection with FIGS. 7A through 7C, embodiments of the interatrial venting device comprise at least one flange segment being longer than the other flange segments. The embodiment schematically shown in FIG. 19A preferably works with such embodiments having at least one flange segment that are longer in relation to the other flange segments; thus the segments shown in the RA have the same reference number as the longer segments in FIGS. 7A through 7C, i.e., 102L. In embodiments utilizing the techniques shown in FIG. 19A, the opening 113a of outer sheath 113 of placement catheter is angled or has a more surface area on one side relative to the other. The placement catheter is oriented during the procedure such that the angled opening (or the plane of the opening itself) is at an angle more normal to the septal wall 107. In the embodiment shown in FIG. 19A, that angle appears to be around 45 degrees with respect to the septal wall 107, but any angle which provides an more normal angle with respect to the septal wall may be used, and any opening which provides more surface area of the outer sheath 113 on one side with respect to the other side may be used. Reference numerals 4000 through 4050 refer to steps in the process described below. The process is largely similar to that described above or with respect to any well-known placement catheter system and process, therefore only the applicable differences will be described. As can be seen at steps 4000 through 4020, the placement catheter is positioned and the device is in the beginning stages of deployment. At steps 4030 and 4040, the as the outer sheath 113 is retracted and on the RA side (or when the inner shaft is advanced while the outer sheath is on the RA side, which is not shown), the opening allows one of the longer flange segments 102L to be deployed after other flange segments have been deployed and are thus in contact with the septum 107. The at least one longer flange segment 102L is retained in the placement catheter system by way of the outer sheath 113, the length of which extends further on one side than the other due to the opening and thus covers the longer segment 102L while the other shorter segments have been deployed. In this way, the operator of the placement catheter can determine if the interatrial device is in the proper position. If not, the operator can still retrieve the device up until the last point prior to full deployment, i.e., when at least one of the longer flange segments (102L for example) is still retained in the placement catheter by the outer sheath 113. If it is in proper position, the deployment may commence.

Figure 19B:
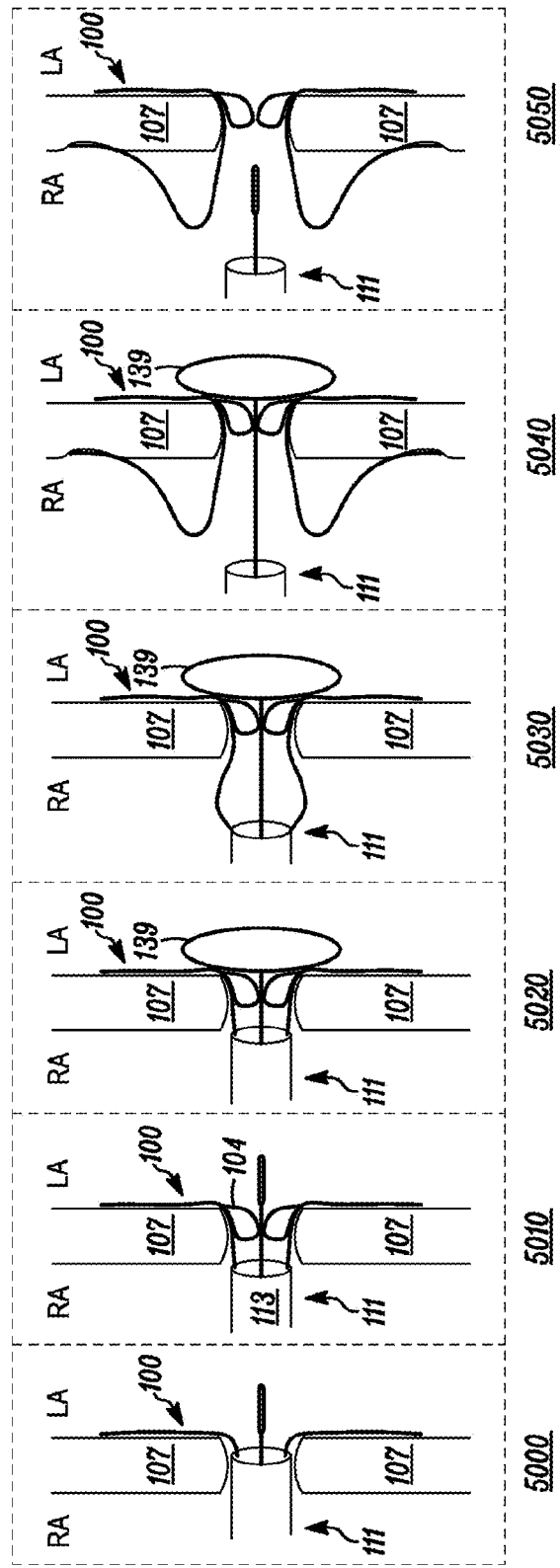
FIG. 19B is schematic depiction of another embodiment of a placement catheter system and deployment process therefor.

Another deployment embodiment is now described in connection with FIG. 19B. This deployment embodiment may be used with any embodiment of the interatrial vent described herein. Reference numerals 5000 through 5050 refer to steps in the process described below. At step 5000, the LA side of the device (generally referred to in this figure as 100) is deployed on the LA side of the heart. Further deployment is shown at step 5010 and the outer sheath is retracted into the RA side of the heart, which allows flow control element 104 to exit the placement catheter. Placement catheter is equipped with a balloon, which is in fluid communication, for example, with lumen 136 described above or guide wire 138. The skilled artisan will appreciate other configurations in which a balloon catheter may be provided in the placement catheter system. Upon deployment of the LA side flange or shortly thereafter, balloon 139 is inflated (shown in step 5020). The inflation of the balloon optionally coupled with a pulling-back motion of the placement catheter 111 holds the device 100 against the LA side of the septal wall 107 and thereby prevents the device 100 from dislodging during deployment and/or moving in a direction away from the septal wall. Step 5040 shows the full deployment of the device 100 while the balloon 139 is inflated. When satisfactory deployment is achieved, the balloon 139 is deflated and the placement catheter system is removed (shown at step 5050). Other embodiments that enhance deployment or retrieval of the device are described throughout.

Figure 20:
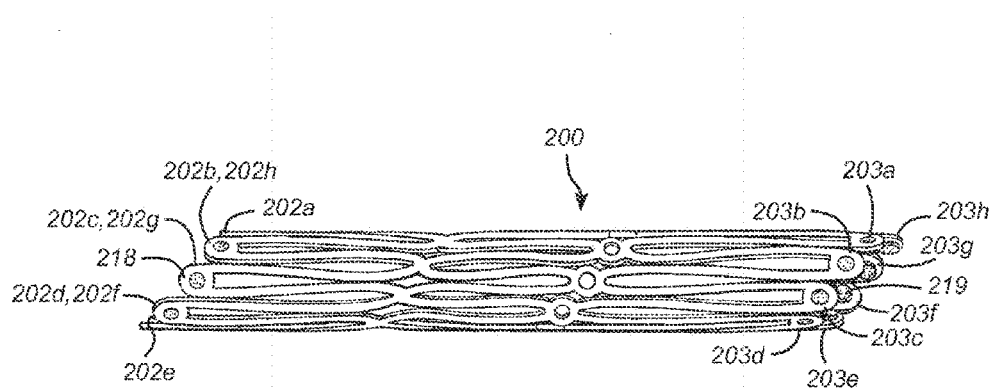
FIG. 20 is a side elevational view of an alternate embodiment of an interatrial pressure vent body with slanted flange segment ends.

Now referring to FIG. 20, an interatrial pressure vent 200 is shown. In embodiments, flange segments 202a-h and 203 a-h can be formed with graduating length to reduce interference between flange segments 202a-h and 203a-h during handling, folding and loading. In embodiments, radiopaque markers 218 and 219 protrude into the inner cylindrical shape of the stowed position of the interatrial pressure vent and each flange segment 202a-h and 203a-h differ in length by at least the width of the radiopaque markers 218 and 219. In embodiments, each flange segment 202a-h and 203a-h differ in length by at least at least 1 mm. In embodiments, each flange segment 202a-h and 203a-h differ in length by at least 2% of the overall length of interatrial pressure vent 200 in the position shown in FIG. 20.

Figure 21:
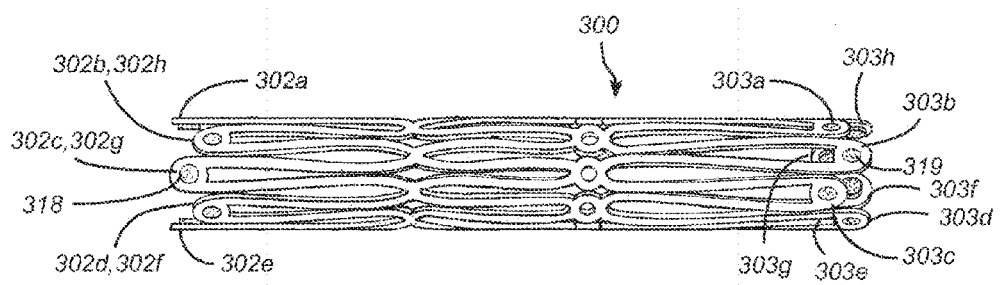
FIG. 21 is a side elevational view of an alternate embodiment of an interatrial pressure vent body with staggered flange segment ends.

Now referring to FIG. 21, an interatrial pressure vent 300 is shown. In embodiments, flange segments 302a-h and 303a-h can be formed with alternating length to reduce interference between flange segments 202a-h and 203a-h during handling, folding and loading. In embodiments radiopaque markers 318 and 319 protrude into the inner cylindrical shape of the stowed position of the interatrial pressure vent 300 and alternating flange segments 302a, c, e, and g are longer than flange segments 302 b, d, f and h, and correspondingly, flange segments 303b, d, f and h are longer than flange segments 303a, c, e and g by at least the width of the radiopaque marker. In embodiments, alternating flange segments 302a, c, e and g are longer than flange segments 302 b, d, f and h and, correspondingly, flange segments 303b, d, f and h are longer than flange segments 303a, c, e and g by at least 1 mm. In one aspect the alternating flange segments 302a, c, e and g are longer than flange segments 302 b, d, f and h and, correspondingly, flange segments 303b, d, f and g are longer than flange segments 303a, c, e and g by at least 2% of the overall length of interatrial pressure vent 300 in the position shown in FIG. 21.

Figure 22:
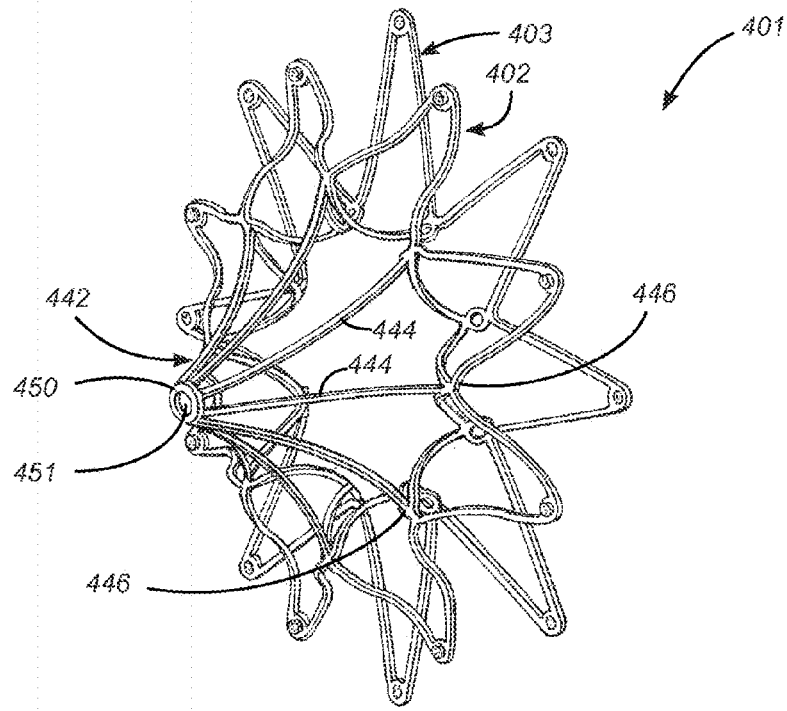
FIG. 22 is a perspective view of an alternate embodiment of an interatrial pressure vent body with an integrated retrieval means and thrombus clot strain.
Figure 23:
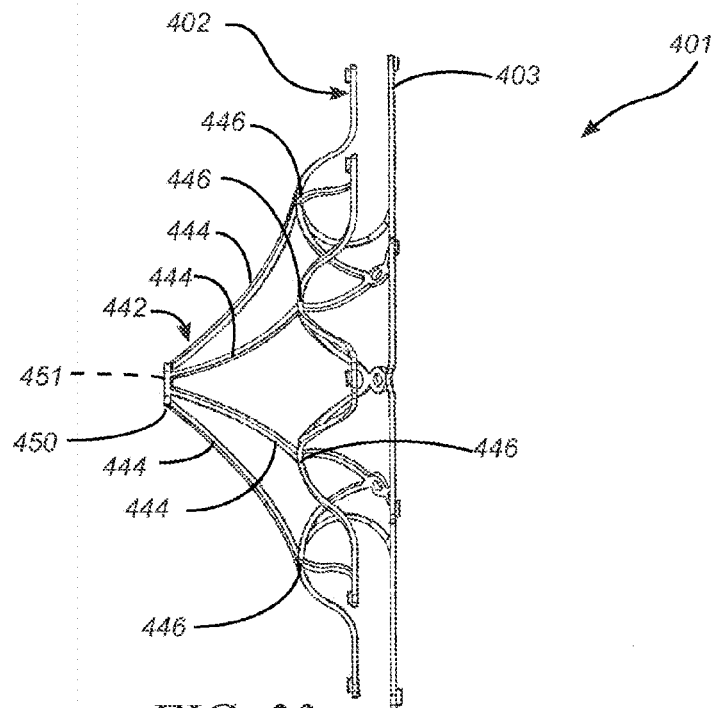
FIG. 23 is a right side view of the body assembly of FIG. 22.

Referring now to FIG. 22 and FIG. 23, the body element 401 of an interatrial pressure vent with integral thrombus filter and retrieval cone 442 is shown. In embodiments, conical struts 444 are affixed to body element 401 at attachment points 446 and converge at apex 450. In embodiments, conical struts 444 comprise single beams of similar material to flange segments 402 and 403 and can be attached to the body element or formed at the same time as the body element using techniques described in this specification, and can thus be integral with the remainder of the device. In embodiments the space between adjacent struts 444 is about 2 mm. In embodiments, the space between adjacent struts 444 is about 4 mm. As can be appreciated, conical struts 444 will protrude into the right atrium of the patient after implant and spaces between conical struts will function to block the passage of solid material larger than the space between adjacent struts 444. This will provide the function of preventing emboli that are larger than the space between the adjacent struts 444 from passing from the right atrium to the left atrium.

Referring again to FIG. 22 and FIG. 23, in embodiments the shape of the conical struts 444 is not straight. In embodiments the shape of the conical struts 444 can be concave when viewed on end as depicted in FIG. 22. In embodiments the conical struts can be curved in a direction away from the chord formed between the apex 450 and the attachment points 446. In embodiments there can be a hole 451 through apex 450 large enough to receive a retrieval snare (not shown). It can be appreciated that conical struts 444 and apex 450 can be used to aid retrieval of the interatrial pressure vent from a patient at some time after the implant procedure using a method as follows: A catheter tube with an internal lumen at least as large as apex 450 can be placed into the patient's right atrium using standard techniques and imaging equipment. A retrieval snare can be fabricated from the proximal end of a guidewire bent sharply by about 180 degrees and this snare can be inserted through the catheter tube and advanced into the patient's right atrium and, with the assistance of fluoroscopy, advanced through hole 451 or around conical struts 444. Once the retrieval snare is engaged in this manner, it will be possible to retract the interatrial pressure vent by advancing a catheter tube while holding slight tension on the snare and thereby guide the catheter tube over apex 450 and onto conical struts 444.

As the catheter tube continues to advance, with some tension on the snare it will be possible to force the conical struts inward, thereby forcing the flange segments 402 to begin folding inwards. When the conical struts are nearly completely in the catheter tube, the catheter tube can be held in a stationary position and the snare wire retracted against it, thereby causing the attachment points 446 between the conical struts 444 and the flange segment 402 to be retracted into the catheter. Flange segments 402 can begin to be retracted into the catheter at this point and the distal ends of flange segments 402 can be diverted toward the patient's left atrium but will also fold inward and into the catheter. Once the flange segments 402 are inside of the catheter tube, the snare can be held stationary and the catheter tube can be advanced further, through the interatrial septum and over flange segments 403. Once the flange segments 403 are retracted into the catheter, the catheter and snare can be moved together to retract the interatrial pressure vent into the patient's right atrium and out through the pathway through which it was introduced.

Figure 24:
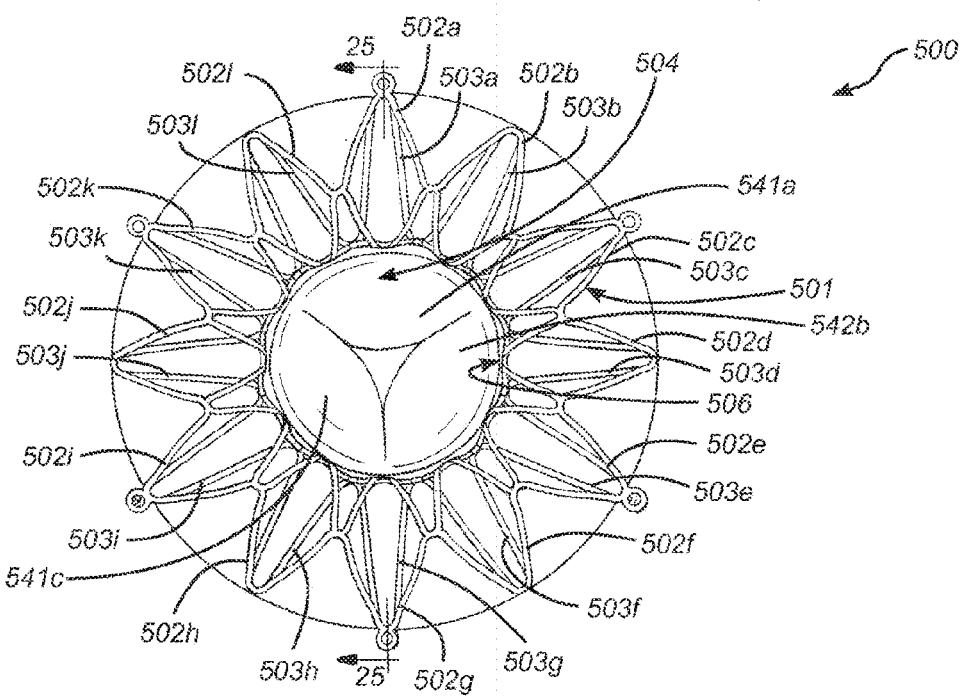
FIG. 24 is an end view of an alternate embodiment of interatrial pressure vent.
Figure 25:
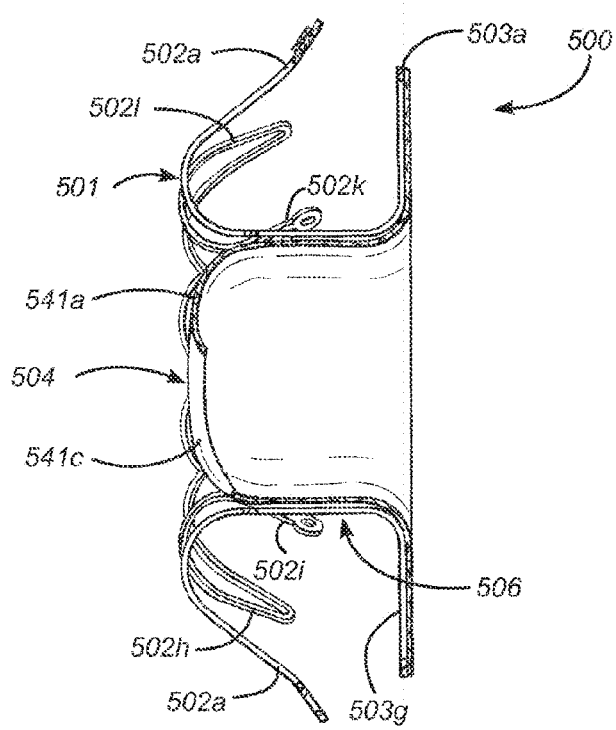
FIG. 25 is a cross-sectional side view taken along line 25-25 of FIG. 24.

Referring now to FIGS. 24 and 25 an alternate embodiment of interatrial pressure vent 500 is shown. In embodiments, flow control element 504 may be comprised of leaflets 541*a*-*c*. Body element 501 may be comprised of core segment 506 and flange segments 502*a*-1 and 503*a*-1 (not fully visible in FIG. 25); the number of flange segments being a multiple of the number of leaflets. This configuration improves the symmetry of strain against the flow control leaflets and also improves the uniformity of motion by the flow control element to changes in blood flow.

In some embodiments, the implantable devices in accordance with the present invention are designed to safeguard against portions of the flange of the inventive device that is to engage the near side of the septum from entering into the space on the far side of the septum, e.g., the left atrium when the delivery is being made from the right atrium. This safeguard is best understood by considering the implantable device in its state of collapse along its longitudinal axis for percutaneous delivery to the patient's heart. In the special case where the inventive device is delivered coaxially with the septal aperture, the safeguard is to provide that the longitudinal distance between the far end of the near flange and the far end of the core segment of the implantable device is greater than the through-thickness of the septal aperture. More generally, this safeguard distance is the quotient of the longitudinal length of the septal aperture into which the device is expected to be implanted divided by the cosine of the angle the longitudinal axis of the implantable device is expected to make during delivery in relation to the longitudinal axis of the septal aperture.

Figure 79:
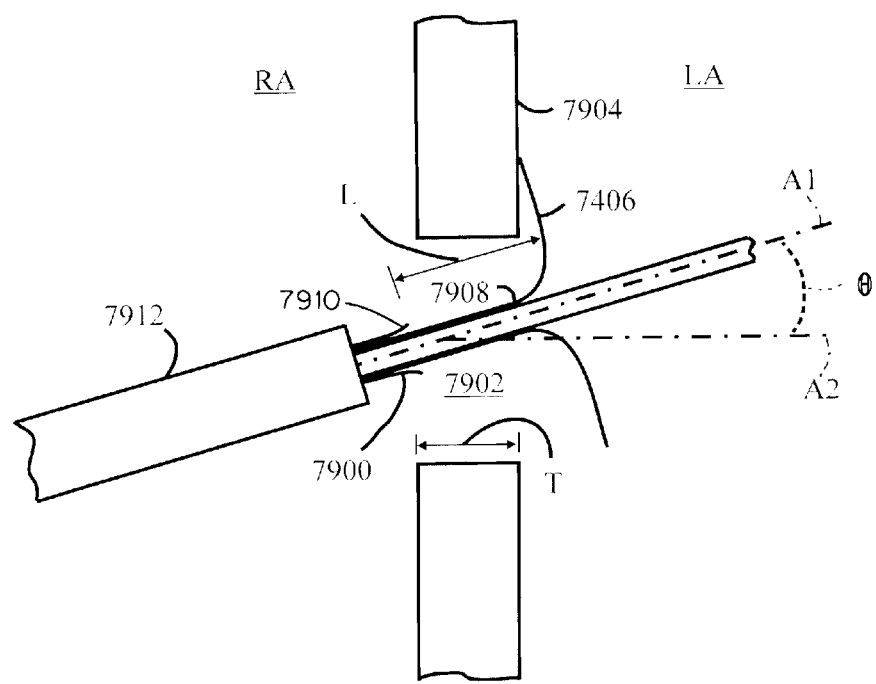
FIG. 79 depicts a device embodiment being deployed at an angle into an orifice in an atrial septum.

This safeguard is explained with reference to FIG. 79 which shows an implantable device 7900 in accordance with an embodiment of the present invention being delivered into an aperture 7902 in the septum 7904 of a patient's heart that divides the left atrium LA from the right atrium RA. At the stage of deployment shown in FIG. 79, the far flange 7906, the core segment 7908, and the far end of the near flange 7910 have emerged from the delivery apparatus 7912. The longitudinal distance L between the far end of the near flange 7910 and the far end of the core segment 7908 is depicted in the drawing. The longitudinal axis A1 of the delivery apparatus 7912 is shown as intersecting the longitudinal axis A2 of the septal aperture 7902 at an angle θ. Thus, for the case shown in the drawing, the length L is to be greater than the quotient of the septal aperture through-thickness T divided by cosine θ.

In view of the fact that during deployment of the implantable device, the septal wall is in a dynamic state and the implantable device may not be completely stationary, this minimum distance may be increased by a factor ranging between 1.1 and 2.0.

An embodiment of the implantable device, device 8000, in which the device is fully retrievable after deployment, is depicted in whole or in part in FIGS. 80A-D. The device 8000 is configured to be collapsible about its longitudinal axis so that the device 8000 may be stored in a delivery apparatus for percutaneous delivery to a hole in the septal wall of a patient's heart. The device 8000 has a body element which includes a plurality of interconnected units 8002, a hub 8004 that is connected to the near end of at least one of the units 8002, a first flange 8006 that is at least in part formed by the junctions 8008 of left and right arm sections 8010, 8012 of adjacent units 8002, a second flange 8014 that is at least in part formed by the far ends of at least some of the units 8002, and a core segment 8016. As is most readily apparent from FIG. 80C, each of first and second flanges 8006, 8014 comprises six individual segments. It is to be understood that the relational terms "right" and "left" are to be applied from the viewpoint of an observer looking at the outside of the body element with the body element oriented so that core segment longitudinal axis is oriented vertically and the hub is at the top.

In the embodiment depicted in FIGS. 80A-D, the device 8000 has six units 8002, although it may have more or less than six in other embodiments. Each unit 8002 has extending from its near end a first diamond section 8018 that connects at its far end to the near end of a second diamond section 8020. Each unit 8002 also has a left arm section 8010 and a right arm section 8012, both of which connect at their respective near ends to the opposite sides of the unit's first diamond section 8018. Each of the left arm sections 8010 is connected at its far end to the far end of the right arm unit 8012 of an adjacent unit 8002 to form a junction 8008 that is one of a first set of junctions. Each of the units 8002 also is connected at its second diamond section 8020 to the respective second diamond sections 8020 of its two adjacent units 8002 to form junctions 8022 which are part of a second set of junctions.

The hub 8004 and the plurality of units 8002 in some embodiments of the present invention form an apex at what would be the near end of the device 8000 within the right atrium of the patient's heart when implanted. The hub 8004 in some instances is adapted to connect to a delivery and/or retrieval apparatus, e.g., such as a catheter-delivered filament or wire. In some instances, the hub 8004 is provided with internal and/or external threads to form such a connection. In some such embodiments, the hub 8004 is provided with a keyslot for making such a connection.

Figure 80A:
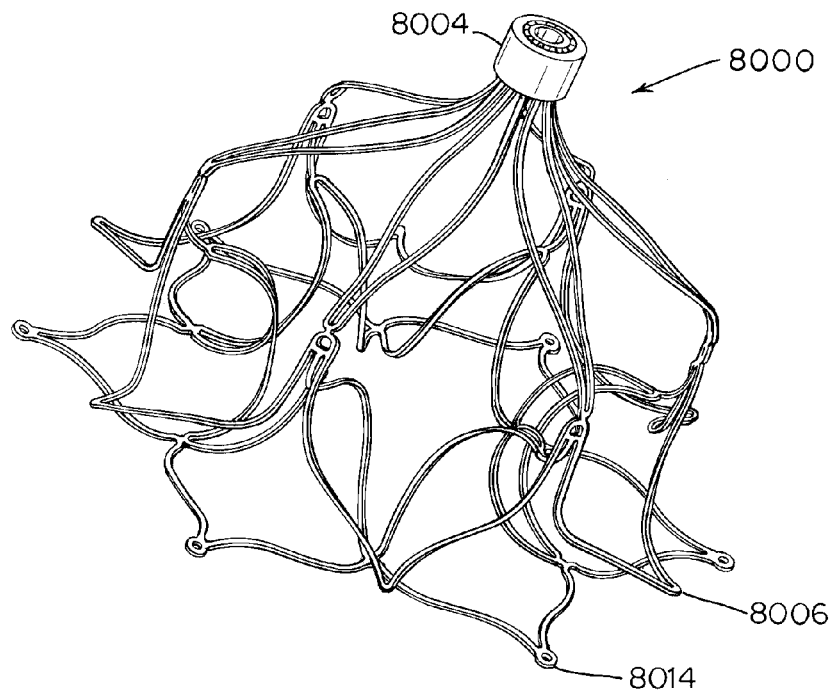
FIG. 80A depicts a perspective view of a device embodiment.
Figure 80B:
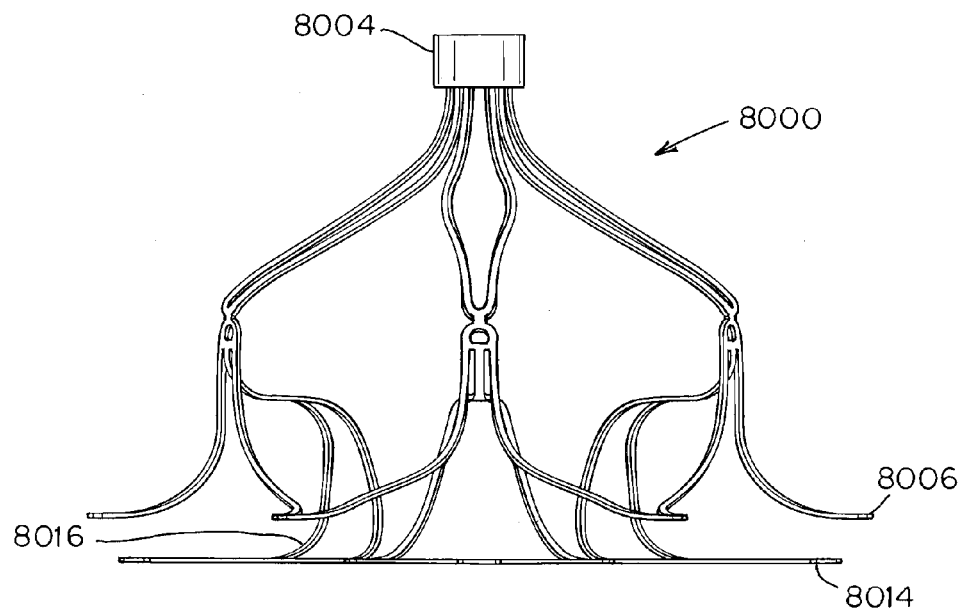
FIG. 80B depicts an elevational side view of the device of FIG. 80A.
Figure 80C:
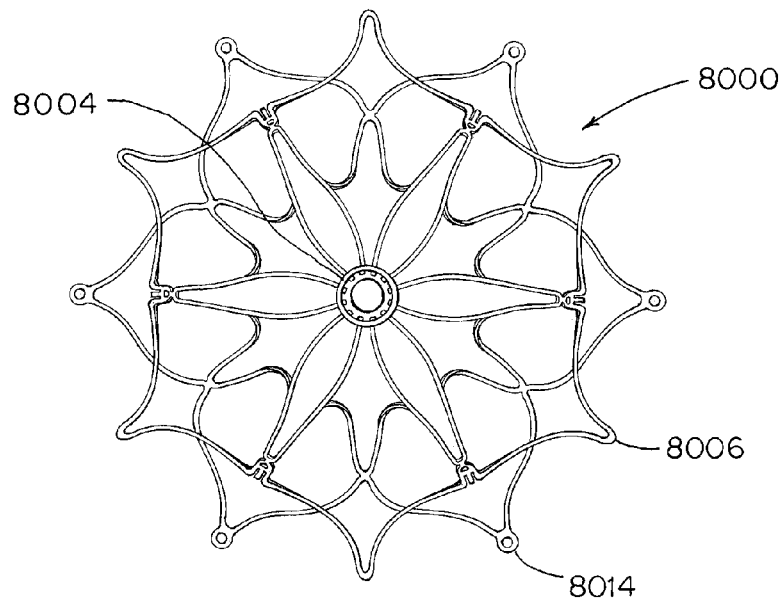
FIG. 80C depicts a top view of the device of FIG. 80A.
Figure 80E:
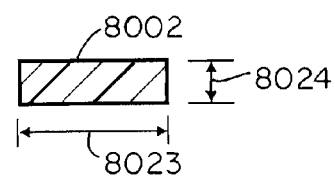
FIG. 80E depicts a cross-section of a strut of the device of FIG. 80D taken across cutting plane 80E-80E.
Figure 80D:
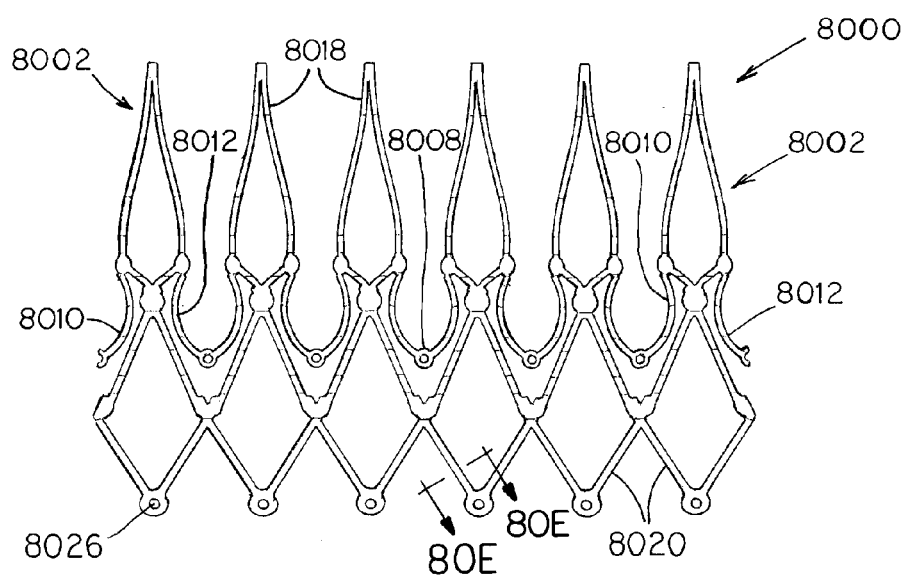
FIG. 80D depicts the device of FIG. 80A having been cut and rolled out into a plane to show its cutting pattern.

The areas or portions of the device 8000 may have a constant width and a constant through-thickness, such as width 8023 and through-thickness 8024 of the cross-section of the arm of the second diamond section 8020 shown in FIG. 80E. In some embodiments of the present invention, however, at least one of the width one area or portion varies in magnitude between a high value and a low value wherein the low value is in the range of between 15 and 99 percent of the high value, and the through-thickness of one area or portion varies in magnitude between a high value and a low value wherein the low value is in the range of between 40 and 99 percent of the high value.

In some embodiments of the present invention, the core segment 8016 comprises one or more junctions 8022 which are part of a second set of junctions. In some instances, at least one of the junctions 8008, 8022 of the first and second sets of junctions and/or at least one of the second diamond sections 8018 includes a radiopaque material, e.g., a radiopaque marker. In some instances, at least one of the junctions 8008, 8022 of the first and second set of junctions and/or at least one of the far ends of the units 8002 has a through-hole, e.g., through-hole 8026, with such a through-hole in some instances being suitable to receive a suture and/or a radiopaque marker.

In some embodiments of the present invention, when the device 8000 is collapsed about its longitudinal axis for percutaneous delivery into the patient's heart, the longitudinal distances between the far ends of the junctions 8008 of the first set of junctions and the far end of the core segment 8016 is greater than the quotient of the through-thickness of the septal aperture in which device 8000 is to be implanted divided by the cosine of the angle the longitudinal axis of the device 8000 is expected to make during delivery in relation to the longitudinal axis of the septal aperture. In some instances, when the device 8000 is collapsed about its longitudinal axis for percutaneous delivery into the patient's heart, the longitudinal distances from the connections of the left and right arm units 8010, 8012 with the first diamond sections 8018 to the far end of the device 8000 are at least three times the longitudinal distances from the connections of the left and right arm units 8010, 8012 with the first diamond sections 8018 with the first diamond sections 8018 to the far ends of each of the junctions 8008 of the first set of junctions.

An embodiment of the implantable device, device 8100, in which the device is fully retrievable after deployment, is depicted in whole or in part in FIGS. 81A-D. The device 8100 is configured to be collapsible about its longitudinal axis so that the device may be stored in a delivery apparatus for percutaneous delivery to a hole in the septal wall of a patient's heart. The device 8100 has a body element which includes a plurality of struts 8102, a hub 8104 that is connected to the near end of at least one of the struts 8102, a first fork section 8106, a second fork section 8108, a third fork section 8110, a first flange 8112, a second flange 8114, and a core segment 8116. As is most readily apparent from FIG. 81B, each of first and second flanges 8110, 8112 comprises six individual segments. It is to be understood that the relational terms "right", "center", and "left" are to be applied from the viewpoint of an observer looking at the outside of the body element with the body element oriented so that core segment longitudinal axis is oriented vertically and the hub is at the top.

Each of the struts 8102 is connected at its far end to the first fork section 8106, which has a left prong 8118, a center prong 8120, and right prong 8122. The center prong 8120 is, in turn, connected at its far end to the second fork section 8108, which has a left prong 8124 and a right prong 8126, each of which is connected at its far end to a different one of the third fork sections 8110. Each of the far ends of the left prongs 8118 of each of the first fork sections 8106 connects to a far end of the right prong 8122 of a different one of the first fork sections 8106 to form a junction 8128 that is a member of a first set of junctions. The first flange 8112 includes at least some of the junctions 8128 of this first set of junctions.

The core segment 8116 comprises one or more the third fork sections 8110. Each of the far ends of the left prongs 8130 of the third fork sections 8110 connects to a far end of the right prong 8132 of a different third fork section 8110 to form a junction 8134 that is a member of a second set of junctions. The second flange 8114 includes at least some of the junctions 8132 of this second set of junctions.

The hub 8104 and the struts 8102 in some embodiments form an apex at what would be the end of the device 8100 which is within the right atrium of the patient's heart when implanted. In some embodiments of the present invention, the hub 8104 is adapted to connect to a delivery and/or retrieval apparatus, e.g., such as a catheter-delivered filament or wire. In such embodiments, the hub 8104 is provided with internal and/or external threads to form such a connection. In some such embodiments, the hub 8104 is provided with a keyslot for making such a connection.

Figure 81A:
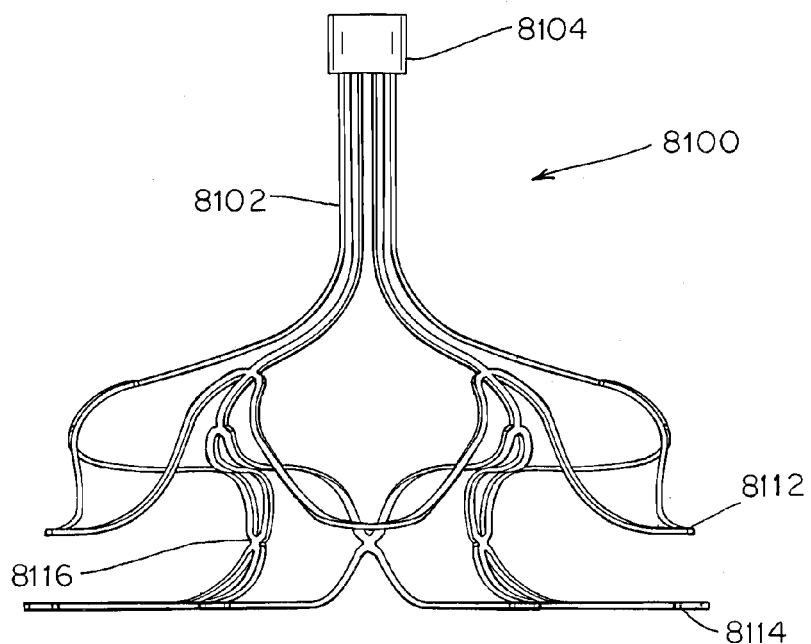
FIG. 81A depicts an elevational view of a device embodiment.
Figure 81B:
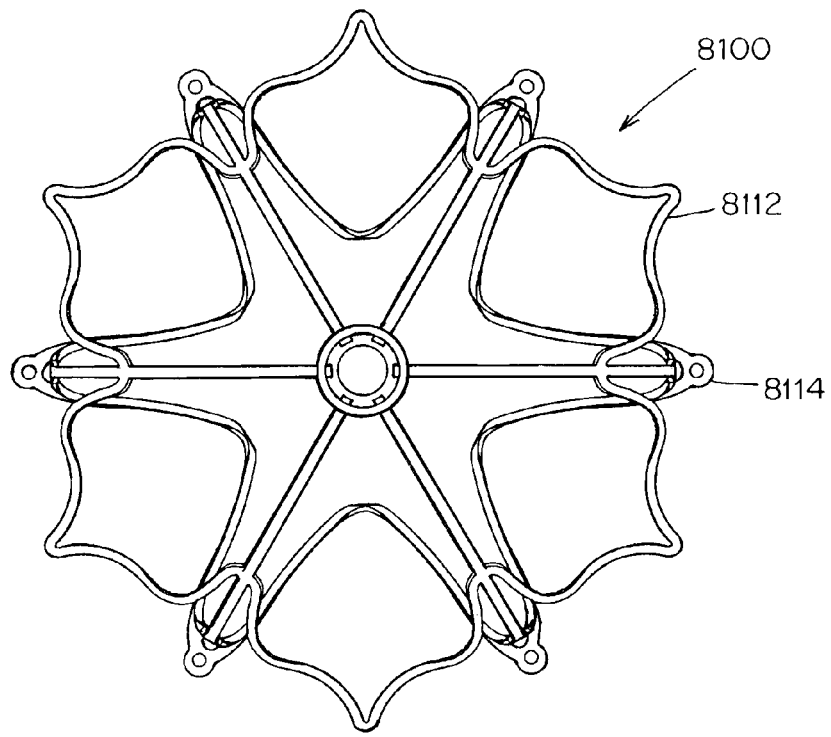
FIG. 81B depicts a top view of the device of FIG. 81A.
Figure 81C:
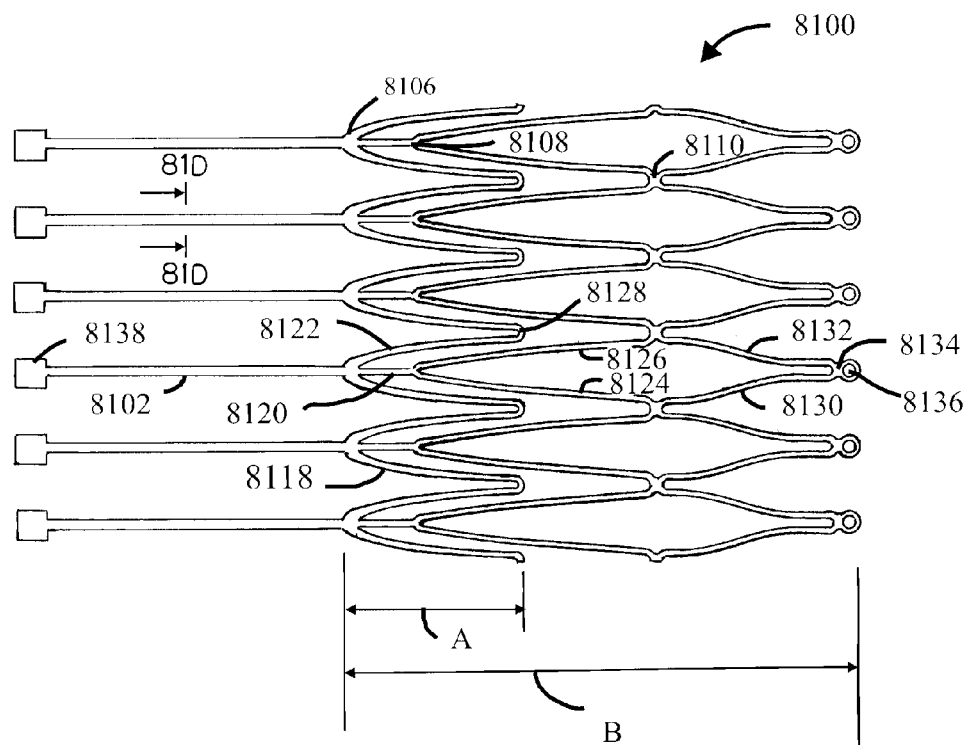
FIG. 81C depicts the device of FIG. 80A having been cut and rolled out into a plane to show its cutting pattern.
Figure 81D:
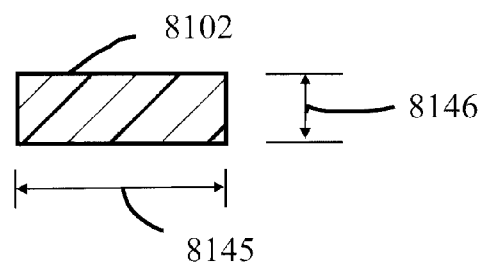
FIG. 81D depicts a cross-section of a strut of the device of FIG. 81C taken across cutting plane 81D-81D.

The areas or portions of the device 8100 may have a constant width and a constant through-thickness, such as width 8145 and through-thickness 8146 of the cross-section of strut 8102 shown in FIG. 81D. In some embodiments of the present invention, however, at least one of the width and the through-thickness of one or more areas or portions of the device varies in magnitude as described herein. In some embodiments, at least one of the width and the through-thickness of at least one of the struts 8102 and/or at least one of the first fork sections 8106, the second fork sections 8108, and the third fork sections 8110 varies in magnitude as described above.

In some embodiments of the present invention, at least one of the junctions 8128 of the first set of junctions and/or at least one of the junctions 8134 of the second sets of junctions and/or at least one of the first fork sections 8106, the second fork sections 8108, and the third fork sections 8110 includes a radiopaque material, e.g., a radiopaque marker. In some embodiments of the present invention, at least one of the junctions 8128, 8134 of the first and second set of junctions has a through-hole, e.g., through-hole 8136, with such a through-hole in some instances being suitable to receive a suture and/or a radiopaque marker.

In some embodiments of the present invention, when the device 8100 is collapsed about its longitudinal axis for percutaneous delivery into the patient's heart, the longitudinal distances between the far ends of the junctions 8128 of the first set of junctions and the far end of the core segment 8116 is greater than the quotient of the through-thickness of the septal aperture into which device 8100 is to be implanted divided by the cosine of the angle which the longitudinal axis of the device 8100 is expected to make during delivery in relation to the longitudinal axis of the septal aperture. This configuration helps to safeguard against portions of the near flange, e.g., the first flange 8112, from inadvertently deploying on the far side of the septum. This is clarified by reference to FIGS. 82A-D.

FIGS. 82A-D is a series of schematic drawings which depict the beginning stages of the deployment of the device 8100 in an aperture 8202 of a septum 8204, which separates the right atrium RA from the left atrium LA, by way of a delivery catheter 8206. In this set of drawings, for simplicity of presentation, the longitudinal axis of the delivery catheter 8206 is coaxial with the longitudinal axis of the aperture 8202 so that the angle of their intersection is zero. Also for simplicity of presentation, the only parts of the device 8100 which are illustrated are planar projections of portions of the first flange 8112, the core segment 8116, and the second flange 8114. In this embodiment, the far ends of junctions 8128 of the first set of junctions of the device 8100 are coincident with the far ends of the first flange 8112, and so, of the two items, reference will be made here only to the first flange 8112.

Figure 82A:
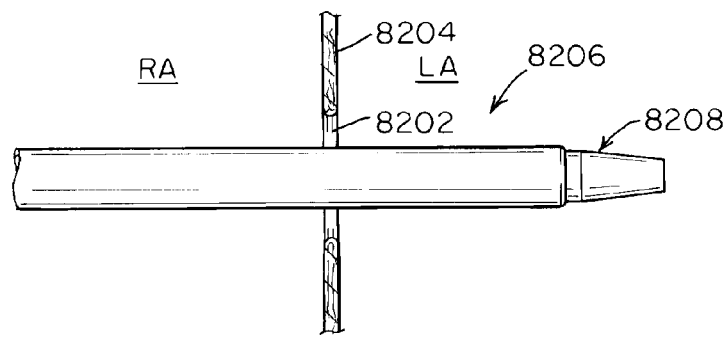
FIGS. 82A-D depict the insertion of a device embodiment into an atrial septum.
Figure 82B:
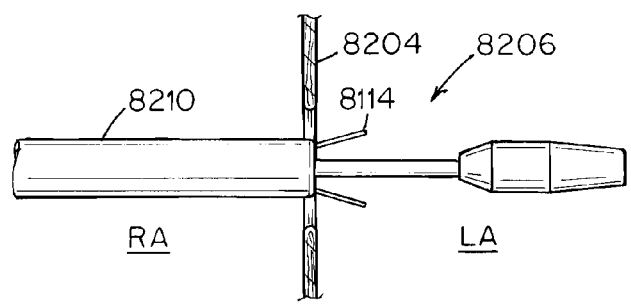
Figure 82C:
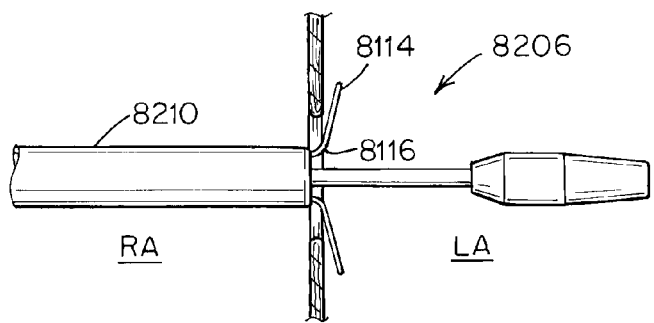
Figure 82D:
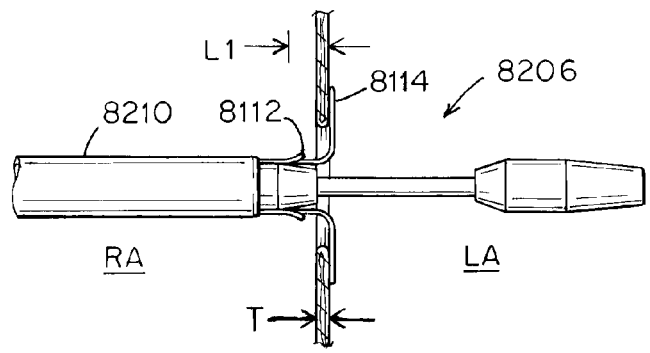

FIG. 82A depicts the delivery catheter 8206 after its tip 8208 has entered the left atrium LA. In the delivery stage depicted in FIG. 82B, the sheath 8210 of the delivery catheter 8206 has been partially withdrawn so that the far end of the second flange 8114 has begun to emerge from the delivery catheter 8206 and to bend radially outward from the longitudinal axis of the delivery catheter 8206. FIG. 82C depicts the deployment at an instant later whereat the sheath 8210 has been drawn back a bit further so that all of the second flange 8114, as well as some of the core segment 8116, has emerged. Finally, FIG. 82D depicts the stage at which the sheath 8210 has been drawn still further back so that the far end of the first flange 8112 has begun to emerge and has just started to bend radially outward from the longitudinal axis of the delivery catheter 8206. At this stage, the second flange 8114 has fully formed and has seated itself against the left atrium LA side of the septum 8204 and the core segment 8116 has fully emerged. From this drawing, by disregarding the slight outward bending of the first flange 8112, it can be understood that for the device 8100 the longitudinal distance L1 between the far end of the first flange 8112 and the far end of the core segment 8116, which in this drawing is coincident with the far end of the septal aperture 8202, is greater than the through-thickness T of the septal aperture 8202. As mentioned, the intersection angle θ between the delivery catheter 8206 and the longitudinal axis of the aperture 8202 in this case is zero, so the cosine of the intersection angle θ is equal to 1 and the quotient of the through-thickness T of the aperture 8202 and the cosine of the intersection angle θ is equal to the through-thickness T. See FIG. 79 and its related discussion herein about the general case wherein the intersection angle θ is non-zero.

Another configuration for device 8100 for safeguarding against the inadvertent deployment of portions of the first flange 8112 on the far side of the septum is described with reference again to FIG. 81C. In this configuration, when the device 8100 is collapsed about its longitudinal axis for percutaneous delivery into the patient's heart, the longitudinal distances B from the far end of each of the struts 8102 to the far end of the device 8100 are at least three times the longitudinal distances A from the far end of each of the struts 8102 to the far end of each of the junctions 8128 of the second set of junctions.

Figure 83A:
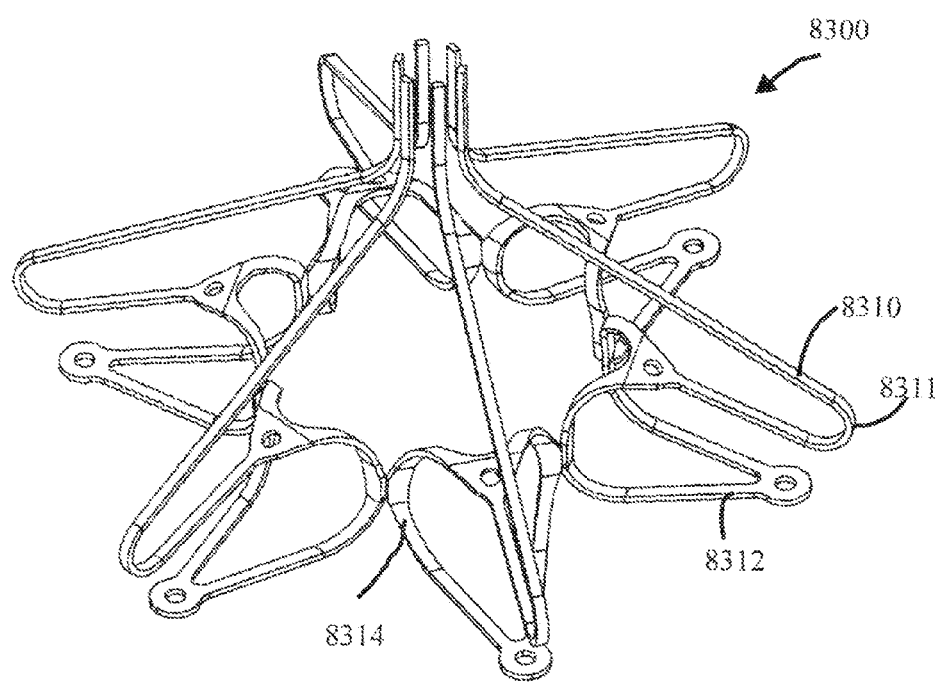
FIG. 83A depicts a perspective view of a device embodiment.
Figure 83B:
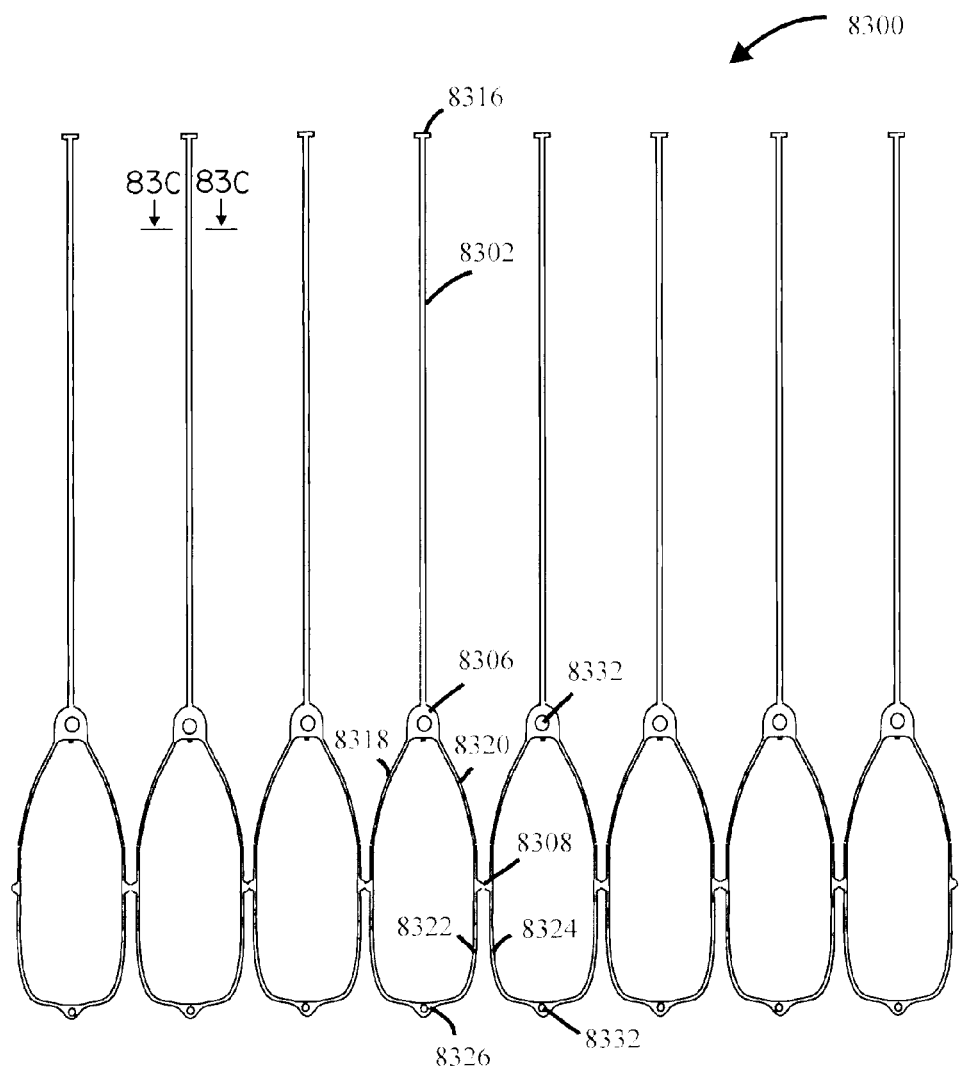
FIG. 83B depicts the device of FIG. 83A having been cut and rolled out into a plane to show its cutting pattern.
Figure 83C:
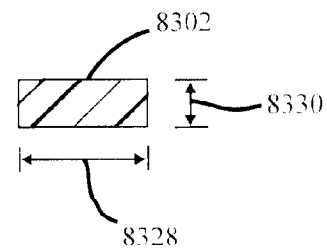
FIG. 83C depicts a cross-section of a strut of the device of FIG. 83B taken across cutting plane 83E-83E.

Another embodiment of the implantable device, device 8300, in which the device is fully retrievable after deployment, is depicted in whole or in part in FIGS. 83A-C. The device 8300 is configured to be collapsible about its longitudinal axis so that the device may be stored in a delivery apparatus for percutaneous delivery to a hole in the septal wall of a patient's heart. The device 8300 has a body assembly which includes a plurality of struts 8302, a hub 8304 that is connected to the near end of at least one of the struts 8302, a plurality of first fork sections 8306, a plurality of second fork sections 8308, a first flange 8310, a second flange 8312, and a core segment 8314. Each of the first and second flanges 8310, 8312 comprises a plurality of individual segments, in this case eight individual segments. Note that each of the first and second flanges 8310, 8312 are annular flanges as each has its flange segments arranged to form an annulus, similar to the annular flanges of other embodiments described herein.

The first flange 8310 comprises two or more of the struts 8302 each having a u-shaped bend that forms one of the radially outer ends 8311 of the first flange 8310.

The near end of each of the struts 8302 optionally has a tab 8316. Each of the struts 8302 is connected at its far end to one of the first fork sections 8306. Each of the first fork sections 8306 has a left prong 8318 and a right prong 8320. Each of the left prongs 8318 of the first fork sections 8306 is connected at its far end to the far end of a right prong 8320 of a different one of the first fork sections 8306 at one of the second fork sections 8308. The core segment 8314 comprises the second fork sections 8308. Each of the second fork sections 8308 has extending from it a left prong 8322 and a right prong 8324. The far end of each of the left prongs 8322 of the second fork sections 8308 connects to a far end of a right prong 8322 of a different one of the second fork section 8308 to form one of a plurality of junctions 8326. The second flange includes two or more of the junctions 8326.

The areas or portions of the device 8300 may have a constant width and a constant through-thickness, such as width 8328 and through-thickness 8330 of the cross-section of strut 8302 shown in FIG. 83C. In some embodiments of the present invention, however, at least one of the width and the through-thickness of one or more areas or portions of the device varies in magnitude as described herein. In some embodiments, at least one of the width and the through-thickness of at least one of the struts 8302 and/or at least one of the first fork sections 8306 and the second fork sections 8308, varies in magnitude as described above.

In some embodiments of the present invention, through-holes may provided in selected portions of the device 8300. In some instances the through-holes are suitable to receive a suture and/or a radiopaque marker. Examples of such through-holes are through-holes 8332.

In some embodiments of the present invention, the segments of the first and second flanges of the device expand in the same direction and/or contract in the same direction. In other embodiments of the present invention, the segments of the first flange expand or contract in an opposite direction from the corresponding segments of the second flange. It is to be understood that these directional characteristics may apply to any device described herein.

Figure 26:
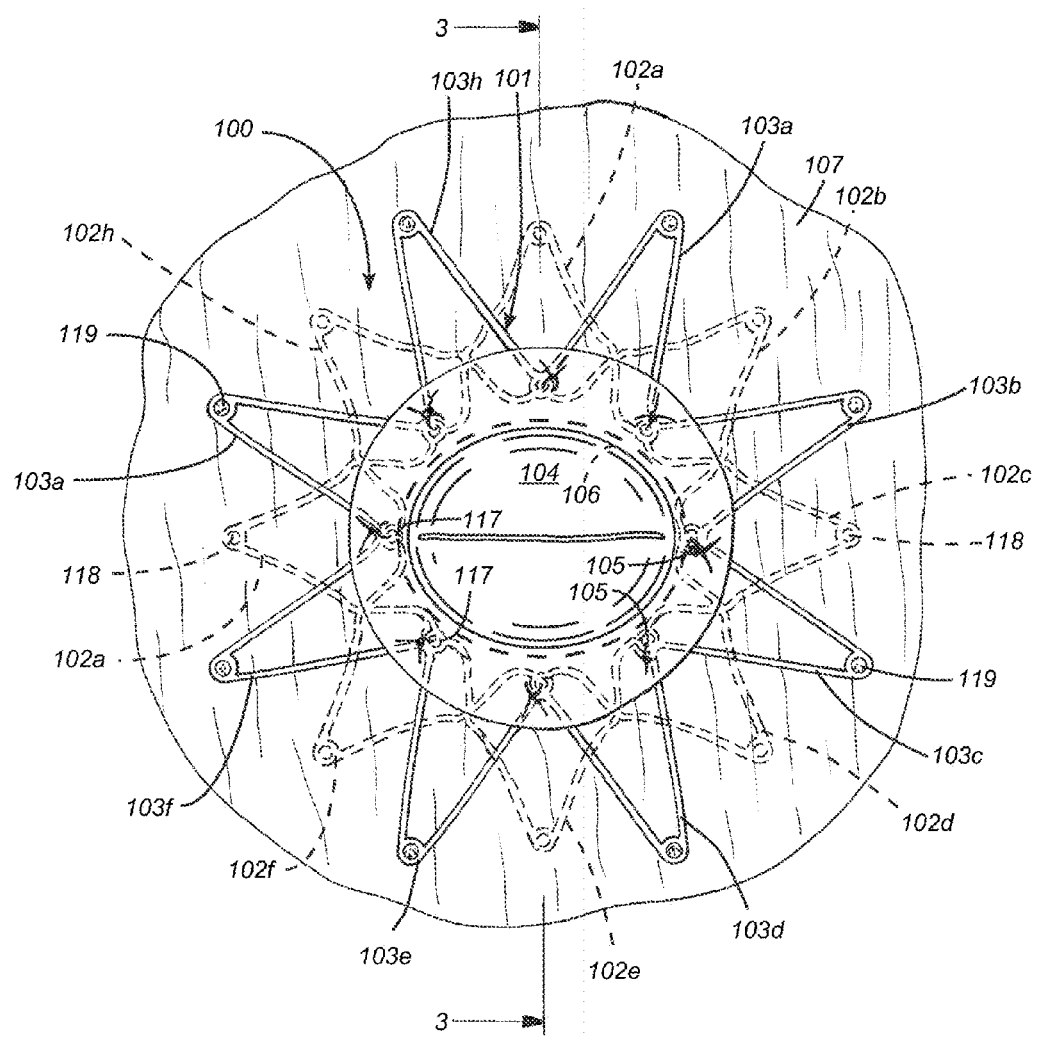
FIG. 26 shows and alternate embodiment wherein the core segment 106 is ovular rather than circular and thus the core segment is a cylindroid or elliptic cylinder rather than a simple cylinder.

FIG. 26 shows and alternate embodiment wherein the core segment 106 is ovular rather than circular and thus the core segment is a cylindroid or elliptic cylinder rather than a simple cylinder. This embodiment is more conducive to a bicuspid (or "duckbill", bivalve, or two-leaflet) configuration for the flow control element. The duckbill configuration is generally referred to as flow control element 104 in this figure. The inventors have found that the bi-valve configuration is able to open more fully when coupled with a core segment in the shape of a cylindroid.

Figure 27:
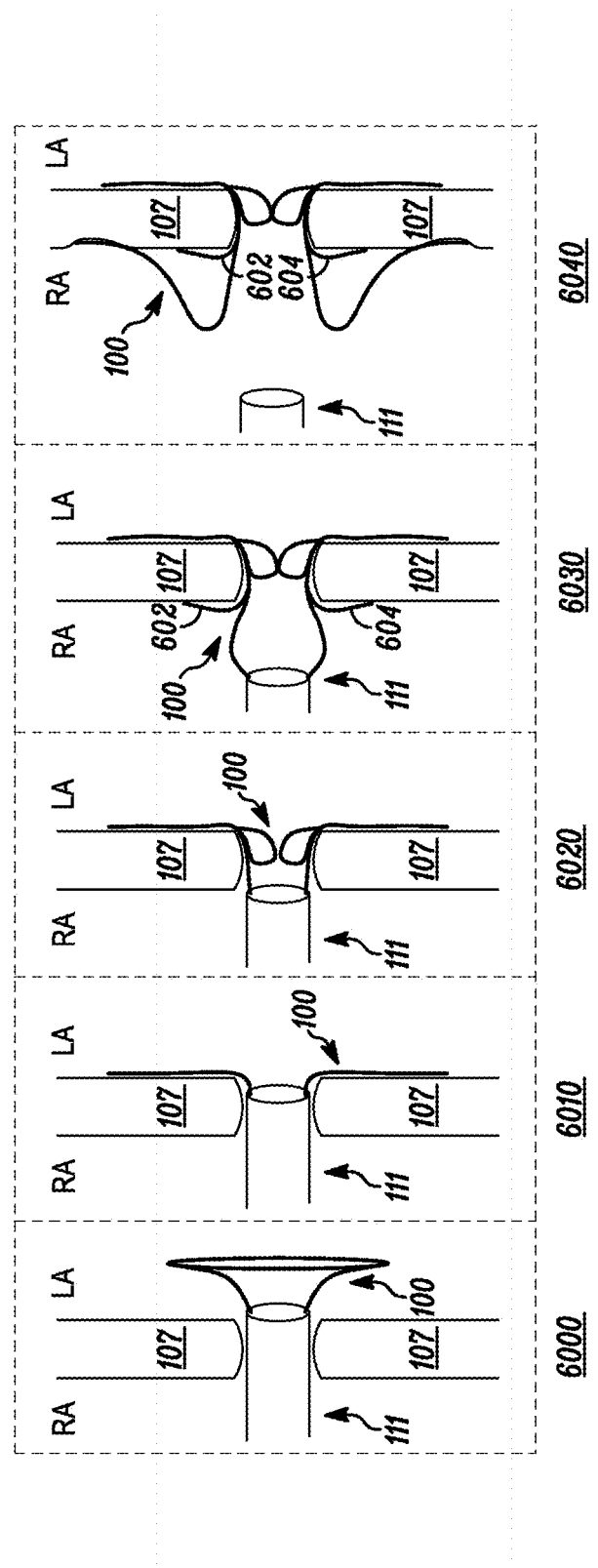
FIG. 27 is schematic depiction of another embodiment of a placement catheter system and interatrial pressure device along with the deployment process therefor.
Figure 27A:
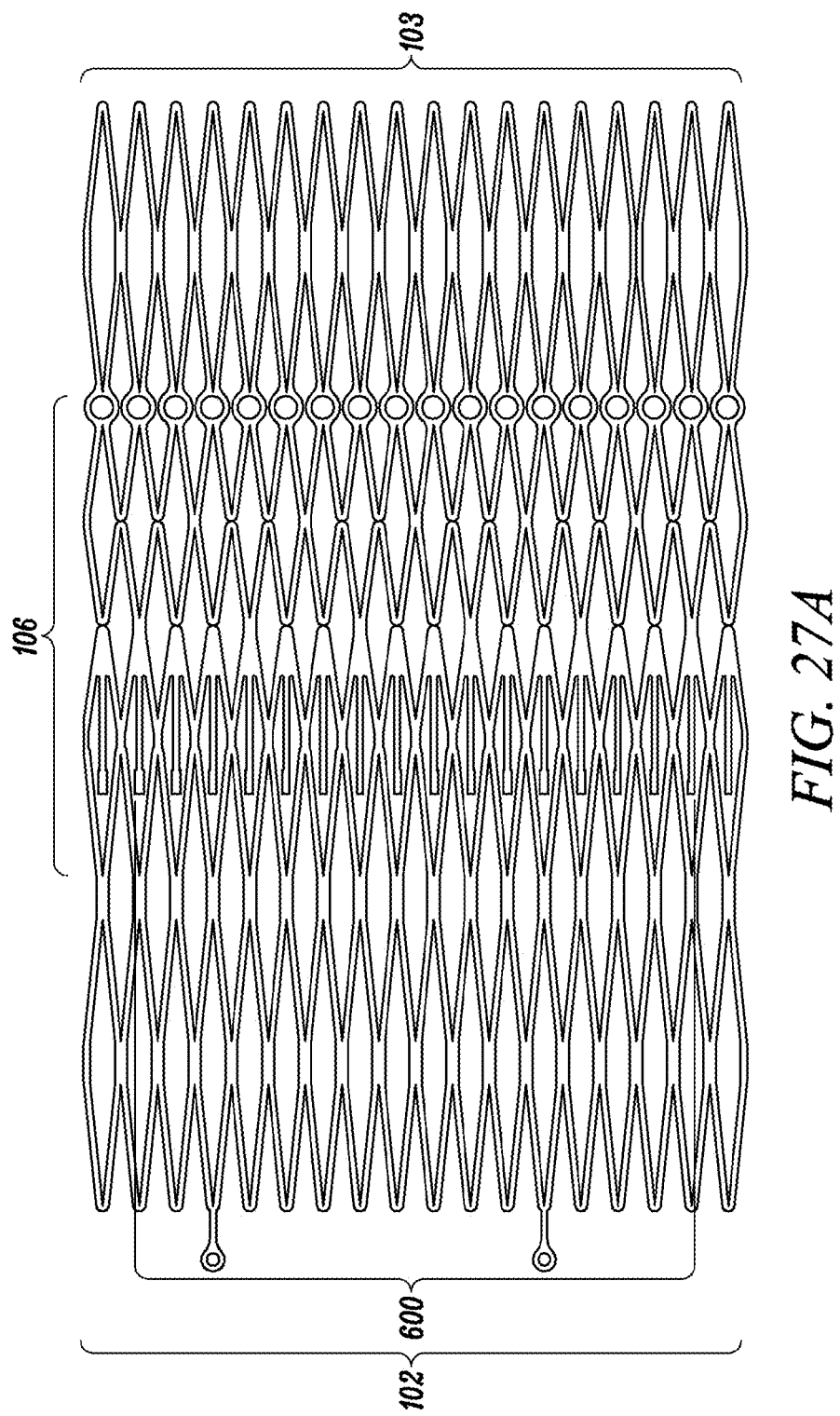
FIG. 27A is a side elevational view of the embodiment described in connection with FIG. 27 in the stowed position.

FIGS. 27 and 27A show another embodiment of an interatrial device having intermediate flange segments for a more secured fit against the septal wall. In embodiment, the device comprises, like many other embodiments disclosed herein, a core segment having an axial length and defining a passage. Like other embodiments disclosed herein there is a first annual flange and a second annular flange. The flanges themselves, similar to other embodiments disclosed herein, may be comprised of segments such as 102*a-h* and 103 *a-h* as shown in FIG. 6 by way of a non-limiting example. However, embodiments with an intermediate flange comprise a flange that contacts the RA or LA side of the septum for better adherence and positioning of the device within the atrial septum. Thus, the intermediate flange may be disposed between the first annular flange and the second annular flange along the core segment axial length Like other flanges disclosed herein the intermediate flange may be annular, and may comprise a plurality of flange segments. The flange segments of the intermediate flange have substantially similar lengths and, in embodiments, those lengths are less than the lengths of the flange segments of the first and second annular flanges. In embodiments, the intermediate flange segments are part of another a third annular flange situated on the same side of the septal wall as one of the other flanges. Reference numerals 6000 through 6040 refer to steps in the deployment of such an embodiment and will be discussed in connection with the structural features of the embodiment to illustrate this embodiment's utility and operation. The deployment process is similar to those described above, and to any commonly-known catheter based delivery process and as such the details of the process will not be discussed herein. Steps 6000 to 6020 show the deployment process steps proceeding in much the same manner as described herein. At step 6030, intermediate flange segments 602 and 604 of intermediate (or third) annular flange are deployed on the RA side. In this embodiment, intermediate flange segments 602 and 604 are shorter than the majority of the flange segments of the RA-side flange. As such, segments 602 and 604 are deployed prior to other longer segments and contact the septal wall 107 at points closer to the septal opening than the contact points of the longer segments. In this manner, the intermediate segments 602 and 604 (and the flange which they comprise) provide increased stability of the device. Any number of intermediate segments may be used although it is preferable to have at least two. As with other embodiments, the stiffness of the intermediate segments may be altered so as to differ from other flange segments of the device to avoid damage to the septal wall, i.e., lesser stiffness/greater flexibility, or to provide increased stability, i.e., greater stiffness/lesser flexibility. The choice of stiffness/flexibility variations must be balanced against the desired goals.

FIG. 27A is a side elevational view of embodiment discussed in connection with FIG. 27. In FIG. 27A the pressure venting device in its stowed configuration. Flanges 102 and 103 are shown with the flange segments that comprise them (flange segments not individually labeled). Core segment is again shown as 106. At a point between the end of the core segment 106 and proximal end of the RA side flange segment 102, the intermediate segments (collectively referred to as 600) emerge. Intermediate segments may be integral with the venting device or attached thereto in the manners described above.

Figure 28A:
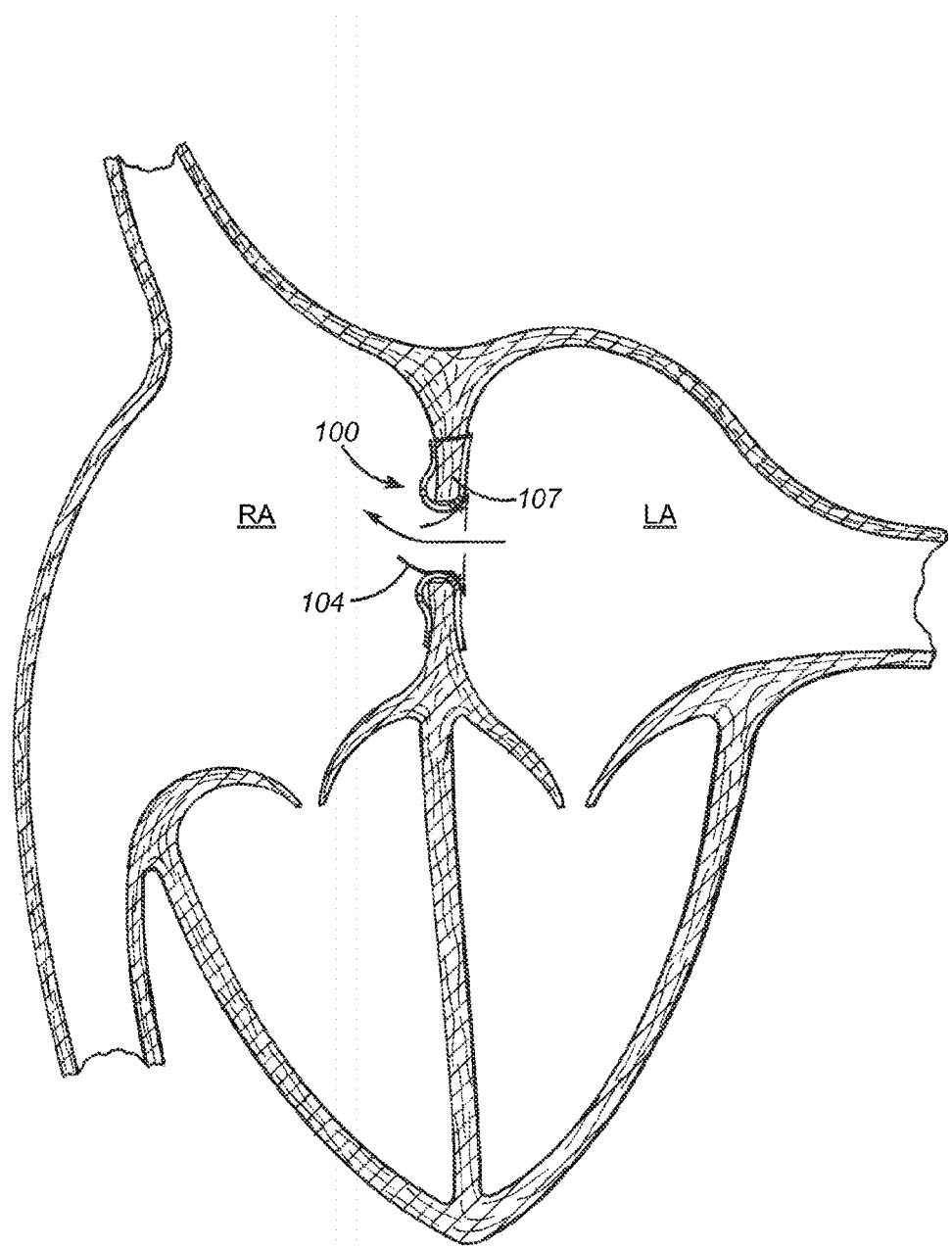

In other embodiments, the flow control element is configured to direct the blood flow in a desired direction. FIGS. 28A through 28C show such embodiments. In FIG. 28A interatrial device 100 is shown implanted in the atrial septum 107 of the heart in the same manner as shown in FIG. 1. Flow control element 104 is configured to aim the flow, shown in this figure as in the direction toward the superior vena cava. FIGS. 28B and 28C show a more detailed view of embodiments that enable the flow to be directed in a desired direction. As shown in FIG. 28B, flow control element may comprise a baffle-like flange 104a that extends at a downward angle and in the corresponding direction. In use, such embodiment directs the flow downward. FIG. 28C shows an embodiment where the flow is directed upward. The valve material (e.g. material for leaflets) can be sized and secured to the 100 in manner to direct the flow. For example, the flow control element may contain a curved tubular member whose opening points toward the direction of flow, or the flow control element may otherwise comprise an opening directed at the area of interest. In embodiments with baffles, the stiffness of the baffle 104a may be varied, for example, made stiffer. The length of the baffle can also be varied depending on the desired flow direction. The baffle can be a separate member attached to the flow control element or it may be made of the material and/or integral with the remainder of the flow control element.

Figure 29A:
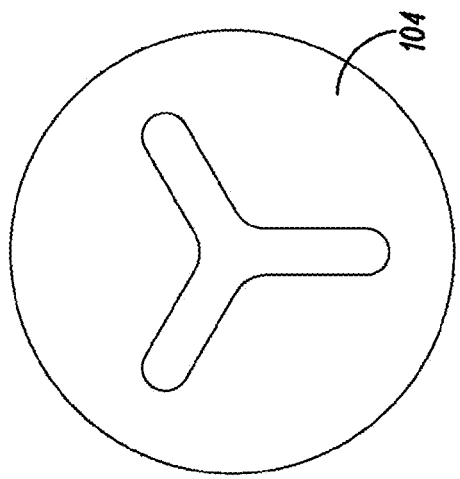
FIGS. 29A, 29B and 29C are end-on views from the RA side of the heart septum showing three different embodiments of exit profiles of the flow control element.
Figure 29B:
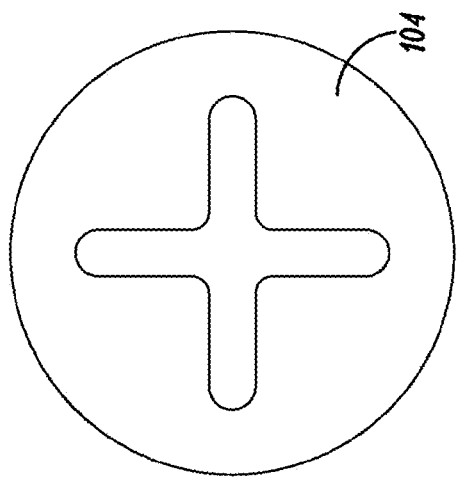
Figure 29C:
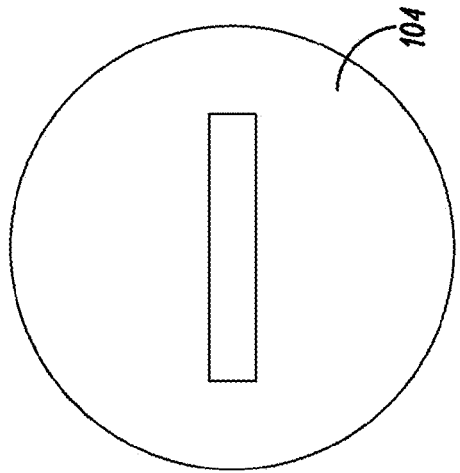

FIGS. 29A through C show exit profile shapes of the flow control element 104. In these figures, the flow control element 104 is being viewed from the RA side and thus the direction of flow is understood to coming out of the page at an angle substantially normal to the page. If the flow control element is a valve as described herein, folding and suturing patterns may be employed to achieved these exit profile shapes. In other embodiments, the end of the flow control element may be provided with a plate, or a partially frustoconical end piece, having an opening defining the two-dimensional shape shown in the Figure. The skilled artisan will appreciate that other exit profile shapes may be fashioned. The selection of an exit profile shape may provide advantages such as directing flow, preventing thrombi from moving across the septal divide, and/or reducing injury to surrounding tissue.

Figure 30:
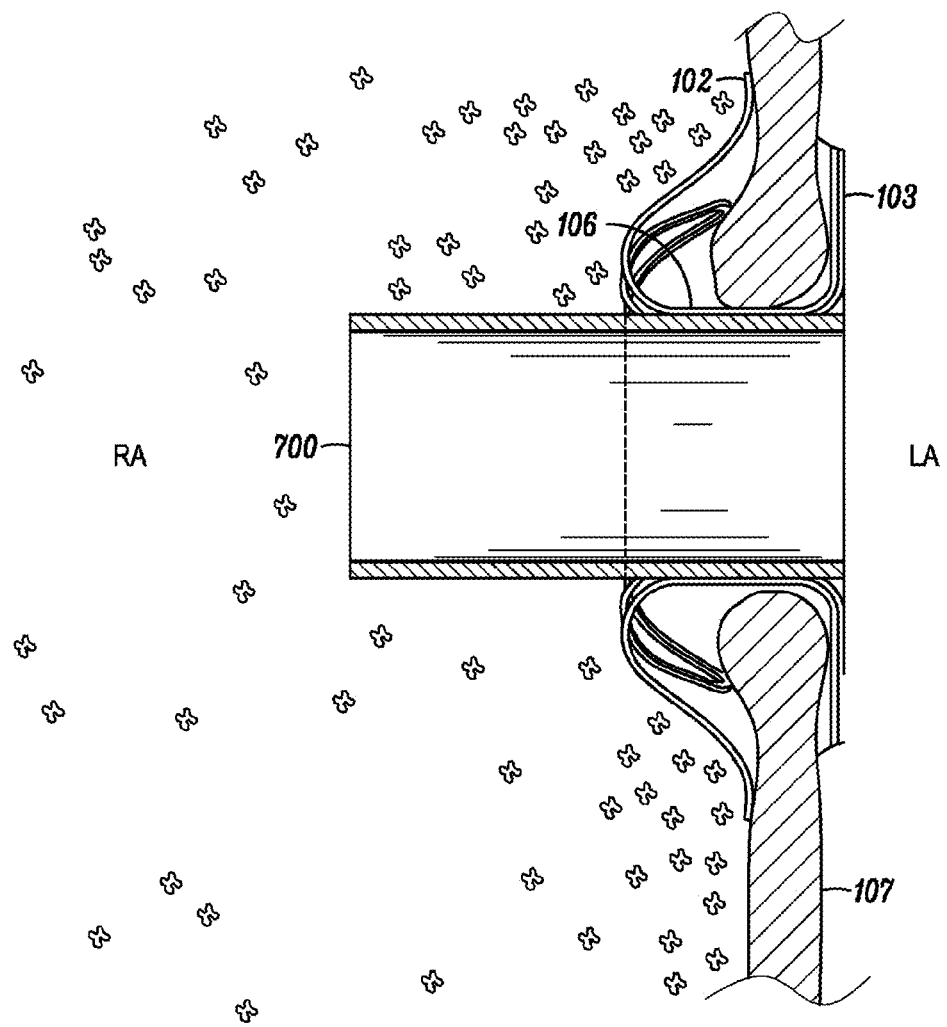
FIG. 30 is a side view of an embodiment of the device having a tube-like extension into the RA side of the heart.

Another embodiment is shown in FIG. 30. In this embodiment, the core segment 106 and flanges 102 and 103 of the device are substantially similar those described herein. Instead of the flow control elements described above (or in addition thereto) a tube-like member 700 is secured to the core segment 106. The tube member 700 is attached to the core segment 700 in a manner to allow the RA end of tube to extend into the RA in an axial direction, thus the tube's length must be sufficient to extend a distance into the RA. It has been found that the tube 700 configured in this manner prevents embolic particles from entering the tube and crossing over the septal divide into the LA. The distance that the tube 700 extends into the RA and beyond the plane of the RA-side flange opening (indicated by dotted line) should be at least a 1 mm but may be up to 2 cm in preferable embodiments. Even at relatively short lengths (such as where the tube extends only a few millimeters into the RA), the inventors have noted the surprisingly unexpected result of a reduction of embolic particles passing through. This is due to, in part, the tendency of embolic particles to collect along the surface of the septal wall and move toward the septal opening (or opening of an implanted device) with each cycle of the heart. By extending away from the septal wall 107, the tube provides an effective barrier to the embolic particles that would otherwise travel toward and possibly through the septal opening.

Figure 31:
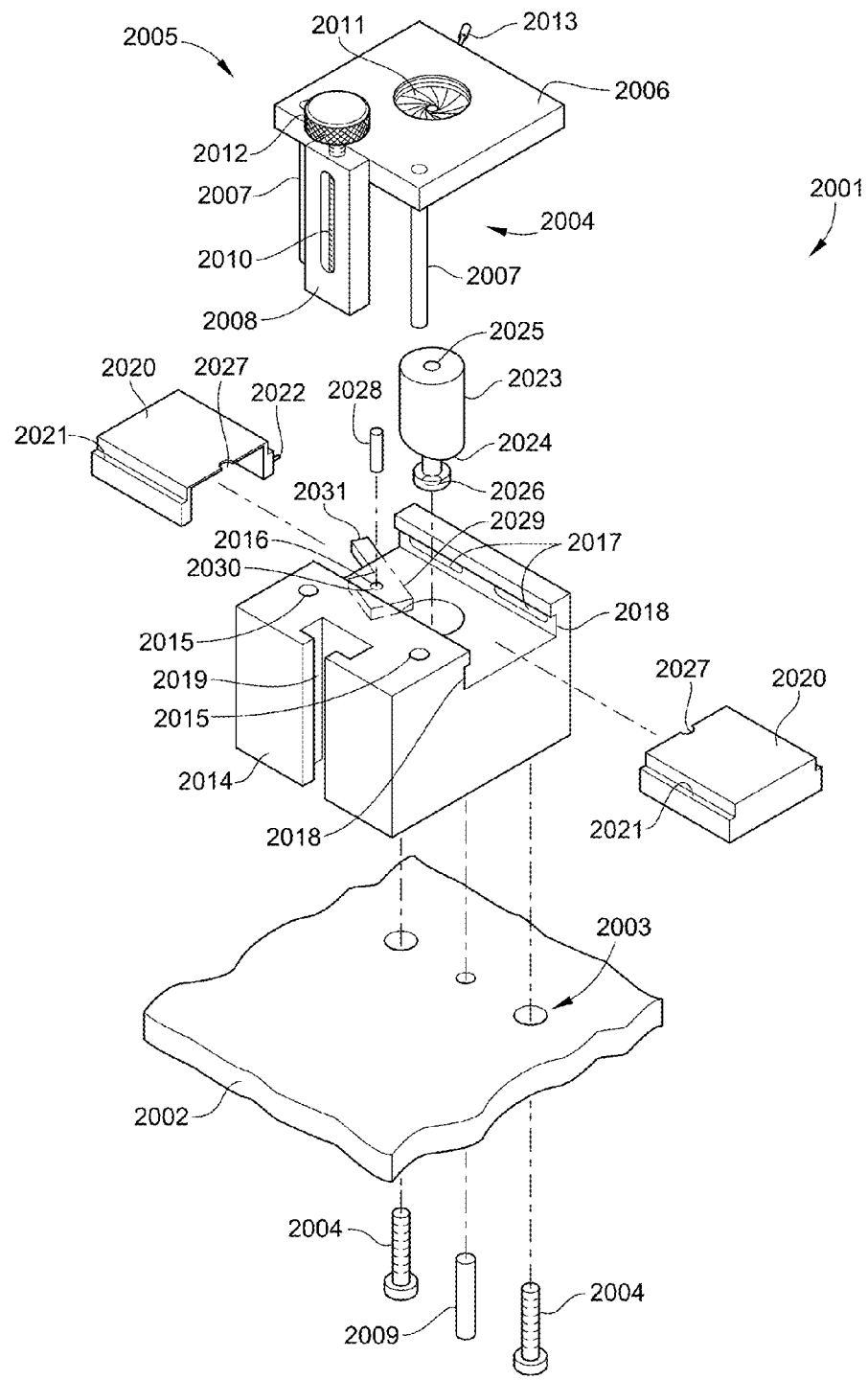
FIG. 31 depicts an exploded view of a first embodiment of a mounting and loading tool for mounting and loading a prosthesis.

FIG. 31 depicts a first embodiment of a mounting and loading tool useful for placing the some embodiments of prosthesis, namely ones having no struts meeting at an apex such as those similar to the embodiments depicted in 2, 4, 5, and 6 for example, onto a catheter or other delivery device for delivery in vivo to a patient. In this embodiment, mounting tool 2001 includes a base plate 2002 with orifices 2003 for securing other components as shown with fasteners 2004 and pin 2009. The principal component is a loader body 2014, mounted via the outer two fasteners and orifices as shown. A mounting platform 2023 is mounted in the center of the loader body via the third orifice and pin 2009. Mounting platform 2023 includes a lower orifice 2026 for mounting to the loader body via the middle loader body orifice with pin 2009. Mounting platform 2023 also includes a slotted cam surface 2024. Pivot 2029 mounts to the loader body 2014 via pivot pin 2028 through pivot orifice 2030 and loader body orifice 2016. Pivot 2029 and lever 2031 mount on the left side of loader body 2014 below the side doors 2020, as seen in FIG. 31. Movement of pivot 2029 and lever 2031 on the cam surface allows a user to raise and lower the mounting platform. The two opposite positions of the mounting platform are the lower and upper positions, achieved by rotating the pivot to the desired position. In other embodiments, the cam surface may simply be a slot or groove in the side of the mounting platform 2023.

The loader body 2014 also mounts the other components of the device. The loader body includes internal side channels 2018 for mounting two side doors 2020 and also includes vertical bores 2015 and a vertical side channel 2019 for mounting top plate 2005. The side doors 2020 include a central orifice 2027 in the shape of a semicircle, for closing against the prosthesis, discussed below. The side doors include shelves 2021 on either side for riding against the channel 2018 of the loader body. The side doors each also include a retaining pin 2022. The pins protrude through side windows 2017 in the loader body and allow the side doors to slide within the loader body while preventing their complete removal from the assembly.

Top plate 2005 includes a top surface 2006, an adjustable internal iris 2011, which functions much like the iris in a camera. The iris has sections that adjust inward and outward to open and to close the central opening of the iris. The adjustable iris decreases the area of the opening and closes in a manner that allows the top section of the implantable device to rest on top of the partially or full closed iris. Opening and closing of the iris is controlled by control lever 2013. The top plate includes two vertical rods 2007 for mounting in the vertical bores 2015 of the loader body and also includes a vertical side guide 2008 with an elevating mechanism 2010 actuated by a top thumbwheel 2012. Raising and lowering via the elevating mechanism allows the user to raise and lower the iris and thus adjust the separation of the left and right flanges of the prosthesis with the iris.

The mounting and loading assembly is used in the following manner. The loader body is positioned conveniently for the user, with the top plate removed and with the doors open. A prosthesis, such as prosthesis 100, is placed on the loading platform, with the left atrium legs or flange facing downward and with the loading platform in the lower position. The doors 2020 are then closed, with the mounting platform still in the lower position, thus placing the left atrium flange below the doors. The mounting platform 2023 is then raised to its upper position by rotating pivot 2029, causing the lower portion (left atrium flange or legs) to be pressed against the under side of the doors 2020. While not shown in FIG. 31, this movement causes the legs of the left atrium flange to be radially spread out.

At this point, the top plate is assembled to the mounting and loading tool and a catheter, such as one of the catheters depicted above in FIGS. 10-12, and also described above, is introduced though the center of the prosthesis. The portion inserted includes the catheter tip and a portion of the catheter control wire connected to the tip. The position of the catheter is adjusted so that the right atrium ball ("RA ball") or other retention device is vertically aligned with the right atrium flange, as discussed above with respect to FIG. 11A. The iris is then partially closed. Vertical alignment may be achieved by raising the top plate 2005 using handwheel 2012. With the doors 2020 closed and the left atrium flange trapped below the doors, raising the top plate will stretch the prosthesis, separate the left and right atrium flanges, and also stretch the prosthesis over the catheter. In one embodiment, the diameter of the orifice made by the two half-circular cut outs 2027 of the side doors is about equal, or slightly less than, a diameter of the catheter intended for use as a delivery device for the prosthesis discussed herein. The diameter may range from about 3 mm (9 Fr) to about 7 mm (21 Fr).

As the iris is raised, the upper (right atrium) flange will approach the retention device, such as the RA ball and the outer sheath of the catheter. The iris may continue to be closed while the top plate is raised, thus bringing the RA flange into contact with the RA ball. If the mounting platform 2023 has not been fully raised, it may also be raised gradually during this process. The entire sequence may be achieved by sequential use of the mounting platform 2023 and pivot 2029, the iris 2011 and handle 2013, and the elevating mechanism 2010 and thumbwheel 2012. When the RA flange has closed over the RA ball, the outer sheath may then be brought over the RA flange, securing the end of the prosthesis in the outer sheath. At this point, the iris 2011 may be opened along with doors 2020 and the catheter and prosthesis removed from the mounting and loading tool. The inner wire, firmly attached to the catheter tip and RA ball, is then retracted, pulling the central portion of the prosthesis and the LA flange into the outer catheter.

The catheter is then processed as discussed above, including assembly to a control device or handle, packaging, and so forth. This process is desirably performed in a sterile environment, with all components, tools, fasteners, and so forth, scrupulously clean and sterile before and during all steps of the process. The mounting and loading tool depicted in FIG. 31 and described above is desirably made from an inert, lubricious and medically-acceptable plastic material, such as a fluoropolymer, fluorinated ethylene-propylene, PTFE, UHMWPE, acetal, polycarbonate, and so forth.

In addition to the mounting and loading tool discussed with respect to FIG. 31, there are other embodiments for mounting a prosthesis and for loading a prosthesis onto a catheter or delivery device. Additional embodiments of useful tools are discussed below. In the discussion below, FIGS. 32-34 concern a discrete mounting tool, while FIG. 35 concerns a separate tool for loading a mounted prosthesis onto a loading tool.

Figure 32:
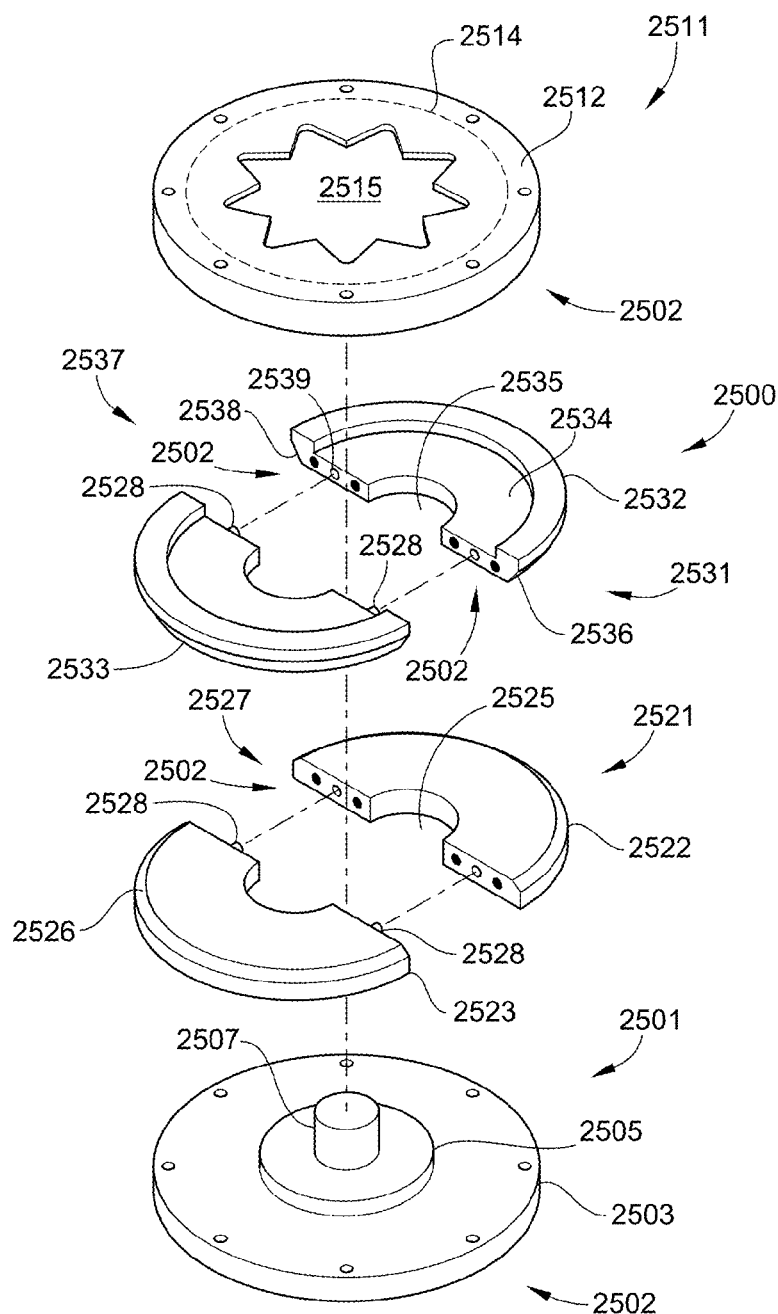
FIG. 32 depicts an exploded view of a second embodiment of a mounting tool for mounting a prosthesis.

FIG. 32 depicts a mounting tool 2500 useful for mounting a prosthesis for relieving intracardial pressure for a mammal, such as a human. The mounting tool includes four principal components. The principal components include a mounting plate 2501, a star-shaped cutout plate 2511, a lower flat disc 2521, also known as a right atrium or RA disc, and an upper counterbored disc 2531, also known as a left atrium or LA disc. The four components are used and stacked in the manner depicted in the drawing, in combination with a prosthesis mounted on the tool. All four components are desirably made from a lubricious, non-allergenic, medically-acceptable plastic, such as a fluoropolymer, fluorinated ethylene-propylene, PTFE, UHMWPE, acetal, polycarbonate, and so forth.

Mounting tool 2500 includes mounting plate 2501 having a cylindrical bottom disc 2503, the disc having a central raised portion 2505 and an additional raised portion 2507 atop the central raised portion. Plate 2501 also includes a plurality of inserts 2502 for attracting and joining with a similar number of inserts in cutout plate 2511. The inserts may be magnets or a combination of magnets and magnetically-attractive materials.

Star-shaped cutout plate 2511 includes a flat top surface 2512 with a cutout in a general shape of a star 2515. While the cutout has the general shape of a star, it is understood that the shape need not be a perfect star with perfectly equal sides and perfect angles between all legs or sides of the star. For example, the tips and corners of each point of the star are rounded rather than sharp. This avoids scratching the prosthesis and also avoids any scratching of personnel assembling the prosthesis to a catheter. A cutout in a general shape of a star is sufficient to accomplish the task described herein. The skilled artisan will appreciate that the shape would be appropriate for accommodating the shape of the device.

The bottom surface includes a counterbore 2514 for most of the entire bottom surface. A counterbored surface typically has an abrupt or right-angle termination, such as achieved by molding or by machining with an end-mill or other flat-bottomed tool. The counterbored surface is preferable to a more gradual change, such as a funnel-shaped countersink or angled approach. As discussed below, the counterbored surface of the cutout plate is used to mount the cutout plate to a loading tool. Thus, having the walls of the counterbore straight rather than angled is helpful, because with sufficiently close tolerances, the counterbore aids in firmly securing the cutout plate to the loading tool used. It is possible, however, that angled walls, i.e., a countersink, may be used instead. Cutout plate 2511 also includes a plurality of inserts 2502 matching the plurality of inserts in mounting plate 2501. In one embodiment, the inserts are polar magnets, i.e., N-S magnets with the poles arranged so that the discs can only be joined in one way.

For example, mounting plate 2501 may have eight N-S magnets molded into the plate with the north poles on the top side, with the raised portions. If cutout plate 2511 has the magnets similarly mounted, north poles on top, south poles on bottom, then the south poles on the bottom of cutout plate 2511 will attract the north poles on the top side of mounting plate 2501, and the two plates may be joined. Because of the polar orientation, there will be no magnetic attraction if one tries to assemble the discs in the incorrect manner, i.e., with the counterbored surface on top. In another incorrect orientation, with the cutout plate 2511 below mounting plate 2501, the plates will be magnetically attracted for assembly, but the star-shaped feature 2515 will be positioned away from the raised portions 2505, 2507. A user will not be able to position the prosthesis on the mounting tool using both the raised surfaces and the star-shaped cutout. Thus the mounting plate 2501 and the cutout plate 2511 have been designed for assembly and for fool-proof assembly.

Right atrium disc or lower flat disc 2521 is made as a two-part assembly, a right half 2522 and a left half 2523. There is a central orifice 2525 and the disc has a chamfer or bevel 2526 on its side. Each side of each half has three bores 2527 within the disc and perpendicular to a radius of the disc, the three bores on each side used to assemble the halves. In one embodiment, the outer two bores are used for magnets to attract the halves together and the central bore is used for a dowel to align the halves. Thus, in one embodiment, right half 2522 has three bores 2527 as shown, the central bore being merely a void for accepting a dowel from the left half, and the two side bores filled with two north-south magnets with the south poles facing outward. Left half 2523 has three bores 2527 on each side, the central bore on each side filled with a protruding dowel 2528 and the two side bores filled with two north-south magnets with the north poles facing outward. Use of the dowel and the void may be considered as a male-female joint. When the two halves are brought into contact, the opposite poles of the magnets will attract and the two halves will be firmly joined.

The left atrium disc 2531, also known as the upper counterbored disc, is also formed as two halves, right half 2532 and left half 2533. Counterbored disc 2531 has a counterbore 2534 on top, the counterbored or void portion removing material from a majority of the top surface. There is a chamfer or bevel 2536 on the side of the disc toward the bottom, such that when counterbored disc 2531 is assembled with lower flat disc 2521, there is a "V" in profile, the "V" formed by the bevels or chamfers on the two discs. Counterbored top disc 2531 also has a central bore 2535 of about the same diameter as central bore 2525 of lower flat disc 2521. Each side of the halves includes three bores 2537 within the disc, the bores perpendicular to a radius of the disc. The bores are voids for accepting devices for joining the two halves, as discussed above for the lower flat disc. In one embodiment, the central bores include a dowel and a void for aligning the two halves, while the outer bores include magnets 2502 with oppositely-facing poles for attracting each other. The dowel and void function for assembly as a tab and a slot in both the right and left atrium discs 2521, 2531. The bores may themselves be considered a slot, for use with a dowel, a tab, a magnet or a magnetic material. The tabs may be made of a plastic material or may be made of durable stainless steel or other non-corroding, medically-acceptable material.

In other embodiments for the side bores on either the lower plate 2521 or the upper counterbored disc 2531, the inserts could include magnets on one half and steel or iron bars on the other half, or one magnet and one steel bar on each half, with a facing magnetically-attractive metal and magnet on the other half.

In one embodiment, the lower flat disc 2521 may be made a different height than the height of the upper counterbored disc 2531. The difference in heights makes it unlikely that an improper assembly could occur between one half of the lower flat disc and one half of the upper counterbored disc. In one embodiment, the magnets of the halves with the central dowels may be assembled with the north poles outward, while the magnets of the halves with the central voids may be assembled with the south poles outward. This would make mis-assembly of the lower flat disc 2521 and the upper counterbored disc 2531 very difficult, since two pieces with dowels (male portions) would be impossible to join. While the two pieces with voids may be magnetically attractive and may join to form a mis-assembly, there would only be one assembled disc, since the two halves with the dowels could not be joined. Thus, use of the magnets and dowels makes assembly of the discs virtually error-proof.

Mounting tool 2500 is used to orient implantable devices that require the loading tool for placement in the loading tool, as discussed below. In practice, a prosthesis for placement in a patient's heart is placed on the mounting plate 2501. In one embodiment, a right atrium (RA) flange is placed on the central portion 2505. The star-shaped cutout plate 2511 is placed atop the mounting plate 2501, with the points of the star placed atop the flange joints of the RA flange, thus locking the prosthesis in place with the oppositely-facing magnets. The left atrium (LA) flange and the barrel, or central portion of the prosthesis, now stand above the raised portions 2505, 2507 of mounting plate 2501. The right atrium disc 2521 is now joined to the assembly between the right atrium flange (lower portion) of the prosthesis and the left atrium flange (upper portion) by bringing the two halves together, such that the bevel 2526 is on the upper side of the disc 2521.

The left atrium disc 2531 is then added to the assembly atop the right atrium disc, also by bringing the two halves together. In this instance, bevel 2536 of the left atrium disc 2531 faces downward. The chamfers or bevels of the two discs are thus adjacent when the mounting tool 2500 is assembly correctly, the bevels together forming a "V" which will be used later by the loading tool, as discussed below. The mounting plate 2501 and the star-shaped cutout plate 2511 may then be removed. When the prosthesis has been placed correctly on the mounting tool and the mounting plate and cutout plate are removed, the left atrium flange protrudes from the left atrium disc and the right atrium flange protrudes from the right atrium disc, as seen in FIGS. 33-34.

Figure 33:
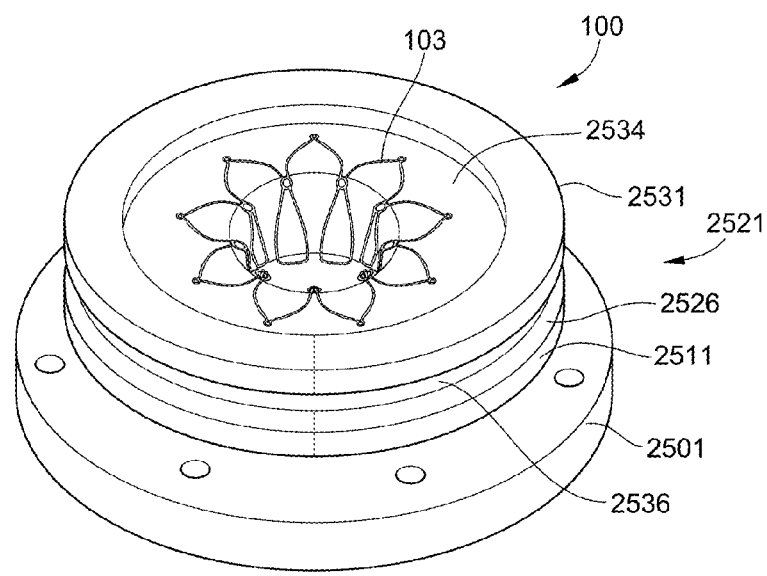
FIGS. 33 and 34 depict the mounting tool with a prosthesis mounted.

The mounting tool is depicted in FIG. 33 after it has been assembled with a prosthesis 100. The mounting tool includes mounting plate 2501 with cutout plate 2511 atop the mounting plate, and with right atrium disc 2521 atop left atrium disc 2531. In this figure, prosthesis 100 is mounted with left atrium flange 103 visible on top. Note the counter bore 2534 visible in the left atrium disc 2531. This is the configuration immediately after the prosthesis has been mounted and the left and right atrium discs have been inserted to separate the left and right atrium flanges. Note also that bevels 2526 and 2536 are adjacent, forming a V when seen from the side.

Figure 34:
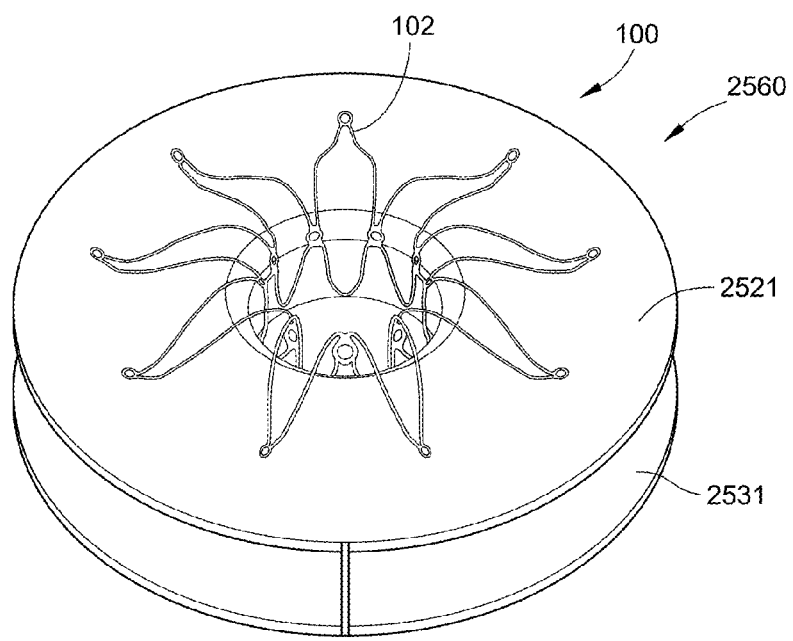

In FIG. 34, the mounting and cutout plates have been removed and the assembly 2560 has been inverted, with right atrium disc 2521 atop left atrium disc 2531 and with the right atrium flange 102 of the prosthesis 100 on top. Note that the right atrium disc 2521 is flat and has no counterbore on the side seen in this view.

Figure 35:
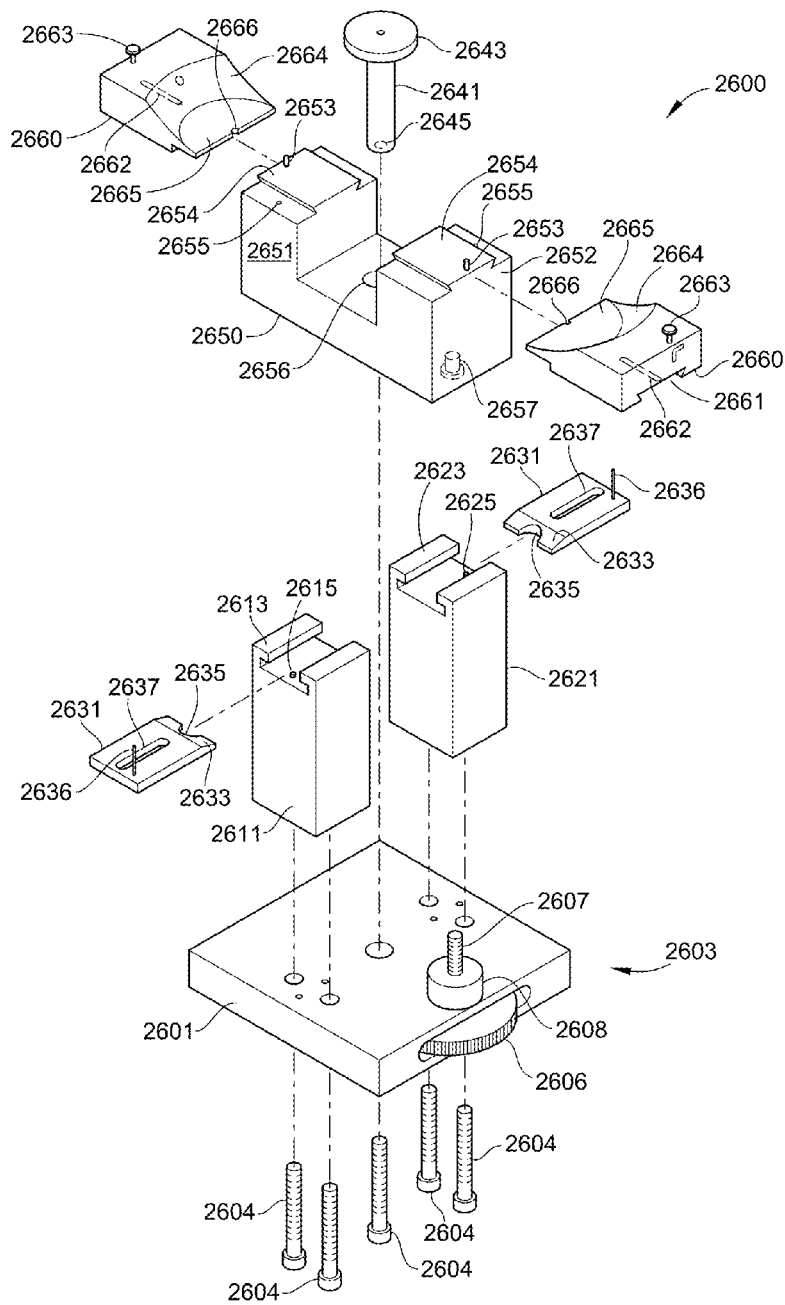
FIG. 35 depicts an exploded view of a loading tool for loading a prosthesis on a mounting tool onto a delivery device.

After the prosthesis has been mounted, a loading tool may be used to assemble the prosthesis and place it into a catheter or other delivery device. A loading tool useful in this process is depicted in FIG. 35 and is herein described.

Loading tool 2600 includes a base plate 2601, side door supports 2611 and 2621, a central column 2641 and a travel subassembly 2650. The base plate, side door supports and central column each mount to the base plate via fasteners 2604, as shown. In one embodiment, the fasteners may mount through the bottom and the heads may reside in countersunk or counterbored recesses in the bottom of the base plate. The base plate also includes a travel control mechanism or thumbwheel 2606, including travel screw 2607 and spacer 2608. In this embodiment, the travel control mechanism 2606, and the thumbwheel travel adjuster are mounted within the base plate, and a portion of the handwheel protrudes through a side of the base plate. Rotating the thumbwheel allows one to advance or retract travel screw 2607 and thus raise or lower travel subassembly 2650.

Side doors 2631 are identical and reside on side door supports 2611, 2621. Main doors 2660 are also substantially identical and reside on travel subassembly 2650. In one embodiment, door supports 2611, 2621 each include a top shelf 2613 for capturing a side door and allowing it to ride back forth, to and fro. In addition, door supports 2611, 2621 also each contain a travel stop or pin 2615, 2625. The pin stands in a groove 2637 within the side door, the pin limiting travel of the door to that allowed by the grooves, e.g., the half-way mark of the central column 2641 and its concentric top surface 2643, on the one side, and retreat from the central column in the opposite direction when appropriate. In this manner, the side doors can slide back and forth symmetrically to meet each other. The side doors have a taper 2633 on their front, as well as a half-circular cutout 2635 on the front. Each side door 2631 also has a vertical pin 2636 for ease of moving the door back and forth and also limiting the forward travel, when the pin touches the shelf 2613. In one embodiment, the diameter of the orifice made by the two half-circular cut outs is about equal, or slightly less than, a diameter of a catheter intended for use as a delivery device for the prosthesis discussed herein. The diameter may range from about 3 mm (9 Fr) to about 20 mm (60 Fr).

Main doors 2660 mount atop the travel subassembly 2650 via main door mounts 2651, 2652. The main doors slide back and forth in a manner orthogonal to the side doors. In this embodiment, the main doors are somewhat larger than the side doors and are used to compress the prosthesis to a diameter suitable for a catheter with a similarly desirably small diameter for delivery to a patient. The front portion of the each of the main doors thus includes a transition 2664 to a frontal semicircular arc 2665 and a semicircular bore 2666 with a radius consistent with such a small diameter. In one embodiment, the desired diameter is about 3.3 mm or 10 Fr, and the radius of the front bore is thus about 1.65 mm. In other embodiments, the radius is from about 1 mm to about 4.5 mm, to accommodate delivery catheters from about 2 mm to about 9 mm, and for catheters with a similar diameter.

The travel subassembly 2650 mounts to the loading tool via an internal threaded bore 2657 that interfaces with threaded screw 2607. Movement of the thumbwheel 2606 moves travel subassembly 2650 up and down as desired. Travel assembly 2650 includes door mounts 2651, 2652 including tongues 2654 atop the mounts and pins 2653 for limiting travel of the main doors. The main doors 2660 are substantially identical and include a groove 2661 along their length of their bottom. Tongues 2653 ride within grooves 2661 of the main doors.

The main doors also include locking pins 2663. Each pin may be used to lock the main door 2660 into the closed position by closing the door fully and depressing the pin to engage orifice 2655 in door mounts 2651, 2652. The pins 2663 may also be used to restrain each door away from the closed position by opening the main doors and depressing the pins outside travel subassembly 2650 so that further inward travel is not possible with the pins depressed. Central column 2641 with mounting surface 2643 mounts to the base plate 2601 via a central orifice 2645 and a fastener from below the base plate. The central column is positioned symmetrically within orifice 2656 of the travel subassembly 2650. The central column and the mounting surface are stationary, while around them the travel subassembly 2650 travels vertically and side doors 2631 and main doors 2660 move horizontally.

The loading tool is used in the following manner, in one embodiment. Other embodiments and other methods may also be used.

The side doors and main doors are opened to their full open positions and the mounted prosthesis assembly 2560 described above is placed onto central column top surface 2643, with the right atrium flange or legs up and the left atrium flange down. Note that in this configuration, the left atrium disc 2531, which is the disc with the large counterbore 2534, faces downward. In one embodiment, the counterbore is sized and oriented to fit precisely onto top mounting surface 2643 of the loading tool 2600, discussed below. Top surface 2643 is the mounting or loading surface for placing the mounted assembly 2560 into the loading tool 2600.

Once the mounted assembly 2560 is placed into the loading tool 2600, the travel subassembly 2650 is raised or lowered so that the side doors align with the "V" formed by the bevels or "V" of the mounted assembly. The side doors 2631 are then closed, bringing the tapered front portions of the side doors into contact with the "V" and urging apart the left atrium and right atrium discs of the mounting tool. The main doors 2660 are then closed against the side doors 2631.

Figure 36:
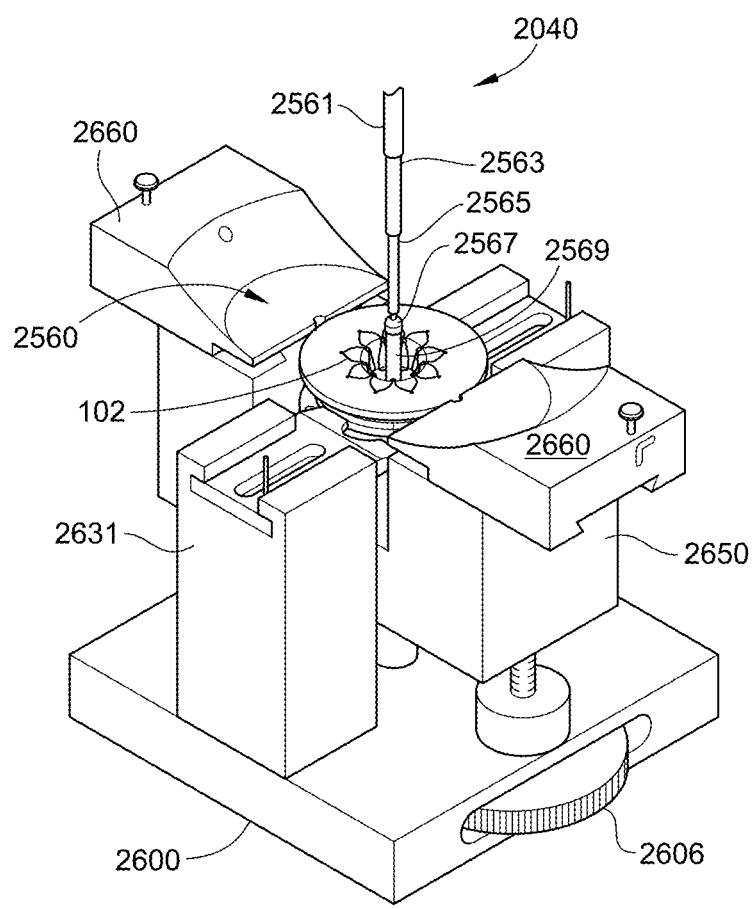
FIG. 36 depicts the prosthesis being loaded into a catheter.

Once this has been accomplished, a delivery catheter 2040 is assembled to the prosthesis, as depicted in FIG. 36. A clear loading tube 2561 is moved over the outer sheath 2563 and the tip (not shown in FIG. 36) of the catheter 2040 is inserted through the central bore of the mounted assembly 2560. Visible in FIG. 36 is the inner sheath 2565, inner control wire 2569 and right atrium ball 2567. As seen in the figure, the right atrium ball 2567 should be aligned with the right atrium flange 102. The thumbwheel 2606 is then adjusted so that the main doors 2660 are above the side doors 2631, such that the main doors 2660 can close. As the closed main doors are raised using thumbwheel 2606, the right atrium disc 2521 will rise, and the right atrium flange 102 will begin to lengthen axially and compress radially. It may be advantageous to insure that no legs or struts of the flange are intermingled or caught in the disc or the doors as the doors rise. Thumbwheel 2606 is used to raise the main doors while the catheter is held in a position that allows the right atrium flange to close around the right atrium ball 2567. When this operation has been correctly accomplished, the legs or struts of the flange are evenly and tightly spaced around the right atrium ball or flange.

The prosthesis is now brought into the catheter. In one embodiment, the following procedure is used. The RA ball acts as a compression device, compressing the right atrium flange. After the right atrium flange is firmly compressed around the right atrium ball, the outer sheath 2563 is held firmly while the inner sheath 2565 and control wire 2569 are pulled back. This pushes outer sheath 2563 over the right atrium flange and ball 2567. The ball 2567 should be pulled into the outer sheath 2563 so that it, and the right atrium flange, are no longer visible. The travel assembly 2650 is now lowered, using the thumbwheel, until it just touches the side doors 2631 (not shown in this view). Both sets of doors are opened and the catheter 2040 and left and right atrium discs 2631, 2621 are removed from the loading tool 2600. The left and right atrium discs are then removed from the catheter by pulling them apart.

The left atrium flange is now lengthened axially and compressed radially. In one embodiment, the clear loading tube 2561 has a larger diameter than the outer sheath 2563. The clear loading tube 2561 is slid over the left atrium flange 103, pushing the left atrium flange legs together. The clear loading tube should be slid forward or distally until it completely covers the prosthesis. The control wire 2569 is then pulled proximally, pulling the inner sheath 2565 and pulling the prosthesis into outer sheath 2563. The clear loading tube 2561 is then removed. The above mounting and loading procedures are accomplished in a sterile environment. Alternatively, the devices and components may be sterilized or re-sterilized after assembly.

Figure 37:
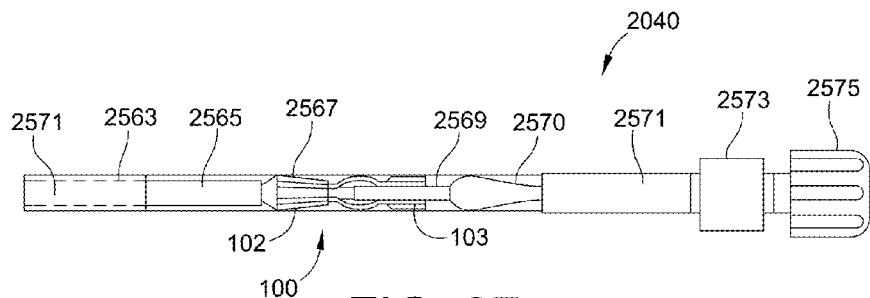
FIG. 37 depicts the loaded catheter with protective packaging.

Any other desired components, such as an outer shipping sheath, may then be added. In one embodiment, an outer shipping sheath is added in a sterile manner, as shown in FIG. 37, over the outer sheath 2563. Sterile outer shipping sheath 2571 with connector 2573 and visible cap 2575 is added over the outer sheath 2563 in such a way that inner sheath 2565, right atrium ball 2567 and right atrium flange 102, the central portion of prosthesis 100, left atrium flange 103, inner control wire 2569 and tip 2570 are visible from the outside of sheath 2571. In the embodiment shown, the prosthesis, including the right atrium flange 102 and right atrium ball 2567, has been advanced using the control wire 2569, or the outer sheath 2563 has been retracted, to allow visibility from the outside of the device. The catheter 2040, with the prosthesis loaded and ready for inspection and deployment, is now ready for shipment to a hospital or other care-giving institution.

Implanting and Deploying the Prosthesis

With this embodiment, and in this configuration, a physician can immediately inspect the prosthesis and determine whether the prosthesis is suitable for implantation into a patient. For example, the physician can immediately inspect, without even opening the outer package, whether the legs or struts of the right atrium flange are intertangled. The physician can also determine whether the left atrium flange or center portion are also suitable for implantation into the patient.

As noted, the shipping sheath is advanced over the outer sheath 2653 of the delivery of deployment catheter 2040. Accordingly, the prosthesis 100 remains within the outer sheath at all times during shipping and during removal of the shipping sheath. In some embodiments, the outer catheter is connected at its proximal end to an irrigation system, described below, suitable for irrigating the outer sheath, and thus the prosthesis, with sterile fluid, a radiopaque dye, or other desired solution. A physician can thus remove the shipping sheath, flush the prosthesis with sterile solution using the irrigation system, and move the prosthesis back and forth within the outer sheath. This allows the physician to remove any possible bubbles from the device and the catheter, at the same time allowing the physician to test the level of effort required to advance and retract the prosthesis or the outer sheath with respect to each other.

More Control Systems for Deploying the Prosthesis

Figure 38A:
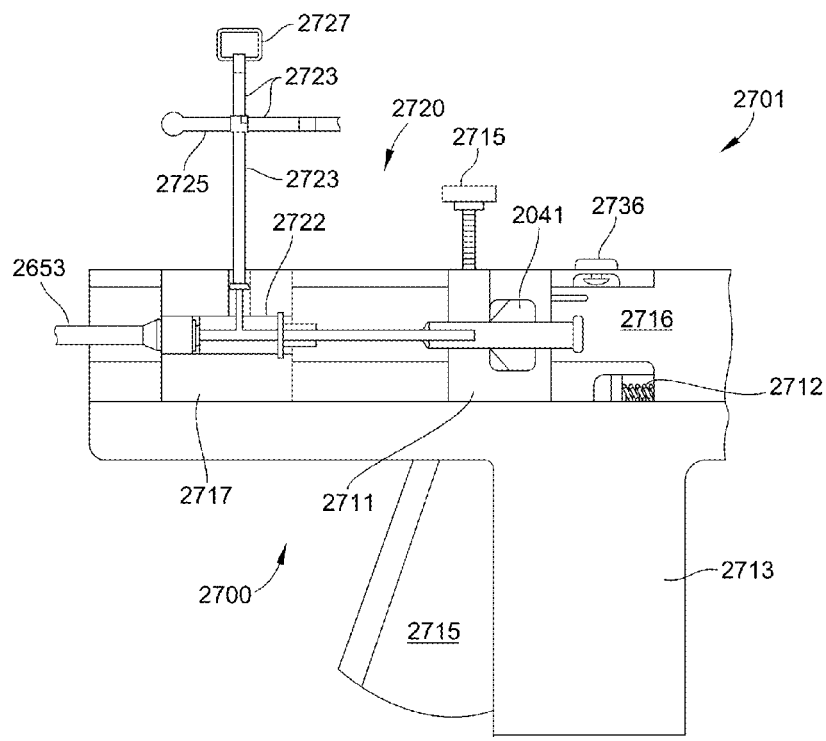
FIGS. 38A and 38B depict an additional embodiment of a control device or handle for deploying the prosthesis.
Figure 38B:
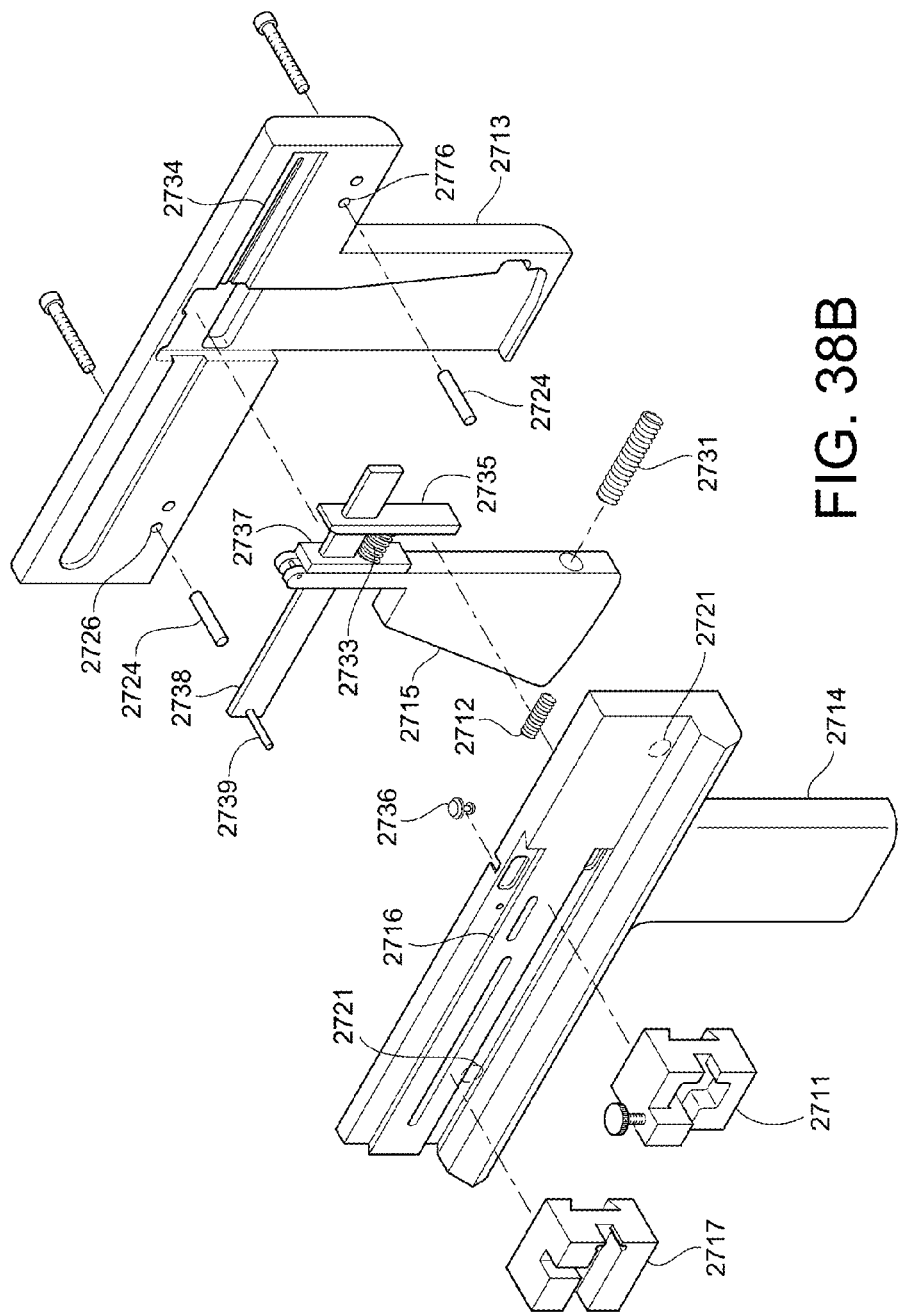

A control system, including a control device or handle, and an irrigation system, may also be usefully employed with the catheter described above. One example of a control system or handle was given above in FIG. 12, and also explained. Another example is depicted in FIGS. 38A and 38B, control system 2700, including control handle 2701 and irrigation system 2720. The control handle 2701 includes a housing or grip 2713 and a control trigger 2715 for a user to retract the outer sheath or advance the inner control wire. The tension or pull required for the trigger 2715 is set with trigger spring 2731. Thus, spring 2731 controls the force needed by the user to deploy the prosthesis, i.e., the force required to release the implant onto the septal wall.

The inner control wire is grounded to the control handle through first plate 2711 via the flange 2041 of the inner control wire and may also be secured with adjustment screw 2715. The position of the first plate within the handle is set by a pin and bore, or set screw or other arrangement (not shown). The second plate 2717 is connected to the outer sheath and the irrigation system, which are secured to the second plate via connector 2722. The second plate is connected via a slot (not shown) on its rear face to a pin (see FIG. 38B) on the actuation mechanism within the handle. The first and second plates 2711, 2717 have slots or mortises on their rear faces for riding on a tenon or shelf 2716 on the side of the front grip cover 2714.

FIG. 38B depicts the internals of the trigger mechanism. Grip 2713 also includes a front cover 2714. The front cover 2714 is assembled to the grip 2713 through fasteners 2724 and orifices 2726 in the grip 2713 and mating parts 2721 in the cover 2714. The mating parts may be molded-in nuts, threaded surfaces, or other appropriate joining components.

The internals of the trigger mechanism are largely contained within the grip 2713. These include a trigger spring 2731, grounded between the trigger 2715 and a pocket in grip 1713. As noted, spring 2731 determines the pull required to activate the trigger. This spring also provides a return for the trigger to its resting or neutral position after each pull by the user. Mounted within a channel 2734 in grip 2713 are a vertical braking/release bar 2735, vertical driving bar 2737 and a driven horizontal bar 2738. Trigger 2715 also has an internal rectangular bore (not shown) for accommodating driven horizontal bar 2738.

Driven bar 2738 in one embodiment has a rectangular cross section, while the driving and braking/release bars 2735, 2737 have bores with rectangular cross sections and are mounted around the driven bar via the rectangular bores. Bar 2738 has a square cross section in one embodiment, as do the matching bores in the braking and driving bars. Other configurations may also be used for the bars 2735, 2737 and 2738, and the corresponding bores. Driven bar 2738 includes a pin 2739, which is connected directly to a bore (not shown) on the rear of the second plate 2717. Biasing spring 2733 is grounded between the driving bar 2737 and braking/release bar 2735, which is somewhat longer than driving bar 2737. Biasing spring 2733 maintains compression and separation between the braking and advancing bars. Trigger 2715 is also mounted around the driven bar 2738 via a rectangular bore in this embodiment. Other embodiments may include different geometries for driven bar 2738 and the corresponding bores in the trigger, the driving bar and the release/braking bar. These shapes may include rounded rectangular, ovate and others.

Compression spring 2712 biases the braking/release bar 2735 to a braking position by maintaining contact between the braking/release bar 2735 and driven bar 2738. Release pin 2736 protrudes above the top of the grip 2713 and is used by the operator to release the driven bar from the braking and driving bars. When a user wishes to return the second plate 2717 to a forward position, or to select a position for the second plate, the user simply presses on pin 2736. Pressing on pin 2736 has the effect of pushing the release/braking bar 2735 to the rear by overcoming the compression of spring 2712. Releasing the braking bar 2735 enables easy manual movement of the driven bar 2738 and thus second plate 2717 and the outer sheath of the catheter.

The trigger mechanism works in this manner, although many other embodiments are also possible, as also discussed in U.S. Pat. No. 7,699,297. When the user activates the control mechanism by pulling the trigger, the driven bar 2738 moves to the rear, to the right in FIGS. 38A and 38B, as does the connected second plate 2717. The outer sheath is also connected to the second plate, and as the second plate moves to the right or rear, the outer sheath does also, thus pulling the outer sheath in a proximal direction and exposing more of the prosthesis and the inner control wire. The distance traveled by the activating bar is determined by outer dimensions of the driven bar, the height of the bore in driving bar 2737, the distance between the driving bar 2737 and the braking/release bar 2535, and length of the vertical distance in the bore of trigger 2715. These lengths or distances determine the angles between the various components and thus limit the distance that is traveled by the trigger, the driving bar and the driven bar, on each pull of the trigger. Thus, each pull of the trigger moves the driven bar 2738, the second plate 2717 and the outer sheath of the catheter 2653 a predetermined distance. This makes it straight-forward for the medical professional to deploy the prosthesis. Each pull of the trigger will retract the outer sheath or advance the control wire a known and repeatable distance.

Returning to FIG. 38A, the outer sheath 2653 is grounded to the second plate 2717 via connector 2722, which provides both a mechanical connection to the control device through second plate 2717 and also a fluid connection to irrigation system 2720. The connector 2722 connects to the irrigation system 2720 through tubing 2723 to a three-way valve 2725. The valve may also include other tubing connections 2723 or to one or more connectors (not shown), and one or more optional caps 2727. As noted above, the irrigation system may be used by the physician to flush the prosthesis and outer sheath with sterile fluid before use, and to check for and remove and bubbles in the catheter and in the prosthesis. Such fluid will exit at the far end of the outer sheath 2653 after connector 2573 and cap 2575 are removed.

In one embodiment, the control system 2700 includes an internal mechanism that determines the amount of movement of the first or second plate when the trigger is pulled, and thus when the outer sheath is retracted or in the control wire and prosthesis is advanced. As noted, the amount of force needed for a single trigger actuation may be set by spring 2731. The remaining internal mechanisms, as discussed above, sets the distance traveled. The catheter is advanced to a point where the catheter and the prosthesis are in the desired location within the patient, as determined by the radiopaque methods described above, or by other desirable, reliable method.

The tip of the catheter is advanced through a surgically-created opening in the atrial septum. The tip is thus in the left atrium at the start of the deployment process. When the trigger is pulled, the outer sheath is retracted a distance sufficient to remove the outer sheath from around the left atrium legs and flange. In embodiments, this distance is about 7 mm. At this point, the left atrium legs are deployed inside of the left atrium, similar to FIG. 27, step 6000, which shows the left flange legs deployed from the outer sheath of catheter 111 into the left atrium. The entire catheter system is then pulled back such that the left atrium legs contact the septal wall, as seen in FIG. 27, step 6010. At this point, the central portion of the interatrial vent and the right atrium legs and flange are still retained by the outer sheath. The central portion, still retained, is located in the septal opening. The right atrium legs, still retained, are located in the right atrium. A second pull of the trigger retracts the outer sheath a distance, about 7 mm, to remove the outer sheath from around the central portion and the right atrium legs, thus deploying the central portion and also deploying the right atrium legs in the right atrium.

While 7 mm is a central value, the actual value may vary from about 3 mm to about 11 mm. In other embodiments, other travel ranges may be used. It will also be understood that this distance may vary, due to tolerance stack ups of the several components, including those of the catheter and the control device.

At this point, the prosthesis has been deployed, and the physician will normally inspect the deployment by one or more of the non-invasive techniques described above to insure correct placement. If deployment is satisfactory, the physician may remove the catheter and all components, including the tip, the outer sheath, the control wire, and so forth, and finally the guide wire used.

During implantation, the physician may use the catheter fluid system to determine the precise placement of the end of the outer sheath and thus the prosthesis. After the device has been advanced through the patient to a point near to the desired implantation point, the radiopaque markers on the left or right atrium flanges or the catheter may be used, along with fluoroscopy, echosound or other non-invasive means, to determine the location of the device within the patient. In addition to, or instead of the radiopaque markers, the irrigation system may use a radiopaque solution, such as a barium solution or other radiopaque solution.

The control device or handle of FIGS. 38A and 38B is merely one example of a delivery or deployment device and control device, as discussed herein, for use with a delivery catheter. Other control devices may also be used, such as additional examples depicted in FIGS. 39A, 39B-39E and 40.

Figure 39A:
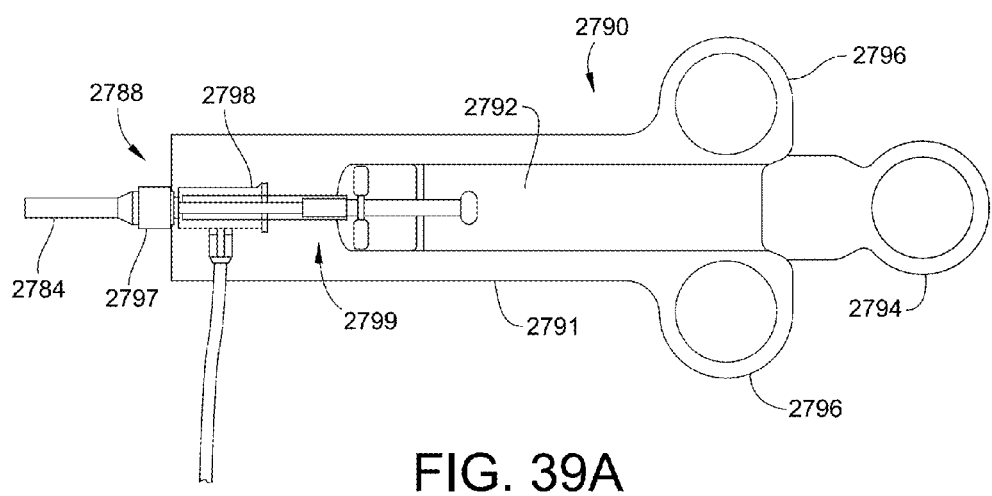
FIGS. 39A through 39E depict another embodiment of a control device for deploying the prosthesis.
Figure 39B:
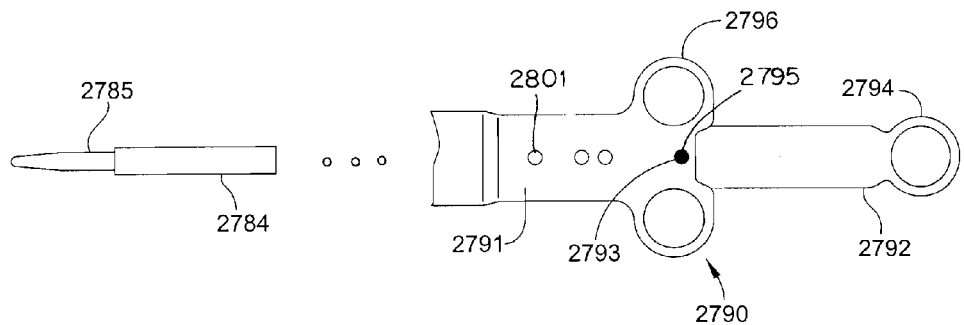
Figure 39C:
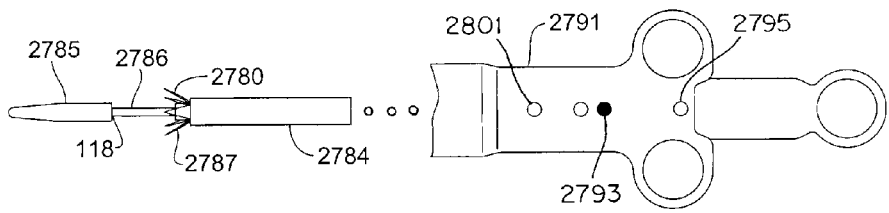
Figure 39D:
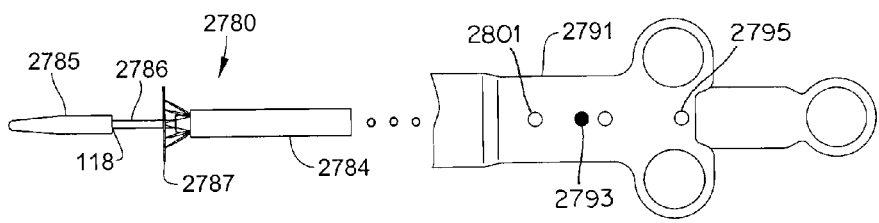
Figure 39E:
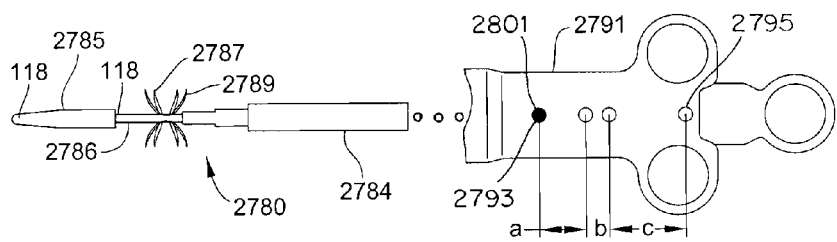

Another embodiment of a control device is depicted in FIGS. 39A and 39B-39E. In this embodiment, as seen in FIG. 39A, control device 2790 connects to delivery catheter 2788 for delivering a prosthesis. Control device 2790 includes a control body 2791 and a control handle 2792. The control body 2791 is attached or connected to the outer sheath 2784 via connector 2797. The moveable control handle 2792 is attached or connected to an inner control wire 2786 (not visible in FIG. 39A) via connector 2799, and as seen in FIG.

39B, connected to the deployable prosthesis 2780. Connector 2798 is a fluid connector for supplying fluid to the inside of catheter 2788 and the inside of outer sheath 2784. The fluid may be sterile fluid, or may be a sterile radiopaque fluid. Control handle 2792 is equipped with a thumb ring 2794, while the control body 2791 includes two finger rings 2796. Handle 2792 is also equipped with a protruding bump or tab 2793, which is sized and designed for sequential positioning in orifices 2795.

In the sequence, depicted in FIGS. 39B-39E, control body 2791 remains stationary, as does outer sheath 2784, while the control handle 2792 moves progressively to the left, i.e., in a distal direction, in a series of discrete steps, as shown. As the tab 2793 moves to the left, from the first of the orifices 2795, on the right to the last orifice 2801 on the left, the tab is visible in one orifice after another, as shown. At the same time, distal tip 2785 also moves progressively to the left, distally, to sequentially deploy more and more of prosthesis 2780. In a first view, (FIG. 39B), there is no deployment. In the middle two views, (FIG. 39C, 39D) left atrium flange 2787 is first partially deployed and then fully deployed. In the final view, (FIG. 39E), both left and right atrium flanges 2787, 2789 are deployed. The final view also allows a close-up of the delivery catheter details, including tip 2785 and non-invasive imaging markers 118 on the tip 2785, just proximal to the tip, and just distal of the deployed prosthesis 2780.

In this embodiment, the control handle 2792 advances control wire 2786 and thus the prosthesis 2780 in a sequenced manner that is controlled by the spacing a, b, c, between the orifices 2795 of the control body 2791. In one embodiment, the distances are 16 mm, 5 mm and 11 mm, respectively. Other embodiments may use other discrete distances. These distances help the medical professional who deploys the prosthesis to more accurately position the prosthesis within the patient. The device and sequence shown in FIGS. 39B-39E uses a stationary outer sheath and a moving inner control wire and prosthesis. It is understood that the handle 2792 could alternately be attached to the outer sheath, so that the tab 2793 begins in the most distal position, as shown in the last movement of the sequence, and then the handle and tab move proximally to retract the outer sheath, thus deploying the prosthesis.

In addition, of course, non-invasive imaging is used to position the catheter outer sheath 2784 and distal tip 2785 to a desired position within the patient, i.e., with the distal top 2785 through an opening in the atrial septum of the patient. Differences between patients may also be studied, and the position of the control handle 2792 may be adjusted slightly for optimal prosthesis placement. As noted in other embodiments, markers for x-ray or echogenic imaging may be placed on the prosthesis, on the delivery device, or both, to assist in accurate placement. Using these markers, the medical professional or surgeon implanting the device may make adjustments to the position of the outer sheath, the prosthesis and the relative distances between them. The prosthesis may then be deployed as desired and the implanting catheter, with its tip, inner control wire, and so forth, retracted from the patient.

Figure 40:
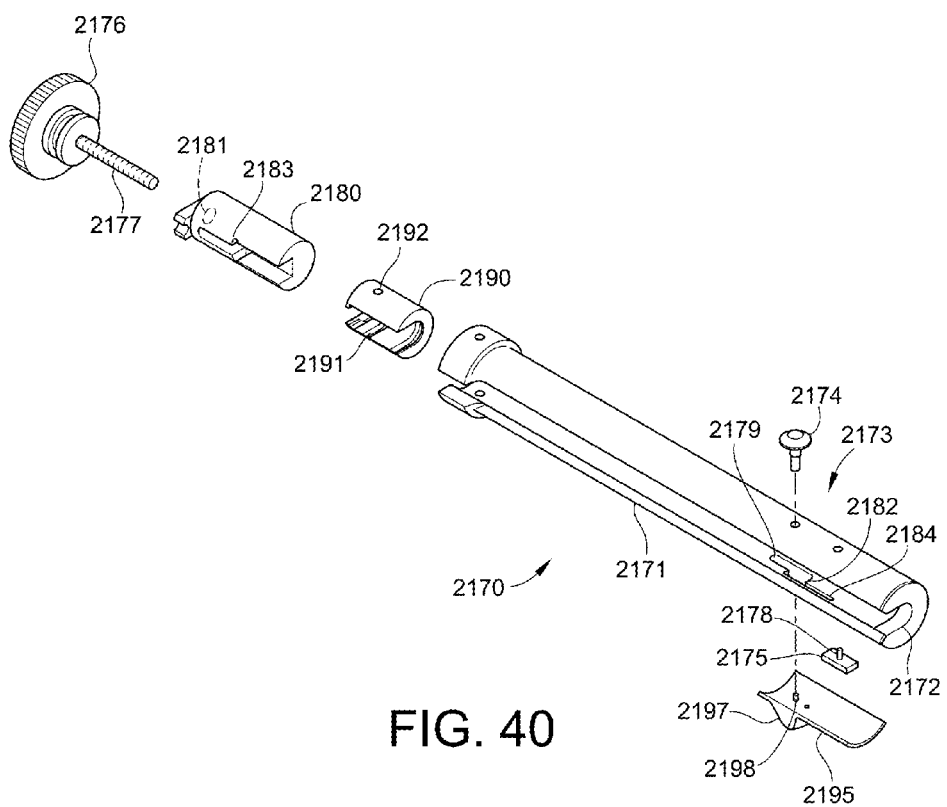
FIG. 40 depicts another embodiment of a control device or handle.

In FIG. 40, another control device 2170 includes a hollow cylindrical body 2171, with a central channel 2172. There is a series of bores 2173 for use with a set pin 2174 to set the position of a front slider 2190 with a hollowed-out portion 2191 for retaining an outer sheath or outer portion of the deployment device. The outer sheath is anchored within slider 2190 and its motion is controlled by a hand actuator 2195 with a thumb grip 2197 for use in moving the slider backward or forwards. The slider 2190 is connected to the hand actuator 2195 via an adapter 2175 and pin 2178. Thus, the slider, and the position of the outer sheath may be retained in place using a bore 2192 in the slider and retaining pin 2174, along with the hand actuator 2195.

Adapter 2175 and pin 2178 connect slider 2190, and an attached outer sheath, to the hand actuator 2195. Pin 2198, also known as a member, on the bottom surface of hand actuator 2195, restrains the movement of the hand actuator to the paths molded into the outer surface of the control device body 2171. These paths include forward track 2184, intermediate track 2182, and rear track 2179. The lengths of the forward and rear tracks are thus fixed or predetermined distances. The forward and rear tracks 2184, 1289 are generally parallel and are separated by intermediate, transverse track 2182.

The control wire of the catheter is connected to a rear retainer 2180 with one or more hollowed-out portions 2183 for securing the control wire or inner portion of the deployment device. The rear retainer 2180 is easily held in place securely and movably by a molded-in retaining nut 2181 and a threaded rod 2177. The handwheel 2176 itself fits snugly into the proximal, enlarged portion of the cylindrical body 2171. The handwheel may be pinned in position and may rotate in place to allow translation of the rear retainer 2180 and thus the inner control wire. The handwheel 2176 and the threaded rod 2177 allow fine adjustments to the position of the control wire with respect to the position of the outer sheath.

In use, the physician or other medical professional will advance the catheter using the non-invasive imaging techniques already described. The prosthesis is advanced to the point where the catheter tip is in the left atrium, while all portions of the prosthesis remain within the outer sheath. The slider 2190 is fixed in a distal position using pin 2174, the forward or most distal orifice of the series of orifices 2173, and orifice 2192 of the slider 2190. At this point, the hand actuator is at its most distal position, and pin 2198 is all the way forward, to the right in right track 2184, i.e., the most distal position.

At this point, the left flange is positioned within the patient's left atrium, still remaining with the outer sheath, and the retainer 2180 is locked in position and not moved further. The outer sheath is then retracted using the slider 2190 and hand actuator 2195, similar to step 6000 in FIG. 27. In one embodiment, the outer sheath is retracted by sliding the hand actuator 2195 straight to the rear and proximally, or to the left in FIG. 40. This movement is allowed by the rearward movement of member or pin 2198 in right track 2184. This movement is a fixed distance, until the pin strikes the rear of the long portion 2184 and the start of transverse portion 2182 of the molded-in paths and can go no further. The length of the long portion 2184 is fixed when the long portion is molded or machined into hollow cylindrical body 2171. The distance is that needed to deploy the left flange of the interatrial pressure vent or prosthesis. The distance may also be that needed to deploy the left flange and the central or valve portion. In one embodiment, this distance is about 7 mm. In other embodiments, the distance may be 5 mm, 6 mm, 8 mm, 9 mm or other desired distance.

After the desired portion has been deployed, the physician may use fluoroscopy or echosound to determine the exact position of the prosthesis with the patient before proceeding. If an adjustment is needed, the prosthesis can readily be retracted into the outer sheath for removal or redeployment at this stage, as will be seen in some of the improved designs for retrieval and redeployment described below.

If continuation is indicated, the surgeon or medical professional will then prepare to deploy the remainder of the interatrial pressure vent or prosthesis. The first step is to rotate the hand actuator 2195 a few degrees to the right so that pin 2198 is now in the other long track 2179. The transverse portion 2182 is only about twice as wide as pin 2198. Rotation of the hand actuator thus does not cause the prosthesis within the patient's heart to translate proximally or distally. The surgeon then moves the hand actuator in a proximal direction, to the left in FIG. 40, further retracting the outer sheath and deploying the right atrium flange into the right atrium of the patient's heart. The length of track 2179 is also a fixed distance, the distance fixed when the track is molded into the hollow cylindrical body 2171. In one embodiment, the distance is 8 mm, a little longer than the length of track 2184. In other embodiments, the distance may vary, as noted above. The distances, or the length of the tracks, may be tailored to fit the patient's anatomy, for example, by determining ahead of time the width of the patient's septum or the dimensions of the patient's heart.

In another embodiment, not shown, the two tracks of predetermined length may be a single length with a pin or other obstacle inserted at a desired point along the length of the track. The pin will prevent further movement of pin 2198 in a proximal direction and will stop the movement of the hand actuator 2195 after it has moved a fixed or predetermined distance, e.g., 7 mm. After the pin is removed, the surgeon or other medical professional may continue to move the hand actuator in a proximal direction along the remainder of the predetermined or fixed length of the track.

As described above there are situations where the deployment may not be satisfactory for any of a number of reasons, and the prosthesis may be removed from the patient. This situation may become apparent before the procedure has been completed. In some cases, the need for removal may become apparent while the guidewire and/or catheter delivery system with which the procedure was begun is still in place, such, for example, the embodiments described in connection with FIG. 19A. In other cases, it may be necessary to introduce a guidewire to begin a removal procedure, while in other cases a guidewire is not used. If the prosthesis has not been fully deployed, removal may be accomplished by retracting the control wire attached to the prosthesis, or by advancing the outer sheath over the prosthesis. Removal is then accomplished by merely withdrawing the outer sheath and all its components. Once the prosthesis has been deployed, different techniques may be needed, as depicted above, and now below. The method of retrieval will depend on the characteristics of the device. Some methods of retrieval have already been discussed above. Below are some other methods.

Figure 41:
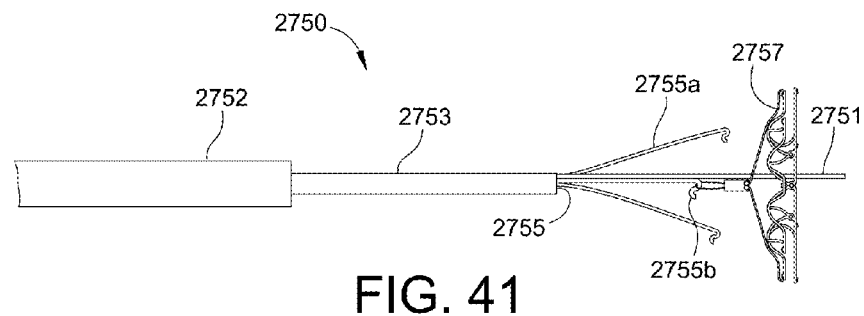
FIG. 41 depicts a retrieval device useful for retrieving a deployed prosthesis.
Figure 42:
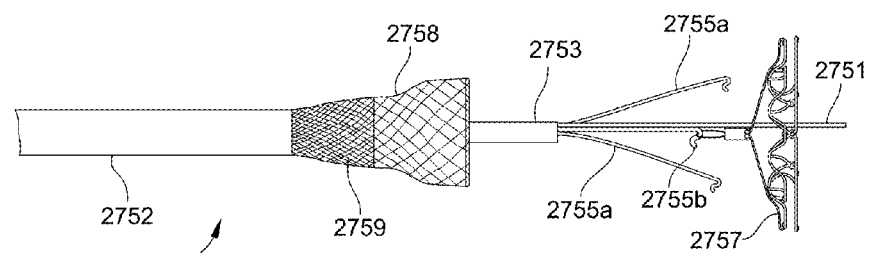
FIG. 42 depicts the retrieval device of FIG. 41 with a retrieval basket deployed.
Figure 43:
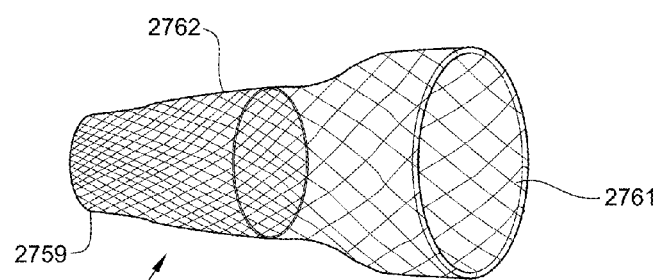
FIG. 43 depicts a closer view of the basket of FIG. 42.

Retrieval of the fully deployed prosthesis is depicted in FIGS. 41 and 42, while the tools used for retrieval are depicted in FIGS. 41, 42 and 43. The retrieval device 2750 is advanced to the desired location within the patient along a guidewire 2751. Components of the retrieval device 2750 include an outer sheath 2752, an inner sheath 2753 and a grasper 2755, such as the three-prong grasper depicted in FIG. 41. In one embodiment, the outer sheath has an outer diameter of about 21 Fr (about 7 mm) while the inner diameter is about 6.7 mm. In the figure, the grasper 2755 has caught the prosthesis 2757 with one of the three prongs 2755*a* and its protruding hook or tab 2755*b*. As noted, the tab 2755*b* may be useful for insertion into an orifice of a prosthesis leg or strut, as seen in FIG. 2A, for retrieval of the prosthesis. In FIG. 2A, legs 103*x* of the flanges meet at a juncture, an apex or an end of two of the legs. Each flange of the prosthesis includes two or more legs, usually in pairs, each pair also forming an apex where the legs meet.

It will be recognized that one or more components of the retrieval device may include radiopaque components or markers for better visibility by non-invasive techniques, such as fluoroscopy, echo-sound, and so forth. In one embodiment, one or more of the prongs of the grasper may be made of a radiopaque metal or material, such as the metals themselves or alloys of gold, platinum, palladium, tungsten and tantalum. In another embodiment, the prongs of may include one or more markers, e.g., a small dot or implant of a radiopaque material or echogenic material that will be easily detected by x-ray, fluoroscopy, echosound or other suitable non-invasive imaging technique.

In use, the retrieval device is advanced to the desired location within the patient, using non-invasive techniques and radiomarkers, echogenic markers, or other indicators on the device. The user has three controls to manipulate the device, in addition to advancing and retracting the entire device 2750, e.g., while the internal portions are contained within the outer sheath 2752. The inner sheath 2753 has a control wire (not shown) as does the grasper 2755 (control wire not shown). The retrieval basket 2758, depicted in FIGS. 42 and 43, also is advanced and retracted using its control wire (not shown), as will be understood by those with skill in minimally-invasive surgery arts. The grasper 2755, as the innermost component and nearest the guide wire, may have a micro-rail, i.e., a lumen or longitudinal cavity, to follow precisely the path of the guide wire. In other embodiments, it is possible to assemble the retriever so that an inner sheath is not used. For example, if the basket is assembled proximally from the grasper, and the grasper sufficiently distal from the basket, an inner sheath and its control wire may not be needed.

The user advances the device 2750 and outer sheath 2752 near the desired point and verifies the location. The user may then advance the inner sheath 2753 out from the outer sheath 2752. The user may then advance the grasper 2755 from the inner sheath and maneuver the grasper and the inner sheath, or the grasper or the sheath separately as desired, to grasp the prosthesis 2757 with the prongs of the grasper. There is no separate closing control for the grasper. The user simply maneuvers the grasper in such a manner that when the grasper is retracted, the prongs approach each other in a manner to grasp and retrieve the prosthesis. The control wire or control handle for the grasper in one embodiment has a locking feature that allows the surgeon to close the grasper and not be concerned about further manipulation of the grasper, except for withdrawal. In one embodiment, the grasper is a three-pronged Hobbs forceps, available from Hobbs Medical, Stamford Springs, Conn., USA. In another embodiment, the grasper or the retrieval device may also have a fluid channel for irrigating the retrieval site, much as the deployment catheter has a fluid channel.

Other graspers or retrievers may be used instead, such as those with four prongs, or even other retrieval devices, such as a single prong or tab. The single tab or prong may be in the form of a short cylinder, suitable for insertion in an orifice of the struts or legs of a flanged atrial septum implantable device, as shown in FIGS. 2A and 7B. The user maneuvers the grasper or tool so that the implantable device is hooked by one or more of the orifices, and then uses this connection to retrieve the implantable device.

In other embodiments, the implanted device may have one or more legs of the right atrium flange longer than most legs of the flange, making it easier to grasp one or more of the legs or struts, as shown above in FIGS. 7B and 7C. In these embodiments, the grasper may more easily approach the implanted device and grasp it, whether a multi-prong grasper is used, or whether a single tab or prong is used to grasp the longer leg. In other embodiments, the implanted device may have a flange more suited for retrieval, such as the conical flanges depicted in FIGS. 22 and 23. In these embodiments, it is relatively easy for a user to grasp the conical apex 450 for retrieving the implant via a grasper, as discussed above. Retrieval is more user-friendly also, since the shape of the implant lends itself to being pulled in the proximal direction, i.e., towards the outside of the body of the patient.

The inner sheath and the grasper are then retracted, as shown in FIG. 42, and the basket 2758 is deployed by advancing its control wire (not shown). Basket 2758 may be made from metal mesh, such as Nitinol or other medically-acceptable, shape-memory material. Nitinol is a good choice because it can be trained to assume the desired basket form as it deploys from the outer sheath. There may also be a barrier layer 2759 to help prevent any undesired piercings by wires or components of the prosthesis. The barrier layer may be made of a suitable medically-acceptable cloth, such as polyester (Dacron®, for example), or other material. Once the prosthesis is grasped and the basket deployed, the grasper 2755 and the prosthesis may be retracted into the basket by advancing the basket or retracting the grasper and prosthesis, or both. The basket, grasper and prosthesis are all withdrawn into the outer sheath, which may then be safely removed from the patient with the retrieved prosthesis.

As noted, basket 2858 may be made from metal mesh, such as a mesh made from Nitinol or other wires. In one embodiment, Nitinol wires may be 0.003 inches in diameter (about 0.08 mm in diameter); in another embodiment, the wires may be 0.020 inches in diameter (about 0.51 mm in diameter). Other embodiments may use flat wires or ovate-shaped wires. Basket 2759 is made from a single layer of Nitinol mesh. Other embodiments, such as the one depicted in FIG. 43, may use a basket 2760 having two layers, i.e., a basket including an inner layer 2761 folded over to form a second, outer layer 2762. The two-layer basket may be better at preventing objects within the basket from protruding outside the basket.

Retrieval Devices with Dilators

It is clear that the outer sheath of a retrieval device, and all components, should be as small and as thin as possible for patient comfort. Accordingly, in one embodiment, the outer sheath has an outer diameter of about 18-20 Fr. In one embodiment, the deployed basket has a largest outer diameter of about 20 mm, which is quite large compared to a 20 Fr outer catheter outer diameter. In other embodiments, the sizes may be larger or smaller, as needed. It is clear from inspection of the basket in FIGS. 42 and 43 that the space used to accommodate devices for retrieving the prosthesis will be somewhat greater than the space typically used to deploy the prosthesis.

Figure 44:
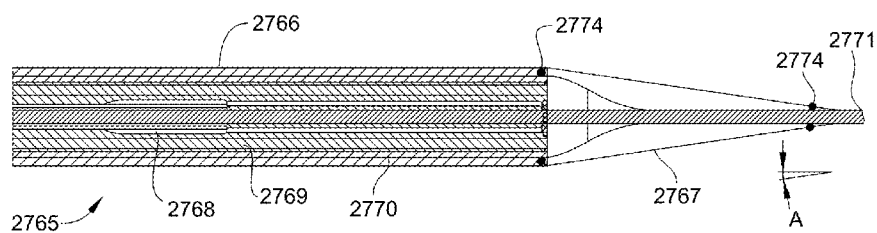
FIGS. 44 and 45 depict retrieval devices using dilators.
Figure 45:
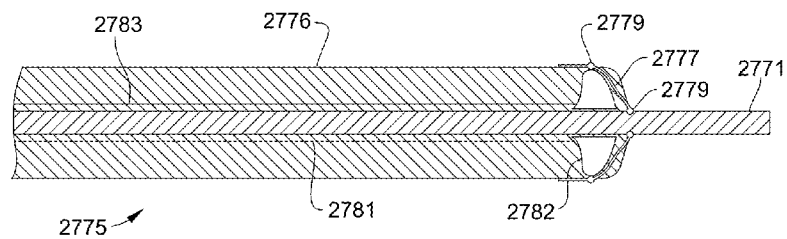

In order to ease the transition, a retrieval device may use a dilator on its distal end. While the tip is nominally termed a dilator, it does not expand, rather its purpose is to maintain the dimension of its widest portion while the forceps or other device within the sheath is deployed behind the tip. Two embodiments are depicted in FIGS. 44 and 45. In FIG. 44, retrieval device 2765 includes an outer sheath 2766 and device tip 2767. The device is introduced into the patient via a guidewire 2771. Retrieval device 2765 includes a grasper or forceps 2768, a jacket or outer covering 2769, as discussed above, and a braided capture sleeve 2770, such as a capture sleeve made from Nitinol mesh. Retrieval device 2765 also includes X-ray or echogenic markers 2774 in useful locations, such as at the distal end of the outer sheath 2766 or the dilator 2767.

In use, the device tip is deployed when the user pushes the forceps 2768 distally, or withdraws the outer sheath 2766 in a proximal direction. The device tip is constrained to move axially along the guidewire 2771, and its location will thus remain in the control of the medical professional deploying or retrieving the prosthesis.

The embodiment of FIG. 44 features a device tip with a rather long transition section. When the user has advanced the retrieval device to the desired location within the patient, the sheath is withdrawn in a proximal direction, or the forceps is advanced in a distal direction to deploy the forceps and the basket. Because the device tip has a very gradual transition, the movement and the disruption to the patient are minimal. In this embodiment, the angle A of the device tip may range from about 10 degrees to about 30 degrees. Other angles may be used. The length of the transition section may vary from about 15 mm to about 25 mm Other lengths may be used.

Another embodiment is depicted in FIG. 45. In this embodiment, the retrieval device 2775 also has an outer sheath 2776 and a separable device tip 2777. As shown in this view, the angle of the device tip is much greater than the previous embodiment, while the length of the device tip is much shorter. Retrieval device 2775 includes an inner sheath 2781 and a balloon 2782 and an inflation/deflation lumen 2783. Retrieval device 2775 also includes X-ray or echogenic markers 2779 in useful locations, such as at the distal end of the outer sheath 2776 or the dilator 2777. The length of the transition section may vary from about 5 mm to about 120 mm. Other lengths may be used.

In this embodiment, the retrieval device is used with the device tip and the internal balloon that is inflated to create a space for the retrieval device. In this embodiment, the retrieval device 2775 does not include a retrieval forceps at the outset. After the device tip is deployed and the balloon is expanded to create a space, the balloon is deflated and retracted and a retrieval forceps and basket are exchanged along the guidewire for the balloon and the inflation equipment. The balloon may be expanded by inflating the balloon to a pressure from 6 atm to 20 atm.

Some Designs for Retrievability and Redeployability

FIGS. 46-49 depict additional embodiments of interatrial implantable prostheses which have been designed for easier retrieval and also for redeployment once they have been retrieved. A first improved embodiment 100*a* is depicted in FIGS. 46A-46B. The drawings depict several views of body element 100*a*, showing how the ends of flange segments 102*a*-102*h*, 103*a*-103*h* are rounded at their distal ends 115 and 116 to reduce stress concentrations against the interatrial septum after placement. These distal ends, or apices where the strut legs intersect, include bores 109*a*, 109*b*, 110*a*, 100*b* into which radiopaque or echogenic markers 118*a*, 118*b* and 119*a*, 119*b* can be positioned. Using these markers, the device may more easily be visualized using radiographic imaging equipment such as with x-ray, fluoroscopy, magnetic resonance, ultrasound or other imaging techniques. Markers as disclosed herein may be applied to the ends of any segments, not just those with holes or eyelets therein. Radiopaque or echogenic markers 118*a*, 118*b*, 119*a*, 119*b* can be swaged, riveted, adhered, or otherwise placed and secured into the bores and dimensioned to be flush with the contours of the segments.

The retrieval legs described herein may be made from nitinol wire, stainless steel wire (such as grades 304, 304L, 316 and 316L, among others), nylon sutures (e.g., polyamide), polypropylene sutures (e.g., Prolene®), or any other material that is medically acceptable and resistant to stretching. Materials that assume a known shape are desirable, as are materials that are visible under echographic or x-ray imaging conditions. The legs may thus take on a filamentary, thread, suture or wire shape, and may comprise a single thread or wire, or more than one suture, filament or wire. Wires made from nitinol or other metals may have a thickness from about 0.004 to 0.025 inches (about 0.11 to 0.64 mm). Sutures may range from about 8-0 to 7 (U.S.P. designations), i.e., from about 18 to 40 AWG, or even a little thinner than 40 gauge. The diameters of such sutures will range from about 0.04 mm to about 0.8 mm, and may apply to collagenous materials, synthetic absorbable materials, and synthetic non-absorbable materials.

Figure 46A:
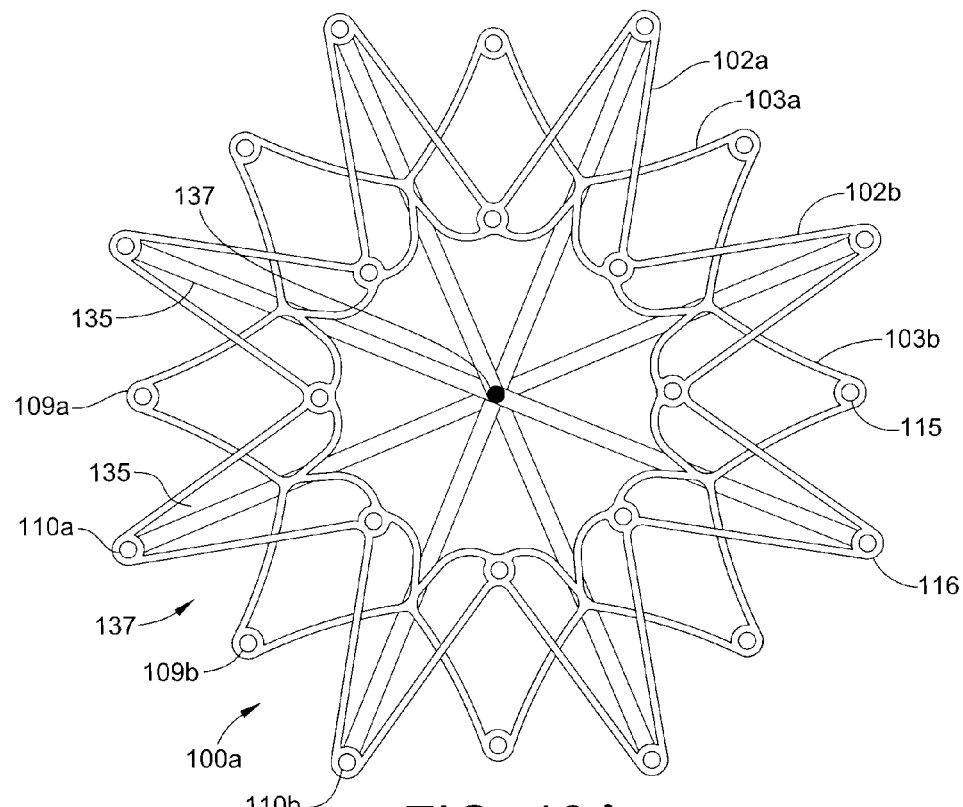
FIGS. 46-49 depict additional embodiments of an implantable prosthesis with retrieval and redeployment features.

FIG. 46A depicts several retrieval legs 135 joined to a central nub 137. The retrieval legs may be made of nitinol wires or of sutures and may be connected to the bores 109 of right atrium flange legs 102a-h, or be formed integrally with the right atrium flange legs, and extend to a central juncture or nub 137. Portions of the sutures or wires may be made from radiopaque materials or MR-visible materials so that the nub 137 is visible using non-invasive imaging techniques. At a juncture, the retrieval legs may be joined into a short tube 175 and crimped into tube 175. A single suture or wire loop 177, or more than one loop, may then extend above the crimp for joining to the inner catheter control wire, or for grasping by a retrieval device. A typical crimp tube is visible under x-ray or echographic (sound) imaging. Thus, the tube may be stainless steel or radiopaque plastic. One embodiment of the tube has a 0.035 inch i.d. (0.90 mm), 0.008 in (about 0.2 mm) wall thickness, and about a 0.050 inch (1.3 mm) o.d. Other embodiments may be used.

Figure 46B:
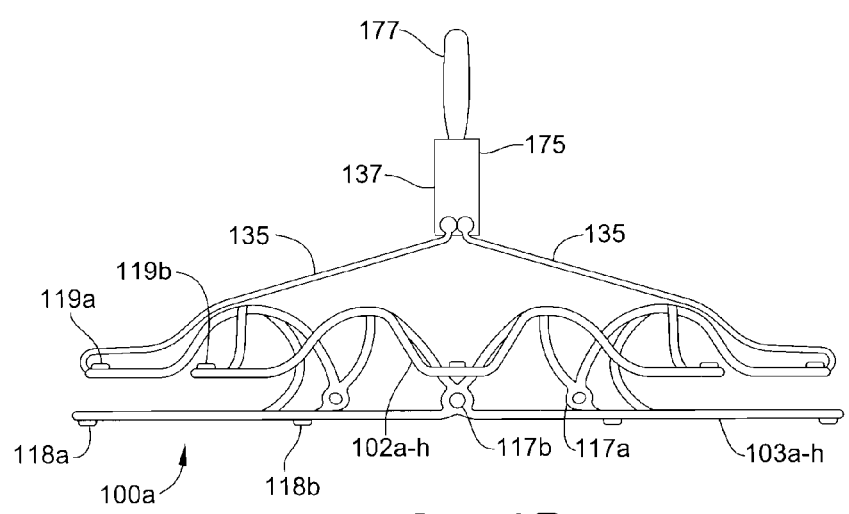

Retrieval loop 177 may be radiopaque or echograpically visible, or may include one or more threads that are radiopaque or echo-visible, such as a gold or platinum thread. The retrieval legs of this design do not interfere with the function of the prosthesis but do extend a short distance proximally, as shown in FIG. 46B. Thus, a filter, such as a thrombus filter, is described. In addition, the flow control elements described above may be used in the central portion of the prosthesis. These include the bivalve of FIG. 26, or a tri-lobal valve, or other embodiments, such as those discussed above with respect to FIGS. 29A-29C.

The prosthesis of FIGS. 46A-46B may be deployed from a catheter, as described above, and is retrieved in a similar manner, described below. The retrieval device secures suture or wire 177 from the central tube or crimp 175 with an appropriate end-effector, hook or grasper on its inner control wire. The inner wire of the retrieval device is then withdrawn proximally, drawing the sutures or wires into a catheter, collapsing the right atrium flange, and then drawing the remainder of the prosthesis into the catheter. The device may then be withdrawn from the patient, or may also be redeployed, perhaps in a better position.

Figure 47A:
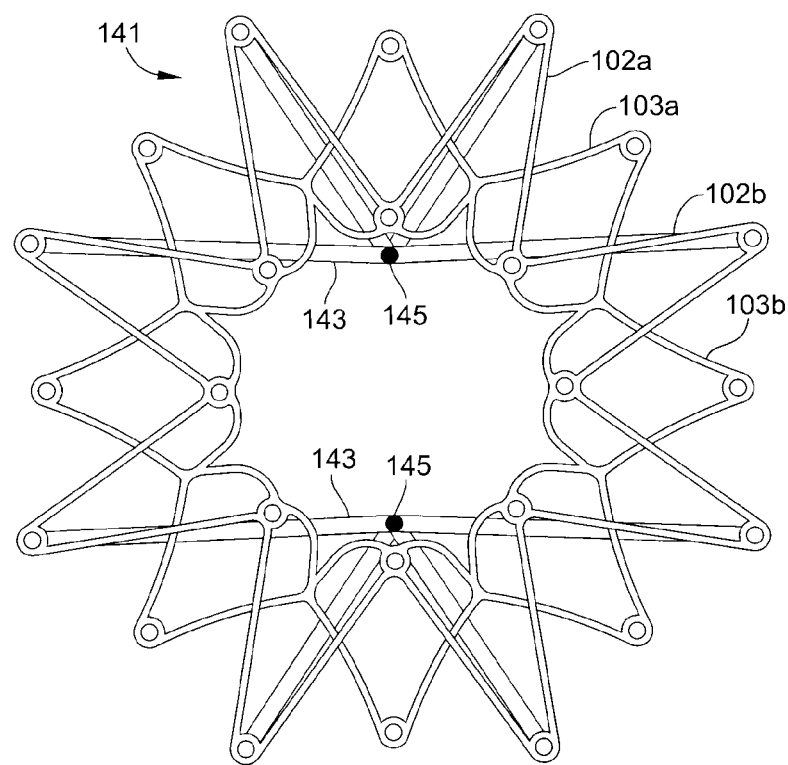
Figure 47B:
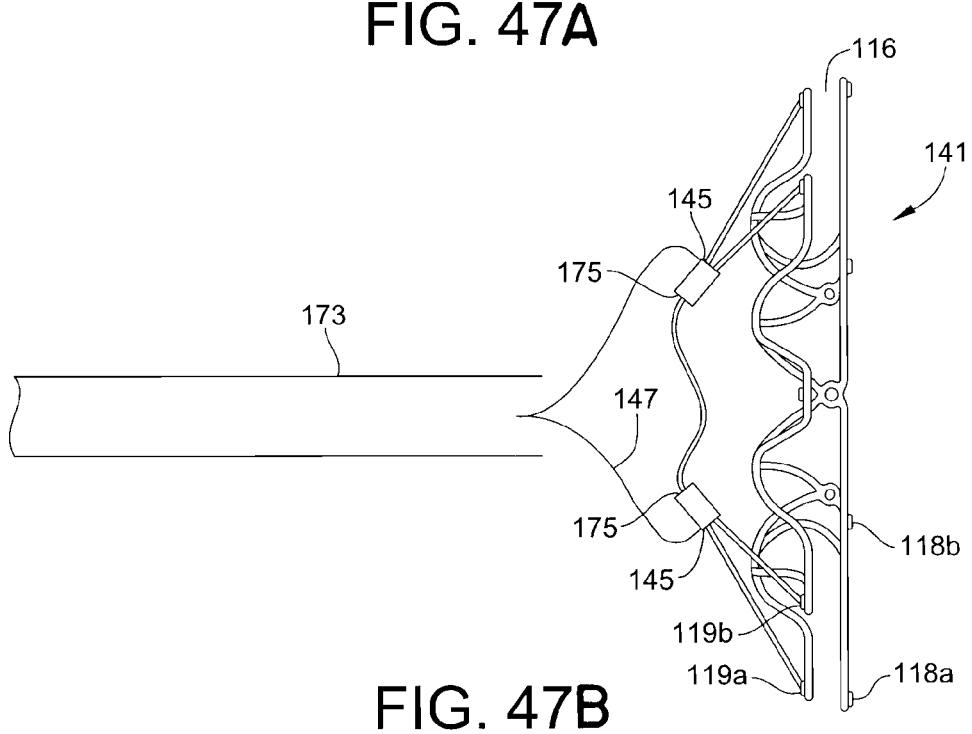

A second design specifically for retrievability is depicted in FIGS. 47A-47B. Prosthesis 141 is similar to prosthesis 100a of FIGS. 46A-46B. FIG. 47A is a top view, depicting prosthesis 141 with retrieval wires or sutures 143 connected to the apices 102a-h of the right atrium flange. In this embodiment, there are two central nubs or points 145, each for about 180 degrees of the flange. The retrieval wires 143 are tied together to form a nub 145 on each side of the right atrium flange. As seen in FIG. 47B, the nubs 145 are then joined with a crimp tube 175, with a loop 147 of one or more retrieval wires or sutures joining the two crimp tubes 175 and sides of the prosthesis for removal. The retrieval wires or sutures, and the nubs, may be made from the materials described above. As depicted in FIG. 47B, the wires or sutures avoid the central area of the prosthesis when deployed from catheter 173 and thus do not interfere with the functioning or deployment of the valve. The wires or sutures are available to assist in withdrawal and removal or redeployment of the prosthesis if needed. Retrieval loop 147 may be radiopaque or echographically visible, or may include one or more threads that are radiopaque or echo-visible, such as a gold or platinum thread.

Figure 48A:
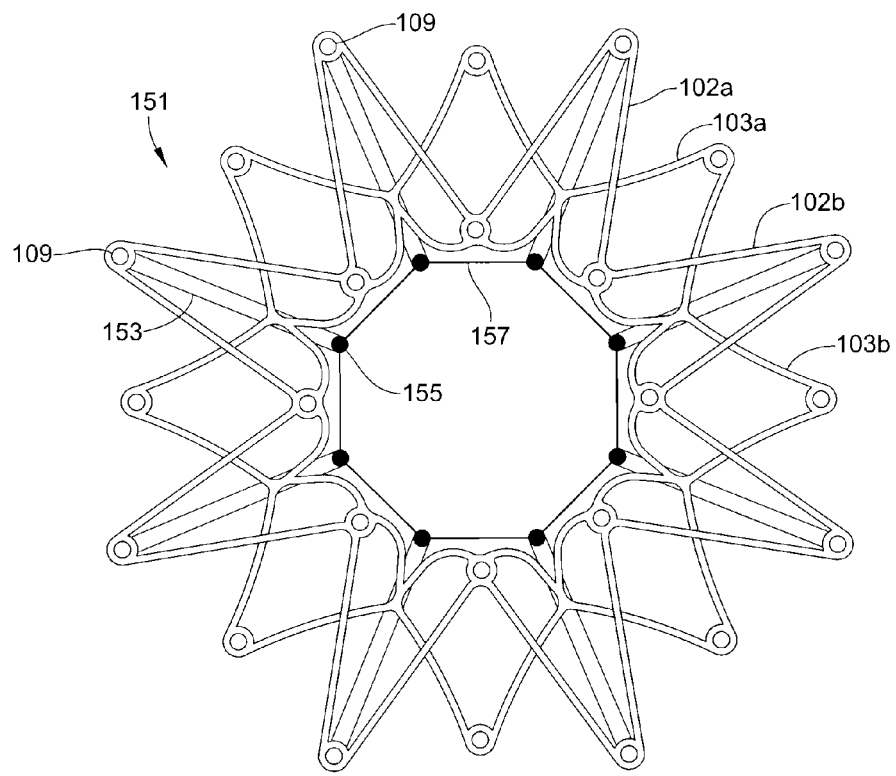
Figure 48B:
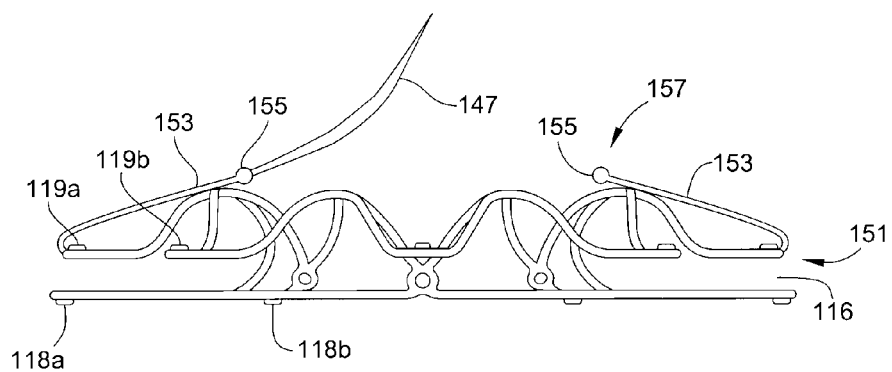

A third embodiment of a design for retrieval is depicted in FIGS. 48A and 48B. In this embodiment, prosthesis 151 is very similar to prosthesis 141 above, including retrieval sutures or wires 153 from bores 109 of the right atrium flange apices 102a-h, to a central annular retrieval suture or wire 157. Each retrieval suture or wire 153 is joined to the central retrieval thread 157 at a juncture 155. The junctures may simply be suture tie-offs; alternatively, the junctures could be orifices in central wire 157 for joining retrieval sutures or wires 153. In some embodiments, an additional retrieval suture or wire 147, suitable for non-invasive imaging, may be tied to the central thread at least at one point for grasping by a retrieval device.

Figure 49:
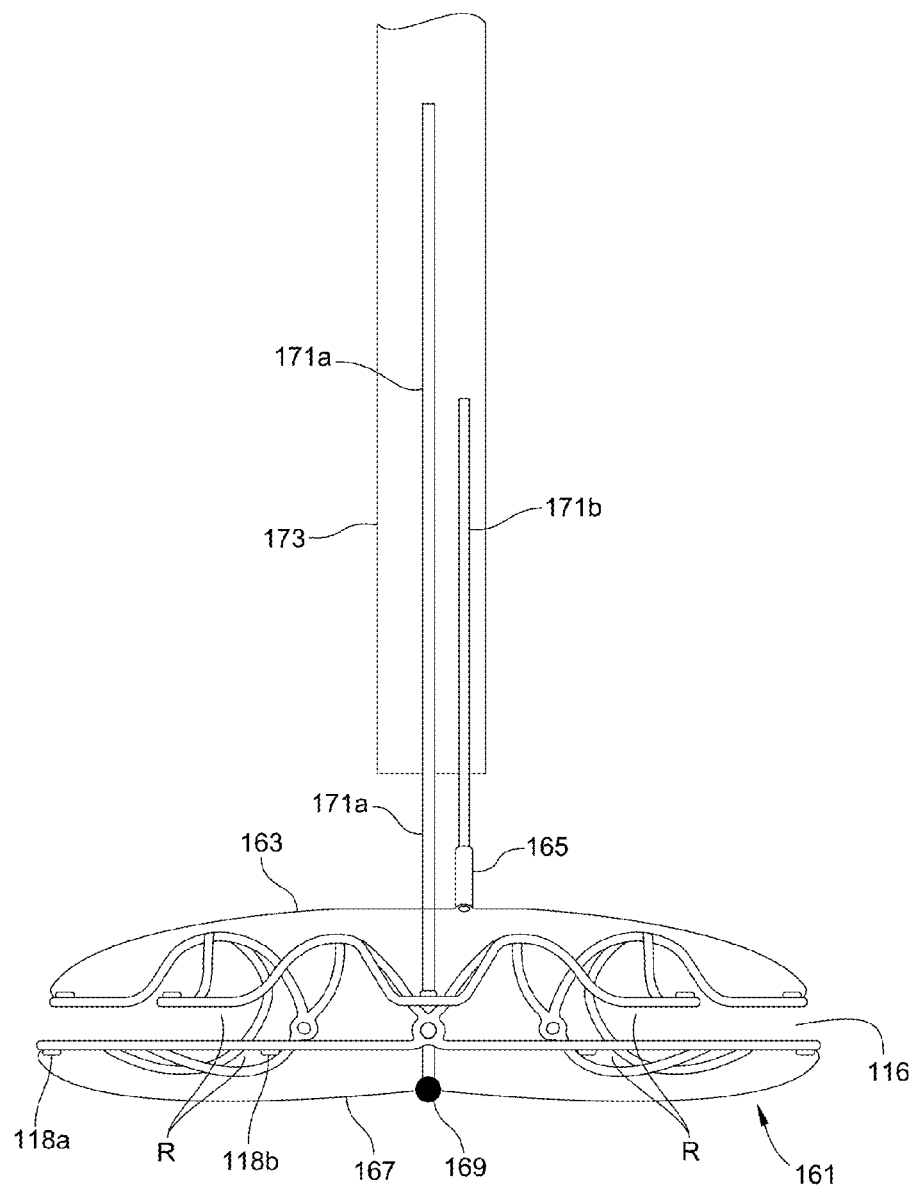

A fourth embodiment of a prosthesis 161 designed for retrieval and redeployment is depicted in FIG. 49. Prosthesis 161 is similar to prosthesis 100a, described above. In the fourth embodiment, there is a retrieval wire or suture 163 secured to each apex 102a-h of the right atrium flange and there is a retrieval wire or suture 167 secured to each apex 103a-h of the left atrium flange. The right atrium flange retrieval wires or sutures are joined to a central point or nub 165 and secured to an inner control wire 171b of a catheter 173. Central nub 165 may be a crimp tube and retrieval suture or wire, as described above. The left atrium flange retrieval wires or sutures are also joined to a central nub 169 and secured to an inner control wire 171a. Central nub 169 may be a crimp tube and retrieval suture or wire, as described above. To deploy the prosthesis 161, the medical professional positions the prosthesis in the correct position within the patient and then releases the left atrium flange, disengaging the inner control wire from nub 169, and also releases the right atrium flange, disengaging the inner control wire from nub 165.

If retrieval is desired, the grasper or retrieval device grasps or engages both nubs 165, 169, preferably separately, with inner control wires 171a, 171b, or with graspers attached to them, to collapse the respective flange and withdraw the prosthesis, as described below. In one embodiment, left atrium flange legs 103a-h have a greater radius R at their root and may even approach the septum wall at an obtuse angle, i.e., as shown in FIG. 49. This larger radius will make it easier to collapse the legs and struts of the flange. Once the prosthesis is withdrawn, it may be redeployed to a better position within the patient. Prosthesis 161 is capable of having both its left and right atrium flanges collapsed. If separate control wires are used, one for each flange, the flanges may be collapsed separately in time, thus requiring less force to withdraw.

Stents for Providing Coronary Sinus Pressure Relief

Per the discussion on heart failure, and consistent with the present invention, it may be beneficial for some patients to relieve pressure in the left atrium. One way to accomplish this is to provide communication between the left atrium and the coronary sinus. The coronary sinus and its tributaries receive approximately eighty-five percent of coronary venous blood. The coronary sinus empties into the posterior of the right atrium, anterior and inferior to the fossa ovalis. A tributary of the coronary sinus is called the great cardiac vein, which courses parallel to the majority of the posterior mitral valve annulus, and is superior to the posterior mitral valve annulus.

Thus, by providing communication between the left atrium and the coronary sinus, inappropriate pressures in the left atrium can be averted, with the blood diverted to the most appropriate blood vessel possible, the coronary sinus. In cases of mitral valve failure or disease, it is possible that providing this communication could allow the patient to put off or forgo mitral valve repair. This could provide additional quality of life to the patient, while avoiding surgery that is more involved and more delicate.

Figure 50:
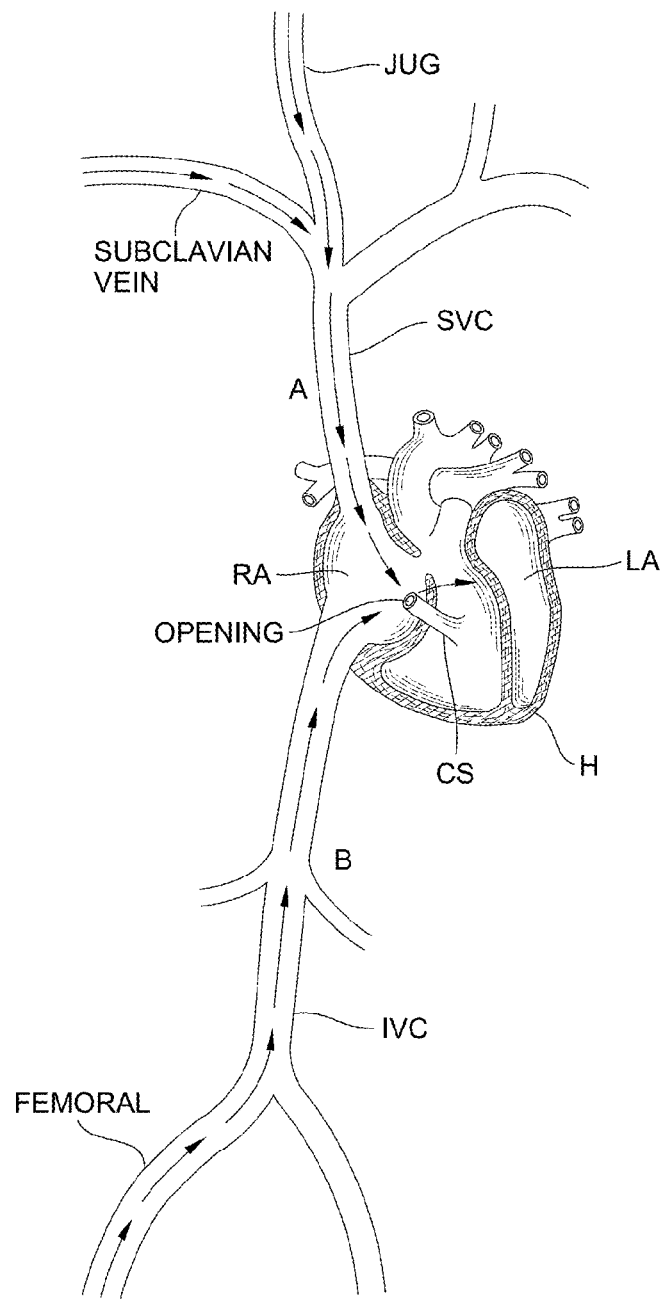
FIG. 50 depicts anatomy of a human being and a human heart, with particular focus on the pathways and natural lumens of the body.

Embodiments of the stent described herein may be placed via minimally-invasive surgery, such as through endoscopic or percutaneous (vascular access) routes, or by traditional surgical methods. Minimally invasive procedures are more easily tolerated by the patients, who may also recover much more quickly from the procedure. In embodiments where the device is implanted into the atrial wall via a minimally invasive procedure, a catheter may be used, as shown generally in FIG. 50. A catheter, such as an introducer catheter is introduced through a jugular vein or a subclavian vein, through the superior vena cava (SVC), along the path of arrows A, and into the coronary sinus CS of the heart H. It is also possible to place the catheter via a femoral vein, through the inferior vena cava (IVC), along the path of arrows B, and into the coronary sinus.

As is well known to those with skill in surgical arts, it is useful to first define the pathway via a guidewire, such as a 0.035 inch diameter (about 0.9 mm) guidewire or 0.038 inch dia. (about 1 mm) guidewire. Guidewires of other diameters may be used as needed or desired. The catheters may be maneuvered to their locations by carefully following the appropriate guidewire. It is also well known to those with skill in surgical arts that other pathways for the catheter may be used, such as through the pulmonary veins, or even through arterial pathways. If patient anatomy suffices, however, the easier method is to go through the route of the SVC as discussed above.

Figure 51:
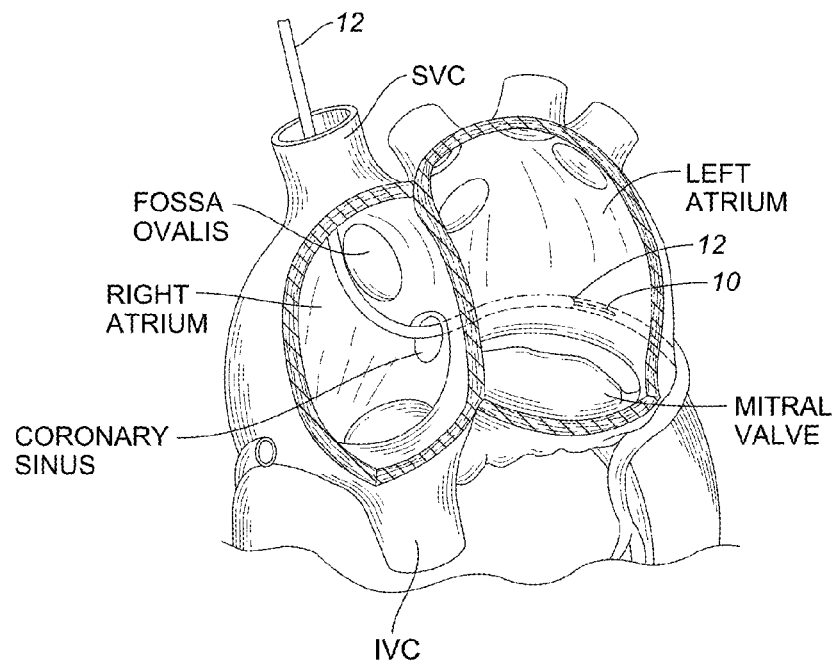
FIG. 51 depicts a closer view of a heart and how guide wires and catheters may be maneuvered in and around the heart to deploy embodiments.

FIG. 51 depicts one method of deploying the stents described herein. In FIG. 51, a guide wire 10 is introduced through the jugular vein (not shown), through the superior vena cava and into the coronary sinus. Once the wire guide provides a path, an introducer sheath 12 may be routed down the guide wire and into position in the coronary sinus. The introducer sheath or introducer catheter is used to provide vascular access. The introducer sheath may be a 16 F or less hemostasis introducer sheath. Alternatively, the subclavian vein may be used. In one embodiment, introducer sheath 12 may be about 30 cm long. The guidewire may be somewhat longer for ease of use. In some embodiments, the introducer catheter may also function only as a dilator and an assistant for preparing an opening in the wall of the left atrium. In these embodiments, a separate placement catheter will be used. In other embodiments, the introducer catheter may be used as the placement catheter also.

Since the coronary sinus is largely contiguous with the left atrium, there are a variety of possible acceptable placements for the stent. The site selected for placement of the stent, may be made in an area where the tissue of the particular patient is less thick or less dense, as determined beforehand by non-invasive diagnostic means, such as a CT scan or radiographic technique, such as fluoroscopy or intravascular coronary echo (IVUS).

Figure 52:
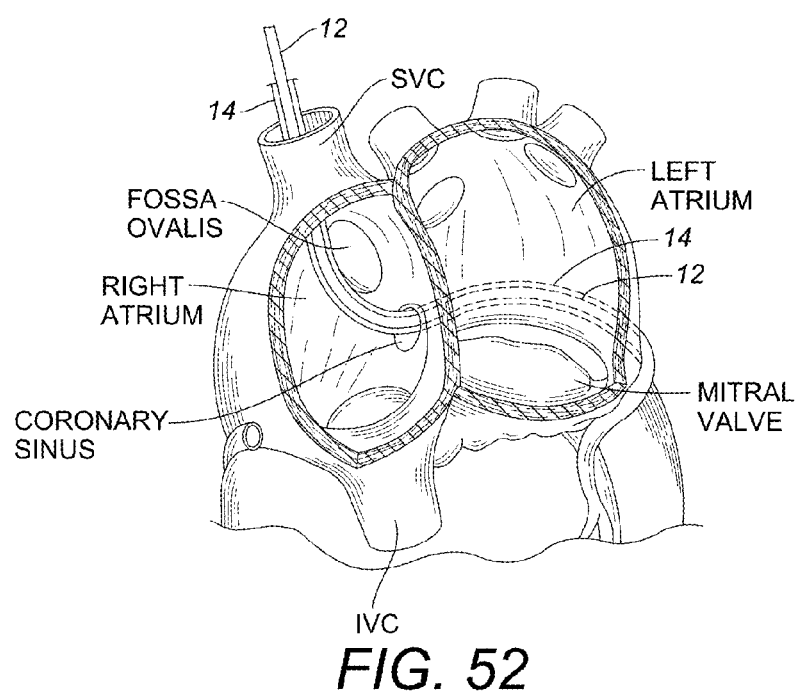
FIG. 52 depicts a first catheter extending from the superior vena cava to the coronary sinus of the heart.
Figure 53:
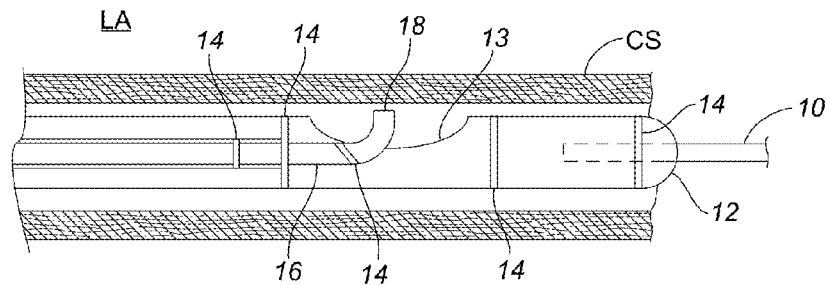
FIG. 53 depicts an ablative catheter in the coronary sinus for creating an opening into the left atrium of the heart.

In FIG. 52, a bending catheter 16 is depicted, guide wire 10 is still in place but is not shown for clarity. In one embodiment, bending catheter 16 may be about 145 cm long. A closer look at the introducer catheter 12 and the bending catheter 16 is depicted in FIG. 53. The introducer catheter 12, equipped with a peripheral opening 13 and at least one marker 14 for radiographic or echogenic location, is shown within the coronary sinus. As noted, the wire guide 10 is still in place. In one embodiment, bending catheter 16 is about 145 cm long and has a very flexible or floppy tip 18 for precisely positioning the catheter. In one embodiment, the tip 18 is capable of a 90° bend so that the medical professional has very close control of its location and can easily use the catheter in the desired location. Bending catheter 16 is also equipped with one or more echogenic or radiographic markers 14 near the tip so its location may be discerned by non-invasive means, such as fluoroscopy or ultrasound techniques. Catheters with very flexible, e.g., floppy 90° distal tips, are available from Baylis Medical Company, Inc., Montreal, Canada.

Figure 54:
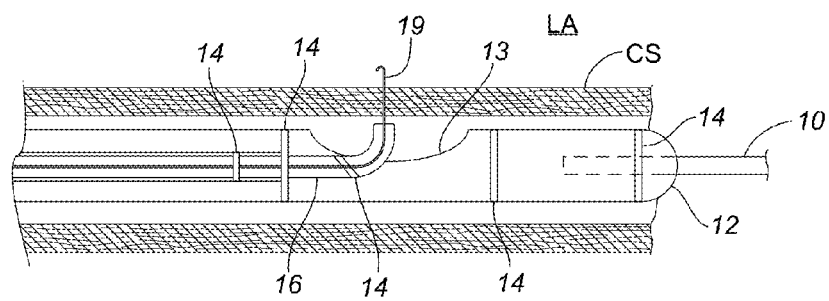
FIG. 54 depicts the ablative catheter creating the opening.

As further shown in FIG. 54, once the bending catheter 16 and very flexible tip 18 are in the proper position, an RF wire 19 will be placed into position through catheter 16 and used to ablate the tissue and to penetrate the wall between the left atrium and the coronary sinus, which is relatively delicate tissue. Care should be taken, however, that tissue remains integral with the wall and that no loose tissue is created when the opening is made.

For example, bipolar or monopolar radio-frequency (RF) energy may be applied to the desired area to ablate or vaporize tissues in the area to form an opening. Several techniques in this area of described in a copending provisional patent application assigned to the assignee of the present application and entitled "Interatrial Pressure Relief Shunt," and filed on Feb. 10, 2011, U.S. Prov. Pat. Appl. 61/441,546, the contents of which are hereby incorporated entirely by reference and relied upon. Additional precautions may be taken in certain of these techniques, such as providing a grounding pad for the patient at least when using monopolar electrical equipment.

Piezoelectric ultrasound techniques and piezoelectric ultrasound sensors or sensor arrays in the desired abrading area, also discussed in the above-mentioned patent document, may instead be used. Typically, DC equipment is used for RF techniques and equipment while AC equipment is used for ultrasound or piezoelectric equipment. The area in the immediate vicinity where ablating is to take place may be protected by heat transfer equipment. For example, cooling coils may be delivered by suitable catheters and placed in the area, such as in an annular ring surrounding the electrodes or sensors that deliver the ablating energy. Cooling fluids, such as saline, may be pumped through the cooling coils to counteract the very hot temperatures generated by the ablating devices. Ablative equipment is available, for example, from Baylis Medical Company, Inc., Montreal, Canada.

Figure 55:
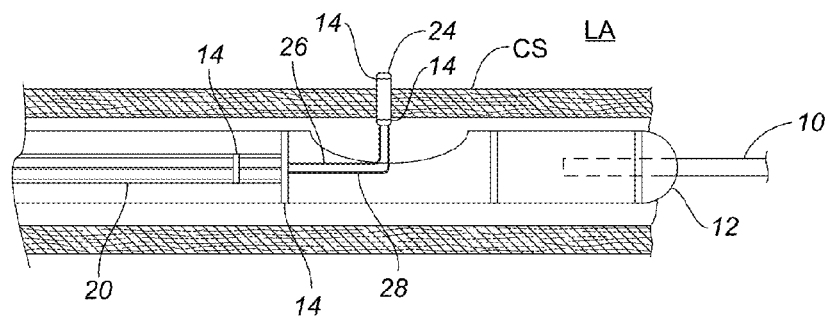
FIG. 55 depicts a balloon catheter for expanding the opening.

In one embodiment, the opening made in the atrial wall by ablation may then be enlarged. The RF wire 19 with its flexible tip may be removed through sheath 16 and a balloon catheter 20, inserted, through sheath 16 as shown in FIG. 55. Balloon catheter 20 may also be equipped with markers 14. In this technique, balloon catheter 20 with tip 22 and with a balloon 24 is guided to the opening and the balloon is inserted into the opening between the coronary sinus and the left atrium. Using inflation lumen 26, the balloon is inflated and the opening enlarged to the desired diameter. When the opening has been made, the balloon may be deflated through deflation lumen 28 and then removed through the sheath 16. Alternatively, any suitable dilator may be used, such as a Mullins™ dilator with a needle or cutting edge or a conical distal tip of a dilator catheter. The method employed must be very reliable and very controllable by the medical professional in all stages of its deployment. The size of the opening desired may range up to about 8 mm, although smaller openings may also be suitable.

Figure 56:
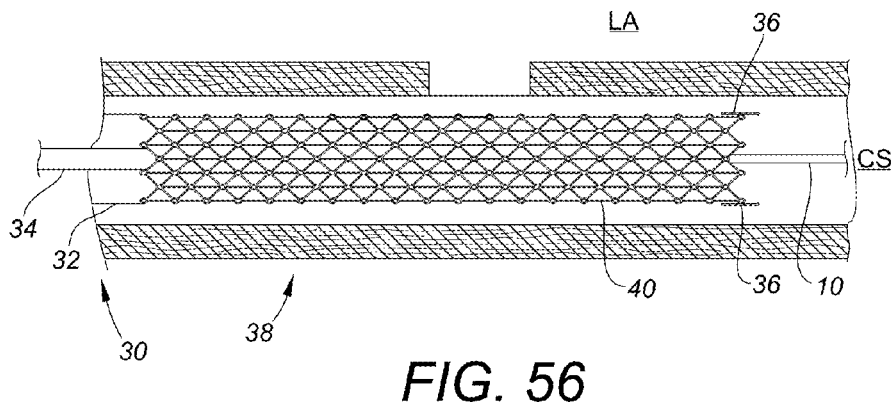
FIG. 56 depicts an embodiment for an implantable device used for coronary sinus pressure relief, the device being in a non-deployed state.

Once the opening is made between the left atrium and the coronary sinus, a deployment catheter 30 is used, as depicted in FIG. 56. Similar depictions are seen in FIGS. 8-11 above, in which the prosthesis is in a compact or folded state prior to deployment. The deployment catheter 30 may be used with a guide wire 10 only or it may be used with a sheath catheter 12, as seen above. In the figures that follow, a sheath catheter is not shown, for simplicity, but it may be used for ease of insertion and then withdrawn before deployment of the stent. The deployment catheter 30 includes an outer sheath 32 and an inner control wire 34. Outer sheath 32 may also include one or more radiographic or echogenic markers 36 so the sheath may be easily seen by non-invasive techniques and its location adjusted as need for proper placement.

Deployment catheter 30 also includes a stent 40 folded up within the catheter. As detailed below, stent 40 may be in generally in a shape of a T, with a longer portion and a shorter perpendicular section. The longer portion is intended for implantation in the coronary sinus, with the perpendicular portion extending into through atrium wall into the left atrium. The stent should extend through the atrium wall, but the extension into the left atrium should be minimal, for example, only 3-4 mm. This distance is believed to insure secure implantation without extending so far as to interfere with movement of the left atrium during normal heart operation.

Stent 40 is deployed using control wire 34, which extends backwards through catheter 30 to a control device or handle (not shown) accessible to a medical professional guiding the catheter. As is well known to those with skill in the art, the catheter is deployed by holding the control wire in place while gently withdrawing the outer sheath 32. As the sheath is withdrawn, the stent expands and deploys in place in the coronary sinus. As is also well known, stent 40 is prepared from medically acceptable prosthesis materials, such as Nitinol, stainless steel, MP35 or other materials. Nitinol or other shape-memory alloys allow manufacturers to prepare stents and train them to assume the desired shape once they are returned to body temperature and are deployed in the body. When freed of the restraints of the confining catheter, the stent will expand and assume the shape for which it was trained.

Figure 57:
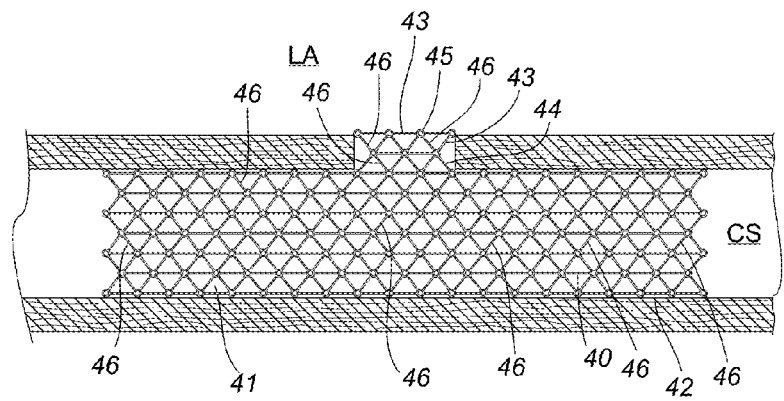
FIG. 57 depicts the stent of FIG. 56 in a deployed state.

Stent 40 is depicted in its undeployed state in FIG. 56 and in its deployed state in FIG. 57. The deployed stent is in a general form of a tube, with longer portions 41, 42 intended for implantation in the coronary sinus and a shorter portion 43, intended to be perpendicular to longer portions 41, 42 and for extension through the orifice made in the wall of the left atrium. In the deployed state, the shorter top portion 43 is intended to protrude through the orifice. In the closer view of FIG. 57, it is seen that both portions of the stent has the appearance of about eight struts 44 joined at apices 45, as also shown in greater detail above in FIG. 2A. In some embodiments, the stents are not made of discrete struts but rather are laser cut or water-jet cut from a thin, solid tube of Nitinol or other desired material. Thus, the stents may better be described as a network, or mesh, of struts and intersections of struts. In one embodiment, at least the shorter portion 43, and also the longer portions 41, 42 include one or more markers 46 made of a radiopaque or echogenic material. In the closer view of FIG. 2A, note that the outer portions are smoothly rounded to avoid any trauma to the heart tissue, for example, with a radius of curvature greater than 0.03 inches (about 0.8 mm).

The stent thus implanted should be capable of two important tasks. The stent should be sized so that the longer part, portions 41, 42 remain in place within the coronary sinus without movement. Accordingly, the diameter of these portions should be in the range of about 8-13 mm, perhaps in the range of 8-11 mm, because the posterior portion of the coronary sinus, in the desired location, is a little smaller than the anterior portion. With the longer portion of the stent fixed in place, the shorter portion, or crown portion 43, will also remain in place.

Once placed, the crown also will not move and will be in a position to keep the orifice open between the left atrium and the coronary sinus. Accordingly, it should not be necessary for the upper portion to exert much force on the opening, and it will be desirable for this portion to be flexible and atraumatic rather than stiff. The coronary sinus is very sensitive to abrasion and the stent portions that reside in the coronary sinus need to be atraumatic while the LA legs need to conform to the curvage or the radius of the opening into the left atrium chamber. At the same time the transverse or crown portion of the stent needs to be strong enough to keep the freshly made opening between the coronary sinus and the left atrium from closing; this would defeat the purpose of the prosthesis. In other embodiments, described below, the upper portion may form a flange, with longer or shorter extensions along the longitudinal direction of the stent, as shown in FIGS. 58 and 59.

Figure 58:
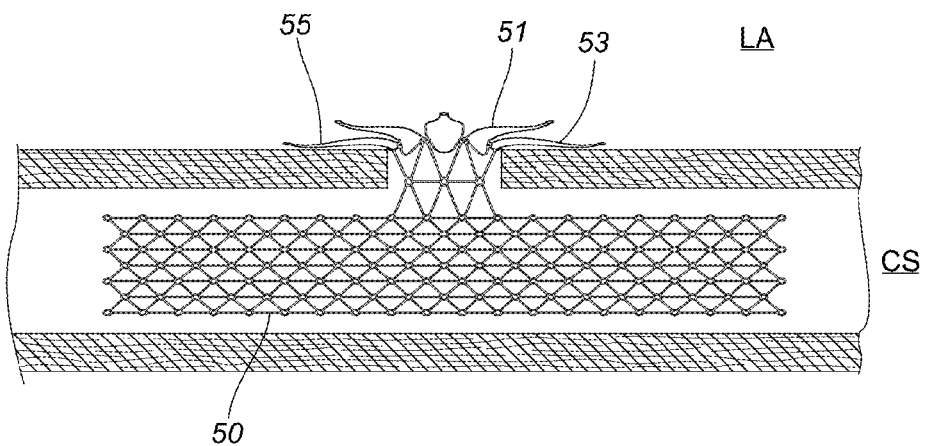
FIG. 58 depicts a first embodiment of a flange for the atrial wall.
Figure 59:
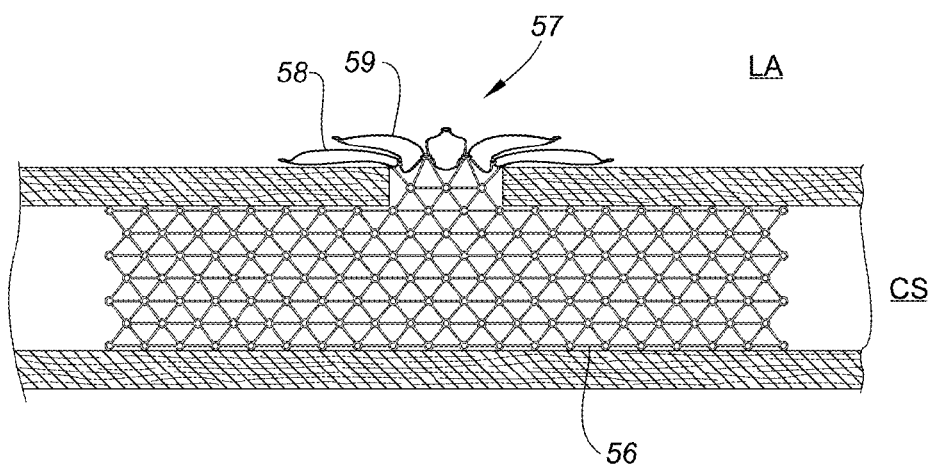
FIG. 59 depicts a second embodiment of a flange for the atrial wall.

In FIG. 58, stent 50 includes a top portion or flange 51 with about 4 protruding triangular struts 53. The radius of curvature is relatively tight, from about 5 mm to 15 mm, so that the flange is not held tightly by the atrial wall in the vicinity of the flange. The flange in this embodiment extends about 2-4 mm in a direction parallel to the coronary sinus. In FIG. 59, stent 56 includes a top portion or flange 57 with about 6 (not all are shown) protruding struts 58. The radius of curvature 59 here is somewhat looser, from about 10 mm to about 40 mm. In one embodiment, the flange extends only about 1-2 mm in a direction parallel to the coronary sinus. Like the annular flange described in connection with intra-atrial stents/devices above, the flange 51 may be annular and comprise a plurality of flange segments in all the same configurations as mentioned above in connection with the intra-atrial stent, including varying flexibility of the flange or flange segments. For example, the flange and/or flange segments may be more flexible than the transverse portion of the stent to achieve the atraumatic contact discussed in the preceding paragraph.

One aspect of the stents for enabling communication between the left atrium and the coronary sinus is that it may be desirable to have only one-way communication. One embodiment of the stent is designed to allow pressure relief of the left atrium by providing an outlet to the coronary sinus without allowing retrograde flow. The coronary sinus directs blood flow from several veins, such as the small, middle, great and oblique cardiac veins, the left marginal vein and the left posterior ventricular vein. It is not desirable, however, to allow flow from the coronary sinus into the left atrium. The stent may thus be restricted to one-way flow by providing the stent with a flow control element of the type disclosed elsewhere herein.

Figure 60:
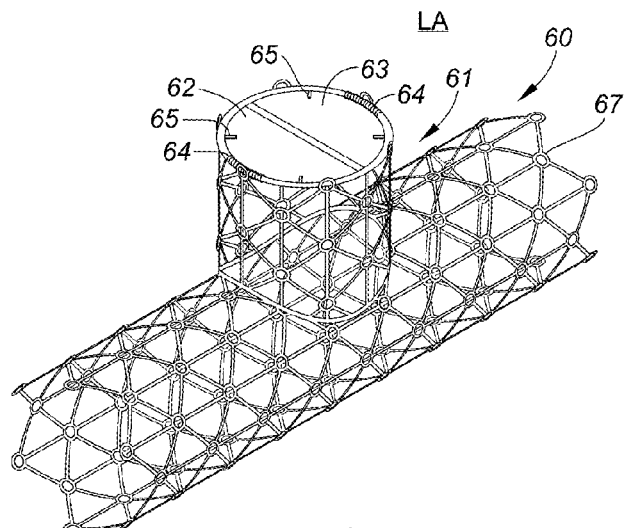
FIG. 60 depicts another embodiment of a stent suitable for ensuring communication between the right atrium and the coronary sinus.
Figure 61:
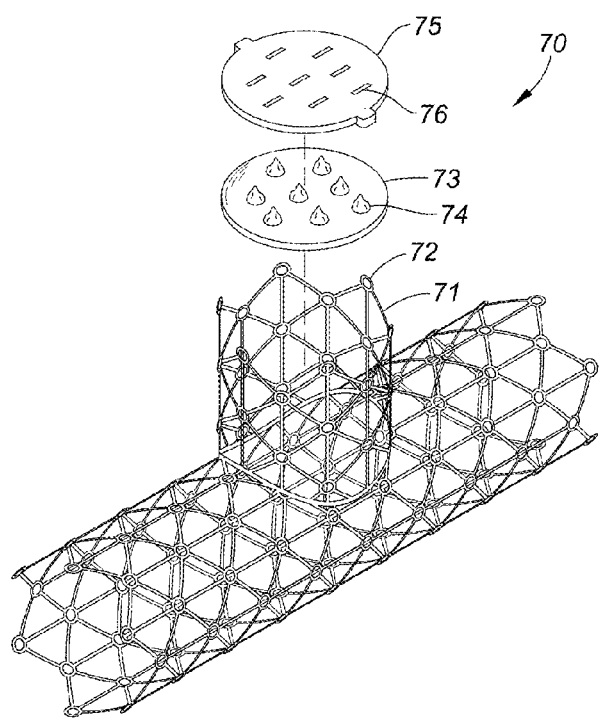
FIG. 61 depicts details of a stent with a one-way valve.

FIGS. 60 and 61 depict two embodiments of a stent limited to one way communication by a restricting valve. In FIG. 60, stent 60 includes a top portion 61 intended for deployment above the wall between the left atrium and the coronary sinus. Stent 60 also includes a transverse portion 67 intended for deployment within the coronary sinus as described above. Top portion 61 in this embodiment includes a multi-part flap valve 63 secured to the top portion 62 of tower 61 with sutures 64. While the flap valve 63 in this embodiment has two portions a bi-valve, that meet roughly along a diameter of the top portion, other embodiments may have three or more portions, again, meeting in the middle. It is also possible to have a single flap, tethered perhaps along one side by about 30-45 degrees of the circumference. This embodiment also includes one or more stops 65 to prevent the valve from opening in the other direction and allowing blood to flow from the coronary sinus into the left atrium. The flow control element could also be a ball and socket valve, a duckbill valve, a butterfly valve, or any other valve component known to those skilled in the art or as those disclosed in the commonly-owned application mentioned above.

As is well known to those with skill in cardiac arts, the valve or flap may be made of mammalian pericardium, such as bovine pericardial tissue, or from ovine or porcine pericardial tissue. Other suitable tissue may also be used. In one embodiment, the tissue is about 0.5 to about 1 mm thick. Other thicknesses may be used. The valve and the flaps are designed so that blood will flow through the one-way valve when the pressure differential reaches about 5-10 mm Hg. Any of the valves/materials disclosed above in connection with intra-atrial stent may also be used.

FIG. 61 depicts another embodiment of a one-way valve useful in the stents disclosed herein. In this exploded view, valve 70 is formed within the top portion 71 of a coronary sinus pressure relieving stent. The valve includes a plate 75 with multiple perforations 76. While perforations 76 are shown as slots, they may be made of any suitable shape. The plate itself made may be made of any material suitable for in vivo contact with blood, including inert polymers such as polycarbonate or polysulfone, or metals such as stainless steels, MP35N or Nitinol. As shown, perforated plate 75 is adjacent the distal end of the stent top portion 71. On the opposite side of the perforated plate 75 is a valve element 73 with flaps 74. In one embodiment, flaps 74 are slightly larger that the gaps beneath the flaps, enabling the flaps to seal tightly if for some reason the pressure in the coronary sinus exceeds the pressure in the left atrium, on the far side of the stent.

During normal operation, when the pressure in the left atrium exceeds the pressure in the coronary sinus, blood will tend to flow from the left atrium through the stent, and in particular at the outset, through the top portion 70. Blood will flow through the perforated plate 75 and since the flaps 74 are free to flap downward, in the embodiment of FIG. 61, the blood will flow through valve element 73 and on into the coronary sinus. However, the flaps 74 are not free to flow in the opposite direction, toward the left atrium, because their movement is prevented by the perforated plate 75. Other embodiments of check valves or one-way valves may also be used.

Figure 62A:
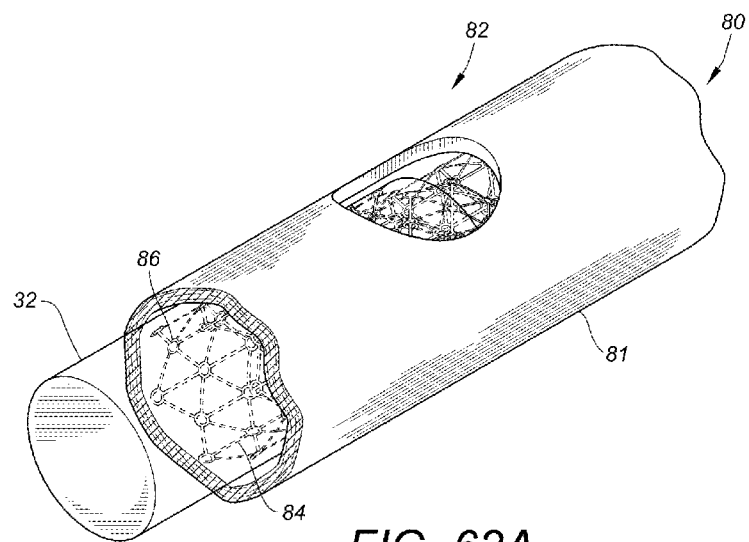
FIGS. 62A and 62B depict another embodiment of a stent.
Figure 62B:
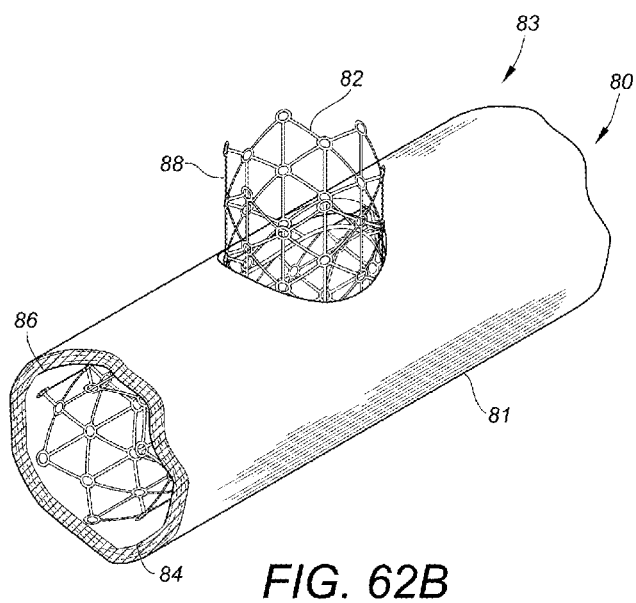

Other embodiments of stents for relieving pressure may have other configurations. For example, FIG. 62A depicts a T-tube stent in a before-deployment configuration. Stent 80 includes a longer portion 81 in a general shape of a cylinder for placement in a coronary sinus of a patient. The stent is constructed of short struts 84 and apices 86 joining the struts, or as mentioned above, an interconnecting network of struts and joining areas. A shorter portion, tower 82 is folded within the longer portion 81. Upon deployment of the stent within a patient, the longer portion will expand if the stent has been trained to do so when the austenitic transition occurs upon warming to body temperature. The tower portion 82 may then be deployed from its retracted position within the longer portion to its deployed position, as shown in FIG. 62B.

The tower will assume its intended shape as it is deployed and as it warms to body temperature. The tower includes a wider portion, i.e., a portion with a larger diameter that will reside within the left atrium. The tower also includes a narrower portion 83 having a diameter about the diameter of the opening which was prepared for the stent. Tower portion 82 may be pushed into place, for example, by a balloon catheter if it fails to deploy properly by the "memory metal" effect. While the principal portion of the stent is constructed of struts and apices, in this embodiment, the tower may be made from many more flexible, thinner wires 88 for greater ease of deployment. In one embodiment, the wires are 0.003 in (0.08 mm) diameter and are thus very flexible. The wires form a porous closed "net" whose openings allow blood to flow from the left atrium to the coronary sinus.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While embodiments have been disclosed and described in detail, it is understood that various modifications and improvements thereon will become readily apparent to those skilled in the art. Accordingly, the spirit and scope of the present invention is not limited by the foregoing examples, but is better understood by the claims below.

What is claimed is:

1. A percutaneously deliverable device for treating a heart condition in a patient comprising: a first flange section having a plurality of flange segments angularly spaced about a longitudinal axis of the device, each flange segment of the first flange section comprising two prongs meeting at a junction; and a second flange section having a plurality of flange segments angularly spaced about the longitudinal axis of the device, each flange segment of the second flange section comprising two elements meeting at a junction; wherein each of the flange segments the each of the first and second flange sections are adapted to fold in the same direction upon the device being drawn into an opening of a percutaneous catheter to assume a collapsed configuration in which the junctions of the flange segments of the first flange section and of the second flange section are disposed distal to their corresponding prongs.

2. The device of claim 1, wherein the device also comprises a hub.

3. The device of claim 2, wherein two or more of the flange segments of the first flange section each has a proximal end connected to the hub.

4. The device of claim 2, wherein the hub has at least one of internal threads and external threads which are adapted to releasably connect with complementary threads of at least one of a delivery device and a retrieval device.

5. The device of claim 2, wherein the hub has a groove, the groove being adapted to cooperate with a collet of at least one of a delivery device and a retrieval device to form a releasable connection.

6. The device of claim 2, wherein the hub has a ball, the ball being adapted to cooperate with a claw device of at least one of a delivery device and a retrieval device to form a releasable connection.

7. The device of claim 2, wherein the hub has a c-shaped connector section, the c-shaped connector section being adapted to cooperate with a complementary c-shaped connector section of at least one of a delivery device and a retrieval device to form a releasable connection.

8. The device of claim 2, wherein the hub has an aperture, the aperture being adapted to receive at least one of a pin or a finger of at least one of a delivery device and a retrieval device to form a releasable connection.

9. The device of claim 1, wherein the device comprises a core section adapted to permit fluid flow therethrough.

10. The device of claim 1, wherein at least one flange segment of at least one of the first and second flange sections has a first region having a first thickness and a first width and a second region having a second thickness and a second width wherein the respective magnitude of at least one of the first thickness and the first width is different than the respective magnitude of, respectively, the second thickness and the second width so that the flexibility of the first region is different from the flexibility of the second region.

11. A reversibly collapsible device for treating a heart condition in a patient comprising a first flange section, a second flange section, and a longitudinal axis, wherein each of the first and second flange sections comprise a plurality of separate, adjacent segments, each segment comprising two prongs meeting at a junction, and is adapted to fold in the same axial direction upon the device being drawn into an opening of a percutaneous catheter to assume a collapsed configuration in which the junctions of the flange segments of the first flange section and of the second flange section are disposed distal to their corresponding prongs.

12. The device of claim 11, wherein the device also comprises a hub.

13. The device of claim 12, wherein two or more of the flange segments of the first flange section each has a proximal end connected to the hub.

14. The device of claim 12, wherein the hub has at least one of internal threads and external threads which are adapted to releasably connect with complementary threads of at least one of a delivery device and a retrieval device.

15. The device of claim 12, wherein the hub has a groove, the groove being adapted to cooperate with a collet of at least one of a delivery device and a retrieval device to form a releasable connection.

16. The device of claim 12, wherein the hub has a ball, the ball being adapted to cooperate with a claw device of at least one of a delivery device and a retrieval device to form a releasable connection.

17. The device of claim 12, wherein the hub has a c-shaped connector section, the c-shaped connector section being adapted to cooperate with a complementary c-shaped connector section of at least one of a delivery device and a retrieval device to form a releasable connection.

18. The device of claim 12, wherein the hub has an aperture, the aperture being adapted to receive at least one of a pin or a finger of at least one of a delivery device and a retrieval device to form a releasable connection.

19. The device of claim 11, wherein the device comprises a core section adapted to permit fluid flow therethrough.

20. The device of claim 11, wherein at least one flange segment of at least one of the first and second flange sections has a first region having a first thickness and a first width and a second region having a second thickness and a second width wherein the respective magnitude of at least one of the first thickness and the first width is different than the respective magnitude of, respectively, the second thickness and the second width so that the flexibility of the first region is different from the flexibility of the second region.

21. A percutaneous deliverable device adapted to be implanted into or retracted from, via a catheter, a patient's atrial septum, comprising: a first annular flange section having a plurality of separate, adjacent flange segments, each flange segment of the first annular flange section comprising two prongs meeting at a junction; and a second annular flange section having a plurality of separate, adjacent flange segments, each flange segment of the first annular flange section comprising two prongs meeting at a junction, wherein the flange segments of the first annular flange section and the flange segments of the second annular flange section are configured to collapse in the same direction upon retraction by said catheter to assume a collapsed configuration in which the junctions of the flange segments of the first flange section and of the second flange section are disposed distal to their corresponding prongs.

22. The device of claim 21, wherein the device also comprises a hub.

23. The device of claim 22, wherein two or more of the flange segments of the first flange section each has a proximal end connected to the hub.

24. The device of claim 22, wherein the hub has at least one of internal threads and external threads which are adapted to releasably connect with complementary threads of at least one of a delivery device and a retrieval device.

25. The device of claim 22, wherein the hub has a groove, the groove being adapted to cooperate with a collet of at least one of a delivery device and a retrieval device to form a releasable connection.

26. The device of claim 22, wherein the hub has a ball, the ball being adapted to cooperate with a claw device of at least one of a delivery device and a retrieval device to form a releasable connection.

27. The device of claim 22, wherein the hub has a c-shaped connector section, the c-shaped connector section being adapted to cooperate with a complementary c-shaped connector section of at least one of a delivery device and a retrieval device to form a releasable connection.

28. The device of claim 22, wherein the hub has an aperture, the aperture being adapted to receive at least one of a pin or a finger of at least one of a delivery device and a retrieval device to form a releasable connection.

29. The device of claim 21, wherein the device comprises a core section adapted to permit fluid flow therethrough.

30. The device of claim 21, wherein at least one flange segment of at least one of the first and second flange sections has a first region having a first thickness and a first width and a second region having a second thickness and a second width wherein the respective magnitude of at least one of the first thickness and the first width is different than the respective magnitude of, respectively, the second thickness and the second width so that the flexibility of the first region is different from the flexibility of the second region.

* * * * *